United States Patent
Stafford et al.

(10) Patent No.: US 10,596,270 B2
(45) Date of Patent: Mar. 24, 2020

(54) ANTI-FOLATE RECEPTOR ANTIBODY CONJUGATES, COMPOSITIONS COMPRISING ANTI-FOLATE RECEPTOR ANTIBODY CONJUGATES, AND METHODS OF MAKING AND USING ANTI-FOLATE RECEPTOR ANTIBODY CONJUGATES

(71) Applicant: Sutro Biopharma, Inc., South San Francisco, CA (US)

(72) Inventors: Ryan Stafford, Emeryville, CA (US); Alice Yam, Tiburon, CA (US); Xiaofan Li, Fremont, CA (US); Gang Yin, South San Francisco, CA (US); Toni Kline, San Francisco, CA (US); Cristina Abrahams, Burlingame, CA (US); Venita De Almeida, San Carlos, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 48 days.

(21) Appl. No.: 16/133,383

(22) Filed: Sep. 17, 2018

(65) Prior Publication Data

US 2019/0083641 A1  Mar. 21, 2019

Related U.S. Application Data

(60) Provisional application No. 62/560,064, filed on Sep. 18, 2017.

(51) Int. Cl.
*A61K 47/64* (2017.01)
*A61K 47/68* (2017.01)
(Continued)

(52) U.S. Cl.
CPC ............ *A61K 47/6425* (2017.08); *A61K 9/19* (2013.01); *A61K 47/6803* (2017.08);
(Continued)

(58) Field of Classification Search
None
See application file for complete search history.

(56) References Cited

U.S. PATENT DOCUMENTS

| | | | |
|---|---|---|---|
| 4,542,225 A | 9/1985 | Blattler et al. | |
| 4,618,492 A | 10/1986 | Blattler et al. | |
| (Continued) | | | |

FOREIGN PATENT DOCUMENTS

| | | |
|---|---|---|
| WO | WO 2013/185115 A1 | 12/2013 |
| WO | WO 2015/006555 A2 | 1/2015 |
| | (Continued) | |

OTHER PUBLICATIONS

International Search Report and Written Opinion of the International Searching Authority of PCT/US2018/051364 dated Dec. 11, 2018, 14 pages.
(Continued)

*Primary Examiner* — Karl J Puttlitz
(74) *Attorney, Agent, or Firm* — Squire Patton Boggs (US) LLP

(57) ABSTRACT

The present disclosure relates to antibody conjugates with binding specificity for folate receptor alpha (FOLR1) and its isoforms and homologs, and compositions comprising the antibody conjugates, including pharmaceutical compositions. Also provided are methods of producing the antibody conjugates and compositions as well as methods of using the antibody conjugates and compositions, such as in therapeutic and diagnostic methods.

24 Claims, 63 Drawing Sheets

Specification includes a Sequence Listing.

(51) Int. Cl.
A61P 35/00 (2006.01)
A61K 9/19 (2006.01)
C07K 16/28 (2006.01)
C07D 487/00 (2006.01)

(52) U.S. Cl.
CPC ...... A61K 47/6811 (2017.08); A61K 47/6849 (2017.08); A61K 47/6877 (2017.08); A61K 47/6889 (2017.08); A61P 35/00 (2018.01); C07K 16/28 (2013.01); C07D 487/00 (2013.01); C07K 2317/92 (2013.01)

(56) References Cited

U.S. PATENT DOCUMENTS

| | | | |
|---|---|---|---|
| 4,625,014 | A | 11/1986 | Senter et al. |
| 4,671,958 | A | 6/1987 | Rodwell et al. |
| 4,816,567 | A | 3/1989 | Cabilly et al. |
| 7,375,078 | B2 | 5/2008 | Feng |
| 8,258,082 | B2 | 9/2012 | Ladner |
| 8,431,558 | B2 | 4/2013 | Bertozzi et al. |
| 8,691,730 | B2 | 4/2014 | Vasquez et al. |
| 8,703,936 | B2 | 4/2014 | Jewett et al. |
| 9,145,361 | B2 | 9/2015 | Gee et al. |
| 9,222,940 | B2 | 12/2015 | Van Delft et al. |
| 2003/0082575 | A1 | 5/2003 | Schultz et al. |
| 2003/0108885 | A1 | 6/2003 | Schultz et al. |
| 2013/0189287 | A1 | 7/2013 | Bregeon et al. |
| 2013/0251783 | A1 | 9/2013 | Parmentier et al. |
| 2014/0356385 | A1 | 12/2014 | Dennler et al. |

FOREIGN PATENT DOCUMENTS

| | | | |
|---|---|---|---|
| WO | WO 2015/196167 | A1 | 12/2015 |
| WO | WO 2016/123582 | A1 | 8/2016 |
| WO | WO 2017/132617 | A1 | 8/2017 |
| WO | 2018071597 | * | 4/2018 |

OTHER PUBLICATIONS

International Search Report and Written Opinion of the International Searching Authority of PCT/US2018/051322 dated Dec. 10, 2018, 14 pages.
Ab et al., "IMGN853, a folate receptor alpha (FRα)-targeting antibody-drug conjugate, exhibits potent targeted anti-tumor activity against FRα-expressing tumors", Jul. 2015, Molecular Cancer Therapeutics, vol. 14, No. 7, pp. 1605-1613.
Cai et al., "A Simplified and Robust Protocol for Immunoglobulin Expression in *Escherichia coli* Cell-Free Protein Synthesis Systems", Biotechnology Progress, 2015, vol. 31, No. 3, pp. 823-831.
Chan et al., "Folate Receptor-α is a Cofactor for Cellular Entry by Marburg and Ebola Viruses", Jul. 13, 2001, Cell, vol. 106, pp. 117-126.
Chronopoulou et al., "Hybridoma Technology for the Generation of Rodent mAbs via Classical Fusion", Methods in Molecular Biology, 2014, vol. 1131, pp. 47-70.
Dreier and Plückthun, "Ribosome Display: A Technology for Selecting and Evolving Proteins from Large Libraries", 2011, Methods in Molecular Biology, vol. 687, pp. 283-306.
Elwood et al., "The Divergent 5' Termini of the a Human Folate Receptor (hFR) mRNAs Originate from Two Tissue-Specific Promoters and Alternative Splicing: Characterization of the a hFR Gene Structure", Biochemistry, 1997, vol. 36, pp. 1467-1478.
Elwood, "Molecular Cloning and Characterization of the Human Folate-binding Protein cDNA from Placenta and Malignant Tissue Culture (KB) Cells", The Journal of Biological Chemistry, Sep. 1989, vol. 264, No. 25, pp. 14893-14901.
Heckman and Pease, "Gene splicing and mutagenesis by PCR-driven overlap extension", Nature Protocols, 2007, vol. 2, No. 4, pp. 924-932.
Johnson and Wu, "Kabat Database and a Bioinformatics Example", Methods in Molecular Biology, vol. 248: Antibody Engineering: Methods and Protocols, pp. 11-25.
Johnson and Wu, "Kabat Database and its applications: 30 years after the first variability plot", Nucleic Acids Research, 2000, vol. 28, No. 1, pp. 214-218.
Lacey et al., "Complementary DNA for the folate binding protein correctly predicts anchoring to the membrane by glycosyl-phosphatidylinositol", Aug. 1989, J. Clinical Investigation, vol. 84, No. 2, pp. 715-720.
Leamon, "Fotate-targeted drug strategies for the treatment of cancer", Curr. Opin. Investig. Drugs, 2008, vol. 9, pp. 1277-1286.
Lee et al., "High-affinity Human Antibodies from Phage-displayed Synthetic Fab Libraries with a Single Framework Scaffold", J. Mol. Biol. 2004, vol. 340, pp. 1073-1093.
Paulos et al., "Folate receptor-mediated targeting of therapeutic and imaging agents to activated macrophages in rheumatoid arthritis", Advanced Drug Delivery Reviews, 2004, vol. 56, pp. 1205-1217.
Stafford et al., "In vitro Fab display: a cell-free system for IgG discovery", Protein Engineering, Design & Selection, 2014, vol. 27, No. 4 pp. 97-109.
Wu and Kabat, "An Analysis of the Sequences of the Variable Regions of Bence Jones Proteins and Myeloma Light Chains and Their Implications for Antibody Complementarity", Received for publication Mar. 26, 1970, pp. 211-249.
Yagodkin and Azhayev, "Improved Synthesis of Trinucleotide Phosphoramidites and Generation of Randomized Oligonucleotide Librarie", Nucleosides, Nucleotides, and Nucleic Acids, 2007, vol. 26, pp. 473-497.
Yin et al., "RFI attenuation enables efficient non-natural amino acid incorporation for production of homogeneous antibody drug conjugates", Scientific Reports, vol. 7, No. 1, Jun. 8, 2017.
Zemlin et al. "Expressed Murine and Human CDR-H3 Intervals of Equal Length Exhibit Distinct Repertoires that Differ in their Amino Acid Composition and Predicted Range of Structures", J. Mol. Biol. 2003, vol. 334, pp. 733-749.

* cited by examiner

| Column # | 1 2 3 4 5 6 7 8 9 10 11 12 13 14 15 16 17 18 19 20 21 22 23 24 25 26 27 28 29 30 31 32 33 34 35 36 37 |
|---|---|
| SRP1848-A01 | E V Q L V E S G G G L V Q P G G S L R L S C A A S G F N I T R Y - - S I H |
| SRP1848-A02 | E V Q L V E S G G G L V Q P G G S L R L S C A A S G F N I S G F - - R I H |
| SRP1848-A04 | E V Q L V E S G G G L V Q P G G S L R L S C A A S G F N I D Q S - - S I H |
| SRP1848-A06 | E V Q L V E S G G G L V Q P G G S L R L S C A A S G F N I G N S - - Y I H |
| SRP1848-A07 | E V Q L V E S G G G L V Q P G G S L R L S C A A S G F N I G Y H - - S I H |
| SRP1848-A08 | E V Q L V E S G G G L V Q P G G S L R L S C A A S G S N I R K H - - S I H |
| SRP1848-A09 | E V Q L V E S G G G L V Q P G G S L R L S C A A S G F N I R K Q - - S I H |
| SRP1848-A10 | E V Q L V E S G G G L V Q P G G S L R L S C A A S G F N I R K Y - - S I H |
| SRP1848-B01 | E V Q L V E S G G G L V Q P G G S L R L S C A A S G F N I R N Y - - S I H |
| SRP1848-B03 | E V Q L V E S G G G L V Q P G G S L R L S C A A S G F N I S M K - - Y I H |
| SRP1848-B04 | E V Q L V E S G G G L V Q P G G S L R L S C A A S S F N I S N H - - S I H |
| SRP1848-B05 | E V Q L V E S G G G L V Q P G G S L R L S C A A S G F N I S N Y - - Y I H |
| SRP1848-B06 | E V Q L V E S G G G L V Q P G G S L R L S C A A S G F N I S N Y - - Y I H |
| SRP1848-B07 | E V Q L V E S G G G L V Q P G G S L R L S C A A S G F N I S R F - - Y I H |
| SRP1848-B09 | E V Q L V E S G G G L V Q P G G S L R L S C A A G G F N I T N Y - - Y I H |
| SRP1848-B10 | E V Q L V E S G G G L V Q P G G S L R L S C A A S G F N T T T K - - S I H |
| SRP1848-B11 | E V Q L V E S G G G L V Q P G G S L R L S C A A S G F N I G N N - - S I H |
| SRP1848-C01 | E V Q L V E S G G G L V Q P G G S L R L S C A A S G F N I G N S - - Y I H |
| SRP1848-C03 | E V Q L V E S G G G L V Q P G G S L R L S C A A S G F N I G V Y - - S I H |
| SRP1848-C04 | E V Q L V E S G G G L V Q P G G S L R L S C A A S G F N I R H Y - - S I H |
| SRP1848-C05 | E V Q L V E S G G G L V Q P G G S L R L S C A A S G F N I R K Y - - S I H |
| SRP1848-C07 | E V Q L V E S G G G L V Q P G G S L R L S C A A S G F N I R K Y - - S I H |
| SRP1848-C10 | E V Q L V E S G G G L V Q P G G S L R L S C A A S G F N I R T Y - - Y I H |
| SRP1848-D02 | E V Q L V E S G G G L V Q P G G S L R L S C A A S G F N I S H N - - Y I H |
| SRP1848-D03 | E V Q L V E S G G G V V Q P G G S L R L S C A A S G F N I R Y F - - S I H |
| SRP1848-D04 | E V Q L V E S G G G L V Q P G G S L R L S C A A S G F N I S H Y - - S I H |
| SRP1848-D05 | E V Q L V E S G G G L V Q P G G S L R L S C A A S G F N I S I S - - Y I H |
| SRP1848-D07 | E V Q L V E S G G G L V Q P G G S L R L S C A A S G F N I S K Y - - Y I H |
| SRP1848-D09 | E V Q L V E S G G G L V Q P G G S L R L S C A A S G F N I S N Y - - Y I H |
| SRP1848-D10 | E V Q L V E S G G G L V Q P G G S L R L S C A A S G F N I S R N - - S I H |
| SRP1848-E01 | E V Q L V E S G G G L V Q P G G S L R L S C A A S G F N I T N K - - Y I H |
| SRP1848-E02 | E V Q L V E S G G G L V Q P G G S L R L S C A A S G F N I G K Y - - S I H |
| SRP1848-E03 | E V Q L V E S G G G L A Q P G G S L R L S C A A S G F N I G N Y - - Y I H |

FIG. 2A

```
Column #     383940414243444546474849505152535455565758596061626364656 66
SRP1848-A01  WVRQAPGKGLEWVAGILPES-GGTSYADS
SRP1848-A02  WVRQAPGKGLEWVAGIYPES-GATYYADS
SRP1848-A04  WVRQAPGKGLEWVGVIYPVD-GTTDYADS
SRP1848-A06  WVRQAPGKGLEWVGGITPID-GNTDYADS
SRP1848-A07  WVRQAPGKGLEWVGEIFPVD-GTTDYADS
SRP1848-A08  WVRQAPGKGLEWVGSIYPND-GTTDYADS
SRP1848-A09  WVRQAPGKGLEWVGSIFPND-GTTDYADS
SRP1848-A10  WARQAPGKGLEWVGDIFPID-DITDYADS
SRP1848-B01  WVRQAPGKGLEWVGEIYPVD-GITDYADS
SRP1848-B03  WVRQAPGKGLEWVGGITPID-GMTDYADS
SRP1848-B04  WVRQAPGKGLEWVGEIYPVD-GITDYADS
SRP1848-B05  WVRQAPGKGLEWVGGISPID-GYTDYADS
SRP1848-B06  WVRQAPGKGLEWVGGITPID-GYTDYADS
SRP1848-B07  WVRQAPGKGLEWVGGISPYD-GFTDYADS
SRP1848-B09  WVRQAPGKGLEWVGGITPVD-GYTDYADR
SRP1848-B10  WVRQAPGKGLEWVGEIYPRD-GITDYADS
SRP1848-B11  WVRQAPGKGLEWVGDISPID-GFTDYADS
SRP1848-C01  WVRQAPGKGLEWVGGVTPND-GYTDYADS
SRP1848-C03  WVRQAPGKGLEWVGEIYPID-GNTDYADS
SRP1848-C04  WVRQAPGKGLEWVGEIYPGP-GNTDYADS
SRP1848-C05  WVRQAPGKGLEWVGDIFPID-GINDYADS
SRP1848-C07  WVRQAPGKGLEWVGDIFPID-GITDYADS
SRP1848-C10  WVRQAPGKGLEWVGGISPID-GYTDYADS
SRP1848-D02  WVRQAPGKGLEWVGGITPQD-GYTDYADS
SRP1848-D03  WVRQAPGKGLEWVGDIFPND-GSTDYADS
SRP1848-D04  WVRQAPGKGLEWVGEIYPRD-GITDYADS
SRP1848-D05  WVRQAPGKGLEWVGGISPID-GYTDYADS
SRP1848-D07  WVRQAPGKGLEWVGGISPND-GYTDYADS
SRP1848-D09  WVRQAPGKGLEWVGGISPND-GYTDYADS
SRP1848-D10  WVRQAPGKGLEWVGWISPND-GTTDYADS
SRP1848-E01  WVRQAPGKGLEWVGGITPFD-GFTDYADS
SRP1848-E02  WVRQAPGKGLEWVGEIYPND-GNTDYADS
SRP1848-E03  WVRQAPGKGLEWVGGITPRD-GFTDYADS
```

FIG. 2B

```
Column #         67 68 69 70 71 72 73 74 75 76 77 78 79 80 81 82 83 84 85 86 87 88 89 90 91 92 93 94 95 96 97 98 99 100
SRP1848-A01      V K G R F T I S A D T S K N T A Y L Q M N S L R A E D T A V Y Y C A
SRP1848-A02      V K G R F T I S A D T S K N T A Y L Q M N S L R A E D T A V Y Y C A
SRP1848-A04      V K G R F T I S A D T S K N T A Y L Q M N S L R A E D T A V Y Y C A
SRP1848-A06      V K G R F T I S A D T S K N T A Y L Q M N S L R A E D T A V Y Y C A
SRP1848-A07      V K G R F T I S A D T S K N T A Y L H M N S L R A E D T A V Y Y C A
SRP1848-A08      V K G R F T I S A D T S K N T A Y L Q M N S L R A E D T A V Y Y C A
SRP1848-A09      V K G R F T I S A D T S K N T A Y L Q V N S L R A E D T A V Y Y C A
SRP1848-A10      V K G R F T I S A D T S K N T A Y L Q M N S L R A E D T A V Y Y C A
SRP1848-A10      V K G R F T I S A D T S K N T A Y L Q M N S L R A E D T A V Y Y C A
SRP1848-B01      V K G R F T I S A D T S K N T A Y L Q M N S L R A E D T A V Y Y C A
SRP1848-B03      V K G R F T I S A D T S K N T A Y L Q M N S L R A E D T A V Y Y C A
SRP1848-B04      M K G R F T I S A D T S K N T A Y L Q M S S L R A E D T A V Y Y C A
SRP1848-B05      V K G R F T I S A D T S K N T A Y L Q M N S L R A E D T A V Y Y C A
SRP1848-B07      V K G R F T I S A D T S K N T A Y L Q M N S L R A E D T A V Y Y C A
SRP1848-B09      V K G R F T I S A D T S K N T A Y L Q M N S L R A E D T A V Y Y C A
SRP1848-B10      V K G R F T I S A D T S K N T A Y L Q M N S L R A E D T A V Y Y C A
SRP1848-B11      V K G R F T I S A D T S K N T A Y L Q M N S L R A E D T A V Y Y C A
SRP1848-C01      V K G R F T I S A D T S K N T T Y L Q M N S L R A E D T A V Y Y C A
SRP1848-C03      V K G R F T I S A D T S K N T A Y L Q M N S L R A E D T A V Y Y C A
SRP1848-C04      V K G R F T I S A D T S K N T A Y L Q M N S L R A E D T A V Y Y C A
SRP1848-C05      V K G R F T I S A D T S K N T A Y L Q M N S L R A E D T A V Y Y C A
SRP1848-C07      M K G R F T I S A D T S K N T A Y L Q M N S L R A E D T A V Y Y C A
SRP1848-C10      V K G R F T I S A D T S K N T A Y L Q M N S L R A E D T A V Y Y C A
SRP1848-D02      V K G R F T I S A D T S K N T A Y L Q M N R L R A E D T A V Y Y C A
SRP1848-D03      V K G R F T I S A D T S K N T A Y L Q M N S L R A E E T A V Y Y C A
SRP1848-D04      V K G R F T I S A D T S K N T A Y L Q M N S L S A E D T A V Y Y C A
SRP1848-D05      V K G R F T I S A D T S K N T A Y L Q M N S L R A E D T A V Y Y C A
SRP1848-D07      V K G R F A I S A D T S K N T A Y L Q M N S L R A E D T A V Y Y C A
SRP1848-D09      V K G R F T I S A D T S K N T A Y L Q M N S L R A E D T A V Y Y C A
SRP1848-D10      V K G R F T I S A D G S K N T A Y L Q M N S L R A E D T A V Y Y C A
SRP1848-E01      V K G R F T I S A D T S K N T A Y L Q M N S L R A E D T A V Y Y C A
SRP1848-E02      V K G R F T I S A D T S K N T A Y L Q M N S L R A E D T A V Y Y C A
SRP1848-E03      V K G R F T I S A D T S K N T A Y L Q V N S L R A E D T A V Y Y C A
```

FIG. 2C

| Column # | 101 102 103 104 105 106 107 108 109 110 111 112 113 114 115 116 117 118 119 120 121 122 123 124 125 126 127 128 |
|---|---|
| SRP1848-A01 | R H I Y P W D W F - S N Y V L D Y W G Q G T L V T V S S |
| SRP1848-A02 | R H L Y V W D W V - L D H V L D Y W G Q G T L V T V S S |
| SRP1848-A04 | R G A W S W R S G - Y G Y Y I D Y W G Q G T L V T V S S |
| SRP1848-A06 | R G A W S W R S G - Y G Y Y I D Y W G Q G T L V T V S S |
| SRP1848-A07 | R G F W A W R S G - Y G Y Y L D Y W G Q G T L V T V S S |
| SRP1848-A08 | R G S W F W R A G - Y G Y Y L D Y W G Q G T L V T V S S |
| SRP1848-A09 | R G S W F W R S G - Y G Y F L E Y W G Q G T L V T V S S |
| SRP1848-A10 | R G S W S W P S G - H S Y Y L D Y W G Q G T L V T V S S |
| SRP1848-B01 | R G F W S W P S G - Y S Y F L D Y W G Q G T L V T V S S |
| SRP1848-B03 | R G S W S W P S G - Y S Y Y L D Y W G Q G T L V T V S S |
| SRP1848-B04 | R G R Y S W R A G - Y S Y Y L D Y W G Q G T L V T V S S |
| SRP1848-B05 | R G S W F W Q S G - Y G Y Y L D Y W G Q G T L V T V S S |
| SRP1848-B06 | R G F W S W P S G - Y G Y Y Q D Y W G Q G T L V T V S S |
| SRP1848-B07 | R G S W S W P A G - Y G Y Y Q D Y W G Q G T L V T V S S |
| SRP1848-B09 | R G A W S W R S G - Y G Y Y M D Y W G Q G T L V T V S S |
| SRP1848-B10 | R G G W H W R S G - Y S Y Y L D Y W G Q G T L V T V S S |
| SRP1848-B11 | R G S W S W R A G - Y G Y Y L D Y W G Q G T L V T V S S |
| SRP1848-C01 | R G S W F W R A G - Y G Y Y L D Y W G Q A L V T V S S |
| SRP1848-C03 | R G S W A W R S G - Y S Y Y L D Y W G Q G T L V T V S S |
| SRP1848-C04 | R G S L S W R A G - Y G Y Y L D Y W G Q G T L V T V S S |
| SRP1848-C05 | R G S W S W K A G - Y G Y Y L D Y W G Q G T L V T V S S |
| SRP1848-C07 | R G S W S W P A G - Y G Y Y Q D Y W G Q G T L V T V S S |
| SRP1848-C10 | R G S W S W P A G - Y G Y Y L D Y W G Q G T L V T V S S |
| SRP1848-D02 | R G A W S W R A G - Y G Y Y L D Y W G Q G T L V T V S S |
| SRP1848-D03 | R G H W S W P S G - Y W Y Y L D Y W G Q G T L V T V S S |
| SRP1848-D04 | R G Y W F W R S G - Y G Y Y L D Y W G Q G T L V T V S S |
| SRP1848-D05 | R G S W S W R A G - Y G Y Y L D Y W G Q G T L V T V S S |
| SRP1848-D07 | R G F W A W R S G - Y G Y Y L D Y W G Q G T L V T V S S |
| SRP1848-D09 | R G S W S W R H G - Y G Y Y L D Y W G Q G T L V T V S S |
| SRP1848-D10 | R G A W S W R S G - Y G Y Y I D Y W G Q G T L V T V S S |
| SRP1848-E01 | R G S W S W P A G - Y G Y Y Q D Y W G Q G T L V T V S S |
| SRP1848-E02 | R G S W S W R S G - Y G Y Y L D Y W G Q G T L V T V S S |
| SRP1848-E03 | R G S W S W P A G - H S Y Y L D Y W G Q G T L V T V S S |

FIG. 2D

```
Column #        1 2 3 4 5 6 7 8 9 10 11 12 13 14 15 16 17 18 19 20 21 22 23 24 25 26 27 28 29 30 31 32 33 34 35 36 37
SRP1848-E05    E V Q L V E S G G G L V Q P G G S L R V S C A A S G F N I G V Y - - Y I H
SRP1848-E06    E V Q L V E S G G G L V Q P S G S L R L S C A A S G F N I N R Y - - Y I H
SRP1848-E07    E V Q L V E S G G G L V Q P G G S L R L S C A A S G F N I R K S - - S I H
SRP1848-F01    E V Q L V E S G G G L V Q P G G S L R L S C A A S G F N I R T Y - - S I H
SRP1848-F02    E V Q L V E S G G G L V Q P G G S L R L S C A A S G F N I R T Y - - S I H
SRP1848-F04    E V Q L V E S G G G L V Q P G G S L R L S C A A S G F N I S N Y - - S I H
SRP1848-F05    E V Q L V E S G G G L V Q P G G S L R L S C A A S G F N I S K S - - S I H
SRP1848-F06    E V Q L V E S G G G L V Q P G G S L R L S C A A S G F N I S L S - - Y I H
SRP1848-F07    E V Q L V E S G G G L V Q P G G S L R L S C A A S G F N I S N H - - S I H
SRP1848-F08    E V Q L V E S G G G L V Q P G G S L R L S C A A G G F N I S N H - - S I H
SRP1848-F09    E V Q L V E S G G G L V Q P G G S L R L S C A A S G F N I S N H - - Y I H
SRP1848-F10    E V Q L V E S G G G L V Q P G G S L R L S C A A S G F N I S N N - - S I H
SRP1848-F11    E V Q L V E S G G G L V Q P G G S L R L S C A A S G F N I S N N - - Y I H
SRP1848-G01    E V Q L V E S G G G L V Q P G G S L R L S C A A S G F N I S R H - - S I H
SRP1848-G03    E V Q L V E S G G G L V Q P G G S L R L S C A A S G F N I S T Y - - Y I H
SRP1848-H01    E V Q L V E S G G G L V Q P G G S L R L S C A A S G F N I R T Q - - S I H
SRP1848-G04    E V Q L V E S G G G L V Q P G G S L R L S C A A S G F N I H S T - - D I H
SRP1848-G06    E V Q L V E S G G G L V Q P G G S L R L S C A A S G F N I R S T - - D I H
SRP1848-G07    E V Q L V E S G G G L V Q P G G S L R L S C A A S G F N I H S T - - D I H
SRP1848-G09    E V Q L V E S G G G L V Q P G G S L R L S C A A S G F N I R G T - - D I H
SRP1848-G10    E V Q L V E S G G G L V Q P G S S L R L S C A A S G F N I R S T - - D I H
SRP1848-G11    E V Q L V E S G G G L V Q P G G S L R L S C A A S G F N I S S T - - D I H
```

FIG. 3A

```
Column #       3839404142434445464748495051525354555657585960616263646566
SRP1848-E05    W V R Q A P G K G L E W V G G I T P N D - G Y T D Y A D S
SRP1848-E06    W V R Q A P G K G L E W V G G I T P N D - G Y T D Y A D S
SRP1848-E07    W V R Q A P G K G L E W V G E I F P Y D - G S T D Y A D N
SRP1848-F01    W V R Q A P G K G L E W V G S I F P N D - G T T D Y A D S
SRP1848-F02    W V R Q A P G K G L E W V G S I F P N D - G T T D Y A D S
SRP1848-F04    W V R Q A P G K G L E W V G E I Y P I D - G I T D Y A D S
SRP1848-F05    W V R Q A P G K G L E W V G E I Y P N D - G S T D Y A D S
SRP1848-F06    W V R Q A P G K G L E W V G G I S P I D - G N T D Y A D S
SRP1848-F07    W V R Q A P G K G L E W V G E I Y P N D - G I T D Y A D S
SRP1848-F08    W V R Q A P G K G V E W V G E I Y P V D - G I T D Y A D S
SRP1848-F09    W V R Q A P G K G L E W V G G I S P L D - G Y T D Y A D S
SRP1848-F10    W V R Q A P G K G L E W V G S I F P N D - G Y T D Y A D S
SRP1848-F11    W V R Q A P G K G L E W V G G I T P I D - G N T D Y A D S
SRP1848-G01    W V R Q A P G K G L E W V G W I A P N D - G S T D Y A D S
SRP1848-G03    W V R Q A P G K G L E W V G G I T P S D - G F T D Y A D S
SRP1848-H01    W V R Q A P G K G L E W I G D I F P I D - G I T D Y A D S
SRP1848-G04    W V R Q A P G K G L E W V A Y I T P A G - G A T F Y A D S
SRP1848-G06    W V R Q A P G K G L E W V A Y I T P A G - G A T Y Y A D N
SRP1848-G07    W V R Q A P G K G L E W V A Y I T P A G - G A T W Y A D S
SRP1848-G09    W V R Q A P G K G L E W V A Y I T P A G - G A T F Y A D S
SRP1848-G10    W V R Q A P G K G L E W V A Y I T P A G - G A T Y Y A D S
SRP1848-G11    W V R Q A P G K G L E W V A Y I T P A G - G A T W Y A D S
```

FIG. 3B

| Column # | 67 68 69 70 71 72 73 74 75 76 77 78 79 80 81 82 83 84 85 86 87 88 89 90 91 92 93 94 95 96 97 98 99 100 |
|---|---|
| SRP1848-E05 | V K G R F T I S A D T S K N T A Y L Q M N S L R A E D T A V Y Y C A |
| SRP1848-E06 | V E G R F T T S A D T S K N T A Y L Q M N S L R A E D T A V Y Y C A |
| SRP1848-E07 | V K G R F T I S A D T S K N T A Y L Q M N S L R A E D T A V Y Y C A |
| SRP1848-F01 | V K G R F T I S A D T S K N T A Y L Q M N S L R A E D T A V Y Y C A |
| SRP1848-F02 | V K G R L T I S A D T S K N T A Y L Q M N S L R A E D T A V Y Y C A |
| SRP1848-F04 | V K G R F T I S A D T S K N T A Y L Q M N S L R A E D T A V Y Y C A |
| SRP1848-F05 | V K G R F T I S A D T S K N T A Y L Q M N S L R A E D T A V Y Y C A |
| SRP1848-F06 | V K G R F T I S A D T S K N T A Y L Q M N S L R A E D T A V Y Y C A |
| SRP1848-F07 | V K G R F T I S A D T S K N T A Y L Q M N S L S A E D T A V Y Y C A |
| SRP1848-F08 | V K G R F T I S A D T S K N T A Y L R M N S L R A E D T A V Y Y C A |
| SRP1848-F09 | V K G R F T I S A D T S K N T A Y L Q M N S L R A E D T A V Y Y C A |
| SRP1848-F10 | V K G R F T I S A D T S K N T A Y L Q M N S L R A E D T A V Y Y C A |
| SRP1848-F11 | V K G R F T I S A D T S M N T A Y L Q M N S L R A E D T A V Y Y C A |
| SRP1848-G01 | V K G R F T I S A D T S K N T A Y L Q M N S L R A E D T A V Y Y C A |
| SRP1848-G03 | V K G R S T I S A D T S K N T A Y L Q M N S L R A E D T A V Y Y C A |
| SRP1848-H01 | V K G R F T I S A D T S K N T A Y L Q M N S L R A E D T A V Y Y C A |
| SRP1848-G04 | V K G R F T I S A D T S K N T A Y L Q M N S L R A E D T A V Y Y C A |
| SRP1848-G06 | V K G R F T I S A D T S K N T A Y L Q M N S L R A E D T A V Y Y C A |
| SRP1848-G07 | V K G R F T I S A D T S K N T A Y L Q M N S L R A E D T A V Y Y C A |
| SRP1848-G09 | V K G R F T I S A D T S K N T A Y L Q M N S L R A E D T A V Y Y C A |
| SRP1848-G10 | V K G R F T I S A D T S K N T A Y L Q M N S L R A E D T A V Y Y C A |
| SRP1848-G11 | V K G R F T I S A D T S K N T A Y L Q M N S L R A E D T A V Y Y C A |

FIG. 3C

```
Column #       101102103104105106107108109110111112113114115116117118119120121122123124125126127128
SRP1848-E05  R G F W A W R S G - Y G Y Y L D Y W G Q G T L V T V S S
SRP1848-E06  R G T W S W P S G - H S Y Y L D Y W G Q G T L V T V S S
SRP1848-E07  R G A W S W R S G - Y G Y Y I D Y W G Q G T L V T V S S
SRP1848-F01  R G S W A W R A G - Y S Y Y L D Y W G Q G T L V T V S S
SRP1848-F02  R G S W S W Q A G - Y G Y Y L D Y W G Q G T L V T V S S
SRP1848-F04  R G S W F W R S G - Y G Y Y L D Y W G Q G T L V T V S S
SRP1848-F05  R G S W A W R S G - Y S Y F L D Y W G Q G T L V T V S S
SRP1848-F06  R G F W A W R S G - Y G Y Y L D Y W G Q G T L V T V S S
SRP1848-F07  R G S W D W R S G - Y S Y Y L D Y W G Q G T L V T V S S
SRP1848-F08  R G S W Y W Q S G - Y S Y Y L D Y W G Q G T L V T V S S
SRP1848-F09  R G A W S W R S G - Y G Y Y I D Y W G Q G T L V T V S S
SRP1848-F10  R G S W F W R S G - Y G Y Y L D Y W G Q G T L V T V S S
SRP1848-F11  R G S W Y W R A G - Y G Y Y L D Y W G Q G A L V T V S S
SRP1848-G01  R G S W A W R S G - Y S Y F L D Y W G Q G T L V T V S S
SRP1848-G03  R G S W S W P S G - H G Y F L D Y W G Q G T L V T V S S
SRP1848-H01  R G S W S W P S G - M D Y Y L D Y W G Q G T L V T V S S
SRP1848-G04  R Y P Y W F A G - - - - - Y M D Y W G Q G T L V T V S S
SRP1848-G06  R Q P Y W F A G - - - - - Y M D Y W G Q G T L V T V S S
SRP1848-G07  R Y P F W F A G - - - - - Y M D Y W G Q G T L V T V S S
SRP1848-G09  R H E Y W F S G - - - - - Y M D Y W G Q G T L V T V S S
SRP1848-G10  R Y P Y W F A G - - - - - Y I D Y W G Q G T L V T V S S
SRP1848-G11  R Y P Y W F S G - - - - - Y M D Y W G Q G T L V T V S S
```

FIG. 3D

```
SRP2060-E10  EVQLLESGGGLVQPGGSLRLSCAFSGFSLSTFGMGVGWVRQAPGKGLEWVSHIWWDD--DKYYHPA
SRP2060-E05  EVQLLESGGGLVQPGGSLRLSCAFSGFSLSTFGMGVGWVRQAPGKGLEWVSHIWWDD--DKYYHPA
SRP2060-B01  EVQLLESGGGLVQPGGSLRLSCALSGFSLSTFGMGVGWVRQATGKGLEWVSHIWWDD--DKYYHPA
SRP2060-A06  EVQLLESGGGLVQPGGSLRLSCAFSGFSLSTFGMGVGWVRQAPGKGLEWVGHIWWDD--DKYYPA

SRP2060-E10  LKGRFTISKDNSKNTVYLQMNSLRAEDTAVYYCGRNHFPHYYGSSHWYFNVWGQGTTVTVSS
SRP2060-E05  LKGRFTVSKDNSKNTVYLQMNSLRAEDTAVYYCGRNHFPHYYGSSHWYFNVWGQGTTVTVSS
SRP2060-B01  LKGRFTISKDNSKNTVHLQMNSLRAEDTAVYYCGRNHFPHYYGSSHWYFNVWGQGTTVTVSS
SRP2060-A06  LKGRFTISKDNSKNTVYLQMNSLRAEDTAVYYCGRNHFPHYYGSSHWYFDVWGQGTTVTVSS
```

FIG. 4

```
Column #      1  2  3  4  5  6  7  8  9 10 11 12 13 14 15 16 17 18 19 20 21 22 23 24 25 26 27 28 29 30 31 32 33 34 35 36 37 38 39 40 41 42 43 44 45 46 47 48 49 50 51 52 53 54 55 56 57 58 59
TRASTUZUMAB   D  I  Q  M  T  Q  S  P  S  S  L  S  A  S  V  G  D  R  V  T  I  T  C  R  A  S  Q  D  V  N  T  A  V  A  W  Y  Q  Q  K  P  G  K  A  P  K  L  L  I  Y  S  A  S  F  L  Y  S  G  V  P
H6D1-LC4      E  I  V  M  T  Q  S  P  A  T  L  S  L  S  P  G  E  R  A  T  L  S  C  K  A  S  Q  D  I  N  S  Y  L  S  W  Y  Q  Q  K  P  G  Q  A  P  R  L  L  I  Y  R  A  N  R  L  V  D  G  I  P
H6D1-LC5      D  I  Q  M  T  Q  S  P  S  T  L  S  A  S  V  G  D  R  V  T  I  T  C  K  A  S  Q  D  I  N  S  Y  L  S  W  Y  Q  Q  K  P  G  K  A  P  K  L  L  I  Y  R  A  N  R  L  V  D  G  V  P Column #     60 61 62 63 64 65 66 67 68 69 70 71 72 73 74 75 76 77 78 79 80 81 82 83 84 85 86 87 88 89 90 91 92 93 94 95 96 97 98 99 100 101 102 103 104 105 106 107 108
TRASTUZUMAB   S  R  F  S  G  S  R  S  G  T  D  F  T  L  T  I  S  S  L  Q  P  E  D  F  A  T  Y  Y  C  Q  Q  H  Y  T  T  -  P  P  T  F   G   Q   G   T   K   V   E   I   K
H6D1-LC4      A  R  F  S  G  S  G  S  G  T  D  Y  T  L  T  I  S  S  L  E  P  E  D  F  A  V  Y  Y  C  L  Q  -  Y  D  E  F  P  Y  T  F   G   G   G   T   K   V   E   I   K
H6D1-LC5      S  R  F  S  G  S  G  S  G  T  E  F  T  L  T  I  S  S  L  Q  P  D  D  F  A  T  Y  Y  C  L  Q  -  Y  D  E  F  P  Y  T  F   G   G   G   T   K   V   E   I   K
```

FIG. 5

SEQUENCE LISTING

<160> NUMBER OF SEQ ID NOS: 382

<210> SEQ ID NO 1
<211> LENGTH: 257
<212> TYPE: PRT
<213> ORGANISM: Homo sapiens
<220> FEATURE:
<221> NAME/KEY: misc_feature
<223> OTHER INFORMATION: Human folate receptor alpha (hFOLR1)

<400> SEQUENCE: 1

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 2
<211> LENGTH: 257
<212> TYPE: PRT
<213> ORGANISM: Macaca fascicularis
<220> FEATURE:
<221> NAME/KEY: misc_feature
<223> OTHER INFORMATION: Cynomolgus folate receptor alpha

<400> SEQUENCE: 2

Met Ala Gln Arg Met Thr Thr Gln Leu Leu Leu Leu Val Trp Val
1               5                   10                  15

Ala Val Val Gly Glu Ala Gln Thr Arg Thr Ala Arg Ala Arg Thr Glu
            20                  25                  30

```
Leu Leu Asn Val Cys Met Asn Ala Lys His His Lys Glu Lys Pro Gly
             35                  40                  45

Pro Glu Asp Lys Leu His Glu Gln Cys Arg Pro Trp Lys Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Arg Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Pro Val Gly Ala Ala Cys Gln
                165                 170                 175

Pro Phe His Phe Tyr Phe Pro Thr Pro Thr Val Leu Cys Asn Glu Ile
                180                 185                 190

Trp Thr Tyr Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Leu Leu Leu Ser Leu Ala Leu Thr Leu Leu Trp Leu Leu
                245                 250                 255

Ser

<210> SEQ ID NO 3
<211> LENGTH: 255
<212> TYPE: PRT
<213> ORGANISM: Mus musculus
<220> FEATURE:
<221> NAME/KEY: misc_feature
<223> OTHER INFORMATION: Murine folate receptor alpha

<400> SEQUENCE: 3

Met Ala His Leu Met Thr Val Gln Leu Leu Leu Leu Val Met Trp Met
 1               5                  10                  15

Ala Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
             35                  40                  45

Asp Asn Leu His Asp Gln Cys Ser Pro Trp Lys Thr Asn Ser Cys Cys
 50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                 85                  90                  95

His Phe Ile Gln Asp Thr Cys Leu Tyr Glu Cys Ser Pro Asn Leu Gly
                100                 105                 110

Pro Trp Ile Gln Gln Val Asp Gln Ser Trp Arg Lys Glu Arg Ile Leu
            115                 120                 125
```

Asp Val Pro Leu Cys Lys Glu Asp Cys Gln Gln Trp Trp Glu Asp Cys
            130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Phe His Gly Thr Trp
225                 230                 235                 240

Pro Leu Leu Cys Ser Leu Ser Leu Val Leu Leu Trp Val Ile Ser
                245                 250                 255

<210> SEQ ID NO 4
<211> LENGTH: 7
<212> TYPE: PRT
<213> ORGANISM: Artificial Sequence
<220> FEATURE:
<223> OTHER INFORMATION: Synthetic: SRP1848-A01, CDR-H1, Chothia

<400> SEQUENCE: 4

Gly Phe Asn Ile Thr Arg Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: SRP1848-A02, CDR-H1, Chothia

<400> SEQUENCE: 5

Gly Phe Asn Ile Ser Gly Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic: SRP1848-A04, CDR-H1, Chothia

<400> SEQUENCE: 6

Gly Phe Asn Ile Asp Gln Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic: SRP1848-A06, CDR-H1, Chothia

<400> SEQUENCE: 7

Gly Phe Asn Ile Gly Asn Ser
1               5

<210> SEQ ID NO 8

```
<211> LENGTH: 7
<212> TYPE: PRT
<213> ORGANISM: Artificial Sequence
<220> FEATURE:
<223> OTHER INFORMATION: Synthetic: SRP1848-A07, CDR-H1, Chothia

<400> SEQUENCE: 8

Gly Phe Asn Ile Gly Tyr His
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic: SRP1848-A08, CDR-H1, Chothia

<400> SEQUENCE: 9

Gly Ser Asn Ile Arg Lys His
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: SRP1848-A09, CDR-H1, Chothia

<400> SEQUENCE: 10

Gly Phe Asn Ile Arg Lys Gln
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: SRP1848-A10, CDR-H1, Chothia

<400> SEQUENCE: 11

Gly Phe Asn Ile Arg Lys Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: SRP1848-B01, CDR-H1, Chothia

<400> SEQUENCE: 12

Gly Phe Asn Ile Arg Asn Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: SRP1848-B03, CDR-H1, Chothia

<400> SEQUENCE: 13

Gly Phe Asn Ile Ser Met Lys
1               5

<210> SEQ ID NO 14
<211> LENGTH: 7
```

```
<212> TYPE: PRT
<213> ORGANISM: Artificial Sequence
<220> FEATURE:
<223> OTHER INFORMATION: Synthetic: SRP1848-B04, CDR-H1, Chothia

<400> SEQUENCE: 14

Ser Phe Asn Ile Ser Asn His
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: SRP1848-B05, CDR-H1, Chothia

<400> SEQUENCE: 15

Gly Phe Asn Ile Ser Asn Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic: SRP1848-B06, CDR-H1, Chothia

<400> SEQUENCE: 16

Gly Phe Asn Ile Ser Asn Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: SRP1848-B07, CDR-H1, Chothia

<400> SEQUENCE: 17

Gly Phe Asn Ile Ser Arg Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic: SRP1848-B09, CDR-H1, Chothia

<400> SEQUENCE: 18

Gly Phe Asn Ile Thr Asn Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: SRP1848-B10, CDR-H1, Chothia

<400> SEQUENCE: 19

Gly Phe Asn Thr Thr Thr Lys
1               5

<210> SEQ ID NO 20
<211> LENGTH: 7
<212> TYPE: PRT
```

```
<213> ORGANISM: Artificial Sequence
<220> FEATURE:
<223> OTHER INFORMATION: Synthetic: SRP1848-B11, CDR-H1, Chothia

<400> SEQUENCE: 20

Gly Phe Asn Ile Gly Asn Asn
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: SRP1848-C01, CDR-H1, Chothia

<400> SEQUENCE: 21

Gly Phe Asn Ile Gly Asn Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: SRP1848-C03, CDR-H1, Chothia

<400> SEQUENCE: 22

Gly Phe Asn Ile Gly Val Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: SRP1848-C04, CDR-H1, Chothia

<400> SEQUENCE: 23

Gly Phe Asn Ile Arg His Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: SRP1848-C05, CDR-H1, Chothia

<400> SEQUENCE: 24

Gly Phe Asn Ile Arg Lys Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: SRP1848-C07, CDR-H1, Chothia

<400> SEQUENCE: 25

Gly Phe Asn Ile Arg Lys Tyr
1               5

<210> SEQ ID NO 26
<211> LENGTH: 7
<212> TYPE: PRT
<213> ORGANISM: Artificial Sequence
```

```
<220> FEATURE:
<223> OTHER INFORMATION: Synthetic: SRP1848-C10, CDR-H1, Chothia

<400> SEQUENCE: 26

Gly Phe Asn Ile Arg Thr Tyr
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic: SRP1848-D02, CDR-H1, Chothia

<400> SEQUENCE: 27

Gly Phe Asn Ile Ser His Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic: SRP1848-D03, CDR-H1, Chothia

<400> SEQUENCE: 28

Gly Phe Asn Ile Arg Tyr Phe
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic: SRP1848-D04, CDR-H1, Chothia

<400> SEQUENCE: 29

Gly Phe Asn Ile Ser His Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic: SRP1848-D05, CDR-H1, Chothia

<400> SEQUENCE: 30

Gly Phe Asn Ile Ser Ile Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic: SRP1848-D07, CDR-H1, Chothia

<400> SEQUENCE: 31

Gly Phe Asn Ile Ser Lys Tyr
1               5

<210> SEQ ID NO 32
<211> LENGTH: 7
<212> TYPE: PRT
<213> ORGANISM: Artificial Sequence
<220> FEATURE:
```

<223> OTHER INFORMATION: Synthetic: SRP1848-D09, CDR-H1, Chothia

<400> SEQUENCE: 32

Gly Phe Asn Ile Ser Asn Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic: SRP1848-D10, CDR-H1, Chothia

<400> SEQUENCE: 33

Gly Phe Asn Ile Ser Arg Asn
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic: SRP1848-E01, CDR-H1, Chothia

<400> SEQUENCE: 34

Gly Phe Asn Ile Thr Asn Lys
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic: SRP1848-E02, CDR-H1, Chothia

<400> SEQUENCE: 35

Gly Phe Asn Ile Gly Lys Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic: SRP1848-E03, CDR-H1, Chothia

<400> SEQUENCE: 36

Gly Phe Asn Ile Gly Asn Tyr
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic: SRP1848-E05, CDR-H1, Chothia

<400> SEQUENCE: 37

Gly Phe Asn Ile Gly Val Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic: SRP1848-E06, CDR-H1, Chothia

```
<400> SEQUENCE: 38

Gly Phe Asn Ile Asn Arg Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic: SRP1848-E07, CDR-H1, Chothia

<400> SEQUENCE: 39

Gly Phe Asn Ile Arg Lys Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic: SRP1848-F01, CDR-H1, Chothia

<400> SEQUENCE: 40

Gly Phe Asn Ile Arg Thr Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic: SRP1848-F02, CDR-H1, Chothia

<400> SEQUENCE: 41

Gly Phe Asn Ile Arg Thr Tyr
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic: SRP1848-F04, CDR-H1, Chothia

<400> SEQUENCE: 42

Gly Phe Asn Ile Ser Asn Tyr
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic: SRP1848-F05, CDR-H1, Chothia

<400> SEQUENCE: 43

Gly Phe Asn Ile Ser Lys Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic: SRP1848-F06, CDR-H1, Chothia
```

```
<400> SEQUENCE: 44

Gly Phe Asn Ile Ser Leu Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic: SRP1848-F07, CDR-H1, Chothia

<400> SEQUENCE: 45

Gly Phe Asn Ile Ser Asn His
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic: SRP1848-F08, CDR-H1, Chothia

<400> SEQUENCE: 46

Gly Phe Asn Ile Ser Asn His
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic: SRP1848-F09, CDR-H1, Chothia

<400> SEQUENCE: 47

Gly Phe Asn Ile Ser Asn His
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic: SRP1848-F10, CDR-H1, Chothia

<400> SEQUENCE: 48

Gly Phe Asn Ile Ser Asn Asn
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic: SRP1848-F11, CDR-H1, Chothia

<400> SEQUENCE: 49

Gly Phe Asn Ile Ser Asn Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic: SRP1848-G01, CDR-H1, Chothia

<400> SEQUENCE: 50
```

```
Gly Phe Asn Ile Ser Arg His
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic: SRP1848-G03, CDR-H1, Chothia

<400> SEQUENCE: 51

Gly Phe Asn Ile Ser Thr Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic: SRP1848-G04, CDR-H1, Chothia

<400> SEQUENCE: 52

Gly Phe Asn Ile His Ser Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic: SRP1848-G06, CDR-H1, Chothia

<400> SEQUENCE: 53

Gly Phe Asn Ile Arg Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic: SRP1848-G07, CDR-H1, Chothia

<400> SEQUENCE: 54

Gly Phe Asn Ile His Ser Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic: SRP1848-G09, CDR-H1, Chothia

<400> SEQUENCE: 55

Gly Phe Asn Ile Arg Gly Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic: SRP1848-G10, CDR-H1, Chothia

<400> SEQUENCE: 56
```

```
Gly Phe Asn Ile Arg Ser Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic: SRP1848-G11, CDR-H1, Chothia

<400> SEQUENCE: 57

Gly Phe Asn Ile Ser Ser Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic: SRP1848-H01, CDR-H1, Chothia

<400> SEQUENCE: 58

Gly Phe Asn Ile Arg Thr Gln
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic: SRP2060-E10, CDR-H1, Chothia

<400> SEQUENCE: 59

Gly Phe Ser Leu Ser Thr Phe Gly Met
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic: SRP2060-E05, CDR-H1, Chothia

<400> SEQUENCE: 60

Gly Phe Ser Leu Ser Thr Phe Gly Met
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic: SRP2060-B01, CDR-H1, Chothia

<400> SEQUENCE: 61

Gly Phe Ser Leu Ser Thr Phe Gly Met
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic: SRP2060-A06, CDR-H1, Chothia

<400> SEQUENCE: 62

Gly Phe Ser Leu Ser Thr Phe Gly Met
```

```
1               5
```

<210> SEQ ID NO 63
<211> LENGTH: 5
<212> TYPE: PRT
<213> ORGANISM: Artificial Sequence
<220> FEATURE:
<223> OTHER INFORMATION: Synthetic: SRP1848-A01, CDR-H1, Kabat

<400> SEQUENCE: 63

```
Arg Tyr Ser Ile His
1               5
```

<210> SEQ ID NO 64
<211> LENGTH: 5
<212> TYPE: PRT
<213> ORGANISM: Artificial Sequence
<220> FEATURE:
<223> OTHER INFORMATION: Synthetic: SRP1848-A02, CDR-H1, Kabat

<400> SEQUENCE: 64

```
Gly Phe Arg Ile His
1               5
```

<210> SEQ ID NO 65
<211> LENGTH: 5
<212> TYPE: PRT
<213> ORGANISM: Artificial Sequence
<220> FEATURE:
<223> OTHER INFORMATION: Synthetic: SRP1848-A04, CDR-H1, Kabat

<400> SEQUENCE: 65

```
Gln Ser Ser Ile His
1               5
```

<210> SEQ ID NO 66
<211> LENGTH: 5
<212> TYPE: PRT
<213> ORGANISM: Artificial Sequence
<220> FEATURE:
<223> OTHER INFORMATION: Synthetic: SRP1848-A06, CDR-H1, Kabat

<400> SEQUENCE: 66

```
Asn Ser Tyr Ile His
1               5
```

<210> SEQ ID NO 67
<211> LENGTH: 5
<212> TYPE: PRT
<213> ORGANISM: Artificial Sequence
<220> FEATURE:
<223> OTHER INFORMATION: Synthetic: SRP1848-A07, CDR-H1, Kabat

<400> SEQUENCE: 67

```
Tyr His Ser Ile His
1               5
```

<210> SEQ ID NO 68
<211> LENGTH: 5
<212> TYPE: PRT
<213> ORGANISM: Artificial Sequence
<220> FEATURE:
<223> OTHER INFORMATION: Synthetic: SRP1848-A08, CDR-H1, Kabat

<400> SEQUENCE: 68

```
Lys His Ser Ile His
1               5
```

```
<210> SEQ ID NO 69
<211> LENGTH: 5
<212> TYPE: PRT
<213> ORGANISM: Artificial Sequence
<220> FEATURE:
<223> OTHER INFORMATION: Synthetic: SRP1848-A09, CDR-H1, Kabat

<400> SEQUENCE: 69

Lys Gln Ser Ile His
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic: SRP1848-A10, CDR-H1, Kabat

<400> SEQUENCE: 70

Lys Tyr Ser Ile His
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic: SRP1848-B01, CDR-H1, Kabat

<400> SEQUENCE: 71

Asn Tyr Ser Ile His
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic: SRP1848-B03, CDR-H1, Kabat

<400> SEQUENCE: 72

Met Lys Tyr Ile His
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic: SRP1848-B04, CDR-H1, Kabat

<400> SEQUENCE: 73

Asn His Ser Ile His
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic: SRP1848-B05, CDR-H1, Kabat

<400> SEQUENCE: 74

Asn Tyr Tyr Ile His
1               5
```

<210> SEQ ID NO 75
<211> LENGTH: 5
<212> TYPE: PRT
<213> ORGANISM: Artificial Sequence
<220> FEATURE:
<223> OTHER INFORMATION: Synthetic: SRP1848-B06, CDR-H1, Kabat

<400> SEQUENCE: 75

Asn Tyr Tyr Ile His
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic: SRP1848-B07, CDR-H1, Kabat

<400> SEQUENCE: 76

Arg Phe Tyr Ile His
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic: SRP1848-B09, CDR-H1, Kabat

<400> SEQUENCE: 77

Asn Tyr Tyr Ile His
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic: SRP1848-B10, CDR-H1, Kabat

<400> SEQUENCE: 78

Thr Lys Ser Ile His
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic: SRP1848-B11, CDR-H1, Kabat

<400> SEQUENCE: 79

Asn Asn Ser Ile His
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic: SRP1848-C01, CDR-H1, Kabat

<400> SEQUENCE: 80

Asn Ser Tyr Ile His
1               5

```
<210> SEQ ID NO 81
<211> LENGTH: 5
<212> TYPE: PRT
<213> ORGANISM: Artificial Sequence
<220> FEATURE:
<223> OTHER INFORMATION: Synthetic: SRP1848-C03, CDR-H1, Kabat

<400> SEQUENCE: 81

Val Tyr Ser Ile His
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic: SRP1848-C04, CDR-H1, Kabat

<400> SEQUENCE: 82

His Tyr Ser Ile His
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic: SRP1848-C05, CDR-H1, Kabat

<400> SEQUENCE: 83

Lys Tyr Ser Ile His
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic: SRP1848-C07, CDR-H1, Kabat

<400> SEQUENCE: 84

Lys Tyr Ser Ile His
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic: SRP1848-C10, CDR-H1, Kabat

<400> SEQUENCE: 85

Thr Tyr Tyr Ile His
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic: SRP1848-D02, CDR-H1, Kabat

<400> SEQUENCE: 86

His Asn Tyr Ile His
1               5

<210> SEQ ID NO 87
```

```
<211> LENGTH: 5
<212> TYPE: PRT
<213> ORGANISM: Artificial Sequence
<220> FEATURE:
<223> OTHER INFORMATION: Synthetic: SRP1848-D03, CDR-H1, Kabat

<400> SEQUENCE: 87

Tyr Phe Ser Ile His
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic: SRP1848-D04, CDR-H1, Kabat

<400> SEQUENCE: 88

His Tyr Ser Ile His
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic: SRP1848-D05, CDR-H1, Kabat

<400> SEQUENCE: 89

Ile Ser Tyr Ile His
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic: SRP1848-D07, CDR-H1, Kabat

<400> SEQUENCE: 90

Lys Tyr Tyr Ile His
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic: SRP1848-D09, CDR-H1, Kabat

<400> SEQUENCE: 91

Asn Tyr Tyr Ile His
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic: SRP1848-D10, CDR-H1, Kabat

<400> SEQUENCE: 92

Arg Asn Ser Ile His
1               5

<210> SEQ ID NO 93
<211> LENGTH: 5
```

```
<212> TYPE: PRT
<213> ORGANISM: Artificial Sequence
<220> FEATURE:
<223> OTHER INFORMATION: Synthetic: SRP1848-E01, CDR-H1, Kabat

<400> SEQUENCE: 93

Asn Lys Tyr Ile His
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic: SRP1848-E02, CDR-H1, Kabat

<400> SEQUENCE: 94

Lys Tyr Ser Ile His
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic: SRP1848-E03, CDR-H1, Kabat

<400> SEQUENCE: 95

Asn Tyr Tyr Ile His
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic: SRP1848-E05, CDR-H1, Kabat

<400> SEQUENCE: 96

Val Tyr Tyr Ile His
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic: SRP1848-E06, CDR-H1, Kabat

<400> SEQUENCE: 97

Arg Tyr Tyr Ile His
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic: SRP1848-E07, CDR-H1, Kabat

<400> SEQUENCE: 98

Lys Ser Ser Ile His
1               5

<210> SEQ ID NO 99
<211> LENGTH: 5
<212> TYPE: PRT
```

```
<213> ORGANISM: Artificial Sequence
<220> FEATURE:
<223> OTHER INFORMATION: Synthetic: SRP1848-F01, CDR-H1, Kabat

<400> SEQUENCE: 99

Thr Tyr Ser Ile His
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic: SRP1848-F02, CDR-H1, Kabat

<400> SEQUENCE: 100

Thr Tyr Ser Ile His
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic: SRP1848-F04, CDR-H1, Kabat

<400> SEQUENCE: 101

Asn Tyr Ser Ile His
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic: SRP1848-F05, CDR-H1, Kabat

<400> SEQUENCE: 102

Lys Ser Ser Ile His
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic: SRP1848-F06, CDR-H1, Kabat

<400> SEQUENCE: 103

Leu Ser Tyr Ile His
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic: SRP1848-F07, CDR-H1, Kabat

<400> SEQUENCE: 104

Asn His Ser Ile His
1               5

<210> SEQ ID NO 105
<211> LENGTH: 5
<212> TYPE: PRT
<213> ORGANISM: Artificial Sequence
```

<220> FEATURE:
<223> OTHER INFORMATION: Synthetic: SRP1848-F08, CDR-H1, Kabat

<400> SEQUENCE: 105

Asn His Ser Ile His
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic: SRP1848-F09, CDR-H1, Kabat

<400> SEQUENCE: 106

Asn His Tyr Ile His
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic: SRP1848-F10, CDR-H1, Kabat

<400> SEQUENCE: 107

Asn Asn Ser Ile His
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic: SRP1848-F11, CDR-H1, Kabat

<400> SEQUENCE: 108

Asn Asn Tyr Ile His
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic: SRP1848-G01, CDR-H1, Kabat

<400> SEQUENCE: 109

Arg His Ser Ile His
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic: SRP1848-G03, CDR-H1, Kabat

<400> SEQUENCE: 110

Thr Tyr Tyr Ile His
1               5

<210> SEQ ID NO 111
<211> LENGTH: 5
<212> TYPE: PRT
<213> ORGANISM: Artificial Sequence
<220> FEATURE:

<223> OTHER INFORMATION: Synthetic: SRP1848-G04, CDR-H1, Kabat

<400> SEQUENCE: 111

Ser Thr Asp Ile His
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic: SRP1848-G06, CDR-H1, Kabat

<400> SEQUENCE: 112

Ser Thr Asp Ile His
1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic: SRP1848-G07, CDR-H1, Kabat

<400> SEQUENCE: 113

Ser Thr Asp Ile His
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic: SRP1848-G09, CDR-H1, Kabat

<400> SEQUENCE: 114

Gly Thr Asp Ile His
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic: SRP1848-G10, CDR-H1, Kabat

<400> SEQUENCE: 115

Ser Thr Asp Ile His
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic: SRP1848-G11, CDR-H1, Kabat

<400> SEQUENCE: 116

Ser Thr Asp Ile His
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic: SRP1848-H01, CDR-H1, Kabat

```
<400> SEQUENCE: 117

Thr Gln Ser Ile His
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic: SRP2060-E10, CDR-H1, Kabat

<400> SEQUENCE: 118

Thr Phe Gly Met Gly Val Gly
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic: SRP2060-E05, CDR-H1, Kabat

<400> SEQUENCE: 119

Thr Phe Gly Met Gly Val Gly
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic: SRP2060-B01, CDR-H1, Kabat

<400> SEQUENCE: 120

Thr Phe Gly Met Gly Val Gly
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic: SRP2060-A06, CDR-H1, Kabat

<400> SEQUENCE: 121

Thr Phe Gly Met Gly Val Gly
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic: SRP1848-A01, CDR-H2, Chothia

<400> SEQUENCE: 122

Leu Pro Glu Ser Gly Gly
1               5

<210> SEQ ID NO 123
<211> LENGTH: 6
<212> TYPE: PRT
<213> ORGANISM: Artificial Sequence
<220> FEATURE:
<223> OTHER INFORMATION: Synthetic: SRP1848-A02, CDR-H2, Chothia
```

```
<400> SEQUENCE: 123

Tyr Pro Glu Ser Gly Ala
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic: SRP1848-A04, CDR-H2, Chothia

<400> SEQUENCE: 124

Tyr Pro Val Asp Gly Thr
1               5

<210> SEQ ID NO 125
<211> LENGTH: 6
<212> TYPE: PRT
<213> ORGANISM: Artificial Sequence
<220> FEATURE:
<223> OTHER INFORMATION: Synthetic: SRP1848-A06, CDR-H2, Chothia

<400> SEQUENCE: 125

Thr Pro Ile Asp Gly Asn
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic: SRP1848-A07, CDR-H2, Chothia

<400> SEQUENCE: 126

Phe Pro Val Asp Gly Thr
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic: SRP1848-A08, CDR-H2, Chothia

<400> SEQUENCE: 127

Tyr Pro Asn Asp Gly Thr
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic: SRP1848-A09, CDR-H2, Chothia

<400> SEQUENCE: 128

Phe Pro Asn Asp Gly Thr
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic: SRP1848-A10, CDR-H2, Chothia

<400> SEQUENCE: 129
```

Phe Pro Ile Asp Asp Ile
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic: SRP1848-B01, CDR-H2, Chothia

<400> SEQUENCE: 130

Tyr Pro Val Asp Gly Ile
1               5

<210> SEQ ID NO 131
<211> LENGTH: 6
<212> TYPE: PRT
<213> ORGANISM: Artificial Sequence
<220> FEATURE:
<223> OTHER INFORMATION: Synthetic: SRP1848-B03, CDR-H2, Chothia

<400> SEQUENCE: 131

Thr Pro Ile Asp Gly Met
1               5

<210> SEQ ID NO 132
<211> LENGTH: 6
<212> TYPE: PRT
<213> ORGANISM: Artificial Sequence
<220> FEATURE:
<223> OTHER INFORMATION: Synthetic: SRP1848-B04, CDR-H2, Chothia

<400> SEQUENCE: 132

Tyr Pro Val Asp Gly Ile
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic: SRP1848-B05, CDR-H2, Chothia

<400> SEQUENCE: 133

Ser Pro Ile Asp Gly Tyr
1               5

<210> SEQ ID NO 134
<211> LENGTH: 6
<212> TYPE: PRT
<213> ORGANISM: Artificial Sequence
<220> FEATURE:
<223> OTHER INFORMATION: Synthetic: SRP1848-B06, CDR-H2, Chothia

<400> SEQUENCE: 134

Thr Pro Ile Asp Gly Tyr
1               5

<210> SEQ ID NO 135
<211> LENGTH: 6
<212> TYPE: PRT
<213> ORGANISM: Artificial Sequence
<220> FEATURE:
<223> OTHER INFORMATION: Synthetic: SRP1848-B07, CDR-H2, Chothia

<400> SEQUENCE: 135

```
Ser Pro Tyr Asp Gly Phe
1               5
```

<210> SEQ ID NO 136
<211> LENGTH: 6
<212> TYPE: PRT
<213> ORGANISM: Artificial Sequence
<220> FEATURE:
<223> OTHER INFORMATION: Synthetic: SRP1848-B09, CDR-H2, Chothia

<400> SEQUENCE: 136

```
Thr Pro Val Asp Gly Tyr
1               5
```

<210> SEQ ID NO 137
<211> LENGTH: 6
<212> TYPE: PRT
<213> ORGANISM: Artificial Sequence
<220> FEATURE:
<223> OTHER INFORMATION: Synthetic: SRP1848-B10, CDR-H2, Chothia

<400> SEQUENCE: 137

```
Tyr Pro Arg Asp Gly Ile
1               5
```

<210> SEQ ID NO 138
<211> LENGTH: 6
<212> TYPE: PRT
<213> ORGANISM: Artificial Sequence
<220> FEATURE:
<223> OTHER INFORMATION: Synthetic: SRP1848-B11, CDR-H2, Chothia

<400> SEQUENCE: 138

```
Ser Pro Ile Asp Gly Phe
1               5
```

<210> SEQ ID NO 139
<211> LENGTH: 6
<212> TYPE: PRT
<213> ORGANISM: Artificial Sequence
<220> FEATURE:
<223> OTHER INFORMATION: Synthetic: SRP1848-C01, CDR-H2, Chothia

<400> SEQUENCE: 139

```
Thr Pro Asn Asp Gly Tyr
1               5
```

<210> SEQ ID NO 140
<211> LENGTH: 6
<212> TYPE: PRT
<213> ORGANISM: Artificial Sequence
<220> FEATURE:
<223> OTHER INFORMATION: Synthetic: SRP1848-C03, CDR-H2, Chothia

<400> SEQUENCE: 140

```
Tyr Pro Ile Asp Gly Asn
1               5
```

<210> SEQ ID NO 141
<211> LENGTH: 6
<212> TYPE: PRT
<213> ORGANISM: Artificial Sequence
<220> FEATURE:
<223> OTHER INFORMATION: Synthetic: SRP1848-C04, CDR-H2, Chothia

<400> SEQUENCE: 141

Tyr Pro Gly Pro Gly Asn

```
1               5

<210> SEQ ID NO 142
<211> LENGTH: 6
<212> TYPE: PRT
<213> ORGANISM: Artificial Sequence
<220> FEATURE:
<223> OTHER INFORMATION: Synthetic: SRP1848-C05, CDR-H2, Chothia

<400> SEQUENCE: 142

Phe Pro Ile Asp Gly Ile
1               5

<210> SEQ ID NO 143
<211> LENGTH: 6
<212> TYPE: PRT
<213> ORGANISM: Artificial Sequence
<220> FEATURE:
<223> OTHER INFORMATION: Synthetic: SRP1848-C07, CDR-H2, Chothia

<400> SEQUENCE: 143

Phe Pro Ile Asp Gly Ile
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic: SRP1848-C10, CDR-H2, Chothia

<400> SEQUENCE: 144

Ser Pro Ile Asp Gly Tyr
1               5

<210> SEQ ID NO 145
<211> LENGTH: 6
<212> TYPE: PRT
<213> ORGANISM: Artificial Sequence
<220> FEATURE:
<223> OTHER INFORMATION: Synthetic: SRP1848-D02, CDR-H2, Chothia

<400> SEQUENCE: 145

Thr Pro Gln Asp Gly Tyr
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic: SRP1848-D03, CDR-H2, Chothia

<400> SEQUENCE: 146

Phe Pro Asn Asp Gly Ser
1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic: SRP1848-D04, CDR-H2, Chothia

<400> SEQUENCE: 147

Tyr Pro Arg Asp Gly Ile
1               5
```

<210> SEQ ID NO 148
<211> LENGTH: 6
<212> TYPE: PRT
<213> ORGANISM: Artificial Sequence
<220> FEATURE:
<223> OTHER INFORMATION: Synthetic: SRP1848-D05, CDR-H2, Chothia

<400> SEQUENCE: 148

Ser Pro Ile Asp Gly Tyr
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic: SRP1848-D07, CDR-H2, Chothia

<400> SEQUENCE: 149

Ser Pro Asn Asp Gly Tyr
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic: SRP1848-D09, CDR-H2, Chothia

<400> SEQUENCE: 150

Ser Pro Asn Asp Gly Tyr
1               5

<210> SEQ ID NO 151
<211> LENGTH: 6
<212> TYPE: PRT
<213> ORGANISM: Artificial Sequence
<220> FEATURE:
<223> OTHER INFORMATION: Synthetic: SRP1848-D10, CDR-H2, Chothia

<400> SEQUENCE: 151

Ser Pro Asn Asp Gly Thr
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic: SRP1848-E01, CDR-H2, Chothia

<400> SEQUENCE: 152

Thr Pro Phe Asp Gly Phe
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic: SRP1848-E02, CDR-H2, Chothia

<400> SEQUENCE: 153

Tyr Pro Asn Asp Gly Asn
1               5

```
<210> SEQ ID NO 154
<211> LENGTH: 6
<212> TYPE: PRT
<213> ORGANISM: Artificial Sequence
<220> FEATURE:
<223> OTHER INFORMATION: Synthetic: SRP1848-E03, CDR-H2, Chothia

<400> SEQUENCE: 154

Thr Pro Arg Asp Gly Phe
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic: SRP1848-E05, CDR-H2, Chothia

<400> SEQUENCE: 155

Thr Pro Asn Asp Gly Tyr
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic: SRP1848-E06, CDR-H2, Chothia

<400> SEQUENCE: 156

Thr Pro Asn Asp Gly Tyr
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic: SRP1848-E07, CDR-H2, Chothia

<400> SEQUENCE: 157

Phe Pro Tyr Asp Gly Ser
1               5

<210> SEQ ID NO 158
<211> LENGTH: 6
<212> TYPE: PRT
<213> ORGANISM: Artificial Sequence
<220> FEATURE:
<223> OTHER INFORMATION: Synthetic: SRP1848-F01, CDR-H2, Chothia

<400> SEQUENCE: 158

Phe Pro Asn Asp Gly Thr
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic: SRP1848-F02, CDR-H2, Chothia

<400> SEQUENCE: 159

Phe Pro Asn Asp Gly Thr
1               5
```

-continued

```
<210> SEQ ID NO 160
<211> LENGTH: 6
<212> TYPE: PRT
<213> ORGANISM: Artificial Sequence
<220> FEATURE:
<223> OTHER INFORMATION: Synthetic: SRP1848-F04, CDR-H2, Chothia

<400> SEQUENCE: 160

Tyr Pro Ile Asp Gly Ile
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic: SRP1848-F05, CDR-H2, Chothia

<400> SEQUENCE: 161

Tyr Pro Asn Asp Gly Ser
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic: SRP1848-F06, CDR-H2, Chothia

<400> SEQUENCE: 162

Ser Pro Ile Asp Gly Asn
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic: SRP1848-F07, CDR-H2, Chothia

<400> SEQUENCE: 163

Tyr Pro Asn Asp Gly Ile
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic: SRP1848-F08, CDR-H2, Chothia

<400> SEQUENCE: 164

Tyr Pro Val Asp Gly Ile
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic: SRP1848-F09, CDR-H2, Chothia

<400> SEQUENCE: 165

Ser Pro Leu Asp Gly Tyr
1               5

<210> SEQ ID NO 166
```

```
<211> LENGTH: 6
<212> TYPE: PRT
<213> ORGANISM: Artificial Sequence
<220> FEATURE:
<223> OTHER INFORMATION: Synthetic: SRP1848-F10, CDR-H2, Chothia

<400> SEQUENCE: 166

Phe Pro Asn Asp Gly Tyr
1               5

<210> SEQ ID NO 167
<211> LENGTH: 6
<212> TYPE: PRT
<213> ORGANISM: Artificial Sequence
<220> FEATURE:
<223> OTHER INFORMATION: Synthetic: SRP1848-F11, CDR-H2, Chothia

<400> SEQUENCE: 167

Thr Pro Ile Asp Gly Asn
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic: SRP1848-G01, CDR-H2, Chothia

<400> SEQUENCE: 168

Ala Pro Asn Asp Gly Ser
1               5

<210> SEQ ID NO 169
<211> LENGTH: 6
<212> TYPE: PRT
<213> ORGANISM: Artificial Sequence
<220> FEATURE:
<223> OTHER INFORMATION: Synthetic: SRP1848-G03, CDR-H2, Chothia

<400> SEQUENCE: 169

Thr Pro Ser Asp Gly Phe
1               5

<210> SEQ ID NO 170
<211> LENGTH: 6
<212> TYPE: PRT
<213> ORGANISM: Artificial Sequence
<220> FEATURE:
<223> OTHER INFORMATION: Synthetic: SRP1848-G04, CDR-H2, Chothia

<400> SEQUENCE: 170

Thr Pro Ala Gly Gly Ala
1               5

<210> SEQ ID NO 171
<211> LENGTH: 6
<212> TYPE: PRT
<213> ORGANISM: Artificial Sequence
<220> FEATURE:
<223> OTHER INFORMATION: Synthetic: SRP1848-G06, CDR-H2, Chothia

<400> SEQUENCE: 171

Thr Pro Ala Gly Gly Ala
1               5

<210> SEQ ID NO 172
<211> LENGTH: 6
```

```
<212> TYPE: PRT
<213> ORGANISM: Artificial Sequence
<220> FEATURE:
<223> OTHER INFORMATION: Synthetic: SRP1848-G07, CDR-H2, Chothia

<400> SEQUENCE: 172

Thr Pro Ala Gly Gly Ala
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic: SRP1848-G09, CDR-H2, Chothia

<400> SEQUENCE: 173

Thr Pro Ala Gly Gly Ala
1               5

<210> SEQ ID NO 174
<211> LENGTH: 6
<212> TYPE: PRT
<213> ORGANISM: Artificial Sequence
<220> FEATURE:
<223> OTHER INFORMATION: Synthetic: SRP1848-G10, CDR-H2, Chothia

<400> SEQUENCE: 174

Thr Pro Ala Gly Gly Ala
1               5

<210> SEQ ID NO 175
<211> LENGTH: 6
<212> TYPE: PRT
<213> ORGANISM: Artificial Sequence
<220> FEATURE:
<223> OTHER INFORMATION: Synthetic: SRP1848-G11, CDR-H2, Chothia

<400> SEQUENCE: 175

Thr Pro Ala Gly Gly Ala
1               5

<210> SEQ ID NO 176
<211> LENGTH: 6
<212> TYPE: PRT
<213> ORGANISM: Artificial Sequence
<220> FEATURE:
<223> OTHER INFORMATION: Synthetic: SRP1848-H01, CDR-H2, Chothia

<400> SEQUENCE: 176

Phe Pro Ile Asp Gly Ile
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic: SRP2060-E10, CDR-H2, Chothia

<400> SEQUENCE: 177

Trp Trp Asp Asp Asp
1               5

<210> SEQ ID NO 178
<211> LENGTH: 5
<212> TYPE: PRT
```

```
<213> ORGANISM: Artificial Sequence
<220> FEATURE:
<223> OTHER INFORMATION: Synthetic: SRP2060-E05, CDR-H2, Chothia

<400> SEQUENCE: 178

Trp Trp Asp Asp Asp
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic: SRP2060-B01, CDR-H2, Chothia

<400> SEQUENCE: 179

Trp Trp Asp Asp Asp
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic: SRP2060-A06, CDR-H2, Chothia

<400> SEQUENCE: 180

Trp Trp Asp Asp Asp
1               5

<210> SEQ ID NO 181
<211> LENGTH: 17
<212> TYPE: PRT
<213> ORGANISM: Artificial Sequence
<220> FEATURE:
<223> OTHER INFORMATION: Synthetic: SRP1848-A01, CDR-H2, Kabat

<400> SEQUENCE: 181

Gly Ile Leu Pro Glu Ser Gly Gly Thr Ser Tyr Ala Asp Ser Val Lys
1               5                   10                  15

Gly

<210> SEQ ID NO 182
<211> LENGTH: 17
<212> TYPE: PRT
<213> ORGANISM: Artificial Sequence
<220> FEATURE:
<223> OTHER INFORMATION: Synthetic: SRP1848-A02, CDR-H2, Kabat

<400> SEQUENCE: 182

Gly Ile Tyr Pro Glu Ser Gly Ala Thr Tyr Tyr Ala Asp Ser Val Lys
1               5                   10                  15

Gly

<210> SEQ ID NO 183
<211> LENGTH: 17
<212> TYPE: PRT
<213> ORGANISM: Artificial Sequence
<220> FEATURE:
<223> OTHER INFORMATION: Synthetic: SRP1848-A04, CDR-H2, Kabat

<400> SEQUENCE: 183

Val Ile Tyr Pro Val Asp Gly Thr Thr Asp Tyr Ala Asp Ser Val Lys
1               5                   10                  15

Gly
```

```
<210> SEQ ID NO 184
<211> LENGTH: 17
<212> TYPE: PRT
<213> ORGANISM: Artificial Sequence
<220> FEATURE:
<223> OTHER INFORMATION: Synthetic: SRP1848-A06, CDR-H2, Kabat

<400> SEQUENCE: 184

Gly Ile Thr Pro Ile Asp Gly Asn Thr Asp Tyr Ala Asp Ser Val Lys
1               5                   10                  15

Gly

<210> SEQ ID NO 185
<211> LENGTH: 17
<212> TYPE: PRT
<213> ORGANISM: Artificial Sequence
<220> FEATURE:
<223> OTHER INFORMATION: Synthetic: SRP1848-A07, CDR-H2, Kabat

<400> SEQUENCE: 185

Glu Ile Phe Pro Val Asp Gly Thr Thr Asp Tyr Ala Asp Ser Val Lys
1               5                   10                  15

Gly

<210> SEQ ID NO 186
<211> LENGTH: 17
<212> TYPE: PRT
<213> ORGANISM: Artificial Sequence
<220> FEATURE:
<223> OTHER INFORMATION: Synthetic: SRP1848-A08, CDR-H2, Kabat

<400> SEQUENCE: 186

Ser Ile Tyr Pro Asn Asp Gly Thr Thr Asp Tyr Ala Asp Ser Val Lys
1               5                   10                  15

Gly

<210> SEQ ID NO 187
<211> LENGTH: 17
<212> TYPE: PRT
<213> ORGANISM: Artificial Sequence
<220> FEATURE:
<223> OTHER INFORMATION: Synthetic: SRP1848-A09, CDR-H2, Kabat

<400> SEQUENCE: 187

Ser Ile Phe Pro Asn Asp Gly Thr Thr Asp Tyr Ala Asp Ser Val Lys
1               5                   10                  15

Gly

<210> SEQ ID NO 188
<211> LENGTH: 17
<212> TYPE: PRT
<213> ORGANISM: Artificial Sequence
<220> FEATURE:
<223> OTHER INFORMATION: Synthetic: SRP1848-A10, CDR-H2, Kabat

<400> SEQUENCE: 188

Asp Ile Phe Pro Ile Asp Asp Ile Thr Asp Tyr Ala Asp Ser Val Lys
1               5                   10                  15

Gly

<210> SEQ ID NO 189
<211> LENGTH: 17
```

<212> TYPE: PRT
<213> ORGANISM: Artificial Sequence
<220> FEATURE:
<223> OTHER INFORMATION: Synthetic: SRP1848-B01, CDR-H2, Kabat

<400> SEQUENCE: 189

Glu Ile Tyr Pro Val Asp Gly Ile Thr Asp Tyr Ala Asp Ser Val Lys
1               5                   10                  15

Gly

<210> SEQ ID NO 190
<211> LENGTH: 17
<212> TYPE: PRT
<213> ORGANISM: Artificial Sequence
<220> FEATURE:
<223> OTHER INFORMATION: Synthetic: SRP1848-B03, CDR-H2, Kabat

<400> SEQUENCE: 190

Gly Ile Thr Pro Ile Asp Gly Met Thr Asp Tyr Ala Asp Ser Val Lys
1               5                   10                  15

Gly

<210> SEQ ID NO 191
<211> LENGTH: 17
<212> TYPE: PRT
<213> ORGANISM: Artificial Sequence
<220> FEATURE:
<223> OTHER INFORMATION: Synthetic: SRP1848-B04, CDR-H2, Kabat

<400> SEQUENCE: 191

Glu Ile Tyr Pro Val Asp Gly Ile Thr Asp Tyr Ala Asp Ser Val Lys
1               5                   10                  15

Gly

<210> SEQ ID NO 192
<211> LENGTH: 17
<212> TYPE: PRT
<213> ORGANISM: Artificial Sequence
<220> FEATURE:
<223> OTHER INFORMATION: Synthetic: SRP1848-B05, CDR-H2, Kabat

<400> SEQUENCE: 192

Gly Ile Ser Pro Ile Asp Gly Tyr Thr Asp Tyr Ala Asp Ser Met Lys
1               5                   10                  15

Gly

<210> SEQ ID NO 193
<211> LENGTH: 17
<212> TYPE: PRT
<213> ORGANISM: Artificial Sequence
<220> FEATURE:
<223> OTHER INFORMATION: Synthetic: SRP1848-B06, CDR-H2, Kabat

<400> SEQUENCE: 193

Gly Ile Thr Pro Ile Asp Gly Tyr Thr Asp Tyr Ala Asp Ser Val Lys
1               5                   10                  15

Gly

<210> SEQ ID NO 194
<211> LENGTH: 17
<212> TYPE: PRT
<213> ORGANISM: Artificial Sequence
<220> FEATURE:
<223> OTHER INFORMATION: Synthetic: SRP1848-B07, CDR-H2, Kabat

<400> SEQUENCE: 194

Gly Ile Ser Pro Tyr Asp Gly Phe Thr Asp Tyr Ala Asp Ser Val Lys
1               5                   10                  15
Gly

<210> SEQ ID NO 195
<211> LENGTH: 17
<212> TYPE: PRT
<213> ORGANISM: Artificial Sequence
<220> FEATURE:
<223> OTHER INFORMATION: Synthetic: SRP1848-B09, CDR-H2, Kabat

<400> SEQUENCE: 195

Gly Ile Thr Pro Val Asp Gly Tyr Thr Asp Tyr Ala Asp Arg Val Lys
1               5                   10                  15
Gly

<210> SEQ ID NO 196
<211> LENGTH: 17
<212> TYPE: PRT
<213> ORGANISM: Artificial Sequence
<220> FEATURE:
<223> OTHER INFORMATION: Synthetic: SRP1848-B10, CDR-H2, Kabat

<400> SEQUENCE: 196

Glu Ile Tyr Pro Arg Asp Gly Ile Thr Asp Tyr Ala Asp Ser Val Lys
1               5                   10                  15
Gly

<210> SEQ ID NO 197
<211> LENGTH: 17
<212> TYPE: PRT
<213> ORGANISM: Artificial Sequence
<220> FEATURE:
<223> OTHER INFORMATION: Synthetic: SRP1848-B11, CDR-H2, Kabat

<400> SEQUENCE: 197

Asp Ile Ser Pro Ile Asp Gly Phe Thr Asp Tyr Ala Asp Ser Val Lys
1               5                   10                  15
Gly

<210> SEQ ID NO 198
<211> LENGTH: 17
<212> TYPE: PRT
<213> ORGANISM: Artificial Sequence
<220> FEATURE:
<223> OTHER INFORMATION: Synthetic: SRP1848-C01, CDR-H2, Kabat

<400> SEQUENCE: 198

Gly Val Thr Pro Asn Asp Gly Tyr Thr Asp Tyr Ala Asp Ser Val Lys
1               5                   10                  15
Gly

<210> SEQ ID NO 199
<211> LENGTH: 17
<212> TYPE: PRT
<213> ORGANISM: Artificial Sequence
<220> FEATURE:
<223> OTHER INFORMATION: Synthetic: SRP1848-C03, CDR-H2, Kabat

<400> SEQUENCE: 199

Glu Ile Tyr Pro Ile Asp Gly Asn Thr Asp Tyr Ala Asp Ser Val Lys

```
<210> SEQ ID NO 200
<211> LENGTH: 17
<212> TYPE: PRT
<213> ORGANISM: Artificial Sequence
<220> FEATURE:
<223> OTHER INFORMATION: Synthetic: SRP1848-C04, CDR-H2, Kabat

<400> SEQUENCE: 200

Glu Ile Tyr Pro Gly Pro Gly Asn Thr Asp Tyr Ala Asp Ser Val Lys
1               5                   10                  15
Gly

<210> SEQ ID NO 201
<211> LENGTH: 17
<212> TYPE: PRT
<213> ORGANISM: Artificial Sequence
<220> FEATURE:
<223> OTHER INFORMATION: Synthetic: SRP1848-C05, CDR-H2, Kabat

<400> SEQUENCE: 201

Asp Ile Phe Pro Ile Asp Gly Ile Asn Asp Tyr Ala Asp Ser Val Lys
1               5                   10                  15
Gly

<210> SEQ ID NO 202
<211> LENGTH: 17
<212> TYPE: PRT
<213> ORGANISM: Artificial Sequence
<220> FEATURE:
<223> OTHER INFORMATION: Synthetic: SRP1848-C07, CDR-H2, Kabat

<400> SEQUENCE: 202

Asp Ile Phe Pro Ile Asp Gly Ile Thr Asp Tyr Ala Asp Ser Val Lys
1               5                   10                  15
Gly

<210> SEQ ID NO 203
<211> LENGTH: 17
<212> TYPE: PRT
<213> ORGANISM: Artificial Sequence
<220> FEATURE:
<223> OTHER INFORMATION: Synthetic: SRP1848-C10, CDR-H2, Kabat

<400> SEQUENCE: 203

Gly Ile Ser Pro Ile Asp Gly Tyr Thr Asp Tyr Ala Asp Ser Met Lys
1               5                   10                  15
Gly

<210> SEQ ID NO 204
<211> LENGTH: 17
<212> TYPE: PRT
<213> ORGANISM: Artificial Sequence
<220> FEATURE:
<223> OTHER INFORMATION: Synthetic: SRP1848-D02, CDR-H2, Kabat

<400> SEQUENCE: 204

Gly Ile Thr Pro Gln Asp Gly Tyr Thr Asp Tyr Ala Asp Ser Val Lys
1               5                   10                  15
Gly
```

<210> SEQ ID NO 205
<211> LENGTH: 17
<212> TYPE: PRT
<213> ORGANISM: Artificial Sequence
<220> FEATURE:
<223> OTHER INFORMATION: Synthetic: SRP1848-D03, CDR-H2, Kabat

<400> SEQUENCE: 205

Asp Ile Phe Pro Asn Asp Gly Ser Thr Asp Tyr Ala Asp Ser Val Lys
1               5                   10                  15
Gly

<210> SEQ ID NO 206
<211> LENGTH: 17
<212> TYPE: PRT
<213> ORGANISM: Artificial Sequence
<220> FEATURE:
<223> OTHER INFORMATION: Synthetic: SRP1848-D04, CDR-H2, Kabat

<400> SEQUENCE: 206

Glu Ile Tyr Pro Arg Asp Gly Ile Thr Asp Tyr Ala Asp Ser Val Lys
1               5                   10                  15
Gly

<210> SEQ ID NO 207
<211> LENGTH: 17
<212> TYPE: PRT
<213> ORGANISM: Artificial Sequence
<220> FEATURE:
<223> OTHER INFORMATION: Synthetic: SRP1848-D05, CDR-H2, Kabat

<400> SEQUENCE: 207

Gly Ile Ser Pro Ile Asp Gly Tyr Thr Asp Tyr Ala Asp Ser Val Lys
1               5                   10                  15
Gly

<210> SEQ ID NO 208
<211> LENGTH: 17
<212> TYPE: PRT
<213> ORGANISM: Artificial Sequence
<220> FEATURE:
<223> OTHER INFORMATION: Synthetic: SRP1848-D07, CDR-H2, Kabat

<400> SEQUENCE: 208

Gly Ile Ser Pro Asn Asp Gly Tyr Thr Asp Tyr Ala Asp Ser Val Lys
1               5                   10                  15
Gly

<210> SEQ ID NO 209
<211> LENGTH: 17
<212> TYPE: PRT
<213> ORGANISM: Artificial Sequence
<220> FEATURE:
<223> OTHER INFORMATION: Synthetic: SRP1848-D09, CDR-H2, Kabat

<400> SEQUENCE: 209

Gly Ile Ser Pro Asn Asp Gly Tyr Thr Asp Tyr Ala Asp Ser Val Lys
1               5                   10                  15
Gly

<210> SEQ ID NO 210
<211> LENGTH: 17
<212> TYPE: PRT

-continued

```
<213> ORGANISM: Artificial Sequence
<220> FEATURE:
<223> OTHER INFORMATION: Synthetic: SRP1848-D10, CDR-H2, Kabat

<400> SEQUENCE: 210

Trp Ile Ser Pro Asn Asp Gly Thr Thr Asp Tyr Ala Asp Ser Val Lys
1               5                   10                  15
Gly

<210> SEQ ID NO 211
<211> LENGTH: 17
<212> TYPE: PRT
<213> ORGANISM: Artificial Sequence
<220> FEATURE:
<223> OTHER INFORMATION: Synthetic: SRP1848-E01, CDR-H2, Kabat

<400> SEQUENCE: 211

Gly Ile Thr Pro Phe Asp Gly Phe Thr Asp Tyr Ala Asp Ser Val Lys
1               5                   10                  15
Gly

<210> SEQ ID NO 212
<211> LENGTH: 17
<212> TYPE: PRT
<213> ORGANISM: Artificial Sequence
<220> FEATURE:
<223> OTHER INFORMATION: Synthetic: SRP1848-E02, CDR-H2, Kabat

<400> SEQUENCE: 212

Glu Ile Tyr Pro Asn Asp Gly Asn Thr Asp Tyr Ala Asp Ser Val Lys
1               5                   10                  15
Gly

<210> SEQ ID NO 213
<211> LENGTH: 17
<212> TYPE: PRT
<213> ORGANISM: Artificial Sequence
<220> FEATURE:
<223> OTHER INFORMATION: Synthetic: SRP1848-E03, CDR-H2, Kabat

<400> SEQUENCE: 213

Gly Ile Thr Pro Arg Asp Gly Phe Thr Asp Tyr Ala Asp Ser Val Lys
1               5                   10                  15
Gly

<210> SEQ ID NO 214
<211> LENGTH: 17
<212> TYPE: PRT
<213> ORGANISM: Artificial Sequence
<220> FEATURE:
<223> OTHER INFORMATION: Synthetic: SRP1848-E05, CDR-H2, Kabat

<400> SEQUENCE: 214

Gly Ile Thr Pro Asn Asp Gly Tyr Thr Asp Tyr Ala Asp Ser Val Lys
1               5                   10                  15
Gly

<210> SEQ ID NO 215
<211> LENGTH: 17
<212> TYPE: PRT
<213> ORGANISM: Artificial Sequence
<220> FEATURE:
<223> OTHER INFORMATION: Synthetic: SRP1848-E06, CDR-H2, Kabat
```

```
<400> SEQUENCE: 215

Gly Ile Thr Pro Asn Asp Gly Tyr Thr Asp Tyr Ala Asp Ser Val Glu
1               5                   10                  15

Gly

<210> SEQ ID NO 216
<211> LENGTH: 17
<212> TYPE: PRT
<213> ORGANISM: Artificial Sequence
<220> FEATURE:
<223> OTHER INFORMATION: Synthetic: SRP1848-E07, CDR-H2, Kabat

<400> SEQUENCE: 216

Glu Ile Phe Pro Tyr Asp Gly Ser Thr Asp Tyr Ala Asp Asn Val Lys
1               5                   10                  15

Gly

<210> SEQ ID NO 217
<211> LENGTH: 17
<212> TYPE: PRT
<213> ORGANISM: Artificial Sequence
<220> FEATURE:
<223> OTHER INFORMATION: Synthetic: SRP1848-F01, CDR-H2, Kabat

<400> SEQUENCE: 217

Ser Ile Phe Pro Asn Asp Gly Thr Thr Asp Tyr Ala Asp Ser Val Lys
1               5                   10                  15

Gly

<210> SEQ ID NO 218
<211> LENGTH: 17
<212> TYPE: PRT
<213> ORGANISM: Artificial Sequence
<220> FEATURE:
<223> OTHER INFORMATION: Synthetic: SRP1848-F02, CDR-H2, Kabat

<400> SEQUENCE: 218

Ser Ile Phe Pro Asn Asp Gly Thr Thr Asp Tyr Ala Asp Ser Val Lys
1               5                   10                  15

Gly

<210> SEQ ID NO 219
<211> LENGTH: 17
<212> TYPE: PRT
<213> ORGANISM: Artificial Sequence
<220> FEATURE:
<223> OTHER INFORMATION: Synthetic: SRP1848-F04, CDR-H2, Kabat

<400> SEQUENCE: 219

Glu Ile Tyr Pro Ile Asp Gly Ile Thr Asp Tyr Ala Asp Ser Val Lys
1               5                   10                  15

Gly

<210> SEQ ID NO 220
<211> LENGTH: 17
<212> TYPE: PRT
<213> ORGANISM: Artificial Sequence
<220> FEATURE:
<223> OTHER INFORMATION: Synthetic: SRP1848-F05, CDR-H2, Kabat

<400> SEQUENCE: 220

Glu Ile Tyr Pro Asn Asp Gly Ser Thr Asp Tyr Ala Asp Ser Val Lys
1               5                   10                  15
```

Gly

<210> SEQ ID NO 221
<211> LENGTH: 17
<212> TYPE: PRT
<213> ORGANISM: Artificial Sequence
<220> FEATURE:
<223> OTHER INFORMATION: Synthetic: SRP1848-F06, CDR-H2, Kabat

<400> SEQUENCE: 221

Gly Ile Ser Pro Ile Asp Gly Asn Thr Asp Tyr Ala Asp Ser Val Lys
1               5                   10                  15

Gly

<210> SEQ ID NO 222
<211> LENGTH: 17
<212> TYPE: PRT
<213> ORGANISM: Artificial Sequence
<220> FEATURE:
<223> OTHER INFORMATION: Synthetic: SRP1848-F07, CDR-H2, Kabat

<400> SEQUENCE: 222

Glu Ile Tyr Pro Asn Asp Gly Ile Thr Asp Tyr Ala Asp Ser Val Lys
1               5                   10                  15

Gly

<210> SEQ ID NO 223
<211> LENGTH: 17
<212> TYPE: PRT
<213> ORGANISM: Artificial Sequence
<220> FEATURE:
<223> OTHER INFORMATION: Synthetic: SRP1848-F08, CDR-H2, Kabat

<400> SEQUENCE: 223

Glu Ile Tyr Pro Val Asp Gly Ile Thr Asp Tyr Ala Asp Ser Val Lys
1               5                   10                  15

Gly

<210> SEQ ID NO 224
<211> LENGTH: 17
<212> TYPE: PRT
<213> ORGANISM: Artificial Sequence
<220> FEATURE:
<223> OTHER INFORMATION: Synthetic: SRP1848-F09, CDR-H2, Kabat

<400> SEQUENCE: 224

Gly Ile Ser Pro Leu Asp Gly Tyr Thr Asp Tyr Ala Asp Ser Val Lys
1               5                   10                  15

Gly

<210> SEQ ID NO 225
<211> LENGTH: 17
<212> TYPE: PRT
<213> ORGANISM: Artificial Sequence
<220> FEATURE:
<223> OTHER INFORMATION: Synthetic: SRP1848-F10, CDR-H2, Kabat

<400> SEQUENCE: 225

Ser Ile Phe Pro Asn Asp Gly Tyr Thr Asp Tyr Ala Asp Ser Val Lys
1               5                   10                  15

Gly

```
<210> SEQ ID NO 226
<211> LENGTH: 17
<212> TYPE: PRT
<213> ORGANISM: Artificial Sequence
<220> FEATURE:
<223> OTHER INFORMATION: Synthetic: SRP1848-F11, CDR-H2, Kabat

<400> SEQUENCE: 226

Gly Ile Thr Pro Ile Asp Gly Asn Thr Asp Tyr Ala Asp Ser Val Lys
1               5                   10                  15

Gly

<210> SEQ ID NO 227
<211> LENGTH: 17
<212> TYPE: PRT
<213> ORGANISM: Artificial Sequence
<220> FEATURE:
<223> OTHER INFORMATION: Synthetic: SRP1848-G01, CDR-H2, Kabat

<400> SEQUENCE: 227

Trp Ile Ala Pro Asn Asp Gly Ser Thr Asp Tyr Ala Asp Ser Val Lys
1               5                   10                  15

Gly

<210> SEQ ID NO 228
<211> LENGTH: 17
<212> TYPE: PRT
<213> ORGANISM: Artificial Sequence
<220> FEATURE:
<223> OTHER INFORMATION: Synthetic: SRP1848-G03, CDR-H2, Kabat

<400> SEQUENCE: 228

Gly Ile Thr Pro Ser Asp Gly Phe Thr Asp Tyr Ala Asp Ser Val Lys
1               5                   10                  15

Gly

<210> SEQ ID NO 229
<211> LENGTH: 17
<212> TYPE: PRT
<213> ORGANISM: Artificial Sequence
<220> FEATURE:
<223> OTHER INFORMATION: Synthetic: SRP1848-G04, CDR-H2, Kabat

<400> SEQUENCE: 229

Tyr Ile Thr Pro Ala Gly Gly Ala Thr Phe Tyr Ala Asp Ser Val Lys
1               5                   10                  15

Gly

<210> SEQ ID NO 230
<211> LENGTH: 17
<212> TYPE: PRT
<213> ORGANISM: Artificial Sequence
<220> FEATURE:
<223> OTHER INFORMATION: Synthetic: SRP1848-G06, CDR-H2, Kabat

<400> SEQUENCE: 230

Tyr Ile Thr Pro Ala Gly Gly Ala Thr Tyr Tyr Ala Asp Asn Val Lys
1               5                   10                  15

Gly

<210> SEQ ID NO 231
<211> LENGTH: 17
<212> TYPE: PRT
<213> ORGANISM: Artificial Sequence
```

<220> FEATURE:
<223> OTHER INFORMATION: Synthetic: SRP1848-G07, CDR-H2, Kabat

<400> SEQUENCE: 231

Tyr Ile Thr Pro Ala Gly Gly Ala Thr Trp Tyr Ala Asp Ser Val Lys
1               5                   10                  15
Gly

<210> SEQ ID NO 232
<211> LENGTH: 17
<212> TYPE: PRT
<213> ORGANISM: Artificial Sequence
<220> FEATURE:
<223> OTHER INFORMATION: Synthetic: SRP1848-G09, CDR-H2, Kabat

<400> SEQUENCE: 232

Tyr Ile Thr Pro Ala Gly Gly Ala Thr Phe Tyr Ala Asp Ser Val Lys
1               5                   10                  15
Gly

<210> SEQ ID NO 233
<211> LENGTH: 17
<212> TYPE: PRT
<213> ORGANISM: Artificial Sequence
<220> FEATURE:
<223> OTHER INFORMATION: Synthetic: SRP1848-G10, CDR-H2, Kabat

<400> SEQUENCE: 233

Tyr Ile Thr Pro Ala Gly Gly Ala Thr Tyr Tyr Ala Asp Ser Val Lys
1               5                   10                  15
Gly

<210> SEQ ID NO 234
<211> LENGTH: 17
<212> TYPE: PRT
<213> ORGANISM: Artificial Sequence
<220> FEATURE:
<223> OTHER INFORMATION: Synthetic: SRP1848-G11, CDR-H2, Kabat

<400> SEQUENCE: 234

Tyr Ile Thr Pro Ala Gly Gly Ala Thr Trp Tyr Ala Asp Ser Val Lys
1               5                   10                  15
Gly

<210> SEQ ID NO 235
<211> LENGTH: 17
<212> TYPE: PRT
<213> ORGANISM: Artificial Sequence
<220> FEATURE:
<223> OTHER INFORMATION: Synthetic: SRP1848-H01, CDR-H2, Kabat

<400> SEQUENCE: 235

Asp Ile Phe Pro Ile Asp Gly Ile Thr Asp Tyr Ala Asp Ser Val Lys
1               5                   10                  15
Gly

<210> SEQ ID NO 236
<211> LENGTH: 16
<212> TYPE: PRT
<213> ORGANISM: Artificial Sequence
<220> FEATURE:
<223> OTHER INFORMATION: Synthetic: SRP2060-E10, CDR-H2, Kabat

<400> SEQUENCE: 236

```
His Ile Trp Trp Asp Asp Asp Lys Tyr Tyr His Pro Ala Leu Lys Gly
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic: SRP2060-E05, CDR-H2, Kabat

<400> SEQUENCE: 237

His Ile Trp Trp Asp Asp Asp Lys Tyr Tyr His Pro Ala Leu Lys Gly
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Synthetic: SRP2060-B01, CDR-H2, Kabat

<400> SEQUENCE: 238

His Ile Trp Trp Asp Asp Asp Lys Tyr Tyr His Pro Ala Leu Lys Gly
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Synthetic: SRP2060-A06, CDR-H2, Kabat

<400> SEQUENCE: 239

His Ile Trp Trp Asp Asp Asp Lys Tyr Tyr Tyr Pro Ala Leu Lys Gly
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Synthetic: SRP1848-A01, CDR-H3

<400> SEQUENCE: 240

His Ile Tyr Pro Trp Asp Trp Phe Ser Asn Tyr Val Leu Asp Tyr
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Synthetic: SRP1848-A02, CDR-H3

<400> SEQUENCE: 241

His Leu Tyr Val Trp Asp Trp Val Leu Asp His Val Leu Asp Tyr
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Synthetic: SRP1848-A04, CDR-H3

<400> SEQUENCE: 242
```

```
Gly Ala Trp Ser Trp Arg Ser Gly Tyr Gly Tyr Tyr Ile Asp Tyr
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Synthetic: SRP1848-A06, CDR-H3

<400> SEQUENCE: 243

Gly Ala Trp Ser Trp Arg Ser Gly Tyr Gly Tyr Tyr Ile Asp Tyr
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Synthetic: SRP1848-A07, CDR-H3

<400> SEQUENCE: 244

Gly Phe Trp Ala Trp Arg Ser Gly Tyr Gly Tyr Tyr Leu Asp Tyr
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Synthetic: SRP1848-A08, CDR-H3

<400> SEQUENCE: 245

Gly Ser Trp Phe Trp Arg Ala Gly Tyr Gly Tyr Tyr Leu Asp Tyr
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Synthetic: SRP1848-A09, CDR-H3

<400> SEQUENCE: 246

Gly Ser Trp Phe Trp Arg Ser Gly Tyr Gly Tyr Phe Leu Glu Tyr
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Synthetic: SRP1848-A10, CDR-H3

<400> SEQUENCE: 247

Gly Ser Trp Ser Trp Pro Ser Gly His Ser Tyr Tyr Leu Asp Tyr
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Synthetic: SRP1848-B01, CDR-H3

<400> SEQUENCE: 248

Gly Phe Trp Ser Trp Pro Ser Gly Tyr Ser Tyr Phe Leu Asp Tyr
```

```
<210> SEQ ID NO 249
<211> LENGTH: 15
<212> TYPE: PRT
<213> ORGANISM: Artificial Sequence
<220> FEATURE:
<223> OTHER INFORMATION: Synthetic: SRP1848-B03, CDR-H3

<400> SEQUENCE: 249

Gly Ser Trp Ser Trp Pro Ser Gly Tyr Ser Tyr Tyr Leu Asp Tyr
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Synthetic: SRP1848-B04, CDR-H3

<400> SEQUENCE: 250

Gly Arg Tyr Ser Trp Arg Ala Gly Tyr Ser Tyr Tyr Leu Asp Tyr
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Synthetic: SRP1848-B05, CDR-H3

<400> SEQUENCE: 251

Gly Ser Trp Phe Trp Gln Ser Gly Tyr Gly Tyr Tyr Leu Asp Tyr
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Synthetic: SRP1848-B06, CDR-H3

<400> SEQUENCE: 252

Gly Phe Trp Ser Trp Pro Ser Gly Tyr Gly Tyr Tyr Gln Asp Tyr
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic: SRP1848-B07, CDR-H3

<400> SEQUENCE: 253

Gly Ser Trp Ser Trp Pro Ala Gly Tyr Gly Tyr Tyr Gln Asp Tyr
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Synthetic: SRP1848-B09, CDR-H3

<400> SEQUENCE: 254

Gly Ala Trp Ser Trp Arg Ser Gly Tyr Gly Tyr Tyr Met Asp Tyr
1               5                   10                  15
```

<210> SEQ ID NO 255
<211> LENGTH: 15
<212> TYPE: PRT
<213> ORGANISM: Artificial Sequence
<220> FEATURE:
<223> OTHER INFORMATION: Synthetic: SRP1848-B10, CDR-H3

<400> SEQUENCE: 255

Gly Gly Trp His Trp Arg Ser Gly Tyr Ser Tyr Tyr Leu Asp Tyr
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthetic: SRP1848-B11, CDR-H3

<400> SEQUENCE: 256

Gly Ser Trp Ser Trp Arg Ala Gly Tyr Gly Tyr Tyr Leu Asp Tyr
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthetic: SRP1848-C01, CDR-H3

<400> SEQUENCE: 257

Gly Ser Trp Phe Trp Arg Ala Gly Tyr Gly Tyr Tyr Leu Asp Tyr
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic: SRP1848-C03, CDR-H3

<400> SEQUENCE: 258

Gly Ser Trp Ala Trp Arg Ser Gly Tyr Ser Tyr Tyr Leu Asp Tyr
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthetic: SRP1848-C04, CDR-H3

<400> SEQUENCE: 259

Gly Ser Leu Ser Trp Arg Ala Gly Tyr Gly Tyr Tyr Leu Asp Tyr
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Synthetic: SRP1848-C05, CDR-H3

<400> SEQUENCE: 260

Gly Ser Trp Ser Trp Lys Ala Gly Tyr Gly Tyr Tyr Leu Asp Tyr
1               5                   10                  15

```
<210> SEQ ID NO 261
<211> LENGTH: 15
<212> TYPE: PRT
<213> ORGANISM: Artificial Sequence
<220> FEATURE:
<223> OTHER INFORMATION: Synthetic: SRP1848-C07, CDR-H3

<400> SEQUENCE: 261

Gly Ser Trp Ser Trp Pro Ala Gly Tyr Gly Tyr Tyr Gln Asp Tyr
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Synthetic: SRP1848-C10, CDR-H3

<400> SEQUENCE: 262

Gly Ser Trp Ser Trp Pro Ala Gly Tyr Gly Tyr Tyr Leu Asp Tyr
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Synthetic: SRP1848-D02, CDR-H3

<400> SEQUENCE: 263

Gly Ala Trp Ser Trp Arg Ala Gly Tyr Gly Tyr Tyr Leu Asp Tyr
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Synthetic: SRP1848-D03, CDR-H3

<400> SEQUENCE: 264

Gly His Trp Ser Trp Pro Ser Gly Tyr Trp Tyr Tyr Leu Asp Tyr
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Synthetic: SRP1848-D04, CDR-H3

<400> SEQUENCE: 265

Gly Tyr Trp Phe Trp Arg Ser Gly Tyr Gly Tyr Tyr Leu Asp Tyr
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Synthetic: SRP1848-D05, CDR-H3

<400> SEQUENCE: 266

Gly Ser Trp Ser Trp Arg Ala Gly Tyr Gly Tyr Tyr Leu Asp Tyr
1               5                   10                  15
```

-continued

```
<210> SEQ ID NO 267
<211> LENGTH: 15
<212> TYPE: PRT
<213> ORGANISM: Artificial Sequence
<220> FEATURE:
<223> OTHER INFORMATION: Synthetic: SRP1848-D07, CDR-H3

<400> SEQUENCE: 267

Gly Phe Trp Ala Trp Arg Ser Gly Tyr Gly Tyr Tyr Leu Asp Tyr
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Synthetic: SRP1848-D09, CDR-H3

<400> SEQUENCE: 268

Gly Ser Trp Ser Trp Arg His Gly Tyr Gly Tyr Tyr Leu Asp Tyr
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Synthetic: SRP1848-D10, CDR-H3

<400> SEQUENCE: 269

Gly Ala Trp Ser Trp Arg Ser Gly Tyr Gly Tyr Tyr Ile Asp Tyr
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthetic: SRP1848-E01, CDR-H3

<400> SEQUENCE: 270

Gly Ser Trp Ser Trp Pro Ala Gly Tyr Gly Tyr Tyr Gln Asp Tyr
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic: SRP1848-E02, CDR-H3

<400> SEQUENCE: 271

Gly Ser Trp Ser Trp Arg Ser Gly Tyr Gly Tyr Tyr Leu Asp Tyr
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic: SRP1848-E03, CDR-H3

<400> SEQUENCE: 272

Gly Ser Trp Ser Trp Pro Ala Gly His Ser Tyr Tyr Leu Asp Tyr
1               5                   10                  15

<210> SEQ ID NO 273
```

```
<211> LENGTH: 15
<212> TYPE: PRT
<213> ORGANISM: Artificial Sequence
<220> FEATURE:
<223> OTHER INFORMATION: Synthetic: SRP1848-E05, CDR-H3

<400> SEQUENCE: 273

Gly Phe Trp Ala Trp Arg Ser Gly Tyr Gly Tyr Tyr Leu Asp Tyr
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Synthetic: SRP1848-E06, CDR-H3

<400> SEQUENCE: 274

Gly Thr Trp Ser Trp Pro Ser Gly His Ser Tyr Tyr Leu Asp Tyr
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Synthetic: SRP1848-E07, CDR-H3

<400> SEQUENCE: 275

Gly Ala Trp Ser Trp Arg Ser Gly Tyr Gly Tyr Tyr Ile Asp Tyr
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Synthetic: SRP1848-F01, CDR-H3

<400> SEQUENCE: 276

Gly Ser Trp Ala Trp Arg Ala Gly Tyr Ser Tyr Tyr Leu Asp Tyr
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Synthetic: SRP1848-F02, CDR-H3

<400> SEQUENCE: 277

Gly Ser Trp Ser Trp Gln Ala Gly Tyr Gly Tyr Tyr Leu Asp Tyr
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Synthetic: SRP1848-F04, CDR-H3

<400> SEQUENCE: 278

Gly Ser Trp Phe Trp Arg Ser Gly Tyr Gly Tyr Tyr Leu Asp Tyr
1               5                   10                  15

<210> SEQ ID NO 279
<211> LENGTH: 15
```

```
<212> TYPE: PRT
<213> ORGANISM: Artificial Sequence
<220> FEATURE:
<223> OTHER INFORMATION: Synthetic: SRP1848-F05, CDR-H3

<400> SEQUENCE: 279

Gly Ser Trp Ala Trp Arg Ser Gly Tyr Ser Tyr Phe Leu Asp Tyr
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Synthetic: SRP1848-F06, CDR-H3

<400> SEQUENCE: 280

Gly Phe Trp Ala Trp Arg Ser Gly Tyr Gly Tyr Tyr Leu Asp Tyr
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Synthetic: SRP1848-F07, CDR-H3

<400> SEQUENCE: 281

Gly Ser Trp Asp Trp Arg Ser Gly Tyr Ser Tyr Tyr Leu Asp Tyr
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: Synthetic: SRP1848-F08, CDR-H3

<400> SEQUENCE: 282

Gly Ser Trp Tyr Trp Gln Ser Gly Tyr Ser Tyr Tyr Leu Asp Tyr
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: Synthetic: SRP1848-F09, CDR-H3

<400> SEQUENCE: 283

Gly Ala Trp Ser Trp Arg Ser Gly Tyr Gly Tyr Tyr Ile Asp Tyr
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Synthetic: SRP1848-F10, CDR-H3

<400> SEQUENCE: 284

Gly Ser Trp Phe Trp Arg Ser Gly Tyr Gly Tyr Tyr Leu Asp Tyr
1               5                   10                  15

<210> SEQ ID NO 285
<211> LENGTH: 15
<212> TYPE: PRT
```

```
<213> ORGANISM: Artificial Sequence
<220> FEATURE:
<223> OTHER INFORMATION: Synthetic: SRP1848-F11, CDR-H3

<400> SEQUENCE: 285

Gly Ser Trp Tyr Trp Arg Ala Gly Tyr Gly Tyr Tyr Leu Asp Tyr
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Synthetic: SRP1848-G01, CDR-H3

<400> SEQUENCE: 286

Gly Ser Trp Ala Trp Arg Ser Gly Tyr Ser Tyr Phe Leu Asp Tyr
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Synthetic: SRP1848-G03, CDR-H3

<400> SEQUENCE: 287

Gly Ser Trp Ser Trp Pro Ser Gly His Gly Tyr Phe Leu Asp Tyr
1               5                   10                  15

<210> SEQ ID NO 288
<211> LENGTH: 11
<212> TYPE: PRT
<213> ORGANISM: Artificial Sequence
<220> FEATURE:
<223> OTHER INFORMATION: Synthetic: SRP1848-G04, CDR-H3

<400> SEQUENCE: 288

Tyr Pro Tyr Trp Phe Ala Gly Tyr Met Asp Tyr
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Synthetic: SRP1848-G06, CDR-H3

<400> SEQUENCE: 289

Gln Pro Tyr Trp Phe Ala Gly Tyr Met Asp Tyr
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Synthetic: SRP1848-G07, CDR-H3

<400> SEQUENCE: 290

Tyr Pro Phe Trp Phe Ala Gly Tyr Met Asp Tyr
1               5                   10

<210> SEQ ID NO 291
<211> LENGTH: 11
<212> TYPE: PRT
<213> ORGANISM: Artificial Sequence
```

```
<220> FEATURE:
<223> OTHER INFORMATION: Synthetic: SRP1848-G09, CDR-H3

<400> SEQUENCE: 291

His Glu Tyr Trp Phe Ser Gly Tyr Met Asp Tyr
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Synthetic: SRP1848-G10, CDR-H3

<400> SEQUENCE: 292

Tyr Pro Tyr Trp Phe Ala Gly Tyr Ile Asp Tyr
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Synthetic: SRP1848-G11, CDR-H3

<400> SEQUENCE: 293

Tyr Pro Tyr Trp Phe Ser Gly Tyr Met Asp Tyr
1               5                   10

<210> SEQ ID NO 294
<211> LENGTH: 15
<212> TYPE: PRT
<213> ORGANISM: Artificial Sequence
<220> FEATURE:
<223> OTHER INFORMATION: Synthetic: SRP1848-H01, CDR-H3

<400> SEQUENCE: 294

Gly Ser Trp Ser Trp Pro Ser Gly Met Asp Tyr Tyr Leu Asp Tyr
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Synthetic: SRP2060-E10, CDR-H3

<400> SEQUENCE: 295

Asn His Phe Pro His Tyr Tyr Gly Ser Ser His Trp Tyr Phe Asn Val
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Synthetic: SRP2060-E05, CDR-H3

<400> SEQUENCE: 296

Asn His Phe Pro His Tyr Tyr Gly Ser Ser His Trp Tyr Phe Asn Val
1               5                   10                  15

<210> SEQ ID NO 297
<211> LENGTH: 16
<212> TYPE: PRT
<213> ORGANISM: Artificial Sequence
<220> FEATURE:
```

-continued

```
<223> OTHER INFORMATION: Synthetic: SRP2060-B01, CDR-H3

<400> SEQUENCE: 297

Asn His Phe Pro His Tyr Tyr Gly Ser Ser His Trp Tyr Phe Asn Val
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Synthetic: SRP2060-A06, CDR-H3

<400> SEQUENCE: 298

Asn His Phe Pro His Tyr Tyr Gly Ser Ser His Trp Tyr Phe Asp Val
1               5                   10                  15

<210> SEQ ID NO 299
<211> LENGTH: 11
<212> TYPE: PRT
<213> ORGANISM: Artificial Sequence
<220> FEATURE:
<223> OTHER INFORMATION: Synthetic: trastuzumab, CDR-L1

<400> SEQUENCE: 299

Arg Ala Ser Gln Asp Val Asn Thr Ala Val Ala
1               5                   10

<210> SEQ ID NO 300
<211> LENGTH: 11
<212> TYPE: PRT
<213> ORGANISM: Artificial Sequence
<220> FEATURE:
<223> OTHER INFORMATION: Synthetic: H6D1-LC4, CDR-L1

<400> SEQUENCE: 300

Lys Ala Ser Gln Asp Ile Asn Ser Tyr Leu Ser
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Synthetic: H6D1-LC5, CDR-L1

<400> SEQUENCE: 301

Lys Ala Ser Gln Asp Ile Asn Ser Tyr Leu Ser
1               5                   10

<210> SEQ ID NO 302
<211> LENGTH: 7
<212> TYPE: PRT
<213> ORGANISM: Artificial Sequence
<220> FEATURE:
<223> OTHER INFORMATION: Synthetic: trastuzumab, CDR-L2

<400> SEQUENCE: 302

Ser Ala Ser Phe Leu Tyr Ser
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic: H6D1-LC4, CDR-L3
```

-continued

<400> SEQUENCE: 303

Arg Ala Asn Arg Leu Val Asp
1               5

<210> SEQ ID NO 304
<211> LENGTH: 7
<212> TYPE: PRT
<213> ORGANISM: Artificial Sequence
<220> FEATURE:
<223> OTHER INFORMATION: Synthetic: H6D1-LC5, CDR-L2

<400> SEQUENCE: 304

Arg Ala Asn Arg Leu Val Asp
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic: trastuzumab, CDR-L3

<400> SEQUENCE: 305

Gln Gln His Tyr Thr Thr Pro Pro Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Synthetic: H6D1-LC4, CDR-L3

<400> SEQUENCE: 306

Leu Gln Tyr Asp Glu Phe Pro Tyr Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Synthetic: H6D1-LC5, CDR-L3

<400> SEQUENCE: 307

Leu Gln Tyr Asp Glu Phe Pro Tyr Thr
1               5

<210> SEQ ID NO 308
<211> LENGTH: 124
<212> TYPE: PRT
<213> ORGANISM: Artificial Sequence
<220> FEATURE:
<223> OTHER INFORMATION: Synthetic: SRP1848-A01, VH

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Thr Arg Tyr
            20                  25                  30

Ser Ile His Trp Val Arg Gln Ala Pro Gly Lys Gly Leu Glu Trp Val
        35                  40                  45

Ala Gly Ile Leu Pro Glu Ser Gly Gly Thr Ser Tyr Ala Asp Ser Val
    50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg His Ile Tyr Pro Trp Asp Trp Phe Ser Asn Tyr Val Leu Asp
            100                 105                 110

Tyr Trp Gly Gln Gly Thr Leu Val Thr Val Ser Ser
        115                 120
```

<210> SEQ ID NO 309
<211> LENGTH: 124
<212> TYPE: PRT
<213> ORGANISM: Artificial Sequence
<220> FEATURE:
<223> OTHER INFORMATION: Synthetic: SRP1848-A02, VH

<400> SEQUENCE: 309

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser Gly Phe
                 20                  25                  30

Arg Ile His Trp Val Arg Gln Ala Pro Gly Lys Gly Leu Glu Trp Val
             35                  40                  45

Ala Gly Ile Tyr Pro Glu Ser Gly Ala Thr Tyr Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg His Leu Tyr Val Trp Asp Trp Val Leu Asp His Val Leu Asp
            100                 105                 110

Tyr Trp Gly Gln Gly Thr Leu Val Thr Val Ser Ser
        115                 120
```

<210> SEQ ID NO 310
<211> LENGTH: 124
<212> TYPE: PRT
<213> ORGANISM: Artificial Sequence
<220> FEATURE:
<223> OTHER INFORMATION: Synthetic: SRP1848-A04, VH

<400> SEQUENCE: 310

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Asp Gln Ser
                 20                  25                  30

Ser Ile His Trp Val Arg Gln Ala Pro Gly Lys Gly Leu Glu Trp Val
             35                  40                  45

Gly Val Ile Tyr Pro Val Asp Gly Thr Thr Asp Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ala Trp Ser Trp Arg Ser Gly Tyr Gly Tyr Tyr Ile Asp
            100                 105                 110

Tyr Trp Gly Gln Gly Thr Leu Val Thr Val Ser Ser
```

<210> SEQ ID NO 311
<211> LENGTH: 124
<212> TYPE: PRT
<213> ORGANISM: Artificial Sequence
<220> FEATURE:
<223> OTHER INFORMATION: Synthetic: SRP1848-A06, VH

<400> SEQUENCE: 311

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Asn Ser
            20                  25                  30

Tyr Ile His Trp Val Arg Gln Ala Pro Gly Lys Gly Leu Glu Trp Val
        35                  40                  45

Gly Gly Ile Thr Pro Ile Asp Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Trp Ser Trp Arg Ser Gly Tyr Gly Tyr Tyr Ile Asp
            100                 105                 110

Tyr Trp Gly Gln Gly Thr Leu Val Thr Val Ser Ser
        115                 120

<210> SEQ ID NO 312
<211> LENGTH: 124
<212> TYPE: PRT
<213> ORGANISM: Artificial Sequence
<220> FEATURE:
<223> OTHER INFORMATION: Synthetic: SRP1848-A07, VH

<400> SEQUENCE: 312

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Tyr His
            20                  25                  30

Ser Ile His Trp Val Arg Gln Ala Pro Gly Lys Gly Leu Glu Trp Val
        35                  40                  45

Gly Glu Ile Phe Pro Val Asp Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu His Met Asn Ser Leu Arg Ala Glu Asp Thr Ala Val Tyr Tyr Cys
                85                  90                  95

Ala Arg Gly Phe Trp Ala Trp Arg Ser Gly Tyr Gly Tyr Tyr Leu Asp
            100                 105                 110

Tyr Trp Gly Gln Gly Thr Leu Val Thr Val Ser Ser
        115                 120

<210> SEQ ID NO 313
<211> LENGTH: 124
<212> TYPE: PRT
<213> ORGANISM: Artificial Sequence
<220> FEATURE:
<223> OTHER INFORMATION: Synthetic: SRP1848-A08, VH

<400> SEQUENCE: 313

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Asn Ile Arg Lys His
            20                  25                  30

Ser Ile His Trp Val Arg Gln Ala Pro Gly Lys Gly Leu Glu Trp Val
        35                  40                  45

Gly Ser Ile Tyr Pro Asn Asp Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Phe Trp Arg Ala Gly Tyr Gly Tyr Tyr Leu Asp
            100                 105                 110

Tyr Trp Gly Gln Gly Thr Leu Val Thr Val Ser Ser
        115                 120
```

<210> SEQ ID NO 314
<211> LENGTH: 124
<212> TYPE: PRT
<213> ORGANISM: Artificial Sequence
<220> FEATURE:
<223> OTHER INFORMATION: Synthetic: SRP1848-A09, VH

<400> SEQUENCE: 314

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Lys Gln
            20                  25                  30

Ser Ile His Trp Val Arg Gln Ala Pro Gly Lys Gly Leu Glu Trp Val
        35                  40                  45

Gly Ser Ile Phe Pro Asn Asp Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Val Asn Ser Leu Arg Ala Glu Asp Thr Ala Val Tyr Tyr Cys
                85                  90                  95

Ala Arg Gly Ser Trp Phe Trp Arg Ser Gly Tyr Gly Tyr Phe Leu Glu
            100                 105                 110

Tyr Trp Gly Gln Gly Thr Leu Val Thr Val Ser Ser
        115                 120
```

<210> SEQ ID NO 315
<211> LENGTH: 124
<212> TYPE: PRT
<213> ORGANISM: Artificial Sequence
<220> FEATURE:
<223> OTHER INFORMATION: Synthetic: SRP1848-A10, VH

<400> SEQUENCE: 315

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Lys Tyr
            20                  25                  30

Ser Ile His Trp Ala Arg Gln Ala Pro Gly Lys Gly Leu Glu Trp Val
        35                  40                  45

Gly Asp Ile Phe Pro Ile Asp Asp Ile Thr Asp Tyr Ala Asp Ser Val
```

```
                    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Gly Ser Trp Ser Trp Pro Ser Gly His Ser Tyr Tyr Leu Asp
                100                 105                 110

Tyr Trp Gly Gln Gly Thr Leu Val Thr Val Ser Ser
            115                 120

<210> SEQ ID NO 316
<211> LENGTH: 124
<212> TYPE: PRT
<213> ORGANISM: Artificial Sequence
<220> FEATURE:
<223> OTHER INFORMATION: Synthetic: SRP1848-B01, VH

<400> SEQUENCE: 316

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Arg Asn Tyr
                 20                  25                  30

Ser Ile His Trp Val Arg Gln Ala Pro Gly Lys Gly Leu Glu Trp Val
             35                  40                  45

Gly Glu Ile Tyr Pro Val Asp Gly Ile Thr Asp Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Gly Phe Trp Ser Trp Pro Ser Gly Tyr Ser Tyr Phe Leu Asp
                100                 105                 110

Tyr Trp Gly Gln Gly Thr Leu Val Thr Val Ser Ser
            115                 120

<210> SEQ ID NO 317
<211> LENGTH: 124
<212> TYPE: PRT
<213> ORGANISM: Artificial Sequence
<220> FEATURE:
<223> OTHER INFORMATION: Synthetic: SRP1848-B03, VH

<400> SEQUENCE: 317

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Ser Met Lys
                 20                  25                  30

Tyr Ile His Trp Val Arg Gln Ala Pro Gly Lys Gly Leu Glu Trp Val
             35                  40                  45

Gly Gly Ile Thr Pro Ile Asp Gly Met Thr Asp Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Gly Ser Trp Ser Trp Pro Ser Gly Tyr Ser Tyr Tyr Leu Asp
                100                 105                 110
```

-continued

```
Tyr Trp Gly Gln Gly Thr Leu Val Thr Val Ser Ser
        115                 120
```

<210> SEQ ID NO 318
<211> LENGTH: 124
<212> TYPE: PRT
<213> ORGANISM: Artificial Sequence
<220> FEATURE:
<223> OTHER INFORMATION: Synthetic: SRP1848-B04, VH

<400> SEQUENCE: 318

```
Glu Val Gln Leu Val Glu Ser Gly Gly Gly Leu Val Gln Pro Gly Gly
1               5                   10                  15

Ser Leu Arg Leu Ser Cys Ala Ala Ser Ser Phe Asn Ile Ser Asn His
            20                  25                  30

Ser Ile His Trp Val Arg Gln Ala Pro Gly Lys Gly Leu Glu Trp Val
        35                  40                  45

Gly Glu Ile Tyr Pro Val Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Arg Tyr Ser Trp Arg Ala Gly Tyr Ser Tyr Tyr Leu Asp
            100                 105                 110

Tyr Trp Gly Gln Gly Thr Leu Val Thr Val Ser Ser
        115                 120
```

<210> SEQ ID NO 319
<211> LENGTH: 124
<212> TYPE: PRT
<213> ORGANISM: Artificial Sequence
<220> FEATURE:
<223> OTHER INFORMATION: Synthetic: SRP1848-B05, VH

<400> SEQUENCE: 319

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
            20                  25                  30

Tyr Ile His Trp Val Arg Gln Ala Pro Gly Lys Gly Leu Glu Trp Val
        35                  40                  45

Gly Gly Ile Ser Pro Ile Asp Gly Tyr Thr Asp Tyr Ala Asp Ser Met
    50                  55                  60

Lys Gly Arg Phe Thr Ile Ser Ala Asp Thr Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Gly Ser Trp Phe Trp Gln Ser Gly Tyr Gly Tyr Tyr Leu Asp
            100                 105                 110

Tyr Trp Gly Gln Gly Thr Leu Val Thr Val Ser Ser
        115                 120
```

<210> SEQ ID NO 320
<211> LENGTH: 124
<212> TYPE: PRT
<213> ORGANISM: Artificial Sequence
<220> FEATURE:
<223> OTHER INFORMATION: Synthetic: SRP1848-B06, VH

```
<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
            20                  25                  30

Tyr Ile His Trp Val Arg Gln Ala Pro Gly Lys Gly Leu Glu Trp Val
        35                  40                  45

Gly Gly Ile Thr Pro Ile Asp Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Trp Ser Trp Pro Ser Gly Tyr Gly Tyr Tyr Gln Asp
            100                 105                 110

Tyr Trp Gly Gln Gly Thr Leu Val Thr Val Ser Ser
        115                 120

<210> SEQ ID NO 321
<211> LENGTH: 124
<212> TYPE: PRT
<213> ORGANISM: Artificial Sequence
<220> FEATURE:
<223> OTHER INFORMATION: Synthetic: SRP1848-B07, VH

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Arg Phe
            20                  25                  30

Tyr Ile His Trp Val Arg Gln Ala Pro Gly Lys Gly Leu Glu Trp Val
        35                  40                  45

Gly Gly Ile Ser Pro Tyr Asp Gly Phe Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ala Gly Tyr Gly Tyr Tyr Gln Asp
            100                 105                 110

Tyr Trp Gly Gln Gly Thr Leu Val Thr Val Ser Ser
        115                 120

<210> SEQ ID NO 322
<211> LENGTH: 124
<212> TYPE: PRT
<213> ORGANISM: Artificial Sequence
<220> FEATURE:
<223> OTHER INFORMATION: Synthetic: SRP1848-B09, VH

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Gly Gly Phe Asn Ile Thr Asn Tyr
            20                  25                  30

Tyr Ile His Trp Val Arg Gln Ala Pro Gly Lys Gly Leu Glu Trp Val
        35                  40                  45
```

Gly Gly Ile Thr Pro Val Asp Gly Tyr Thr Asp Tyr Ala Asp Arg Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ala Trp Ser Trp Arg Ser Gly Tyr Gly Tyr Tyr Met Asp
            100                 105                 110

Tyr Trp Gly Gln Gly Thr Leu Val Thr Val Ser Ser
            115                 120

<210> SEQ ID NO 323
<211> LENGTH: 124
<212> TYPE: PRT
<213> ORGANISM: Artificial Sequence
<220> FEATURE:
<223> OTHER INFORMATION: Synthetic: SRP1848-B10, VH

<400> SEQUENCE: 323

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Thr Thr Thr Lys
             20                  25                  30

Ser Ile His Trp Val Arg Gln Ala Pro Gly Lys Gly Leu Glu Trp Val
         35                  40                  45

Gly Glu Ile Tyr Pro Arg Asp Gly Ile Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Gly Trp His Trp Arg Ser Gly Tyr Ser Tyr Tyr Leu Asp
            100                 105                 110

Tyr Trp Gly Gln Gly Thr Leu Val Thr Val Ser Ser
            115                 120

<210> SEQ ID NO 324
<211> LENGTH: 124
<212> TYPE: PRT
<213> ORGANISM: Artificial Sequence
<220> FEATURE:
<223> OTHER INFORMATION: Synthetic: SRP1848-B11, VH

<400> SEQUENCE: 324

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Gly Asn Asn
             20                  25                  30

Ser Ile His Trp Val Arg Gln Ala Pro Gly Lys Gly Leu Glu Trp Val
         35                  40                  45

Gly Asp Ile Ser Pro Ile Asp Gly Phe Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ser Trp Ser Trp Arg Ala Gly Tyr Gly Tyr Tyr Leu Asp
            100                 105                 110

Tyr Trp Gly Gln Gly Thr Leu Val Thr Val Ser Ser
        115                 120

<210> SEQ ID NO 325
<211> LENGTH: 124
<212> TYPE: PRT
<213> ORGANISM: Artificial Sequence
<220> FEATURE:
<223> OTHER INFORMATION: Synthetic: SRP1848-C01, VH

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Asn Ser
            20                  25                  30

Tyr Ile His Trp Val Arg Gln Ala Pro Gly Lys Gly Leu Glu Trp Val
        35                  40                  45

Gly Gly Val Thr Pro Asn Asp Gly Tyr Thr Asp Tyr Ala Asp Ser Val
    50                  55                  60

Lys Gly Arg Phe Thr Ile Ser Ala Asp Thr Ser Lys Asn Thr Thr Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Phe Trp Arg Ala Gly Tyr Gly Tyr Tyr Leu Asp
            100                 105                 110

Tyr Trp Gly Gln Gly Ala Leu Val Thr Val Ser Ser
        115                 120

<210> SEQ ID NO 326
<211> LENGTH: 124
<212> TYPE: PRT
<213> ORGANISM: Artificial Sequence
<220> FEATURE:
<223> OTHER INFORMATION: Synthetic: SRP1848-C03, VH

<400> SEQUENCE: 326

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Val Tyr
            20                  25                  30

Ser Ile His Trp Val Arg Gln Ala Pro Gly Lys Gly Leu Glu Trp Val
        35                  40                  45

Gly Glu Ile Tyr Pro Ile Asp Gly Asn Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ala Trp Arg Ser Gly Tyr Ser Tyr Tyr Leu Asp
            100                 105                 110

Tyr Trp Gly Gln Gly Thr Leu Val Thr Val Ser Ser
        115                 120

<210> SEQ ID NO 327
<211> LENGTH: 124
<212> TYPE: PRT
<213> ORGANISM: Artificial Sequence
<220> FEATURE:
<223> OTHER INFORMATION: Synthetic: SRP1848-C04, VH

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg His Tyr
            20                  25                  30

Ser Ile His Trp Val Arg Gln Ala Pro Gly Lys Gly Leu Glu Trp Val
        35                  40                  45

Gly Glu Ile Tyr Pro Gly Pro Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Ser Trp Arg Ala Gly Tyr Gly Tyr Tyr Leu Asp
            100                 105                 110

Tyr Trp Gly Gln Gly Thr Leu Val Thr Val Ser Ser
        115                 120

<210> SEQ ID NO 328
<211> LENGTH: 124
<212> TYPE: PRT
<213> ORGANISM: Artificial Sequence
<220> FEATURE:
<223> OTHER INFORMATION: Synthetic: SRP1848-C05, VH

<400> SEQUENCE: 328

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Lys Tyr
            20                  25                  30

Ser Ile His Trp Val Arg Gln Ala Pro Gly Lys Gly Leu Glu Trp Val
        35                  40                  45

Gly Asp Ile Phe Pro Ile Asp Gly Ile Asn Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Lys Ala Gly Tyr Gly Tyr Tyr Leu Asp
            100                 105                 110

Tyr Trp Gly Gln Gly Thr Leu Val Thr Val Ser Ser
        115                 120

<210> SEQ ID NO 329
<211> LENGTH: 124
<212> TYPE: PRT
<213> ORGANISM: Artificial Sequence
<220> FEATURE:
<223> OTHER INFORMATION: Synthetic: SRP1848-C07, VH

<400> SEQUENCE: 329

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Lys Tyr
            20                  25                  30

Ser Ile His Trp Val Arg Gln Ala Pro Gly Lys Gly Leu Glu Trp Val
        35                  40                  45

```
Gly Asp Ile Phe Pro Ile Asp Gly Ile Thr Asp Tyr Ala Asp Ser Met
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ala Gly Tyr Gly Tyr Tyr Gln Asp
                100                 105                 110

Tyr Trp Gly Gln Gly Thr Leu Val Thr Val Ser Ser
            115                 120

<210> SEQ ID NO 330
<211> LENGTH: 124
<212> TYPE: PRT
<213> ORGANISM: Artificial Sequence
<220> FEATURE:
<223> OTHER INFORMATION: Synthetic: SRP1848-C10, VH

<400> SEQUENCE: 330

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Arg Thr Tyr
                20                  25                  30

Tyr Ile His Trp Val Arg Gln Ala Pro Gly Lys Gly Leu Glu Trp Val
            35                  40                  45

Gly Gly Ile Ser Pro Ile Asp Gly Tyr Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ala Gly Tyr Gly Tyr Tyr Leu Asp
                100                 105                 110

Tyr Trp Gly Gln Gly Thr Leu Val Thr Val Ser Ser
            115                 120

<210> SEQ ID NO 331
<211> LENGTH: 124
<212> TYPE: PRT
<213> ORGANISM: Artificial Sequence
<220> FEATURE:
<223> OTHER INFORMATION: Synthetic: SRP1848-D02, VH

<400> SEQUENCE: 331

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser His Asn
                20                  25                  30

Tyr Ile His Trp Val Arg Gln Ala Pro Gly Lys Gly Leu Glu Trp Val
            35                  40                  45

Gly Gly Ile Thr Pro Gln Asp Gly Tyr Thr Asp Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Arg Leu Arg Ala Glu Asp Thr Ala Val Tyr Tyr Cys
                85                  90                  95

Ala Arg Gly Ala Trp Ser Trp Arg Ala Gly Tyr Gly Tyr Tyr Leu Asp
```

100                 105                 110

Tyr Trp Gly Gln Gly Thr Leu Val Thr Val Ser Ser
        115                 120

<210> SEQ ID NO 332
<211> LENGTH: 124
<212> TYPE: PRT
<213> ORGANISM: Artificial Sequence
<220> FEATURE:
<223> OTHER INFORMATION: Synthetic: SRP1848-D03, VH

<400> SEQUENCE: 332

Glu Val Gln Leu Val Glu Ser Gly Gly Val Val Gln Pro Gly Gly
1               5                   10                  15

Ser Leu Arg Leu Ser Cys Ala Ala Ser Gly Phe Asn Ile Arg Tyr Phe
            20                  25                  30

Ser Ile His Trp Val Arg Gln Ala Pro Gly Lys Gly Leu Glu Trp Val
        35                  40                  45

Gly Asp Ile Phe Pro Asn Asp Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Thr Ala Val Tyr Tyr Cys
                85                  90                  95

Ala Arg Gly His Trp Ser Trp Pro Ser Gly Tyr Trp Tyr Tyr Leu Asp
            100                 105                 110

Tyr Trp Gly Gln Gly Thr Leu Val Thr Val Ser Ser
        115                 120

<210> SEQ ID NO 333
<211> LENGTH: 124
<212> TYPE: PRT
<213> ORGANISM: Artificial Sequence
<220> FEATURE:
<223> OTHER INFORMATION: Synthetic: SRP1848-D04, VH

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser His Tyr
            20                  25                  30

Ser Ile His Trp Val Arg Gln Ala Pro Gly Lys Gly Leu Glu Trp Val
        35                  40                  45

Gly Glu Ile Tyr Pro Arg Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Ser Ala Glu Asp Thr Ala Val Tyr Tyr Cys
                85                  90                  95

Ala Arg Gly Tyr Trp Phe Trp Arg Ser Gly Tyr Gly Tyr Tyr Leu Asp
            100                 105                 110

Tyr Trp Gly Gln Gly Thr Leu Val Thr Val Ser Ser
        115                 120

<210> SEQ ID NO 334
<211> LENGTH: 124
<212> TYPE: PRT
<213> ORGANISM: Artificial Sequence
<220> FEATURE:

<223> OTHER INFORMATION: Synthetic: SRP1848-D05, VH

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ile Ser
            20                  25                  30

Tyr Ile His Trp Val Arg Gln Ala Pro Gly Lys Gly Leu Glu Trp Val
        35                  40                  45

Gly Gly Ile Ser Pro Ile Asp Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Arg Ala Gly Tyr Gly Tyr Tyr Leu Asp
            100                 105                 110

Tyr Trp Gly Gln Gly Thr Leu Val Thr Val Ser Ser
        115                 120

<210> SEQ ID NO 335
<211> LENGTH: 124
<212> TYPE: PRT
<213> ORGANISM: Artificial Sequence
<220> FEATURE:
<223> OTHER INFORMATION: Synthetic: SRP1848-D07, VH

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Lys Tyr
            20                  25                  30

Tyr Ile His Trp Val Arg Gln Ala Pro Gly Lys Gly Leu Glu Trp Val
        35                  40                  45

Gly Gly Ile Ser Pro Asn Asp Gly Tyr Thr Asp Tyr Ala Asp Ser Val
    50                  55                  60

Lys Gly Arg Phe Ala Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Trp Ala Trp Arg Ser Gly Tyr Gly Tyr Tyr Leu Asp
            100                 105                 110

Tyr Trp Gly Gln Gly Thr Leu Val Thr Val Ser Ser
        115                 120

<210> SEQ ID NO 336
<211> LENGTH: 124
<212> TYPE: PRT
<213> ORGANISM: Artificial Sequence
<220> FEATURE:
<223> OTHER INFORMATION: Synthetic: SRP1848-D09, VH

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
            20                  25                  30

Tyr Ile His Trp Val Arg Gln Ala Pro Gly Lys Gly Leu Glu Trp Val

```
                35                  40                  45
Gly Gly Ile Ser Pro Asn Asp Gly Tyr Thr Asp Tyr Ala Asp Ser Val
     50                   55                  60

Lys Gly Arg Phe Thr Ile Ser Ala Asp Thr Ser Lys Asn Thr Ala Tyr
 65                   70                  75                  80

Leu Gln Met Asn Ser Leu Arg Ala Glu Asp Thr Ala Val Tyr Tyr Cys
                 85                  90                  95

Ala Arg Gly Ser Trp Ser Trp Arg His Gly Tyr Gly Tyr Tyr Leu Asp
             100                 105                 110

Tyr Trp Gly Gln Gly Thr Leu Val Thr Val Ser Ser
        115                 120

<210> SEQ ID NO 337
<211> LENGTH: 124
<212> TYPE: PRT
<213> ORGANISM: Artificial Sequence
<220> FEATURE:
<223> OTHER INFORMATION: Synthetic: SRP1848-D10, VH

<400> SEQUENCE: 337

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Ser Arg Asn
             20                  25                  30

Ser Ile His Trp Val Arg Gln Ala Pro Gly Lys Gly Leu Glu Trp Val
         35                  40                  45

Gly Trp Ile Ser Pro Asn Asp Gly Thr Thr Asp Tyr Ala Asp Ser Val
     50                  55                  60

Lys Gly Arg Phe Thr Ile Ser Ala Asp Gly Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ala Trp Ser Trp Arg Ser Gly Tyr Gly Tyr Tyr Ile Asp
             100                 105                 110

Tyr Trp Gly Gln Gly Thr Leu Val Thr Val Ser Ser
        115                 120

<210> SEQ ID NO 338
<211> LENGTH: 124
<212> TYPE: PRT
<213> ORGANISM: Artificial Sequence
<220> FEATURE:
<223> OTHER INFORMATION: Synthetic: SRP1848-E01, VH

<400> SEQUENCE: 338

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Thr Asn Lys
             20                  25                  30

Tyr Ile His Trp Val Arg Gln Ala Pro Gly Lys Gly Leu Glu Trp Val
         35                  40                  45

Gly Gly Ile Thr Pro Phe Asp Gly Phe Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95
```

Ala Arg Gly Ser Trp Ser Trp Pro Ala Gly Tyr Gly Tyr Tyr Gln Asp
            100                 105                 110

Tyr Trp Gly Gln Gly Thr Leu Val Thr Val Ser Ser
            115                 120

<210> SEQ ID NO 339
<211> LENGTH: 124
<212> TYPE: PRT
<213> ORGANISM: Artificial Sequence
<220> FEATURE:
<223> OTHER INFORMATION: Synthetic: SRP1848-E02, VH

<400> SEQUENCE: 339

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Gly Lys Tyr
            20                  25                  30

Ser Ile His Trp Val Arg Gln Ala Pro Gly Lys Gly Leu Glu Trp Val
        35                  40                  45

Gly Glu Ile Tyr Pro Asn Asp Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Arg Ser Gly Tyr Gly Tyr Tyr Leu Asp
            100                 105                 110

Tyr Trp Gly Gln Gly Thr Leu Val Thr Val Ser Ser
            115                 120

<210> SEQ ID NO 340
<211> LENGTH: 124
<212> TYPE: PRT
<213> ORGANISM: Artificial Sequence
<220> FEATURE:
<223> OTHER INFORMATION: Synthetic: SRP1848-E03, VH

<400> SEQUENCE: 340

Glu Val Gln Leu Val Glu Ser Gly Gly Gly Leu Ala Gln Pro Gly Gly
1               5                   10                  15

Ser Leu Arg Leu Ser Cys Ala Ala Ser Gly Phe Asn Ile Gly Asn Tyr
            20                  25                  30

Tyr Ile His Trp Val Arg Gln Ala Pro Gly Lys Gly Leu Glu Trp Val
        35                  40                  45

Gly Gly Ile Thr Pro Arg Asp Gly Phe Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Val Asn Ser Leu Arg Ala Glu Asp Thr Ala Val Tyr Tyr Cys
                85                  90                  95

Ala Arg Gly Ser Trp Ser Trp Pro Ala Gly His Ser Tyr Tyr Leu Asp
            100                 105                 110

Tyr Trp Gly Gln Gly Thr Leu Val Thr Val Ser Ser
            115                 120

<210> SEQ ID NO 341
<211> LENGTH: 124
<212> TYPE: PRT
<213> ORGANISM: Artificial Sequence

```
<220> FEATURE:
<223> OTHER INFORMATION: Synthetic: SRP1848-E05, VH

<400> SEQUENCE: 341
```

| Glu | Val | Gln | Leu | Val | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Leu Arg Val Ser Cys Ala Ala Ser Gly Phe Asn Ile Gly Val Tyr
            20                  25                  30

Tyr Ile His Trp Val Arg Gln Ala Pro Gly Lys Gly Leu Glu Trp Val
            35                  40                  45

Gly Gly Ile Thr Pro Asn Asp Gly Tyr Thr Asp Tyr Ala Asp Ser Val
50                      55                  60

Lys Gly Arg Phe Thr Ile Ser Ala Asp Thr Ser Lys Asn Thr Ala Tyr
65                      70                  75                  80

Leu Gln Met Asn Ser Leu Arg Ala Glu Asp Thr Ala Val Tyr Tyr Cys
            85                  90                  95

Ala Arg Gly Phe Trp Ala Trp Arg Ser Gly Tyr Gly Tyr Tyr Leu Asp
            100                 105                 110

Tyr Trp Gly Gln Gly Thr Leu Val Thr Val Ser Ser
        115                 120

```
<210> SEQ ID NO 342
<211> LENGTH: 124
<212> TYPE: PRT
<213> ORGANISM: Artificial Sequence
<220> FEATURE:
<223> OTHER INFORMATION: Synthetic: SRP1848-E06, VH

<400> SEQUENCE: 342
```

Glu Val Gln Leu Val Glu Ser Gly Gly Gly Leu Val Gln Pro Ser Gly
1               5                   10                  15

Ser Leu Arg Leu Ser Cys Ala Ala Ser Gly Phe Asn Ile Asn Arg Tyr
            20                  25                  30

Tyr Ile His Trp Val Arg Gln Ala Pro Gly Lys Gly Leu Glu Trp Val
            35                  40                  45

Gly Gly Ile Thr Pro Asn Asp Gly Tyr Thr Asp Tyr Ala Asp Ser Val
50                      55                  60

Glu Gly Arg Phe Thr Thr Ser Ala Asp Thr Ser Lys Asn Thr Ala Tyr
65                      70                  75                  80

Leu Gln Met Asn Ser Leu Arg Ala Glu Asp Thr Ala Val Tyr Tyr Cys
            85                  90                  95

Ala Arg Gly Thr Trp Ser Trp Pro Ser Gly His Ser Tyr Tyr Leu Asp
            100                 105                 110

Tyr Trp Gly Gln Gly Thr Leu Val Thr Val Ser Ser
        115                 120

```
<210> SEQ ID NO 343
<211> LENGTH: 124
<212> TYPE: PRT
<213> ORGANISM: Artificial Sequence
<220> FEATURE:
<223> OTHER INFORMATION: Synthetic: SRP1848-E07, VH

<400> SEQUENCE: 343
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Lys Ser
            20                  25                  30

```
Ser Ile His Trp Val Arg Gln Ala Pro Gly Lys Gly Leu Glu Trp Val
        35                  40                  45

Gly Glu Ile Phe Pro Tyr Asp Gly Ser Thr Asp Tyr Ala Asp Asn Val
 50                  55                  60

Lys Gly Arg Phe Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                 85                  90                  95

Ala Arg Gly Ala Trp Ser Trp Arg Ser Gly Tyr Gly Tyr Ile Asp
            100                 105                 110

Tyr Trp Gly Gln Gly Thr Leu Val Thr Val Ser Ser
        115                 120
```

<210> SEQ ID NO 344
<211> LENGTH: 124
<212> TYPE: PRT
<213> ORGANISM: Artificial Sequence
<220> FEATURE:
<223> OTHER INFORMATION: Synthetic: SRP1848-F01, VH

<400> SEQUENCE: 344

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Tyr
            20                  25                  30

Ser Ile His Trp Val Arg Gln Ala Pro Gly Lys Gly Leu Glu Trp Val
        35                  40                  45

Gly Ser Ile Phe Pro Asn Asp Gly Thr Thr Asp Tyr Ala Asp Ser Val
 50                  55                  60

Lys Gly Arg Phe Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                 85                  90                  95

Ala Arg Gly Ser Trp Ala Trp Arg Ala Gly Tyr Ser Tyr Tyr Leu Asp
            100                 105                 110

Tyr Trp Gly Gln Gly Thr Leu Val Thr Val Ser Ser
        115                 120
```

<210> SEQ ID NO 345
<211> LENGTH: 124
<212> TYPE: PRT
<213> ORGANISM: Artificial Sequence
<220> FEATURE:
<223> OTHER INFORMATION: Synthetic: SRP1848-F02, VH

<400> SEQUENCE: 345

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Tyr
            20                  25                  30

Ser Ile His Trp Val Arg Gln Ala Pro Gly Lys Gly Leu Glu Trp Val
        35                  40                  45

Gly Ser Ile Phe Pro Asn Asp Gly Thr Thr Asp Tyr Ala Asp Ser Val
 50                  55                  60

Lys Gly Arg Leu Thr Ile Ser Ala Asp Thr Ser Lys Asn Thr Ala Tyr
65                   70                  75                  80

Leu Gln Met Asn Ser Leu Arg Ala Glu Asp Thr Ala Val Tyr Tyr Cys
                 85                  90                  95
```

-continued

```
Ala Arg Gly Ser Trp Ser Trp Gln Ala Gly Tyr Gly Tyr Tyr Leu Asp
            100                 105                 110

Tyr Trp Gly Gln Gly Thr Leu Val Thr Val Ser Ser
        115                 120

<210> SEQ ID NO 346
<211> LENGTH: 124
<212> TYPE: PRT
<213> ORGANISM: Artificial Sequence
<220> FEATURE:
<223> OTHER INFORMATION: Synthetic: SRP1848-F04, VH

<400> SEQUENCE: 346

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Tyr
            20                  25                  30

Ser Ile His Trp Val Arg Gln Ala Pro Gly Lys Gly Leu Glu Trp Val
        35                  40                  45

Gly Glu Ile Tyr Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Phe Trp Arg Ser Gly Tyr Gly Tyr Tyr Leu Asp
            100                 105                 110

Tyr Trp Gly Gln Gly Thr Leu Val Thr Val Ser Ser
        115                 120

<210> SEQ ID NO 347
<211> LENGTH: 124
<212> TYPE: PRT
<213> ORGANISM: Artificial Sequence
<220> FEATURE:
<223> OTHER INFORMATION: Synthetic: SRP1848-F05, VH

<400> SEQUENCE: 347

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Lys Ser
            20                  25                  30

Ser Ile His Trp Val Arg Gln Ala Pro Gly Lys Gly Leu Glu Trp Val
        35                  40                  45

Gly Glu Ile Tyr Pro Asn Asp Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ala Trp Arg Ser Gly Tyr Ser Tyr Phe Leu Asp
            100                 105                 110

Tyr Trp Gly Gln Gly Thr Leu Val Thr Val Ser Ser
        115                 120

<210> SEQ ID NO 348
<211> LENGTH: 124
<212> TYPE: PRT
```

<213> ORGANISM: Artificial Sequence
<220> FEATURE:
<223> OTHER INFORMATION: Synthetic: SRP1848-F06, VH

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Leu Ser
            20                  25                  30

Tyr Ile His Trp Val Arg Gln Ala Pro Gly Lys Gly Leu Glu Trp Val
        35                  40                  45

Gly Gly Ile Ser Pro Ile Asp Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Trp Ala Trp Arg Ser Gly Tyr Gly Tyr Tyr Leu Asp
            100                 105                 110

Tyr Trp Gly Gln Gly Thr Leu Val Thr Val Ser Ser
        115                 120

<210> SEQ ID NO 349
<211> LENGTH: 124
<212> TYPE: PRT
<213> ORGANISM: Artificial Sequence
<220> FEATURE:
<223> OTHER INFORMATION: Synthetic: SRP1848-F07, VH

<400> SEQUENCE: 349

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn His
            20                  25                  30

Ser Ile His Trp Val Arg Gln Ala Pro Gly Lys Gly Leu Glu Trp Val
        35                  40                  45

Gly Glu Ile Tyr Pro Asn Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Ser Ala Glu Asp Thr Ala Val Tyr Tyr Cys
                85                  90                  95

Ala Arg Gly Ser Trp Asp Trp Arg Ser Gly Tyr Ser Tyr Tyr Leu Asp
            100                 105                 110

Tyr Trp Gly Gln Gly Thr Leu Val Thr Val Ser Ser
        115                 120

<210> SEQ ID NO 350
<211> LENGTH: 124
<212> TYPE: PRT
<213> ORGANISM: Artificial Sequence
<220> FEATURE:
<223> OTHER INFORMATION: Synthetic: SRP1848-F08, VH

<400> SEQUENCE: 350

Glu Val Gln Leu Val Glu Ser Gly Gly Gly Leu Val Gln Pro Gly Gly
1               5                   10                  15

Ser Leu Arg Leu Ser Cys Ala Ala Gly Gly Phe Asn Ile Ser Asn His
            20                  25                  30

Ser Ile His Trp Val Arg Gln Ala Pro Gly Lys Gly Val Glu Trp Val
        35                  40                  45

Gly Glu Ile Tyr Pro Val Asp Gly Ile Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Arg Met Asn Ser Leu Arg Ala Glu Asp Thr Ala Val Tyr Tyr Cys
                85                  90                  95

Ala Arg Gly Ser Trp Tyr Trp Gln Ser Gly Tyr Ser Tyr Tyr Leu Asp
                100                 105                 110

Tyr Trp Gly Gln Gly Thr Leu Val Thr Val Ser Ser
                115                 120

<210> SEQ ID NO 351
<211> LENGTH: 124
<212> TYPE: PRT
<213> ORGANISM: Artificial Sequence
<220> FEATURE:
<223> OTHER INFORMATION: Synthetic: SRP1848-F09, VH

<400> SEQUENCE: 351

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn His
            20                  25                  30

Tyr Ile His Trp Val Arg Gln Ala Pro Gly Lys Gly Leu Glu Trp Val
        35                  40                  45

Gly Gly Ile Ser Pro Leu Asp Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Trp Ser Trp Arg Ser Gly Tyr Gly Tyr Tyr Ile Asp
                100                 105                 110

Tyr Trp Gly Gln Gly Thr Leu Val Thr Val Ser Ser
                115                 120

<210> SEQ ID NO 352
<211> LENGTH: 124
<212> TYPE: PRT
<213> ORGANISM: Artificial Sequence
<220> FEATURE:
<223> OTHER INFORMATION: Synthetic: SRP1848-F10, VH

<400> SEQUENCE: 352

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Asn
            20                  25                  30

Ser Ile His Trp Val Arg Gln Ala Pro Gly Lys Gly Leu Glu Trp Val
        35                  40                  45

Gly Ser Ile Phe Pro Asn Asp Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                        85                  90                  95

Ala Arg Gly Ser Trp Phe Trp Arg Ser Gly Tyr Gly Tyr Tyr Leu Asp
                100                 105                 110

Tyr Trp Gly Gln Gly Thr Leu Val Thr Val Ser Ser
        115                 120

<210> SEQ ID NO 353
<211> LENGTH: 124
<212> TYPE: PRT
<213> ORGANISM: Artificial Sequence
<220> FEATURE:
<223> OTHER INFORMATION: Synthetic: SRP1848-F11, VH

<400> SEQUENCE: 353

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Asn Asn
            20                  25                  30

Tyr Ile His Trp Val Arg Gln Ala Pro Gly Lys Gly Leu Glu Trp Val
        35                  40                  45

Gly Gly Ile Thr Pro Ile Asp Gly Asn Thr Asp Tyr Ala Asp Ser Val
    50                  55                  60

Lys Gly Arg Phe Thr Ile Ser Ala Asp Thr Ser Met Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Tyr Trp Arg Ala Gly Tyr Gly Tyr Tyr Leu Asp
                100                 105                 110

Tyr Trp Gly Gln Gly Ala Leu Val Thr Val Ser Ser
        115                 120

<210> SEQ ID NO 354
<211> LENGTH: 124
<212> TYPE: PRT
<213> ORGANISM: Artificial Sequence
<220> FEATURE:
<223> OTHER INFORMATION: Synthetic: SRP1848-G01, VH

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Arg His
            20                  25                  30

Ser Ile His Trp Val Arg Gln Ala Pro Gly Lys Gly Leu Glu Trp Val
        35                  40                  45

Gly Trp Ile Ala Pro Asn Asp Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ala Trp Arg Ser Gly Tyr Ser Tyr Phe Leu Asp
                100                 105                 110

Tyr Trp Gly Gln Gly Thr Leu Val Thr Val Ser Ser
        115                 120

<210> SEQ ID NO 355
<211> LENGTH: 124
```

```
<212> TYPE: PRT
<213> ORGANISM: Artificial Sequence
<220> FEATURE:
<223> OTHER INFORMATION: Synthetic: SRP1848-G03, VH

<400> SEQUENCE: 355

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Thr Tyr
            20                  25                  30

Tyr Ile His Trp Val Arg Gln Ala Pro Gly Lys Gly Leu Glu Trp Val
        35                  40                  45

Gly Gly Ile Thr Pro Ser Asp Gly Phe Thr Asp Tyr Ala Asp Ser Val
    50                  55                  60

Lys Gly Arg Ser Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly His Gly Tyr Phe Leu Asp
            100                 105                 110

Tyr Trp Gly Gln Gly Thr Leu Val Thr Val Ser Ser
        115                 120

<210> SEQ ID NO 356
<211> LENGTH: 120
<212> TYPE: PRT
<213> ORGANISM: Artificial Sequence
<220> FEATURE:
<223> OTHER INFORMATION: Synthetic: SRP1848-G04, VH

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile His Ser Thr
            20                  25                  30

Asp Ile His Trp Val Arg Gln Ala Pro Gly Lys Gly Leu Glu Trp Val
        35                  40                  45

Ala Tyr Ile Thr Pro Ala Gly Gly Ala Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Trp Phe Ala Gly Tyr Met Asp Tyr Trp Gly Gln
            100                 105                 110

Gly Thr Leu Val Thr Val Ser Ser
        115                 120

<210> SEQ ID NO 357
<211> LENGTH: 120
<212> TYPE: PRT
<213> ORGANISM: Artificial Sequence
<220> FEATURE:
<223> OTHER INFORMATION: Synthetic: SRP1848-G06, VH

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Ser Thr
```

```
            20                  25                  30
Asp Ile His Trp Val Arg Gln Ala Pro Gly Lys Gly Leu Glu Trp Val
        35                  40                  45

Ala Tyr Ile Thr Pro Ala Gly Gly Ala Thr Tyr Tyr Ala Asp Asn Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Pro Tyr Trp Phe Ala Gly Tyr Met Asp Tyr Trp Gly Gln
            100                 105                 110

Gly Thr Leu Val Thr Val Ser Ser
        115                 120

<210> SEQ ID NO 358
<211> LENGTH: 120
<212> TYPE: PRT
<213> ORGANISM: Artificial Sequence
<220> FEATURE:
<223> OTHER INFORMATION: Synthetic: SRP1848-G07, VH

<400> SEQUENCE: 358

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile His Ser Thr
            20                  25                  30

Asp Ile His Trp Val Arg Gln Ala Pro Gly Lys Gly Leu Glu Trp Val
        35                  40                  45

Ala Tyr Ile Thr Pro Ala Gly Gly Ala Thr Trp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Phe Trp Phe Ala Gly Tyr Met Asp Tyr Trp Gly Gln
            100                 105                 110

Gly Thr Leu Val Thr Val Ser Ser
        115                 120

<210> SEQ ID NO 359
<211> LENGTH: 120
<212> TYPE: PRT
<213> ORGANISM: Artificial Sequence
<220> FEATURE:
<223> OTHER INFORMATION: Synthetic: SRP1848-G09, VH

<400> SEQUENCE: 359

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Gly Thr
            20                  25                  30

Asp Ile His Trp Val Arg Gln Ala Pro Gly Lys Gly Leu Glu Trp Val
        35                  40                  45

Ala Tyr Ile Thr Pro Ala Gly Gly Ala Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg His Glu Tyr Trp Phe Ser Gly Tyr Met Asp Tyr Trp Gly Gln
            100                 105                 110

Gly Thr Leu Val Thr Val Ser Ser
        115                 120

<210> SEQ ID NO 360
<211> LENGTH: 120
<212> TYPE: PRT
<213> ORGANISM: Artificial Sequence
<220> FEATURE:
<223> OTHER INFORMATION: Synthetic: SRP1848-G10, VH

<400> SEQUENCE: 360

Glu Val Gln Leu Val Glu Ser Gly Gly Gly Leu Val Gln Pro Gly Ser
1               5                   10                  15

Ser Leu Arg Leu Ser Cys Ala Ala Ser Gly Phe Asn Ile Arg Ser Thr
            20                  25                  30

Asp Ile His Trp Val Arg Gln Ala Pro Gly Lys Gly Leu Glu Trp Val
        35                  40                  45

Ala Tyr Ile Thr Pro Ala Gly Gly Ala Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Trp Phe Ala Gly Tyr Ile Asp Tyr Trp Gly Gln
            100                 105                 110

Gly Thr Leu Val Thr Val Ser Ser
        115                 120

<210> SEQ ID NO 361
<211> LENGTH: 120
<212> TYPE: PRT
<213> ORGANISM: Artificial Sequence
<220> FEATURE:
<223> OTHER INFORMATION: Synthetic: SRP1848-G11, VH

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Thr
            20                  25                  30

Asp Ile His Trp Val Arg Gln Ala Pro Gly Lys Gly Leu Glu Trp Val
        35                  40                  45

Ala Tyr Ile Thr Pro Ala Gly Gly Ala Thr Trp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Trp Phe Ser Gly Tyr Met Asp Tyr Trp Gly Gln
            100                 105                 110

Gly Thr Leu Val Thr Val Ser Ser
        115                 120

<210> SEQ ID NO 362
```

```
<211> LENGTH: 124
<212> TYPE: PRT
<213> ORGANISM: Artificial Sequence
<220> FEATURE:
<223> OTHER INFORMATION: Synthetic: SRP1848-H01, VH

<400> SEQUENCE: 362

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Thr Gln
            20                  25                  30

Ser Ile His Trp Val Arg Gln Ala Pro Gly Lys Gly Leu Glu Trp Ile
        35                  40                  45

Gly Asp Ile Phe Pro Ile Asp Gly Ile Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Trp Ser Trp Pro Ser Gly Met Asp Tyr Tyr Leu Asp
            100                 105                 110

Tyr Trp Gly Gln Gly Thr Leu Val Thr Val Ser Ser
        115                 120

<210> SEQ ID NO 363
<211> LENGTH: 126
<212> TYPE: PRT
<213> ORGANISM: Artificial Sequence
<220> FEATURE:
<223> OTHER INFORMATION: Synthetic: SRP2060-E10, VH

<400> SEQUENCE: 363

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Ser Leu Ser Thr Phe
            20                  25                  30

Gly Met Gly Val Gly Trp Val Arg Gln Ala Pro Gly Lys Gly Leu Glu
        35                  40                  45

Trp Val Ser His Ile Trp Trp Asp Asp Lys Tyr Tyr His Pro Ala
    50                  55                  60

Leu Lys Gly Arg Phe Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Gly Arg Asn His Phe Pro His Tyr Tyr Gly Ser Ser His Trp Tyr
            100                 105                 110

Phe Asn Val Trp Gly Gln Gly Thr Thr Val Thr Val Ser Ser
        115                 120                 125

<210> SEQ ID NO 364
<211> LENGTH: 126
<212> TYPE: PRT
<213> ORGANISM: Artificial Sequence
<220> FEATURE:
<223> OTHER INFORMATION: Synthetic: SRP2060-E05, VH

<400> SEQUENCE: 364

Glu Val Gln Leu Leu Glu Ser Gly Gly Gly Leu Val Gln Pro Gly Gly
1               5                   10                  15
```

Ser Leu Arg Leu Ser Cys Ala Phe Ser Gly Phe Ser Leu Ser Thr Phe
            20                  25                  30

Gly Met Gly Val Gly Trp Val Arg Gln Ala Pro Gly Lys Gly Leu Glu
            35                  40                  45

Trp Val Ser His Ile Trp Trp Asp Asp Lys Tyr Tyr His Pro Ala
    50                  55                  60

Leu Lys Gly Arg Phe Thr Val Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Gly Arg Asn His Phe Pro His Tyr Tyr Gly Ser Ser His Trp Tyr
            100                 105                 110

Phe Asn Val Trp Gly Gln Gly Thr Thr Val Thr Val Ser Ser
            115                 120                 125

<210> SEQ ID NO 365
<211> LENGTH: 126
<212> TYPE: PRT
<213> ORGANISM: Artificial Sequence
<220> FEATURE:
<223> OTHER INFORMATION: Synthetic: SRP2060-B01, VH

<400> SEQUENCE: 365

Glu Val Gln Leu Leu Glu Ser Gly Gly Gly Leu Val Gln Pro Gly Gly
1               5                   10                  15

Ser Leu Arg Leu Ser Cys Ala Leu Ser Gly Phe Ser Leu Ser Thr Phe
            20                  25                  30

Gly Met Gly Val Gly Trp Val Arg Gln Ala Thr Gly Lys Gly Leu Glu
            35                  40                  45

Trp Val Ser His Ile Trp Trp Asp Asp Lys Tyr Tyr His Pro Ala
    50                  55                  60

Leu Lys Gly Arg Phe Thr Ile Ser Lys Asp Asn Ser Lys Asn Thr Val
65                  70                  75                  80

His Leu Gln Met Asn Ser Leu Arg Ala Glu Asp Thr Ala Val Tyr Tyr
                85                  90                  95

Cys Gly Arg Asn His Phe Pro His Tyr Tyr Gly Ser Ser His Trp Tyr
            100                 105                 110

Phe Asn Val Trp Gly Gln Gly Thr Thr Val Thr Val Ser Ser
            115                 120                 125

<210> SEQ ID NO 366
<211> LENGTH: 126
<212> TYPE: PRT
<213> ORGANISM: Artificial Sequence
<220> FEATURE:
<223> OTHER INFORMATION: Synthetic: SRP2060-A06, VH

<400> SEQUENCE: 366

Glu Val Gln Leu Leu Glu Ser Gly Gly Gly Leu Val Gln Pro Gly Gly
1               5                   10                  15

Ser Leu Arg Leu Ser Cys Ala Phe Ser Gly Phe Ser Leu Ser Thr Phe
            20                  25                  30

Gly Met Gly Val Gly Trp Val Arg Gln Ala Pro Gly Lys Gly Leu Glu
            35                  40                  45

Trp Val Gly His Ile Trp Trp Asp Asp Lys Tyr Tyr Tyr Pro Ala
    50                  55                  60

Leu Lys Gly Arg Phe Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Gly Arg Asn His Phe Pro His Tyr Tyr Gly Ser Ser His Trp Tyr
            100                 105                 110

Phe Asp Val Trp Gly Gln Gly Thr Thr Val Thr Val Ser Ser
        115                 120                 125

<210> SEQ ID NO 367
<211> LENGTH: 107
<212> TYPE: PRT
<213> ORGANISM: Artificial Sequence
<220> FEATURE:
<223> OTHER INFORMATION: Synthetic: trastuzumab, VL

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 368
<211> LENGTH: 107
<212> TYPE: PRT
<213> ORGANISM: Artificial Sequence
<220> FEATURE:
<223> OTHER INFORMATION: Synthetic: H6D1-LC4, VL

<400> SEQUENCE: 368

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asp Ile Asn Ser Tyr
            20                  25                  30

Leu Ser Trp Tyr Gln Gln Lys Pro Gly Gln Ala Pro Arg Leu Leu Ile
        35                  40                  45

Tyr Arg Ala Asn Arg Leu Val Asp Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 369
<211> LENGTH: 107
<212> TYPE: PRT
<213> ORGANISM: Artificial Sequence
<220> FEATURE:
<223> OTHER INFORMATION: Synthetic: H6D1-LC5, VL

<400> SEQUENCE: 369

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 370
<211> LENGTH: 330
<212> TYPE: PRT
<213> ORGANISM: Homo sapiens
<220> FEATURE:
<221> NAME/KEY: misc_feature
<223> OTHER INFORMATION: Human IgG1 HC Constant

<400> SEQUENCE: 370

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

-continued

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 371
<211> LENGTH: 107
<212> TYPE: PRT
<213> ORGANISM: Homo sapiens
<220> FEATURE:
<221> NAME/KEY: misc_feature
<223> OTHER INFORMATION: Human IgG LC Constant Ckappa

<400> SEQUENCE: 371

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 372
<211> LENGTH: 323
<212> TYPE: PRT
<213> ORGANISM: Mus musculus
<220> FEATURE:
<221> NAME/KEY: misc_feature
<223> OTHER INFORMATION: Mouse IgG1 HC Constant

<400> SEQUENCE: 372

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95
```

```
Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
                115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
                210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
                290                 295                 300

Leu His Glu Gly Leu His Asn His His Thr Glu Lys Ser Leu Ser His
305                 310                 315                 320

Ser Pro Gly

<210> SEQ ID NO 373
<211> LENGTH: 107
<212> TYPE: PRT
<213> ORGANISM: Mus musculus
<220> FEATURE:
<221> NAME/KEY: misc_feature
<223> OTHER INFORMATION: Mouse IgG LC Constant Ckappa

<400> SEQUENCE: 373

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
                35                  40                  45

Gln Asn Gly Val Leu Asn Ser Trp Thr Asp Gln Asp Ser Lys Asp Ser
                50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

<210> SEQ ID NO 374
```

```
<211> LENGTH: 108
<212> TYPE: PRT
<213> ORGANISM: Artificial Sequence
<220> FEATURE:
<223> OTHER INFORMATION: Synthetic: Kappa LC

<400> SEQUENCE: 374

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 375
<211> LENGTH: 106
<212> TYPE: PRT
<213> ORGANISM: Artificial Sequence
<220> FEATURE:
<223> OTHER INFORMATION: Synthetic: Lambda LD

<400> SEQUENCE: 375

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 376
<211> LENGTH: 20
<212> TYPE: PRT
<213> ORGANISM: Artificial Sequence
<220> FEATURE:
<223> OTHER INFORMATION: Synthetic: FlagHis Tag

<400> SEQUENCE: 376

Gly Ser Gly Asp Tyr Lys Asp Asp Asp Lys Gly Ser Gly His His
1               5                   10                  15

His His His His
            20

<210> SEQ ID NO 377
<211> LENGTH: 15
```

```
<212> TYPE: PRT
<213> ORGANISM: Artificial Sequence
<220> FEATURE:
<223> OTHER INFORMATION: Synthetic: Linker

<400> SEQUENCE: 377

Gly Gly Gly Gly Ser Gly Gly Gly Gly Ser Gly Gly Gly Gly Ser
1               5                   10                  15

<210> SEQ ID NO 378
<211> LENGTH: 11
<212> TYPE: PRT
<213> ORGANISM: Artificial Sequence
<220> FEATURE:
<223> OTHER INFORMATION: Synthetic: Linker

<400> SEQUENCE: 378

Ala Ala Gly Ser Asp Gln Glu Pro Lys Ser Ser
1               5                   10

<210> SEQ ID NO 379
<211> LENGTH: 247
<212> TYPE: PRT
<213> ORGANISM: Artificial Sequence
<220> FEATURE:
<223> OTHER INFORMATION: Synthetic: 1848-B10-VH-(G4S)3-VL, scFv

<400> SEQUENCE: 379

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Thr Thr Thr
            20                  25                  30

Lys Ser Ile His Trp Val Arg Gln Ala Pro Gly Lys Gly Leu Glu Trp
        35                  40                  45

Val Gly Glu Ile Tyr Pro Arg Asp Gly Ile Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Gly Gly Trp His Trp Arg Ser Gly Tyr Ser Tyr Tyr Leu
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys
```

<210> SEQ ID NO 380
<211> LENGTH: 247
<212> TYPE: PRT
<213> ORGANISM: Artificial Sequence
<220> FEATURE:
<223> OTHER INFORMATION: Synthetic: 1848-B10-VL-(G4S)3-VH, scFv

<400> SEQUENCE: 380

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Thr Thr Lys Ser Ile His Trp Val
145                 150                 155                 160

Arg Gln Ala Pro Gly Lys Gly Leu Glu Trp Val Gly Ile Tyr Pro
                165                 170                 175

Arg Asp Gly Ile Thr Asp Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Gly Gly Trp
    210                 215                 220

His Trp Arg Ser Gly Tyr Ser Tyr Tyr Leu Asp Tyr Trp Gly Gln Gly
225                 230                 235                 240

Thr Leu Val Thr Val Ser Ser
                245
```

<210> SEQ ID NO 381
<211> LENGTH: 485
<212> TYPE: PRT
<213> ORGANISM: Artificial Sequence
<220> FEATURE:
<223> OTHER INFORMATION: Synthetic: 1848-B10-VH-(G4S)3-VL, scFv-Fc

<400> SEQUENCE: 381

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Thr Thr Thr
            20                  25                  30

Lys Ser Ile His Trp Val Arg Gln Ala Pro Gly Lys Gly Leu Glu Trp
        35                  40                  45
```

```
Val Gly Glu Ile Tyr Pro Arg Asp Gly Ile Thr Asp Tyr Ala Asp Ser
 50                  55                  60
Val Lys Gly Arg Phe Thr Ile Ser Ala Asp Thr Ser Lys Asn Thr Ala
 65                  70                  75                  80
Tyr Leu Gln Met Asn Ser Leu Arg Ala Glu Asp Thr Ala Val Tyr Tyr
                 85                  90                  95
Cys Ala Arg Gly Gly Trp His Trp Arg Ser Gly Tyr Ser Tyr Tyr Leu
            100                 105                 110
Asp Tyr Trp Gly Gln Gly Thr Leu Val Thr Val Ser Ser Gly Gly Gly
            115                 120                 125
Gly Ser Gly Gly Gly Gly Ser Gly Gly Gly Gly Ser Asp Ile Gln Met
        130                 135                 140
Thr Gln Ser Pro Ser Ser Leu Ser Ala Ser Val Gly Asp Arg Val Thr
145                 150                 155                 160
Ile Thr Cys Arg Ala Ser Gln Asp Val Asn Thr Ala Val Ala Trp Tyr
                165                 170                 175
Gln Gln Lys Pro Gly Lys Ala Pro Lys Leu Leu Ile Tyr Ser Ala Ser
            180                 185                 190
Phe Leu Tyr Ser Gly Val Pro Ser Arg Phe Ser Gly Ser Arg Ser Gly
            195                 200                 205
Thr Asp Phe Thr Leu Thr Ile Ser Ser Leu Gln Pro Glu Asp Phe Ala
        210                 215                 220
Thr Tyr Tyr Cys Gln Gln His Tyr Thr Thr Pro Pro Thr Phe Gly Gln
225                 230                 235                 240
Gly Thr Lys Val Glu Ile Lys Ala Ala Gly Ser Asp Gln Glu Pro Lys
                245                 250                 255
Ser Ser Asp Lys Thr His Thr Cys Pro Pro Cys Pro Ala Pro Glu Leu
            260                 265                 270
Leu Gly Gly Pro Ser Val Phe Leu Phe Pro Pro Lys Pro Lys Asp Thr
            275                 280                 285
Leu Met Ile Ser Arg Thr Pro Glu Val Thr Cys Val Val Val Asp Val
        290                 295                 300
Ser His Glu Asp Pro Glu Val Lys Phe Asn Trp Tyr Val Asp Gly Val
305                 310                 315                 320
Glu Val His Asn Ala Lys Thr Lys Pro Arg Glu Glu Gln Tyr Asn Ser
                325                 330                 335
Thr Tyr Arg Val Val Ser Val Leu Thr Val Leu His Gln Asp Trp Leu
            340                 345                 350
Asn Gly Lys Glu Tyr Lys Cys Lys Val Ser Asn Lys Ala Leu Pro Ala
            355                 360                 365
Pro Ile Glu Lys Thr Ile Ser Lys Ala Lys Gly Gln Pro Arg Glu Pro
        370                 375                 380
Gln Val Tyr Thr Leu Pro Pro Ser Arg Glu Glu Met Thr Lys Asn Gln
385                 390                 395                 400
Val Ser Leu Thr Cys Leu Val Lys Gly Phe Tyr Pro Ser Asp Ile Ala
                405                 410                 415
Val Glu Trp Glu Ser Asn Gly Gln Pro Glu Asn Asn Tyr Lys Thr Thr
            420                 425                 430
Pro Pro Val Leu Asp Ser Asp Gly Ser Phe Phe Leu Tyr Ser Lys Leu
            435                 440                 445
Thr Val Asp Lys Ser Arg Trp Gln Gln Gly Asn Val Phe Ser Cys Ser
        450                 455                 460
Val Met His Glu Ala Leu His Asn His Tyr Thr Gln Lys Ser Leu Ser
```

Leu Ser Pro Gly Lys
            485

<210> SEQ ID NO 382
<211> LENGTH: 485
<212> TYPE: PRT
<213> ORGANISM: Artificial Sequence
<220> FEATURE:
<223> OTHER INFORMATION: Synthetic: 1848-B10-VL-(G4S)3-VH, scFv-Fc

<400> SEQUENCE: 382

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Thr Thr Thr Lys Ser Ile His Trp Val
145                 150                 155                 160

Arg Gln Ala Pro Gly Lys Gly Leu Glu Trp Val Gly Glu Ile Tyr Pro
                165                 170                 175

Arg Asp Gly Ile Thr Asp Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Gly Gly Trp
    210                 215                 220

His Trp Arg Ser Gly Tyr Ser Tyr Tyr Leu Asp Tyr Trp Gly Gln Gly
225                 230                 235                 240

Thr Leu Val Thr Val Ser Ser Ala Ala Gly Ser Asp Gln Glu Pro Lys
                245                 250                 255

Ser Ser Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu

-continued

```
                340                 345                 350
Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
        370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
                420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
        450                 455                 460

Val Met His Glu Ala Leu His Asn His Tyr Thr Gln Lys Ser Leu Ser
465                 470                 475                 480

Leu Ser Pro Gly Lys
                485
```

ANTI-FOLATE RECEPTOR ANTIBODY CONJUGATES, COMPOSITIONS COMPRISING ANTI-FOLATE RECEPTOR ANTIBODY CONJUGATES, AND METHODS OF MAKING AND USING ANTI-FOLATE RECEPTOR ANTIBODY CONJUGATES

CROSS-REFERENCE TO RELATED APPLICATION

This application claims the benefit of U.S. Provisional Patent Application No. 62/560,064, filed Sep. 18, 2017, which is incorporated herein by reference in its entirety.

FIELD OF THE INVENTION

Provided herein are antibody conjugates with binding specificity for folate receptor alpha (FolRα or FOLR1) and compositions comprising the antibody conjugates, including pharmaceutical compositions, methods of producing the conjugates, and methods of using the conjugates and compositions for therapy. The conjugates and compositions are useful in methods of treatment and prevention of cell proliferation and cancer, methods of detection of cell proliferation and cancer, and methods of diagnosis of cell proliferation and cancer. The conjugates and compositions are also useful in methods of treatment, prevention, detection, and diagnosis of autoimmune diseases, infectious diseases, and inflammatory conditions.

BACKGROUND

Folate receptors, or folate binding proteins (FBPs), include single chain glycoproteins that bind and contribute to the update of folates and other compounds in vivo. Elwood, 1989, *J. Biol. Chem.* 264:14893-14901. Certain folate receptors are single-chain glycoproteins with a high affinity binding site for folate and other compounds such as methotrexate. Elwood, p. 14893. The human FOLR1 gene encodes the adult folate receptor, a 30 kDa polypeptide with about 257 amino acids with three potential N-linked glycosylation sites. Elwood, p. 14893; Lacey et al., 1989, *J. Clin. Invest.* 84:715-720. Homologous genes and polypeptides have been identified in dozens of species.

The mature folate receptor glycoprotein has a size of about 42 kDa and has been observed to participate in the internalization of folates and antifolates into cells. Elwood et al., 1997, *Biochemistry* 36:1467-1478. Expression has been observed in human cerebellum and kidney cells, along with human cancer cell lines. Elwood et al., 1997, p. 1467. In addition to internalization of folate, a folate receptor has been shown to be a significant cofactor for cellular entry of viruses, particularly Marburg and Ebola viruses. Chan et al., 2001, *Cell* 106:117-126. Due to these internalization properties, the folate receptor has been proposed as a target for diagnostic and therapeutic agents. For instance, diagnostic and therapeutic agents have been linked to folate for internalization into cells expressing the folate receptor. See, e.g., Leamon, 2008, *Curr. Opin. Investig. Drugs* 9:1277-1286; Paulos et al., 2004, *Adv. Drug Del. Rev.* 56:1205-1217.

Folate receptor alpha (FolRα or FOLR1) is a glycosylphosphatidylinositol linked cell-surface glycoprotein that has high affinity for folates. Except for low levels in kidney and lung, most normal tissues do not express FOLR1, but high levels of FOLR1 have been found in serous and endometrioid epithelial ovarian cancer, endometrial adenocarcinoma, non-small cell lung carcinoma (NSCLC) of the adenocarcinoma subtype, and triple-negative breast cancer (TNBC). FOLR1 expression is maintained in metastatic foci and recurrent carcinomas in ovarian cancer patients, and FOLR1 expression has been observed after chemotherapy in epithelial ovarian and endometrial cancers. These properties, together with the highly restricted expression of FOLR1 on normal tissues, make FOLR1 a highly promising target for cancer therapy. As such, the folate receptor provides a potential target for diagnostics and therapeutics for cancers and inflammatory conditions. New antibodies are needed for specific binding and targeting of these folate receptors.

There is a need for improved methods of modulating the immune regulation of folate receptor alpha (FOLR1) and the downstream signaling processes activated by folate receptor alpha (FOLR1). Moreover, given the specific expression of folate receptor alpha (FOLR1) in cancer- and carcinoma-transformed cells and lower expression in non-cancer tissue, there is a need for improved therapeutics that can specifically target cells and tissues that overexpress folate receptor alpha (FOLR1). Antibody conjugates to FOLR1 could be used to deliver therapeutic or diagnostic payload moieties to target cells expressing folate receptor alpha for the treatment or diagnosis of such diseases.

SUMMARY

Provided herein are antibody conjugates that selectively bind folate receptor alpha (FOLR1). The antibody conjugates comprise an antibody that binds folate receptor alpha (FOLR1) linked to one or more payload moieties. The antibody can be linked to the payload directly by a covalent bond or indirectly by way of a linker. Folate receptor alpha (FOLR1) antibodies are described in detail herein, as are useful payload moieties, and useful linkers.

In another aspect, provided are compositions comprising the antibody conjugates. In some embodiments, the compositions are pharmaceutical compositions. Any suitable pharmaceutical composition may be used. In some embodiments, the pharmaceutical composition is a composition for parenteral administration. In a further aspect, provided herein are kits comprising the antibody conjugates or pharmaceutical compositions.

In another aspect, provide herein are methods of using the anti-FOLR1 antibody conjugates. In some embodiments, the methods are methods of delivering one or more payload moieties to a target cell or tissue expressing folate receptor alpha. In some embodiments, the methods are methods of treatment. In some embodiments, the methods are diagnostic methods. In some embodiments, the methods are analytical methods. In some embodiments, the antibody conjugates are used to treat a disease or condition. In some aspects, the disease or condition is selected from a cancer, autoimmune disease, and infection.

In some embodiments, the antibody conjugates bind human folate receptor alpha. In some embodiments, the antibody conjugates also bind homologs of human folate receptor alpha. In some aspects, the antibody conjugates also bind homologs of cynomolgus monkey and/or mouse folate receptor alpha.

BRIEF DESCRIPTION OF THE DRAWINGS

FIG. 2(A-D), FIG. 3(A-D), and FIG. 4 provide alignments of the VH sequences (SEQ ID NOs: 308-366) from the variant antibodies provided herein. CDRs according to Chothia are highlighted, and CDRs according to Kabat are boxed.

FIG. 5 provides alignments of the VL sequences (SEQ ID NOs: 367-369) from trastuzumab and the variant antibodies provided herein. CDRs according to Chothia are highlighted, and CDRs according to Kabat are underlined.

DETAILED DESCRIPTION OF THE EMBODIMENTS

1. Definitions

Figure 1:
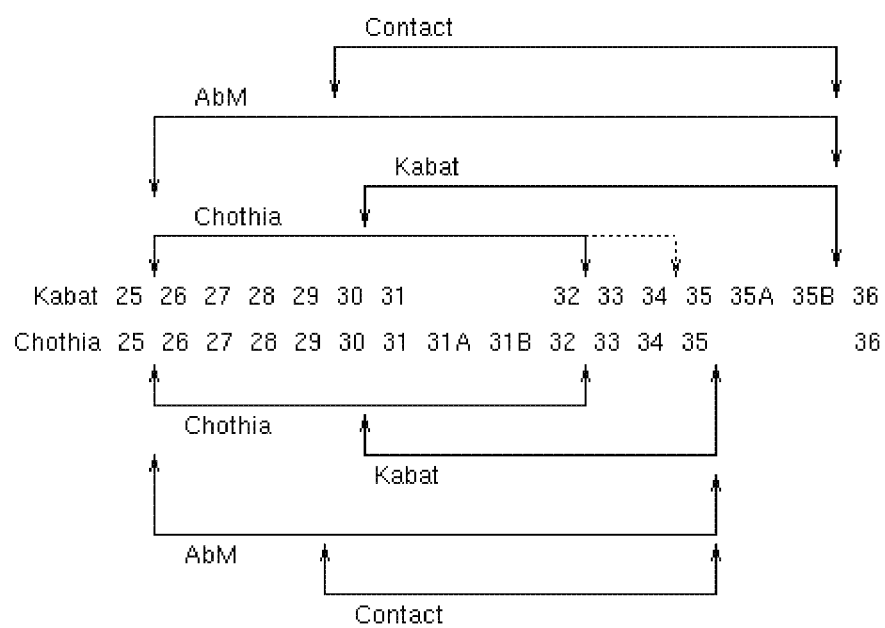
FIG. 1 provides a comparison of the Kabat and Chothia numbering systems for CDR-H1. Adapted from Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value±one standard deviation of that value.

The term "combinations thereof" includes every possible combination of elements to which the term refers to. For example, a sentence stating that "if $\alpha_2$ is A, then $\alpha_3$ is not D; $\alpha_5$ is not S; or $\alpha_6$ is not S; or combinations thereof" includes the following combinations when $\alpha_2$ is A: (1) $\alpha_3$ is not D; (2) $\alpha_5$ is not S; (3) $\alpha_6$ is not S; (4) $\alpha_3$ is not D; as is not S; and $\alpha_6$ is not S; (5) $\alpha_3$ is not D and $\alpha_5$ is not S; (6) $\alpha_3$ is not D and $\alpha_6$ is not S; and (7) $\alpha_5$ is not S and $\alpha_6$ is not S.

The terms "folate receptor alpha" and "folate receptor 1" are used interchangeably herein. Folate receptor alpha is also known by synonyms, including FOLR1, FolRα, folate binding protein, FBP, adult folate binding protein, Folbp1, FR-alpha, FRα, KB cells FBP, and ovarian tumor-associated antigen MOv18, among others. Unless specified otherwise, the terms include any variants, isoforms and species homologs of human folate receptor alpha that are naturally expressed by cells, or that are expressed by cells transfected with a folate receptor alpha or FOLR1 gene. Folate receptor alpha proteins include, for example, human folate receptor alpha (SEQ ID NO: 1). In some embodiments, folate receptor alpha proteins include cynomolgus monkey folate receptor alpha (SEQ ID NO: 2). In some embodiments, folate receptor alpha proteins include murine folate receptor alpha (SEQ ID NO: 3).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$—$V_L$ dimer. A "folate receptor alpha antibody," "anti-folate receptor alpha antibody," "folate receptor alpha Ab," "folate receptor alpha-specific antibody," "anti-folate receptor alpha Ab," "FOLR1 antibody," "FolRα antibody," "anti-FOLR1 antibody," "anti-FolRα antibody," "FOLR1 Ab," "FolRα. Ab," "FOLR1-specific antibody," "FolRα-specific antibody," "anti-FolRα Ab," or "anti-FOLR1 Ab" is an antibody, as described herein, which binds specifically to folate receptor alpha or FOLR1. In some embodiments, the antibody binds the extracellular domain of folate receptor alpha (FOLR1).

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., Sequences of Proteins of Immunological Interest 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Pluckthun A. (1994). In some embodiments, the linker is SEQ ID NO: 377. In some embodiments, the linker is SEQ ID NO: 378. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 370, or a portion thereof. SEQ ID NO: 370 provides the sequence of $C_{H1}$, $C_{H2}$, and $C_{H3}$ of the human IgG1 constant region.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant (KO. Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" ($M^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., folate receptor alpha, or FOLR1). In one exemplary assay, FOLR1 is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to variants of folate receptor alpha (FOLR1) with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The term "conjugate" or "antibody conjugate" refers to an antibody linked to one or more payload moieties. The antibody can be any antibody described herein. The payload can be any payload described herein. The antibody can be directly linked to the payload via a covalent bond, or the antibody can be linked to the payload indirectly via a linker. Typically, the linker is covalently bonded to the antibody and also covalently bonded to the payload. The term "antibody drug conjugate" or "ADC" refers to a conjugate wherein at least one payload is a therapeutic moiety such as a drug.

The term "payload" refers to a molecular moiety that can be conjugated to an antibody. In particular embodiments, payloads are selected from the group consisting of therapeutic moieties and labelling moieties.

The term "linker" refers to a molecular moiety that is capable of forming at least two covalent bonds. Typically, a linker is capable of forming at least one covalent bond to an antibody and at least another covalent bond to a payload. In certain embodiments, a linker can form more than one covalent bond to an antibody. In certain embodiments, a linker can form more than one covalent bond to a payload or can form covalent bonds to more than one payload. After a linker forms a bond to an antibody, or a payload, or both, the remaining structure, i.e. the residue of the linker after one or more covalent bonds are formed, may still be referred to as a "linker" herein. The term "linker precursor" refers to a linker having one or more reactive groups capable of forming a covalent bond with an antibody or payload, or both. In some embodiments, the linker is a cleavable linker. For example, a cleavable linker can be one that is released by an bio-labile function, which may or may not be engineered. In some embodiments, the linker is a non-cleavable linker. For example, a non-cleavable linker can be one that is released upon degradation of the antibody.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder. In some embodiments, a therapeutically effective amount or effective amount refers to an amount of an antibody or composition that when administered to a subject is effective to prevent or ameliorate a disease or the progression of the disease, or result in amelioration of symptoms.

As used herein, the term "inhibits growth" (e.g. referring to cells, such as tumor cells) is intended to include any measurable decrease in cell growth (e.g., tumor cell growth) when contacted with a folate receptor alpha (FOLR1) antibody, as compared to the growth of the same cells not in contact with a FOLR1 antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a disease that can be treated or diagnosed with an antibody provided herein. In some embodiments, the disease is gastric carcinoma, colorectal carcinoma, renal cell carcinoma, cervical carcinoma, non-small cell lung carcinoma, ovarian cancer, breast cancer, triple-negative breast cancer, endometrial cancer, prostate cancer, and/or a cancer of epithelial origin.

In some chemical structures illustrated herein, certain substituents, chemical groups, and atoms are depicted with a curvy/wavy line (e.g., 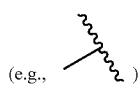 )

that intersects a bond or bonds to indicate the atom through which the substituents, chemical groups, and atoms are bonded. For example, in some structures, such as but not limited to

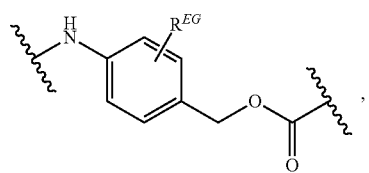

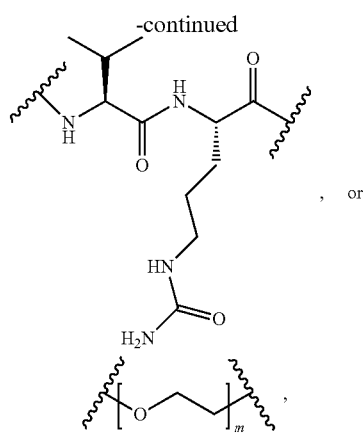

this curvy/wavy line indicates the atoms in the backbone of a conjugate or linker-payload structure to which the illustrated chemical entity is bonded. In some structures, such as but not limited to

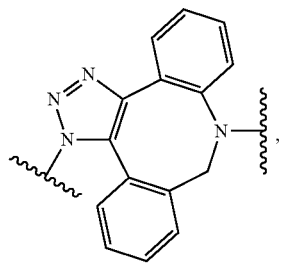 [SMILES: *N1Cc2ccccc2-c2c(nnn2*)-c2ccccc21]

this curvy/wavy line indicates the atoms in the antibody or antibody fragment as well as the atoms in the backbone of a conjugate or linker-payload structure to which the illustrated chemical entity is bonded.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Conjugates

Provided herein are conjugates of antibodies to folate receptor alpha (FOLR1 or FolRα). The conjugates comprise an antibody to FOLR1 covalently linked directly or indirectly, via a linker, to a payload. In certain embodiments, the antibody is linked to one payload. In further embodiments, the antibody is linked to more than one payload. In certain embodiments, the antibody is linked to two, three, four, five, six, seven, eight, or more payloads.

The payload can be any payload deemed useful by the practitioner of skill. In certain embodiments, the payload is a therapeutic moiety. In certain embodiments, the payload is a diagnostic moiety, e.g. a label. Useful payloads are described in the sections and examples below.

The linker can be any linker capable of forming at least one bond to the antibody and at least one bond to a payload. Useful linkers are described the sections and examples below.

In the conjugates provided herein, the antibody can be any antibody with binding specificity for folate receptor alpha (FOLR1 or FolRα). The FOLR1 can be from any species. In certain embodiments, the FOLR1 is a vertebrate FOLR1. In certain embodiments, the FOLR1 is a mammalian FOLR1. In certain embodiments, the FOLR1 is human FOLR1. In certain embodiments, the FOLR1 is mouse FOLR1. In certain embodiments, the FOLR1 is cynomolgus FOLR1.

In certain embodiments, the antibody to folate receptor alpha (FOLR1 or FolRα) competes with an antibody described herein for binding. In certain embodiments, the antibody to FOLR1 binds to the same epitope as an antibody described herein.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair).

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Further reactive groups are described in the sections and examples below.

In further embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

The non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

In certain embodiments, the antibodies provided herein comprise one or more non-natural amino acids each at a position selected from the group consisting of heavy chain or light chain residues HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, or HC-S70 according to the Kabat or Chothia or EU numbering scheme, or a post-translationally modified variant thereof. In these designations, HC indicates a heavy chain residue, and LC indicates a light chain residue.

In certain embodiments, provided herein are conjugates according to Formula (C1) or (C2):

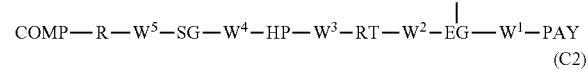

(C1)

(C2)

COMP—R—W⁵—SG—W⁴—HP—W³—RT—W²—RT—W¹—PAY or a pharmaceutically acceptable salt, solvate, stereoisomer, regioisomer, or tautomer thereof, wherein:

COMP is a residue of an anti-FOLR1 antibody;
PAY is a payload moiety;
$W^1$, $W^2$, $W^3$, $W^4$, and $W^5$ are each independently a single bond, absent, or a divalent attaching group;
EG is absent, or an eliminator group;
each RT is a release trigger group, in the backbone of Formula (C1) or (C2) or bonded to EG, wherein each RT is optional;
HP is a single bond, absent, or a divalent hydrophilic group;
SG is a single bond, absent, or a divalent spacer group; and
R is hydrogen, a terminal conjugating group, or a divalent residue of a terminal conjugating group.

In some embodiments, a conjugate according to Formula (C1) or (C2) comprises n number of PAY moieties, wherein n is an integer from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise —C(O)—, —O—, —C(O)NH—, —C(O)NH-alkyl-, —OC(O)NH—, —SC(O)NH—, —NH—, —NH-alkyl-, —N(CH₃)CH₂CH₂N(CH₃)—, —S—, —S—S—, OCH₂CH₂O—, or the reverse (e.g. —NHC(O)—) thereof, or a combination thereof.

Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

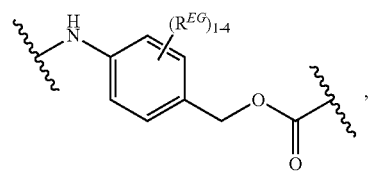

19

-continued

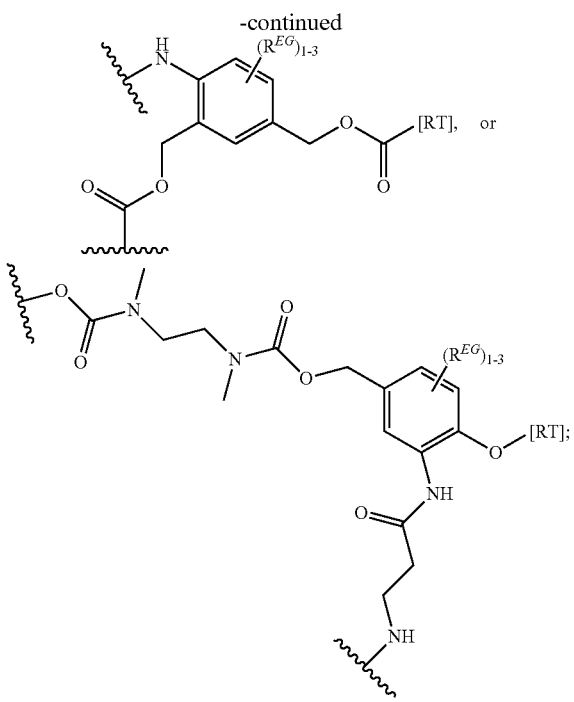

[RT], or;

wherein R$^{EG}$ is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four R$^{EG}$ groups. In the second and third structures, those of skill will recognize that EG is bonded to an RT that is not within the backbone of formula (C1) as indicated in the above description of formula (C1). In some embodiments, R$^{EG}$ is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, R$^{EG}$ is selected from the group consisting of hydrogen, —NO$_2$, —CN, fluoro, bromo, and chloro. In certain embodiments, the eliminator group is

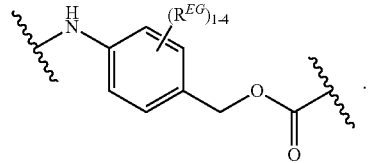

In certain embodiments, the eliminator group is

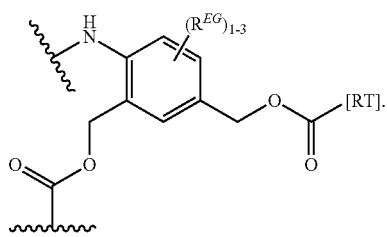

20

In certain embodiments, the eliminator group is

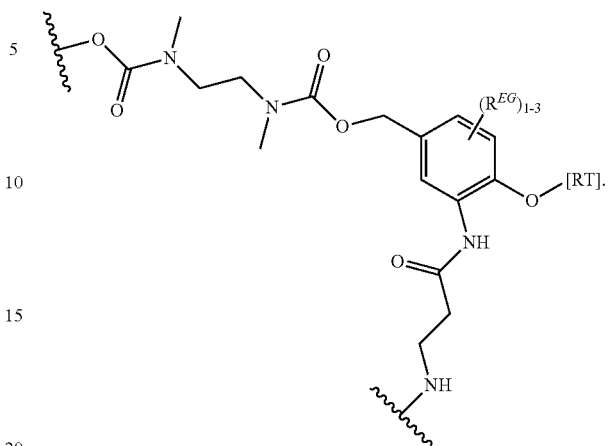

In some embodiments, the eliminator group is:

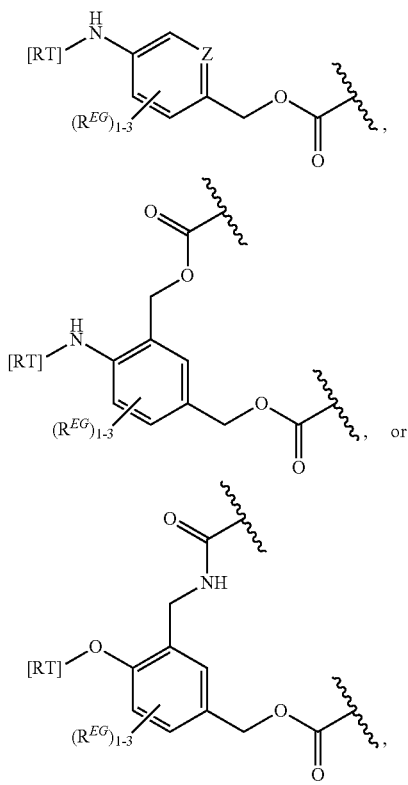

wherein Z may be CH or N, R$^{EG}$ is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four R$^{EG}$ groups. In the first and second structures, those of skill will recognize that EG is bonded to an RT that is not within the backbone of formula (C1) as indicated in the above description of formula (C1). In some embodiments, R$^{EG}$ is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —NO$_2$, —CN, fluoro, bromo, and chloro. In some embodiments, each $R^{EG}$ in the EG is hydrogen. In certain embodiments, the eliminator group is

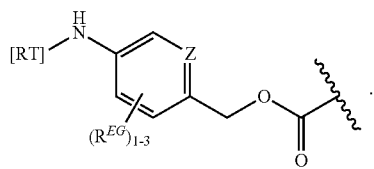

In certain embodiments, the eliminator group is

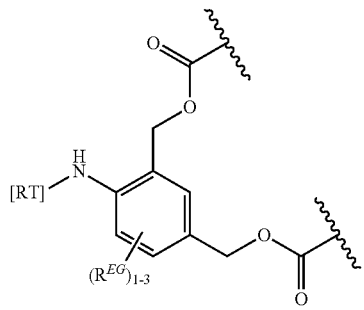

In certain embodiments, the eliminator group is

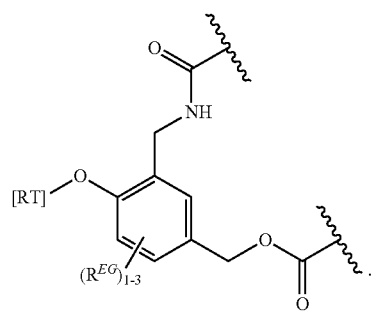

Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiment, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

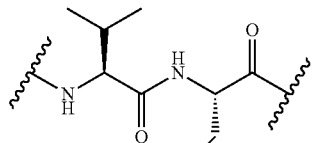

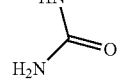

or

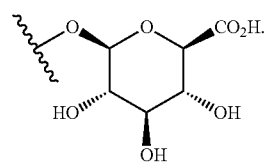

Those of skill will recognize that the first structure is divalent and can be bonded within the backbone of Formula (C1) or as depicted in Formula (C2), and that the second structure is monovalent and can be bonded to EG as depicted in formula (C1) above.

In certain embodiments, the release trigger group is

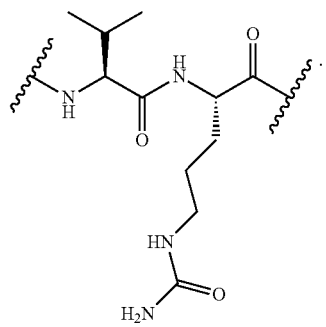 [SMILES: *N[C@H](C(=O)N[C@@H](CCCNC(N)=O)C(*)=O)C(C)C]

In certain embodiments, the release trigger group is

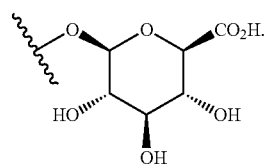 [SMILES: *O[C@H]1O[C@@H](C(=O)O)[C@H](O)[C@@H](O)[C@@H]1O]

In some embodiments, the release trigger group is a protease-cleavable $R_1$-Val-X peptide having the structure of:

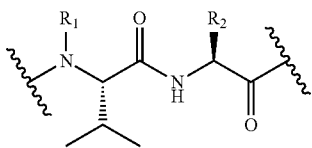

wherein $R_1$ is H or

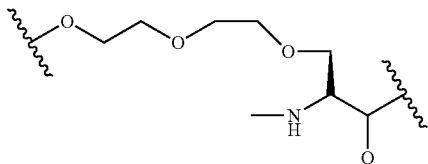

and $R_2$ is $CH_3$, $CH_2CH_2CO_2H$, or $(CH_2)_3NHCONH_2$; a legumain-cleavable Ala-Ala-Asn or Ala-Ala-Asp peptide having the structure of:

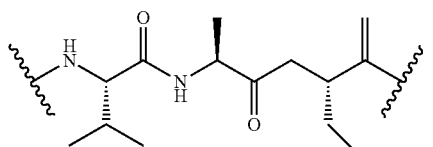

where Z is OH or $NH_2$; or a β-glucuronidase-cleavable β-glucuronide having the structure of:

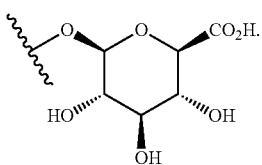

Those of skill will recognize that

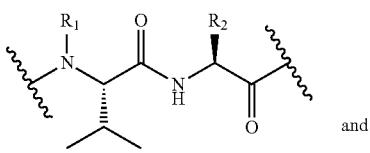

and

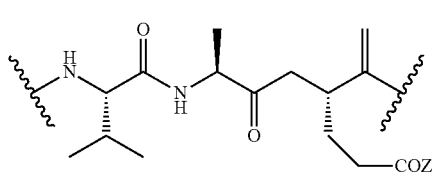

are divalent structures and can be bonded within the backbone of Formula (C1) or as depicted in Formula (C2). The structure

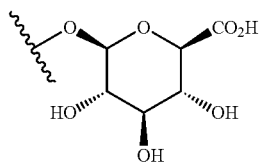 [SMILES: *O[C@H]1O[C@@H](C(=O)O)[C@H](O)[C@@H](O)[C@@H]1O]

is monovalent and can be bonded to EG as depicted in formula (C1) above.

Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

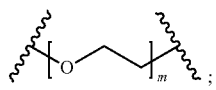

wherein m is an integer from 1 to 13, optionally 1 to 4, optionally 2 to 4, or optionally 4 to 8.

In some embodiments, the hydrophilic group is a divalent poly(ethylene glycol) having the following formula:

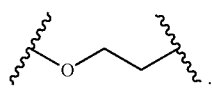 [SMILES: *CCO*]

In some other embodiments, the hydrophilic group is a divalent poly(ethylene glycol) having the following formula:

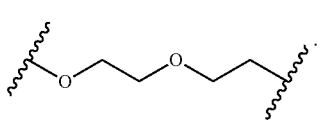 [SMILES: *CCOCCO*]

In other embodiments, the hydrophilic group is a divalent poly(ethylene glycol) having the following formula:

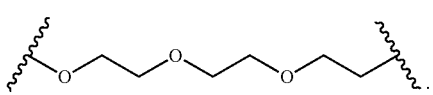 [SMILES: *CCOCCOCCO*]

In other embodiments, the hydrophilic group is a divalent poly(ethylene glycol) having the following formula:

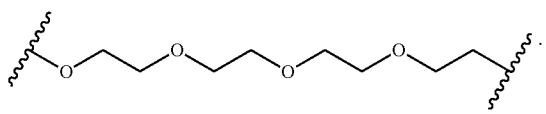 [SMILES: *CCOCCOCCOCCO*]

In some embodiments, the hydrophilic group can bear a chain-presented sulfonic acid having the formula:

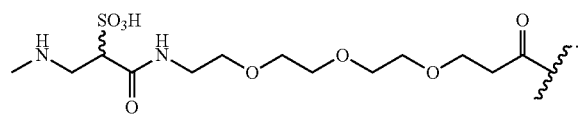 [SMILES: *C(=O)CCOCCOCCOCCNC(=O)C(CNC)S(=O)(=O)O]

Spacer Groups

Spacer groups facilitate spacing of the conjugating group from the other groups of the compounds described herein. This spacing can lead to more efficient conjugation of the compounds described herein to a second compound as well as more efficient cleavage of the active catabolite. The spacer group can also stabilize the conjugating group and lead to improved overall antibody-drug conjugate properties.

In certain embodiments, the spacer group is designated SP herein. Useful spacer groups include those described herein. In certain embodiments, the spacer group is:

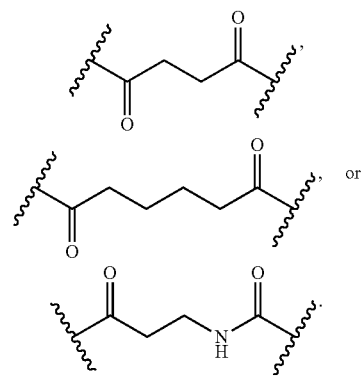

In certain embodiments, the spacer group, $W^4$, and the hydrophilic group combine to form a divalent poly(ethylene glycol) according to the formula:

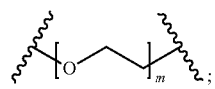

wherein m is an integer from 1 to 13, optionally 1 to 4, optionally 2 to 4, or optionally 4 to 8.

In some embodiments, the SP is

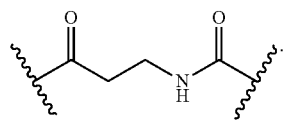 [SMILES: *C(=O)CCNC(*)=O]

In some embodiments, the divalent poly(ethylene glycol) has the following formula:

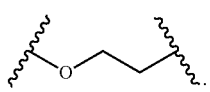

In some other embodiments, the divalent poly(ethylene glycol) has the following formula:

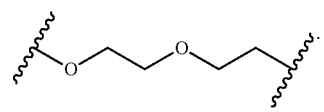 [SMILES: *CCOCCO*]

In other embodiments, the divalent poly(ethylene glycol) has the following formula:

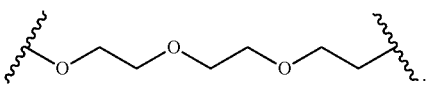 [SMILES: *CCOCCOCCO*]

In other embodiments, the divalent poly(ethylene glycol) has the following formula:

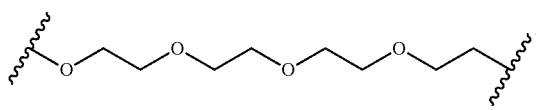

In some embodiments, the hydrophilic group can bear a chain-presented sulfonic acid having the formula:

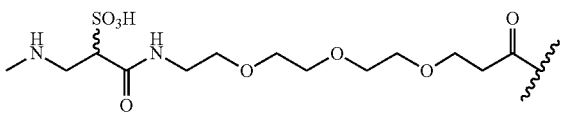

Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

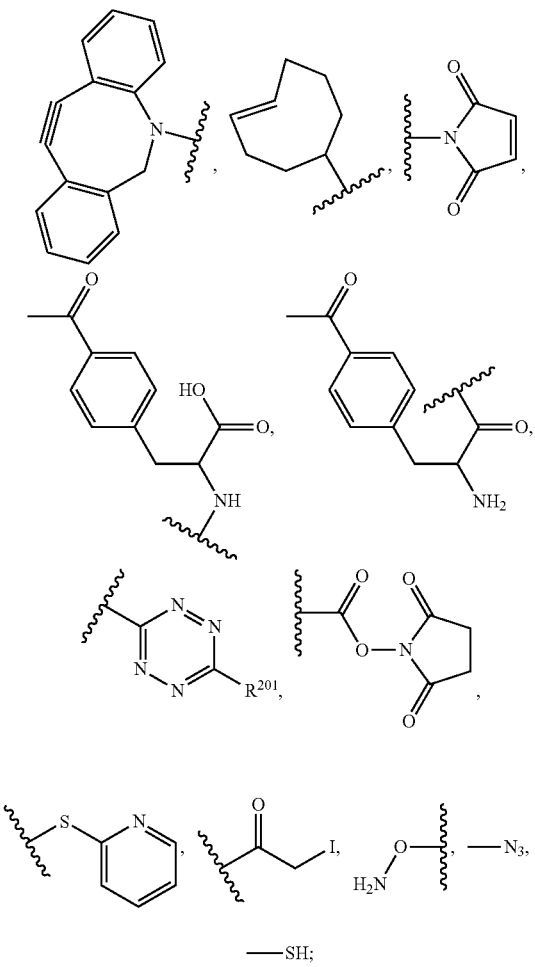

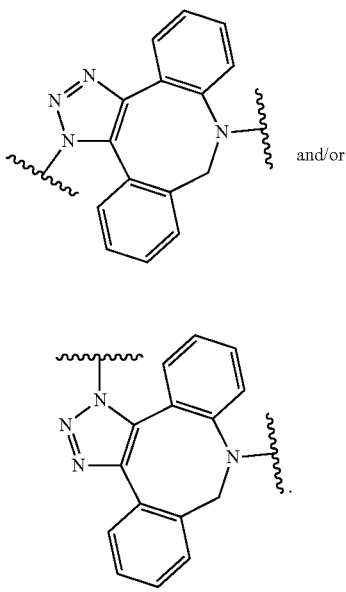 and/or

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

In an embodiment, provided herein is a conjugate according to any of Formulas 101a-104b, where COMP indicates a residue of the anti-FOLR1 antibody and PAY indicates a payload moiety:

(101a)

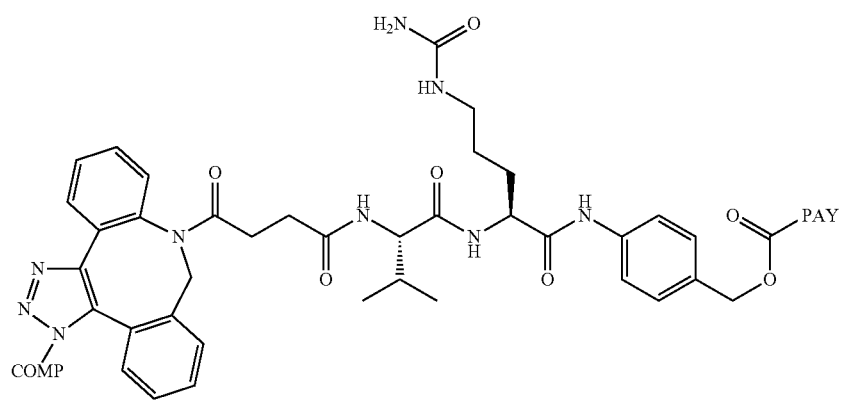

(101b)
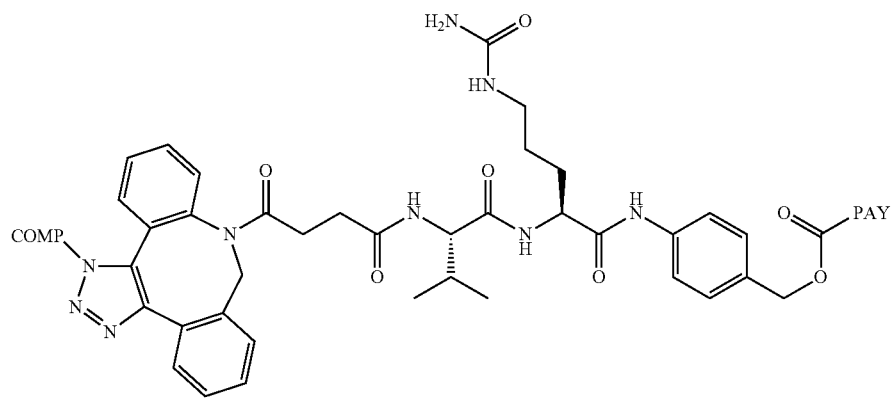
(102a)
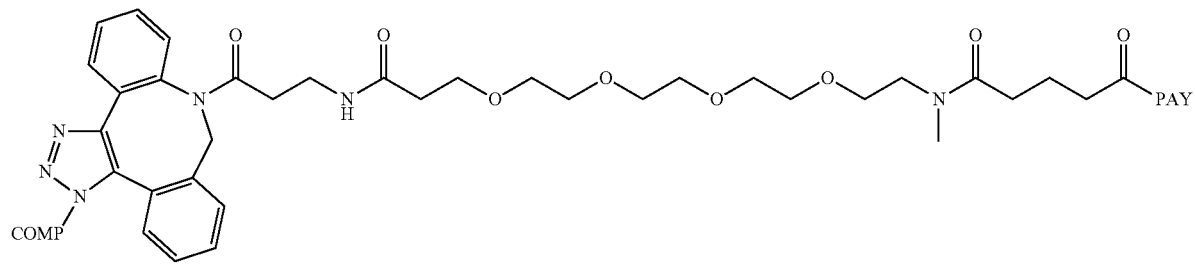
(102b)
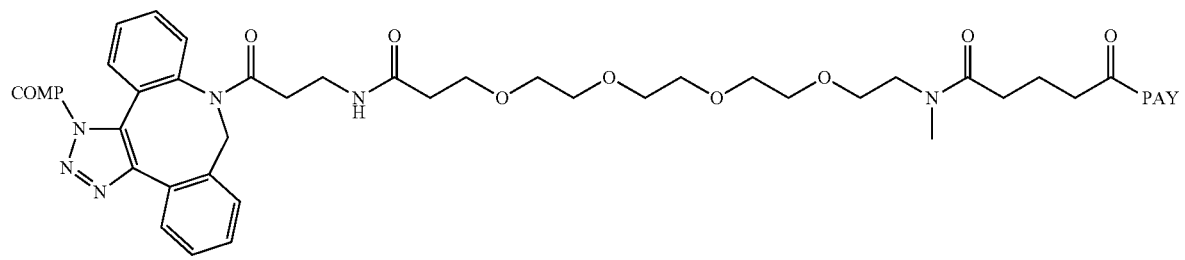
(103a)
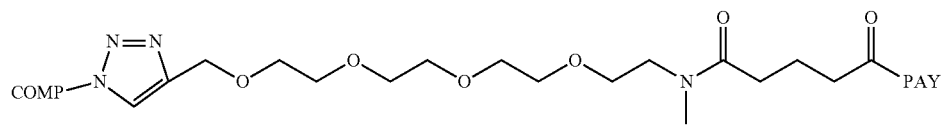
(103b)
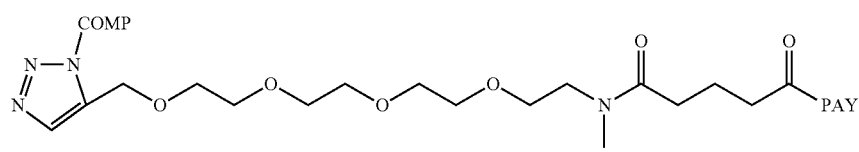
(104a) (104b)
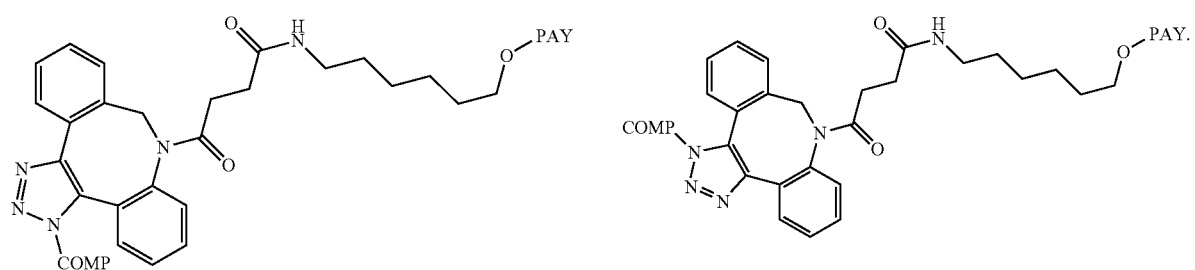
In any of the foregoing embodiments, the conjugate comprises n number of PAY moieties, wherein n is an integer from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

In particular embodiments, provided herein are anti-FOLR1 conjugates according to any of Formulas 101a-104b wherein COMP indicates a residue of the non-natural amino acid according to Formula (30), below. In particular embodiments, provided herein are anti-FOLR1 conjugates according to any of Formulas 101a-104b wherein COMP indicates a residue of the non-natural amino acid according to Formula (30), below, at heavy chain position 404 according to the EU numbering system. In particular embodiments, provided herein are anti-FOLR1 conjugates according to any of Formulas 101a-104b wherein COMP indicates a residue of the non-natural amino acid according to Formula (30), below, at heavy chain position 180 according to the EU numbering system. In particular embodiments, provided herein are anti-FOLR1 conjugates according to any of Formulas 101a-104b wherein COMP indicates a residue of the non-natural amino acid according to Formula (30), below, at heavy chain position 241 according to the EU numbering system. In particular embodiments, provided herein are anti-FOLR1 conjugates according to any of Formulas 101a-104b wherein COMP indicates a residue of the non-natural amino acid according to Formula (30), below, at heavy chain position 222 according to the EU numbering system. In particular embodiments, provided herein are anti-FOLR1 conjugates according to any of Formulas 101a-104b wherein COMP indicates a residue of the non-natural amino acid according to Formula (30), below, at light chain position 7 according to the Kabat or Chothia numbering system. In particular embodiments, provided herein are anti-FOLR1 conjugates according to any of Formulas 101a-104b wherein COMP indicates a residue of the non-natural amino acid according to Formula (30), below, at light chain position 42 according to the Kabat or Chothia numbering system. In certain embodiments, PAY is selected from the group consisting of maytansine, hemiasterlin, amanitin, monomethyl auristatin F (MMAF), and monomethyl auristatin E (MMAE). In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

(30)

In particular embodiments, provided herein are anti-FOLR1 conjugates according to any of Formulas 101a-104b wherein COMP indicates a residue of the non-natural amino acid according to Formula (56), below. In particular embodiments, provided herein are anti-FOLR1 conjugates according to any of Formulas 101a-104b wherein COMP indicates a residue of the non-natural amino acid according to Formula (56), below, at heavy chain position 404 according to the EU numbering system. In particular embodiments, provided herein are anti-FOLR1 conjugates according to any of Formulas 101a-104b wherein COMP indicates a residue of the non-natural amino acid according to Formula (56), below, at heavy chain position 180 according to the EU numbering system. In particular embodiments, provided herein are anti-FOLR1 conjugates according to any of Formulas 101a-104b wherein COMP indicates a residue of the non-natural amino acid according to Formula (56), below, at heavy chain position 241 according to the EU numbering system. In particular embodiments, provided herein are anti-FOLR1 conjugates according to any of Formulas 101a-104b wherein COMP indicates a residue of the non-natural amino acid according to Formula (56), below, at heavy chain position 222 according to the EU numbering system. In particular embodiments, provided herein are anti-FOLR1 conjugates according to any of Formulas 101a-104b wherein COMP indicates a residue of the non-natural amino acid according to Formula (56), below, at light chain position 7 according to the Kabat or Chothia numbering system. In particular embodiments, provided herein are anti-FOLR1 conjugates according to any of Formulas 101a-104b wherein COMP indicates a residue of the non-natural amino acid according to Formula (56), below, at light chain position 42 according to the Kabat or Chothia numbering system. In certain embodiments, PAY is selected from the group consisting of maytansine, hemiasterlin, amanitin, MMAF, and MMAE. In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

(56)

In particular embodiments, provided herein are anti-FOLR1 conjugates according to any of Formulas 101a-104b wherein COMP indicates a non-natural amino acid residue of para-azido-L-phenylalanine. In particular embodiments, provided herein are anti-FOLR1 conjugates according to any of Formulas 101a-104b wherein COMP indicates the non-natural amino acid residue para-azido-phenylalanine at heavy chain position 404 according to the EU numbering system. In particular embodiments, provided herein are anti-FOLR1 conjugates according to any of Formulas 101a-104b wherein COMP indicates a non-natural amino acid residue of para-azido-L-phenylalanine at heavy chain position 180 according to the EU numbering system. In particular embodiments, provided herein are anti-FOLR1 conjugates according to any of Formulas 101a-104b wherein COMP indicates a non-natural amino acid residue para-azido-L-phenylalanine at heavy chain position 241 according to the EU numbering system. In particular embodiments, provided herein are anti-FOLR1 conjugates according to any of Formulas 101a-104b wherein COMP indicates a non-natural amino acid residue para-azido-L-phenylalanine at heavy chain position 222 according to the EU numbering system. In particular embodiments, provided herein are anti-FOLR1 conjugates according to any of Formulas 101a-104b wherein COMP indicates a non-natural amino acid residue para-azido-L-phenylalanine at light chain position 7 according to the Kabat or Chothia numbering system. In particular embodiments, provided herein are anti-FOLR1 conjugates according to any of Formulas 101a-104b wherein COMP indicates a non-natural amino acid residue para-azido-L-phenylalanine at light chain position 42 according to the Kabat or Chothia numbering system. In certain embodiments, PAY is selected from the group consisting of maytansine, hemiasterlin, amanitin, MMAF, and MMAE. In certain embodiments, the PAY is maytansine. In certain embodiments, PAY is hemiasterlin. In certain embodiments, PAY is amanitin. In certain embodiments, PAY is MMAF. In certain embodiments, PAY is MMAE.

In some embodiments, provided herein are anti-FOLR1 conjugates comprising a modified hemiasterlin and linker as described, for example, in PCT Publication No. WO 2016/123582. For example, the conjugate can have a structure comprising any of Formulas 1000-1000b, 1001-1001b, 1002-1002b, and I-XIXb-2, 101-111b, or 1-8b as described in PCT Publication No. WO 2016/2016/123582. Examples of conjugates comprising a modified hemiasterlin and linker are provided below.

In some embodiments, provided herein are anti-FOLR1 conjugates having the structure of Conjugate M:

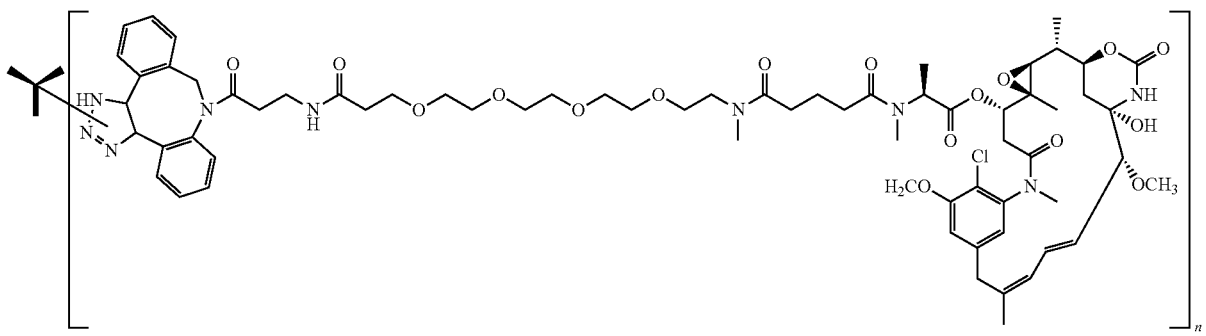

where n is an integer from 1 to 6. In some embodiments, n is an integer from 1 to 4. In some embodiments, n is 2. For example, in some embodiments, the anti-FOLR1 conjugate has the structure:

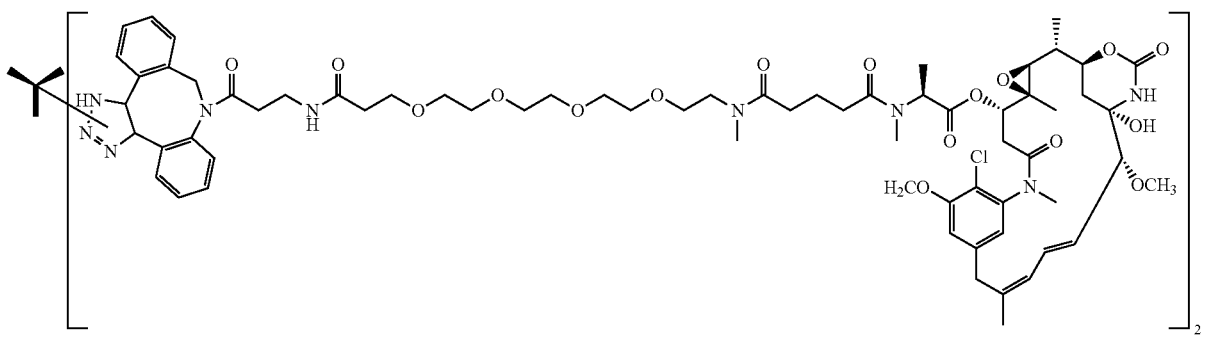

In some embodiments, n is 4. For example, in some embodiments, the anti-FOLR1 conjugate has the structure:

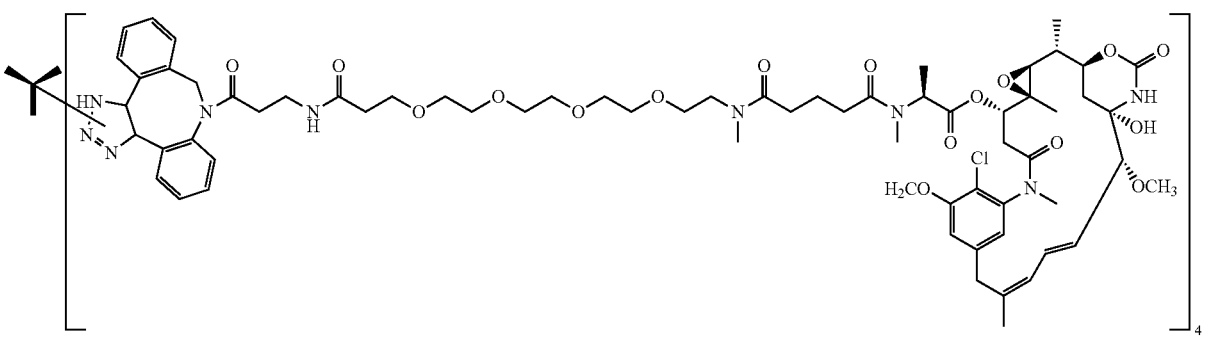

In some embodiments, provided herein are anti-FOLR1 conjugates having the structure of Conjugate P:

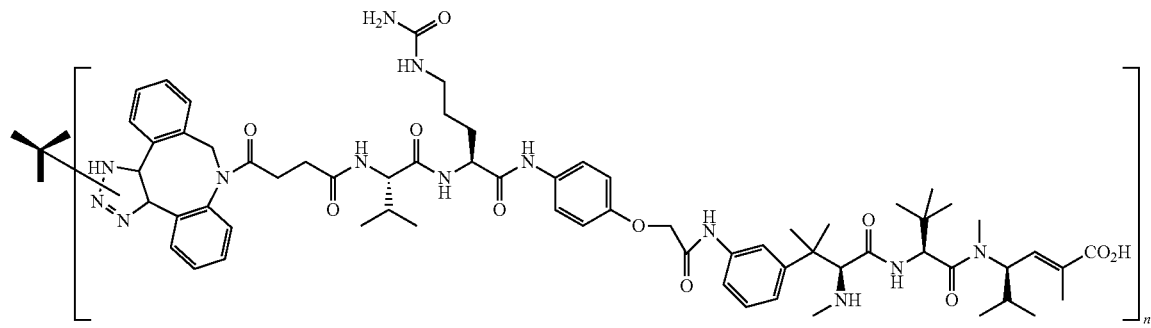

where n is an integer from 1 to 6. In some embodiments, n is an integer from 1 to 4. In some embodiments, n is 2. For example, in some embodiments, the anti-FOLR1 conjugate has the structure:

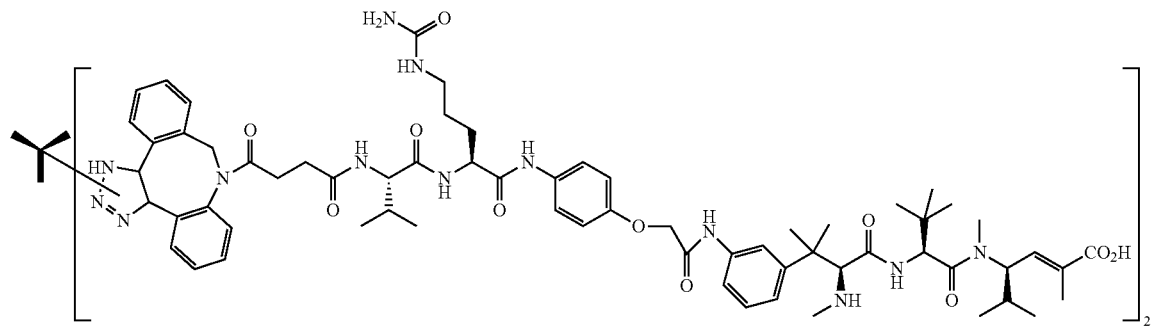

In some embodiments, n is 4. For example, in some embodiments, the anti-FOLR1 conjugate has the structure:

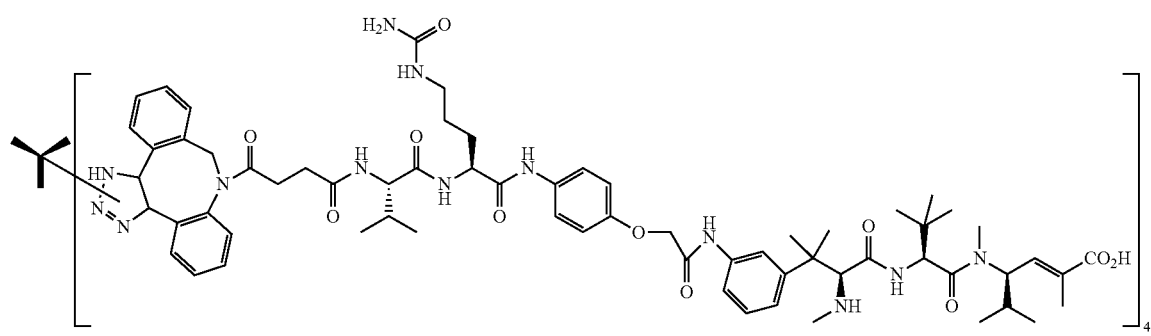

In some embodiments, provided herein are anti-FOLR1 conjugates having the structure of Conjugate Q:

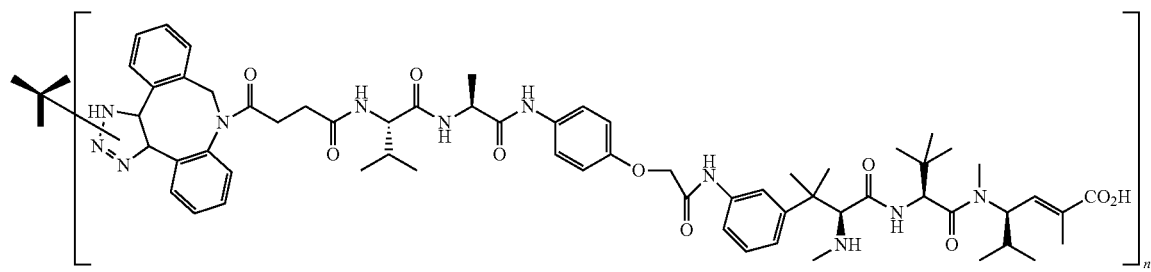

where n is an integer from 1 to 6. In some embodiments, n is an integer from 1 to 4. In some embodiments, n is 2. For example, in some embodiments, the anti-FOLR1 conjugate has the structure:

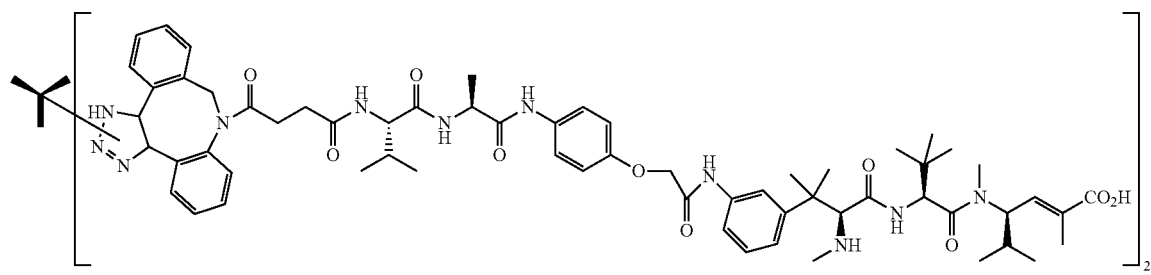

In some embodiments, n is 4. For example, in some embodiments, the anti-FOLR1 conjugate has the structure:

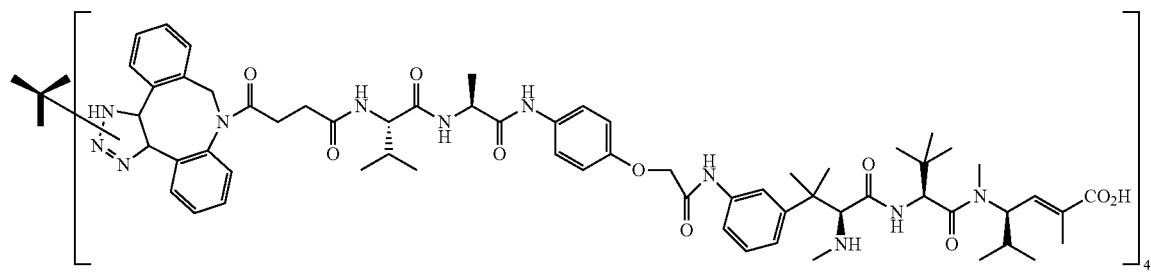

In any of the foregoing embodiments wherein the anti-FOLR1 conjugate has a structure according to Conjugate M, Conjugate P, or Conjugate Q, the bracketed structure can be covalently bonded to one or more non-natural amino acids of the antibody, wherein the one or more non-natural amino acids are located at sites selected from the group consisting of: HC-F404, HC-Y180, and LC-K42 according to the Kabat or EU numbering scheme of Kabat. In some embodiments, the bracketed structure is covalently bonded to one or more non-natural amino acids at site HC-F404 of the antibody. In some embodiments, the bracketed structure is covalently bonded to one or more non-natural amino acids at site HC-Y180 of the antibody. In some embodiments, the bracketed structure is covalently bonded to one or more non-natural amino acids at site LC-K42 of the antibody. In some embodiments, the bracketed structure is covalently bonded to one or more non-natural amino acids at sites HC-F404 and HC-Y180 of the antibody. In some embodiments, at least one bracketed structure is covalently bonded to a non-natural amino acid at site HC-F404 of the antibody, and at least one bracketed structure is covalently bonded a non-natural amino acid at site HC-Y180 of the antibody. In some embodiments, the bracketed structure is covalently bonded to one or more non-natural amino acids at sites HC-Y180 and LC-K42 of the antibody. In some embodiments, at least one bracketed structure is covalently bonded to a non-natural amino acid at site HC-Y180 of the antibody, and at least one bracketed structure is covalently bonded a non-natural amino acid at site LC-K32 of the antibody.

3. Payloads

In addition to the payloads described above, the molecular payload can be any molecular entity that one of skill in the art might desire to conjugate to the polypeptide. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the polypeptide to its target. In certain embodiments, the payload is a cytotoxic moiety. In such embodiments, the antibody conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, an antibody conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

4. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarlyene, and substituted heteroarylene. In certain embodiments, the linker is $C_{1-10}$ alkylene or $C_{1-10}$ heteroalkylene. In some embodiments, the $C_{1-10}$heteroalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of: N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl)cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit), glycine-glycine-glycine (gly-gly-gly), and glycine-methoxyethoxy-ethyl)serine-valine (gly-val-citalanine OMESerValAla).

In some embodiments, a linker comprises a self-immolative spacer. In certain embodiments, the self-immolative spacer comprises p-aminobenzyl. In some embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. 55:5867). Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as citValCit-PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

Additional linkers are disclosed herein, such as, for example, the linker precursors (A)-(L) described below.

5. Antibody Specificity

The conjugates comprise antibodies that selectively bind human folate receptor alpha. In some aspects, the antibody selectively binds to the extracellular domain of human folate receptor alpha (human FOLR1).

In some embodiments, the antibody binds to a homolog of human FOLR1. In some aspects, the antibody binds to a homolog of human FOLR1 from a species selected from monkeys, mice, dogs, cats, rats, cows, horses, goats and sheep. In some aspects, the homolog is a cynomolgus monkey homolog. In some aspects, the homolog is a mouse or murine analog.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, or a variant thereof. In some aspects, the variant is a variant with a conservative amino acid substitution.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 13, 14, 15, 16, or 17 residues in length.

In some aspects, the Kabat/Chothia CDR-L1 of the antibody is 11, 12, 13, 14, 15, 16, 17, or 18 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

The antibodies provided herein may be useful for the treatment of a variety of diseases and conditions including cancers. In some embodiments, the antibodies provided herein may be useful for the treatment of cancers of solid tumors. For example, the antibodies provided herein can be useful for the treatment of colorectal cancer.

5.1 CDR-H3 Sequences

In some embodiments, the antibody comprises a CDR-H3 sequence comprising, consisting of, or consisting essentially of a CDR-H3 sequence of an illustrative antibody or $V_H$ sequence provided herein. In some aspects, the CDR-H3 sequence is a CDR-H3 sequence of a $V_H$ sequence provided in SEQ ID NOs.: 308-366.

In some embodiments, the antibody comprises a CDR-H3 sequence comprising, consisting of, or consisting essentially of a sequence selected from SEQ ID NOs.: 240-298. In some aspects, the antibody comprises a CDR-H3 sequence comprising, consisting of, or consisting essentially of SEQ ID NO: 255. In some aspects, the antibody comprises a CDR-H3 sequence comprising, consisting of, or consisting essentially of SEQ ID NO: 294.

5.2 $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof. In some embodiments, the CDR-H sequences comprise, consist of, or consist essentially of one or more CDR-H sequences provided in a $V_H$ sequence selected from SEQ ID NOs: 308-366.

5.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

5.2.1.1. Kabat CDR-H3

In some embodiments, the antibody comprises a $V_H$ sequence comprising a CDR-H3 sequence, wherein the CDR-H3 sequence comprises, consists of, or consists essentially of a Kabat CDR-H3 sequence of an illustrative antibody or $V_H$ sequence provided herein. In some aspects, the Kabat CDR-H3 sequence is a Kabat CDR-H3 sequence of a $V_H$ sequence provided in SEQ ID NOs: 308-366.

In some embodiments, the antibody comprises a $V_H$ sequence comprising a Kabat CDR-H3 sequence comprising, consisting of, or consisting essentially of a sequence selected from SEQ ID NOs.: 240-298. In some aspects, the antibody comprises a $V_H$ sequence comprising a Kabat CDR-H3 sequence comprising, consisting of, or consisting essentially of SEQ ID NO: 255. In some aspects, the antibody comprises a $V_H$ sequence comprising a Kabat CDR-H3 sequence comprising, consisting of, or consisting essentially of SEQ ID NO: 294.

5.2.1.2. Kabat CDR-H2

In some embodiments, the antibody comprises a $V_H$ sequence comprising a CDR-H2 sequence, wherein the CDR-H2 sequence comprises, consists of, or consists essentially of a Kabat CDR-H2 sequence of an illustrative antibody or $V_H$ sequence provided herein. In some aspects, the Kabat CDR-H2 sequence is a Kabat CDR-H2 sequence of a $V_H$ sequence provided in SEQ ID NOs: 308-366.

In some embodiments, the antibody comprises a $V_H$ sequence comprising a Kabat CDR-H2 sequence comprising, consisting of, or consisting essentially of a sequence selected from SEQ ID NOs: 181-239. In some aspects, the antibody comprises a $V_H$ sequence comprising a Kabat CDR-H2 sequence comprising, consisting of, or consisting essentially of SEQ ID NO: 196. In some aspects, the antibody comprises a $V_H$ sequence comprising a Kabat CDR-H2 sequence comprising, consisting of, or consisting essentially of SEQ ID NO: 235.

5.2.1.3. Kabat CDR-H1

In some embodiments, the antibody comprises a $V_H$ sequence comprising a CDR-H1 sequence, wherein the CDR-H1 sequence comprises, consists of, or consists essentially of a Kabat CDR-H1 sequence of an illustrative antibody or $V_H$ sequence provided herein. In some aspects, the Kabat CDR-H1 sequence is a Kabat CDR-H1 sequence of a $V_H$ sequence provided in SEQ ID NOs: 308-366.

In some embodiments, the antibody comprises a $V_H$ sequence comprising a Kabat CDR-H1 sequence comprising, consisting of, or consisting essentially of a sequence selected from SEQ ID NOs: 63-121. In some aspects, the antibody comprises a $V_H$ sequence comprising a Kabat CDR-H1 sequence comprising, consisting of, or consisting essentially of SEQ ID NO: 78. In some aspects, the antibody comprises a $V_H$ sequence comprising a Kabat CDR-H1 sequence comprising, consisting of, or consisting essentially of SEQ ID NO: 117.

5.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 240-298, and a Kabat CDR-H2 sequence comprising, consisting of, or consisting essentially of a sequence selected from SEQ ID NOs: 181-239. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 308-366.

5.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 240-298, and a Kabat CDR-H1 sequence comprising, consisting of, or consisting essentially of a sequence selected from SEQ ID NOs: 63-121. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 308-366.

5.2.1.6. Kabat CDR-H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 63-121 and a Kabat CDR-H2 sequence comprising, consisting of, or consisting essentially of a sequence selected from SEQ ID NOs: 181-239. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 308-366.

5.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 63-121, a Kabat CDR-H2 sequence comprising, consisting of, or consisting essentially of a sequence selected from SEQ ID NOs: 181-239, and a Kabat CDR-H3 sequence comprising, consisting of, or consisting essentially of a sequence selected from SEQ ID NOs: 240-298. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 308-366.

5.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

5.2.2.1. Chothia CDR-H3

In some embodiments, the antibody comprises a $V_H$ sequence comprising a CDR-H3 sequence, wherein the CDR-H3 sequence comprises, consists of, or consists essentially of a Chothia CDR-H3 sequence of an illustrative antibody or $V_H$ sequence provided herein. In some aspects, the Chothia CDR-H3 sequence is a Chothia CDR-H3 sequence of a $V_H$ sequence provided in SEQ ID NOs: 308-366.

In some embodiments, the antibody comprises a $V_H$ sequence comprising a Chothia CDR-H3 sequence comprising, consisting of, or consisting essentially of a sequence selected from SEQ ID NOs: 240-298. In some aspects, the antibody comprises a $V_H$ sequence comprising a Chothia CDR-H3 sequence comprising, consisting of, or consisting essentially of SEQ ID NO: 255. In some aspects, the antibody comprises a $V_H$ sequence comprising a Chothia CDR-H3 sequence comprising, consisting of, or consisting essentially of SEQ ID NO: 294.

5.2.2.2. Chothia CDR-H2

In some embodiments, the antibody comprises a $V_H$ sequence comprising a CDR-H2 sequence, wherein the CDR-H2 sequence comprises, consists of, or consists essentially of a Chothia CDR-H2 sequence of an illustrative antibody or $V_H$ sequence provided herein. In some aspects, the Chothia CDR-H2 sequence is a Chothia CDR-H2 sequence of a $V_H$ sequence provided in SEQ ID NOs: 308-366.

In some embodiments, the antibody comprises a $V_H$ sequence comprising a Chothia CDR-H2 sequence comprising, consisting of, or consisting essentially of a sequence selected from SEQ ID NOs: 122-180. In some aspects, the antibody comprises a $V_H$ sequence comprising a Chothia CDR-H2 sequence comprising, consisting of, or consisting essentially of SEQ ID NO: 137. In some aspects, the antibody comprises a $V_H$ sequence comprising a Chothia CDR-H2 sequence comprising, consisting of, or consisting essentially of SEQ ID NO: 176.

5.2.2.3. Chothia CDR-H1

In some embodiments, the antibody comprises a $V_H$ sequence comprising a CDR-H1 sequence, wherein the CDR-H1 sequence comprises, consists of, or consists essentially of a Chothia CDR-H1 sequence of an illustrative antibody or $V_H$ sequence provided herein. In some aspects, the Chothia CDR-H1 sequence is a Chothia CDR-H1 sequence of a $V_H$ sequence provided in SEQ ID NOs: 308-366.

In some embodiments, the antibody comprises a $V_H$ sequence comprising a Chothia CDR-H1 sequence comprising, consisting of, or consisting essentially of a sequence selected from SEQ ID NOs: 4-62. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 58.

5.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs: 240-298, and a Chothia CDR-H2 sequence comprising, consisting of, or consisting essentially of a sequence selected from SEQ ID NOs: 122-180. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 308-366.

5.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 240-298, and a Chothia CDR-H1 sequence comprising, consisting of, or consisting essentially of a sequence selected from SEQ ID NOs: 4-62. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 308-366.

5.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 4-62 and a Chothia CDR-H2 sequence comprising, consisting of, or consisting essentially of a sequence selected from SEQ ID NOs: 122-180. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 308-366.

5.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 4-62, a Chothia CDR-H2 sequence comprising, consisting of, or consisting essentially of a sequence selected from SEQ ID NOs: 122-180, and a Chothia CDR-H3 sequence comprising, consisting of, or consisting essentially of a sequence selected from SEQ ID NOs: 240-298. In some aspects, the Chothia CDR-H1 sequence, Chothia CDR-H2 sequence, and Chothia CDR- H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 308-366.

5.3. $V_H$ Sequences

In some embodiments, the antibody comprises, consists of, or consists essentially of a $V_H$ sequence provided in SEQ ID NOs: 308-366.

In some embodiments, the antibody comprises a $V_H$ sequence comprising, consisting of, or consisting essentially of a sequence selected from SEQ ID NOs: 308-366. In some aspects, the antibody comprises a $V_H$ sequence comprising, consisting of, or consisting essentially of SEQ ID NO: 323. In some aspects, the antibody comprises a $V_H$ sequence comprising, consisting of, or consisting essentially of SEQ ID NO: 362.

5.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.4. CDR-L3 Sequences

In some embodiments, the antibody comprises a CDR-L3 sequence comprising, consisting of, or consisting essentially of a CDR-L3 sequence of an illustrative antibody or $V_L$ sequence provided herein. In some aspects, the CDR-L3 sequence is a CDR-L3 sequence of a $V_L$ sequence provided in SEQ ID NOs.: 367-369.

In some embodiments, the antibody comprises a CDR-L3 sequence comprising, consisting of, or consisting essentially of a sequence selected from SEQ ID NOs: 305-307. In some aspects, the antibody comprises a CDR-L3 sequence comprising, consisting of, or consisting essentially of SEQ ID NO: 305. In some aspects, the antibody comprises a CDR-L3 sequence comprising, consisting of, or consisting essentially of SEQ ID NO: 306. In some aspects, the antibody comprises a CDR-L3 sequence comprising, consisting of, or consisting essentially of SEQ ID NO: 307.

5.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

5.5.1. CDR-L3

In some embodiments, the antibody comprises a $V_L$ sequence comprising a CDR-L3 sequence, wherein the CDR-L3 sequence comprises, consists of, or consists essentially of a CDR-L3 sequence of an illustrative antibody or $V_L$ sequence provided herein. In some aspects, the CDR-L3 sequence is a CDR-L3 sequence of a $V_L$ sequence provided in SEQ ID NOs.: 367-369.

In some embodiments, the antibody comprises a $V_L$ sequence comprising a CDR-L3 sequence comprising, consisting of, or consisting essentially of a sequence selected from SEQ ID NOs: 305-307. In some aspects, the antibody comprises a $V_L$ sequence comprising a CDR-L3 sequence comprising, consisting of, or consisting essentially of SEQ ID NO: 305. In some aspects, the antibody comprises a $V_L$ sequence comprising a CDR-L3 sequence comprising, consisting of, or consisting essentially of SEQ ID NO: 306. In some aspects, the antibody comprises a $V_L$ sequence comprising a CDR-L3 sequence comprising, consisting of, or consisting essentially of SEQ ID NO: 307.

5.5.2. CDR-L2

In some embodiments, the antibody comprises a $V_L$ sequence comprising a CDR-L2 sequence, wherein the CDR-L2 sequence comprises, consists of, or consists essentially of a CDR-L2 sequence of an illustrative antibody or $V_L$ sequence provided herein. In some aspects, the CDR-L2 sequence is a CDR-L2 sequence of a $V_L$ sequence provided in SEQ ID NOs.: 367-369.

In some embodiments, the antibody comprises a $V_L$ sequence comprising a CDR-L2 sequence comprising, consisting of, or consisting essentially of a sequence selected from SEQ ID NOs: 302-304. In some aspects, the antibody comprises a $V_L$ sequence comprising a CDR-L2 sequence comprising, consisting of, or consisting essentially of SEQ ID NO: 302. In some aspects, the antibody comprises a $V_L$ sequence comprising a CDR-L2 sequence comprising, consisting of, or consisting essentially of SEQ ID NO: 303. In some aspects, the antibody comprises a $V_L$ sequence comprising a CDR-L2 sequence comprising, consisting of, or consisting essentially of SEQ ID NO: 304.

5.5.3. CDR-L1

In some embodiments, the antibody comprises a $V_L$ sequence comprising a CDR-L1 sequence, wherein the CDR-L1 sequence comprises, consists of, or consists essentially of a CDR-L1 sequence of an illustrative antibody or $V_L$ sequence provided herein. In some aspects, the CDR-L1 sequence is a CDR-L1 sequence of a $V_L$ sequence provided in SEQ ID NOs.: 367-369.

In some embodiments, the antibody comprises a $V_L$ sequence comprising a CDR-L1 sequence comprising, consisting of, or consisting essentially of a sequence selected from SEQ ID NOs: 299-301. In some aspects, the antibody comprises a $V_L$ sequence comprising a CDR-L1 sequence comprising, consisting of, or consisting essentially of SEQ ID NO: 299. In some aspects, the antibody comprises a $V_L$ sequence comprising a CDR-L1 sequence comprising, consisting of, or consisting essentially of SEQ ID NO: 300. In some aspects, the antibody comprises a $V_L$ sequence comprising a CDR-L1 sequence comprising, consisting of, or consisting essentially of SEQ ID NO: 301.

5.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 305-307 and a CDR-L2 sequence comprising, consisting of, or consisting essentially of a sequence selected from SEQ ID NOs: 302-304. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs.: 367-369.

5.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 305-307 and a CDR-L1 sequence comprising, consisting of, or consisting essentially of a sequence selected from SEQ ID NOs: 299-301. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs.: 367-369.

5.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 299-301 and a CDR-L2 sequence comprising, consisting of, or consisting essentially of a sequence selected from SEQ ID NOs: 302-304. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs.: 367-369.

5.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 299-301, a CDR-L2 sequence comprising, consisting of, or consisting essentially of a sequence selected from SEQ ID NOs: 302-304, and a CDR-L3 sequence comprising, consisting of, or consisting essentially of a sequence selected from SEQ ID NOs: 305-307. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs.: 367-369.

5.6. $V_L$ Sequences

In some embodiments, the antibody comprises, consists of, or consists essentially of a $V_L$ sequence provided in SEQ ID NOs.: 367-369.

In some embodiments, the antibody comprises a $V_L$ sequence comprising, consisting of, or consisting essentially of a sequence selected from SEQ ID NOs.: 367-369. In some aspects, the antibody comprises a $V_L$ sequence comprising, consisting of, or consisting essentially of SEQ ID NO: 367. In some aspects, the antibody comprises a $V_L$ sequence comprising, consisting of, or consisting essentially of SEQ ID NO: 368. In some aspects, the antibody comprises a $V_L$ sequence comprising, consisting of, or consisting essentially of SEQ ID NO: 369.

5.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.7. Pairs

5.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 240-298, and the CDR-L3 sequence is a CDR-L3 sequence comprising, consisting of, or consisting essentially of SEQ ID NOs: 305-307.

In some aspects, the CDR-H3-CDR-L3 pairs are selected from SEQ ID NO: 305 and SEQ ID NO: 255; and SEQ ID NO: 305 and SEQ ID NO: 294.

In some aspects, the CDR-H3-CDR-L3 pairs are selected from SEQ ID NO: 306 and SEQ ID NO: 255; and SEQ ID NO: 306 and SEQ ID NO: 294.

In some aspects, the CDR-H3-CDR-L3 pairs are selected from SEQ ID NO: 307 and SEQ ID NO: 255; and SEQ ID NO: 307 and SEQ ID NO: 294.

5.7.2. CDR-H1-CDR-L1 Pairs

In some embodiments, the antibody comprises a CDR-H1 sequence and a CDR-L1 sequence. In some aspects, the CDR-H1 sequence is part of a $V_H$ and the CDR-L1 sequence is part of a $V_L$.

In some aspects, the CDR-H1 sequence is a Chothia CDR-H1 sequence comprising, consisting of, or consisting essentially of SEQ ID NOs: 4-62, and the CDR-L1 sequence is a CDR-L1 sequence comprising, consisting of, or consisting essentially of SEQ ID NOs: 299-301.

In some aspects, the CDR-H1 sequence is a Kabat CDR-H1 sequence comprising, consisting of, or consisting essentially of SEQ ID NOs: 63-121, and the CDR-L1 sequence is a CDR-L1 sequence comprising, consisting of, or consisting essentially of SEQ ID NOs: 299-301.

5.7.3. CDR-H2-CDR-L2 Pairs

In some embodiments, the antibody comprises a CDR-H2 sequence and a CDR-L2 sequence. In some aspects, the CDR-H2 sequence is part of a $V_H$ and the CDR-L2 sequence is part of a $V_L$.

In some aspects, the CDR-H2 sequence is a Chothia CDR-H2 sequence comprising, consisting of, or consisting essentially of SEQ ID NOs: 122-180, and the CDR-L2 sequence is a CDR-L2 sequence comprising, consisting of, or consisting essentially of SEQ ID NOs: 302-304.

In some aspects, the CDR-H1 sequence is a Kabat CDR-H2 sequence comprising, consisting of, or consisting essentially of SEQ ID NOs: 181-239, and the CDR-L2 sequence is a CDR-L2 sequence comprising, consisting of, or consisting essentially of SEQ ID NOs: 302-304.

5.7.4. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 308-366, and the $V_L$ sequence is a $V_L$ sequence comprising, consisting of, or consisting essentially of SEQ ID NOs: 367-369.

In some aspects, the $V_H$-$V_L$ pairs are selected from SEQ ID NO: 367 and SEQ ID NO: 323; and SEQ ID NO: 367 and SEQ ID NO: 362.

In some aspects, the $V_H$-$V_L$ pairs are selected from SEQ ID NO: 368 and SEQ ID NO: 323; and SEQ ID NO: 368 and SEQ ID NO: 362.

In some aspects, the $V_H$-$V_L$ pairs are selected from SEQ ID NO: 369 and SEQ ID NO: 323; and SEQ ID NO: 369 and SEQ ID NO: 362.

5.7.4.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.8. Antibodies Comprising all Six CDRs

In some embodiments, the antibody comprises a CDR-H1 sequence, a CDR-H2 sequence, a CDR-H3 sequence, a CDR-L1 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 4-62; the CDR-H2 sequence is a Chothia CDR-H2 sequence comprising, consisting of, or consisting essentially of SEQ ID NOs: 122-180; the CDR-H3 sequence is a CDR-H3 sequence comprising, consisting of, or consisting essentially of SEQ ID NOs: 240-298; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

In some aspects, the CDR-H1 sequence is a Chothia CDR-H1 sequence comprising, consisting of, or consisting essentially of SEQ ID NO: 19; the CDR-H2 sequence is a Chothia CDR-H2 sequence comprising, consisting of, or consisting essentially of SEQ ID NO: 137; the CDR-H3 sequence is a CDR-H3 sequence comprising, consisting of, or consisting essentially of SEQ ID NO: 255; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

In some aspects, the CDR-H1 sequence is a Chothia CDR-H1 sequence comprising, consisting of, or consisting essentially of SEQ ID NO: 58; the CDR-H2 sequence is a Chothia CDR-H2 sequence comprising, consisting of, or consisting essentially of SEQ ID NO: 176; the CDR-H3 sequence is a CDR-H3 sequence comprising, consisting of, or consisting essentially of SEQ ID NO: 294; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

In some aspects, the CDR-H1 sequence is a Kabat CDR-H1 sequence comprising, consisting of, or consisting essentially of SEQ ID NOs: 63-121; the CDR-H2 sequence is a Kabat CDR-H2 sequence comprising, consisting of, or consisting essentially of SEQ ID NOs: 181-239; the CDR-H3 sequence is a CDR-H3 sequence comprising, consisting of, or consisting essentially of SEQ ID NOs: 240-298; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

In some aspects, the CDR-H1 sequence is a Kabat CDR-H1 sequence comprising, consisting of, or consisting essentially of SEQ ID NO: 78; the CDR-H2 sequence is a Kabat CDR-H2 sequence comprising, consisting of, or consisting essentially of SEQ ID NO: 196; the CDR-H3 sequence is a CDR-H3 sequence comprising, consisting of, or consisting essentially of SEQ ID NO: 255; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

In some aspects, the CDR-H1 sequence is a Kabat CDR-H1 sequence comprising, consisting of, or consisting essentially of SEQ ID NO: 117; the CDR-H2 sequence is a Kabat CDR-H2 sequence comprising, consisting of, or consisting essentially of SEQ ID NO: 235; the CDR-H3 sequence is a CDR-H3 sequence comprising, consisting of, or consisting essentially of SEQ ID NO: 294; the CDR-L1 sequence is a CDR-L1 sequence comprising, consisting of, or consisting essentially of SEQ ID NOs: 299-301; the CDR-L2 sequence is a CDR-L2 sequence comprising, consisting of, or consisting essentially of SEQ ID NOs: 302-304; and the CDR-L3 sequence is a CDR-L3 sequence comprising, consisting of, or consisting essentially of SEQ ID NOs: 305-307.

6. Germline

In some embodiments, the antibody that specifically binds folate receptor alpha is an antibody comprising a variable region that is encoded by a particular germline gene, or a variant thereof. The illustrative antibodies provided herein comprise variable regions that are encoded by the heavy chain variable region germline genes VH1-18, VH3-33, VH2-5, VH2-70, and VH4-30-4, or variants thereof; and the light chain variable region germline genes Vκ1-5, Vκ3-11, Vκ2-20, Vκ1-33, and Vκ1-16, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H1$, $V_H2$, $V_H3$, or $V_H4$ families, or a variant thereof. In some embodiments, a CDR-L sequence provided herein may be combined with a variable region encoded by a variable region germline gene selected from the Vκ1, Vκ2, or Vκ3, or a variant thereof.

7. Affinity

In some embodiments, the affinity of the antibody for folate receptor alpha as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-9}$ M and $10^{-10}$ M.

In some embodiments, the affinity of the antibody for human folate receptor alpha, as determined by surface plasmon resonance at 25° C., and as indicated by $K_D$, is from about $0.36 \times 10^{-9}$ M to about $2.21 \times 10^{-9}$ M. In some embodiments, the affinity of the antibody for human folate receptor alpha, as determined by surface plasmon resonance at 25° C., and as indicated by $K_D$, is from about $8.55 \times 10^{-10}$ M to about $1.70 \times 10^{-8}$ M. In some embodiments, the affinity of the antibody for human folate receptor alpha, as determined by surface plasmon resonance at 25° C., and as indicated by $K_D$, is from about $5.71 \times 10^{-10}$ M to about $2.58 \times 10^{-8}$ M. In some embodiments, the affinity of the antibody for human folate receptor alpha is about any of the $K_D$ values reported for human folate receptor alpha in the examples below.

In some embodiments the antibody has a $k_a$ of at least about $10^4$ $M^{-1} \times sec^{-1}$. In some embodiments the antibody has a $k_a$ of at least about $10^5$ $M^{-1} \times sec^{-1}$. In some embodiments the antibody has a $k_a$ of at least about $10^6$ $M^{-1} \times sec^{-1}$. In some embodiments the antibody has a $k_a$ of at least about $10^7$ $M^{-1} \times sec^{-1}$. In some embodiments the antibody has a $k_a$ of at least about $10^8$ $M^{-1} \times sec^{-1}$. In some embodiments the antibody has a $k_a$ of at least about $10^9$ $M^{-1} \times sec^{-1}$. In some embodiments the antibody has a $k_a$ of between about $10^4$ $M^{-1} \times sec^{-1}$ and about $10^{10}$ $M^{-1} \times sec^{-1}$. In some embodiments the antibody has a $k_a$ of between about $10^5$ $M^{-1} \times sec^{-1}$ and about $10^{10}$ $M^{-1} \times sec^{-1}$. In some embodiments the antibody has a $k_a$ of between about $10^6$ $M^{-1} \times sec^{-1}$ and about $10^{10}$ $M^{-1} \times sec^{-1}$. In some embodiments the antibody has a $k_a$ of between about $10^7$ $M^{-1} \times sec^{-1}$ and about $10^{10}$ $M^{-1} \times sec^{-1}$.

In some embodiments the antibody has a $k_a$ when associating with human folate receptor alpha, as determined by surface plasmon resonance at 25° C., of from about $4.44 \times 10^5$ $M^{-1} \times sec^{-1}$ to about $1.61 \times 10^5$ $M^{-1} \times sec^{-1}$. In some embodiments the antibody has a $k_a$ when associating with human folate receptor alpha, as determined by surface plasmon resonance at 25° C., of from about $2.90 \times 10^5$ $M^{-1} \times sec^{-1}$ to about $9.64 \times 10^9$ $M^{-1} \times sec^{-1}$. In some embodiments the antibody has a $k_a$ when associating with human folate receptor alpha of about any of the $k_a$ values reported for human folate receptor alpha in the examples below.

In some embodiments the antibody has a $k_d$ of about $10^{-5}$ $sec^{-1}$ or less. In some embodiments the antibody has a $k_d$ of about $10^{-4}$ $sec^{-1}$ or less. In some embodiments the antibody has a $k_d$ of about $10^{-3}$ $sec^{-1}$ or less. In some embodiments the antibody has a $k_d$ of between about $10^{-2}$ $sec^{-1}$ and about $10^{-5}$ $sec^{-1}$. In some embodiments the antibody has a $k_d$ of between about $10^{-2}$ $sec^{-1}$ and about $10^{-4}$ $sec^{-1}$. In some embodiments the antibody has a $k_d$ of between about $10^{-3}$ $sec^{-1}$ and about $10^{-5}$ $sec^{-1}$.

In some embodiments the antibody has a $k_d$ when dissociating from human folate receptor alpha, as determined by surface plasmon resonance at 25° C., of from about $8.66 \times 10^{-4}$ $sec^{-1}$ to about $1.08 \times 10^{-2}$ $sec^{-1}$. In some embodiments the antibody has a $k_d$ when dissociating from human folate receptor alpha, as determined by surface plasmon resonance at 25° C., of from about $2.28 \times 10^{-4}$ $sec^{-1}$ to about $4.82 \times 10^1$ $sec^{-1}$. In some embodiments the antibody has a $k_d$ when dissociating from human folate receptor alpha of about any of the $k_d$ values reported for human folate receptor alpha in the examples below.

In some embodiments, the affinity of the antibody for cynomolgus folate receptor alpha, as determined by surface plasmon resonance at 25° C., and as indicated by $K_D$, is from about $0.19 \times 10^{-9}$ M to about $2.84 \times 10^{-9}$ M. In some embodiments, the affinity of the antibody for cynomolgus folate receptor alpha is about any of the $K_D$ values reported for cynomolgus folate receptor alpha in the examples below.

In some embodiments, the affinity of the antibody for mouse folate receptor alpha, as determined by surface plasmon resonance at 25° C., and as indicated by $K_D$, is from about $0.5 \times 10^{-9}$ M to about $9.07 \times 10^{-8}$ M. In some embodiments, the affinity of the antibody for mouse folate receptor alpha is about any of the $K_D$ values reported for mouse folate receptor alpha in the examples below.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

8. Epitope Bins

In some embodiments, the antibody binds the same epitope as an antibody encompassing any of SEQ ID NOs: 308-366. In some embodiments, the antibody binds the same epitope as an antibody comprising any of the $V_H$-$V_L$ pairs, above. In some embodiments, the antibody competes for epitope binding with an antibody encompassing any of SEQ ID NOs: 308-366. In some embodiments, the antibody competes for epitope binding with an antibody comprising any of the $V_H$-$V_L$ pairs, above.

9. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

10. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc comprises one or more modifications in at least one of the $C_H3$ sequences. In some embodiments, the Fc comprises one or more modifications in at least one of the $C_H2$ sequences. For example, the Fc can include one or modifications selected from the group consisting of: V262E, V262D, V262K, V262R, V262S, V264S, V303R, and V305R. In some embodiments, an Fc is a single polypeptide. In some embodiments, an Fc is multiple peptides, e.g., two polypeptides. Exemplary modifications in the Fc region are described, for example, in International Patent Application No. PCT/US2017/037545, filed Jun. 14, 2017.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, Ann. Rev. Immunol., 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., Proc. Natl. Acad. Sci. U.S.A., 1986, 83:7059-7063; Hellstrom et al., Proc. Natl. Acad. Sci. U.S.A., 1985, 82:1499-1502; and Bruggemann et al., J. Exp. Med., 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. Proc. Natl. Acad. Sci. U.S.A., 1998, 95:652-656, incorporated by reference in its entirety.

C1q binding assays may also be carried out to confirm that the antibody is unable to bind C1 q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., J. Immunol. Methods, 1996, 202:163-171; Cragg et al., Blood, 2003, 101: 1045-1052; and Cragg and Glennie, Blood, 2004, 103:2738-2743; each of which is incorporated by reference in its entirety.

FcRn binding and in vivo clearance (half-life determination) can also be measured, for example, using the methods described in Petkova et al., Intl. Immunol., 2006, 18:1759-1769, incorporated by reference in its entirety.

11. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido and alkynyl. Modified amino acids are also described in, for example, WO 2013/185115 and WO 2015/006555, each of which is incorporated herein by reference in its entirety.

In certain embodiments, the amino acid residue is according to any of the following formulas:

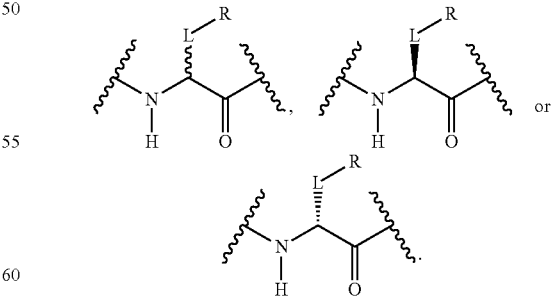

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^1NR^2R^3$, $R^1C(=O)R^2$, $R^1C(=O)OR^2$, $R^1N_3$, $R^1C(\equiv CH)$. In these embodiments, $R^1$ is selected from the group consisting of a bond, alkylene, heteroalkylene, arylene, heteroarylene. $R^2$ and $R^3$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-α-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenyl-alanine, isopropyl-L-phenylalanine, p-azido-methyl-L-phenyl alanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. One particularly useful non-natural amino acid is p-azido phenylalanine. This amino acid residue is known to those of skill in the art to facilitate Huisgen [3+2] cyloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the cognate reactive group (e.g., alpha carbon) of the non-natural amino acid. Useful divalent linkers are a bond, alkylene, substituted alkylene, heteroalkylene, substituted heteroalkylene, arylene, substituted arylene, heteroarylene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

In particular embodiments, the non-natural amino acid is selected from the group consisting of:

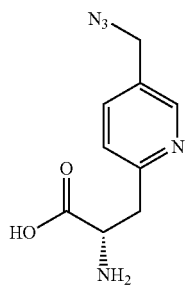
(1)

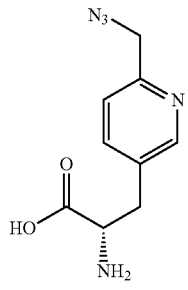
(2)

(3)

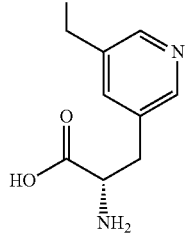
(4)

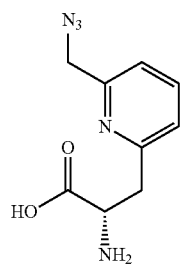
(5)

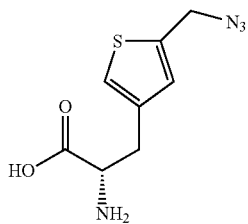
(6)

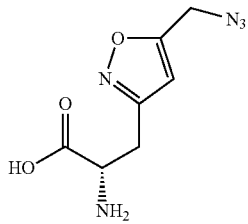
(7)

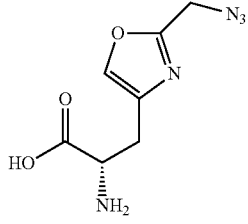
(8)

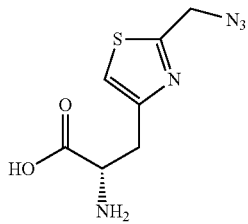
(9)

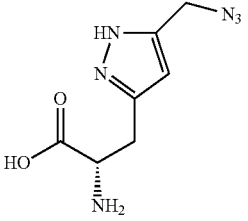
(10)

(11) 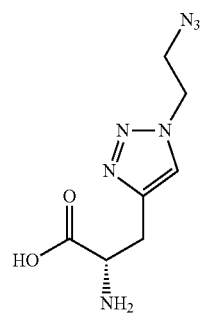
(12) 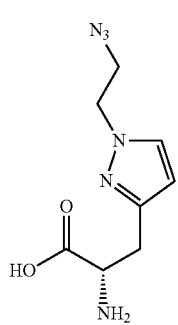
(13) 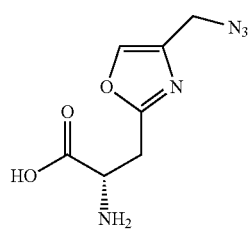
(14) 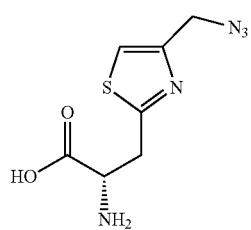
(15) 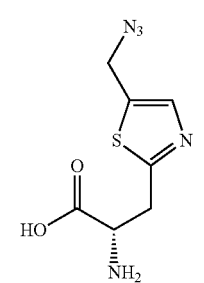
(16) 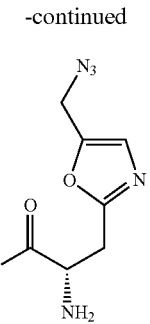
(17) 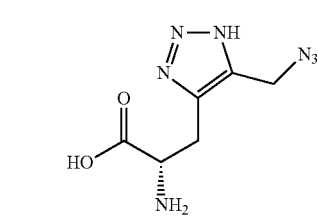
(18) 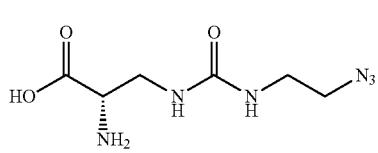
(19) 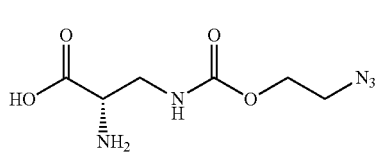
(20) 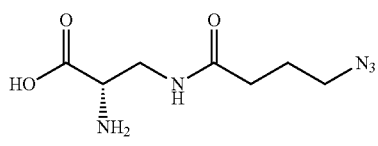
(21) 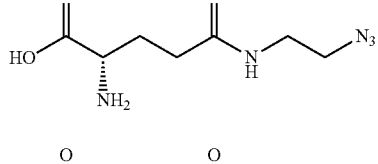
(22) 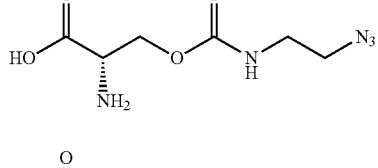
(23) 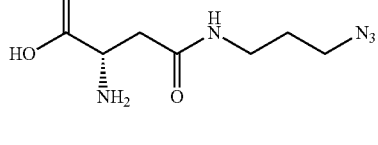
(24) 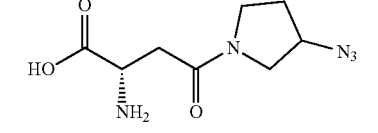

-continued
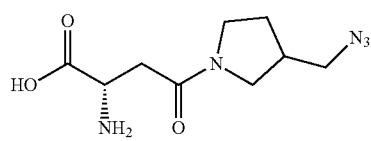 (25)
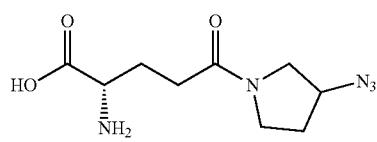 (26)
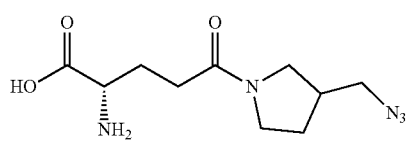 (27)
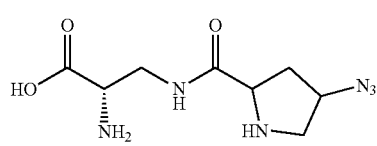 (28)
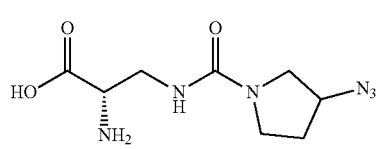 (29)
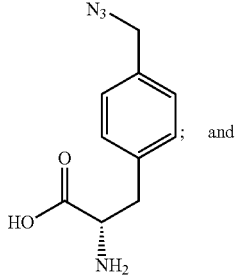 (30)
; and
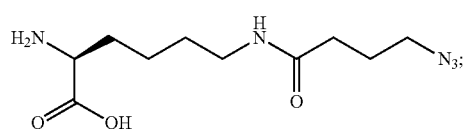 (31)
or a salt thereof. Such non-natural amino acids may be in the form of a salt, or may be incorporated into a non-natural amino acid polypeptide, polymer, polysaccharide, or a polynucleotide and optionally post translationally modified.
In certain embodiments, the modified amino acid is according to any of formulas 51-62:
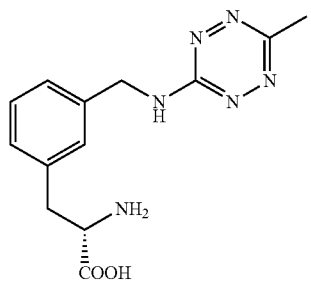 (51)
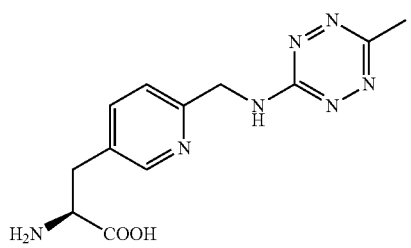 (52)
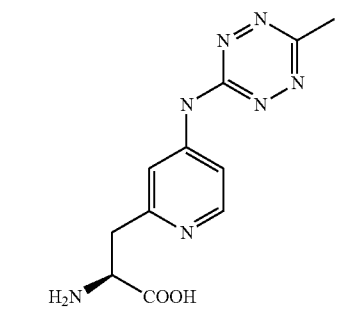 (53)
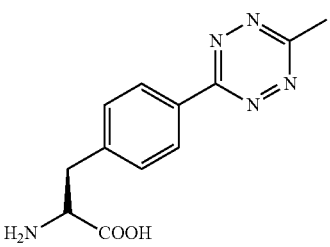 (54)
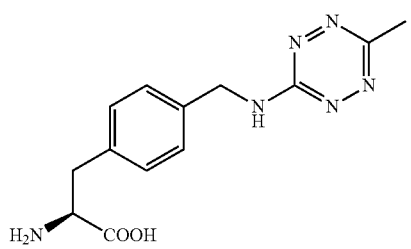 (55)
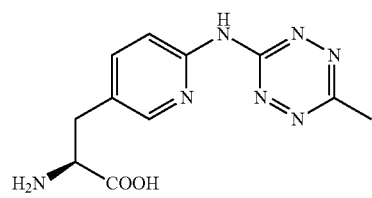 (56)

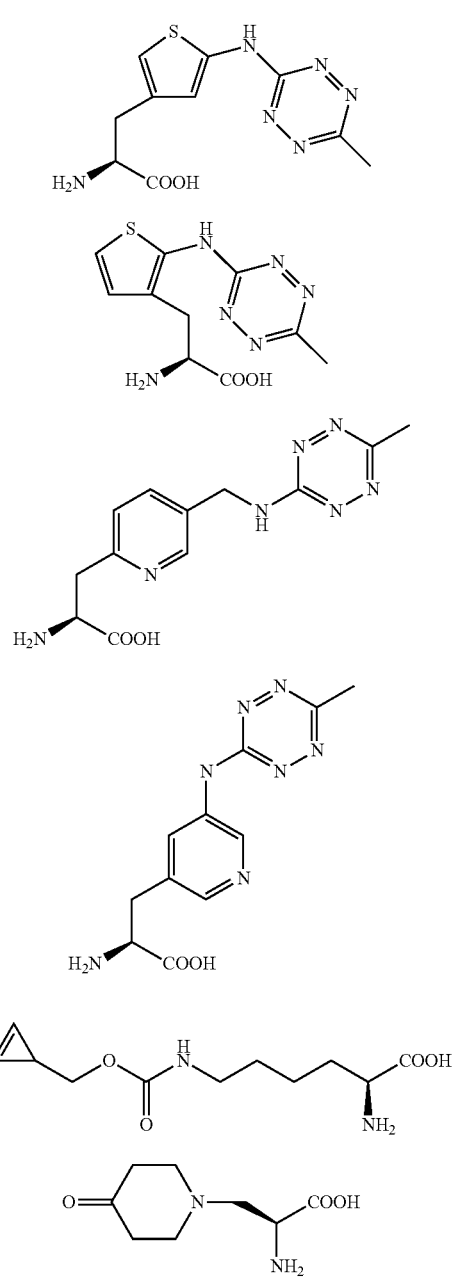

or a salt thereof.

In certain embodiments, the non-natural amino acid is selected from the group consisting of compounds 30, 53, 56, 59, 60, 61, and 62 above. In certain embodiments, the non-natural amino acid is compound 30. In certain embodiments, the non-natural amino acid is compound 56. In some embodiments, the non-natural amino acid is compound 61. In some embodiments, the non-natural amino acid is compound 62.

12. Preparation of Antibody Conjugates 12.1. Antigen Preparation

The FOLR1 protein to be used for isolation of the antibodies may be intact FOLR1 or a fragment of FOLR1. The intact FOLR1 protein, or fragment of FOLR1, may be in the form of an isolated protein or protein expressed by a cell. Other forms of FOLR1 useful for generating antibodies will be apparent to those skilled in the art.

12.2. Monoclonal Antibodies

Monoclonal antibodies may be obtained, for example, using the hybridoma method first described by Kohler et al., Nature, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., Monoclonal Antibodies: Principles and Practice 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, J. Immunol., 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., E. coli), yeast (e.g., Saccharomyces or Pichia sp.), COS cells, Chinese hamster ovary (CHO) cells, or myeloma cells that do not otherwise produce antibody, to produce the monoclonal antibodies.

12.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370; each of which is incorporated by reference in its entirety.

12.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

12.5. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, an anti-FOLR1 conjugate is prepared by contacting an anti-FOLR1 antibody as disclosed herein with a linker precursor having a structure of any of (A)-(L):

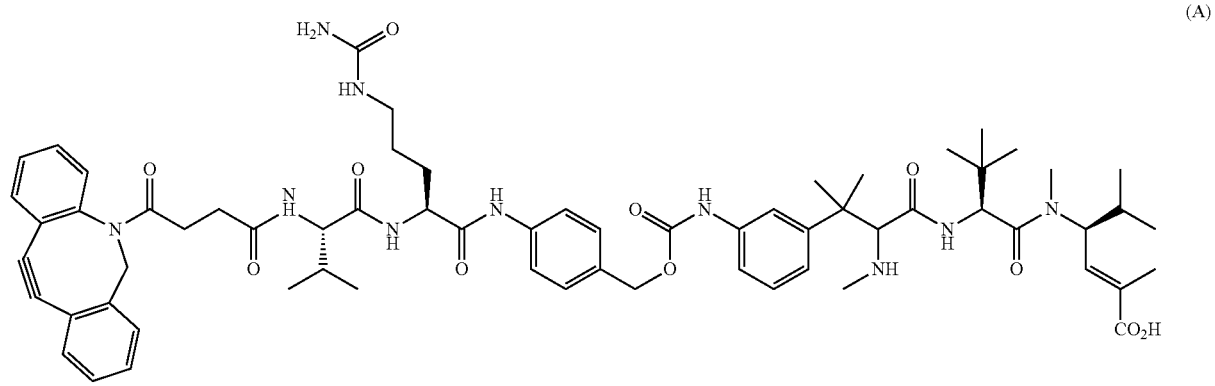

(A)

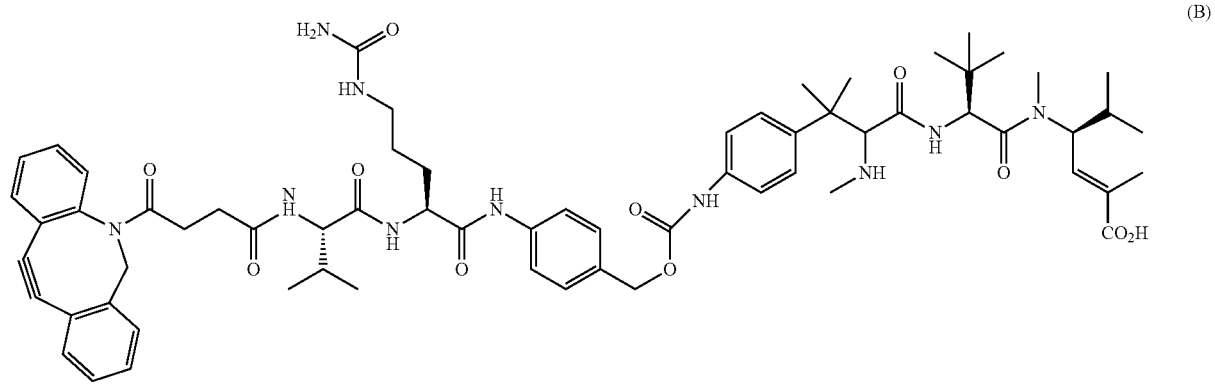

(B)

-continued
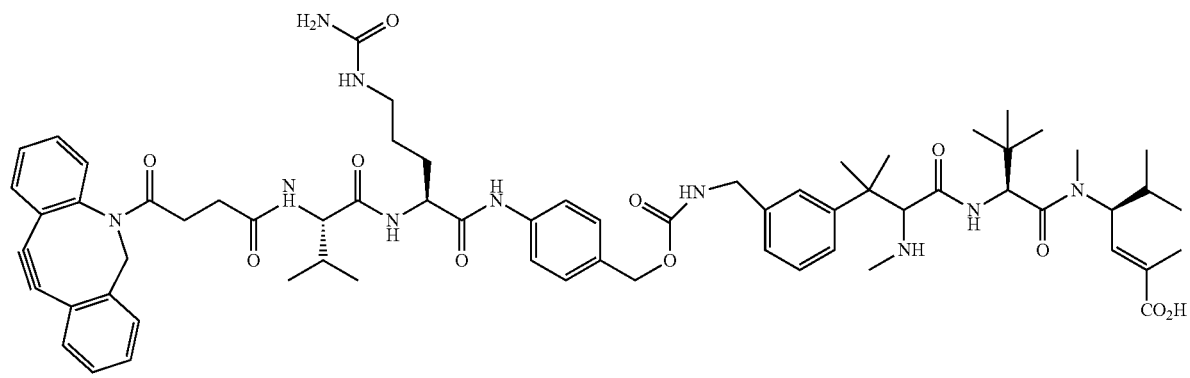
(C)
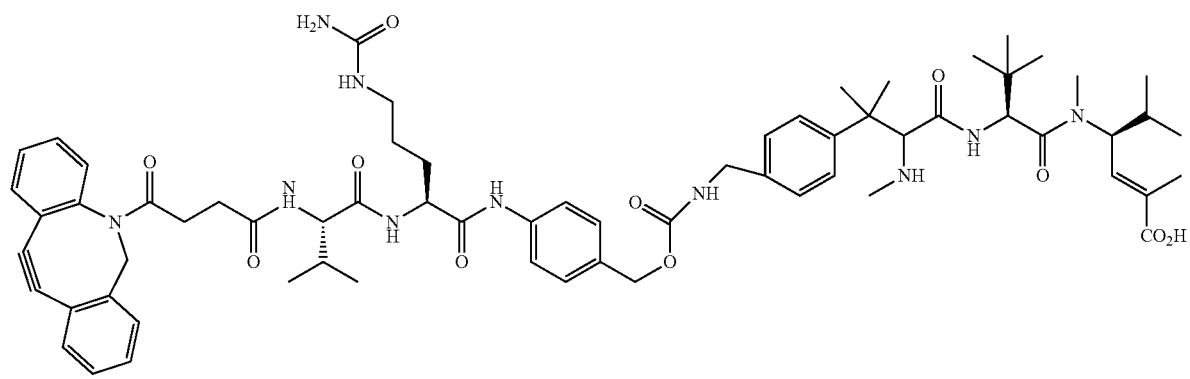
(D)
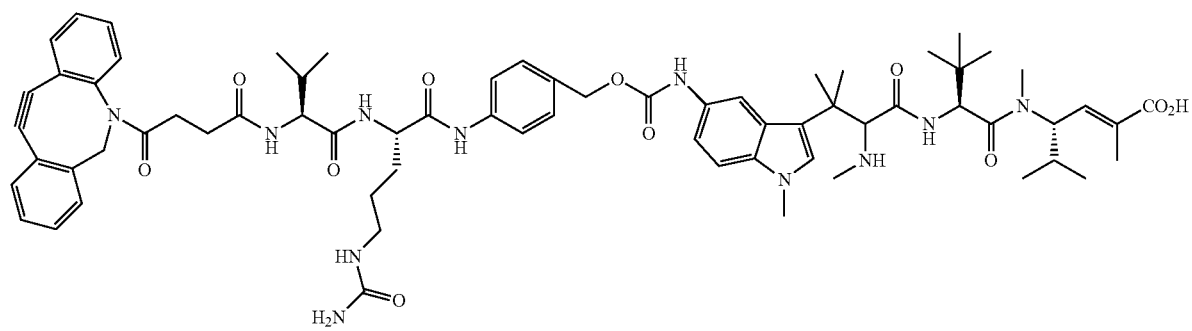
(E)
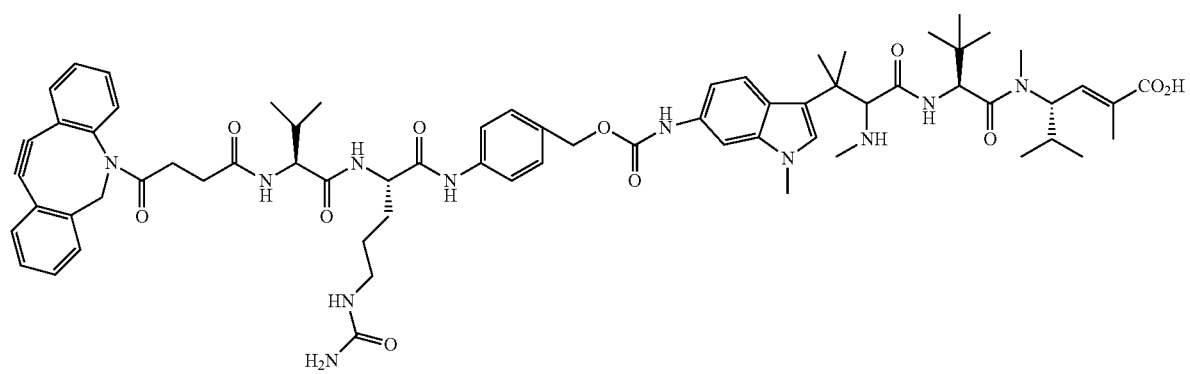
(F)

-continued
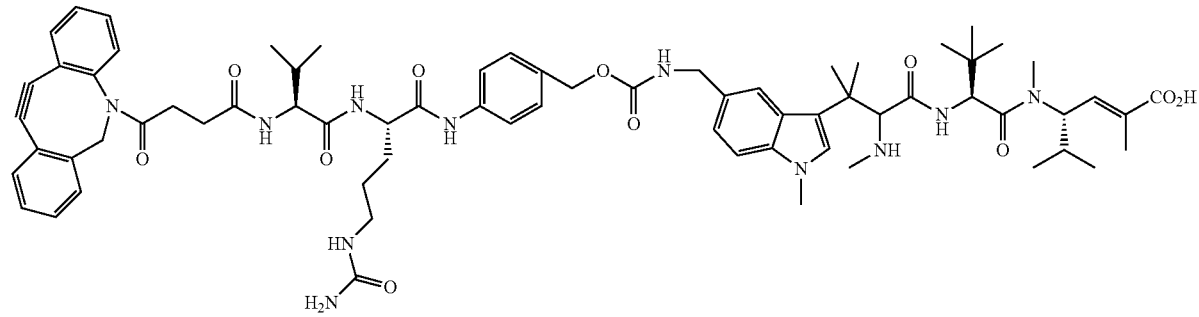
(G)
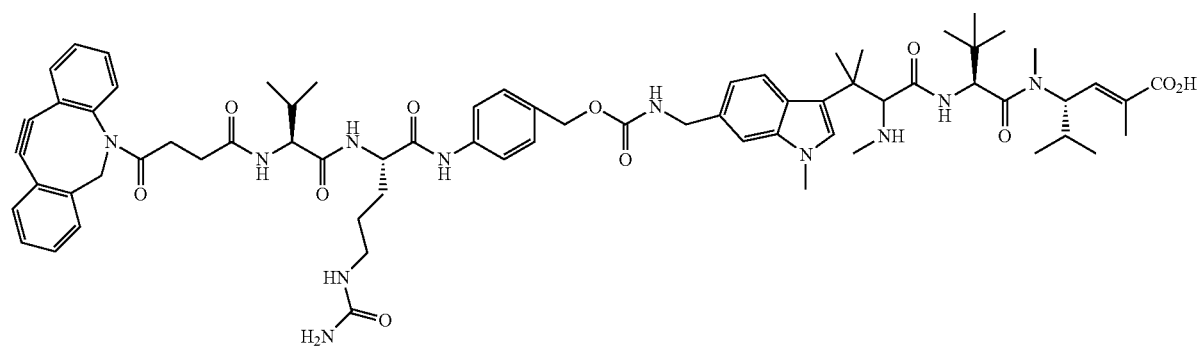
(H)
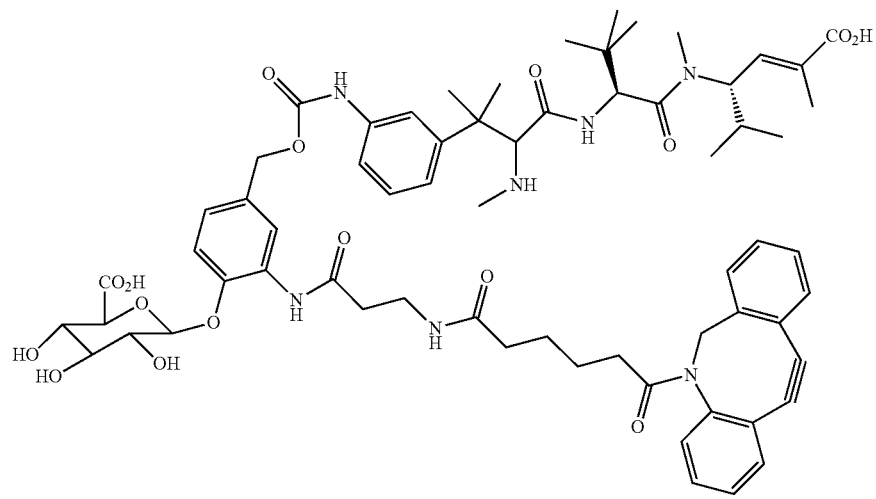
(I)
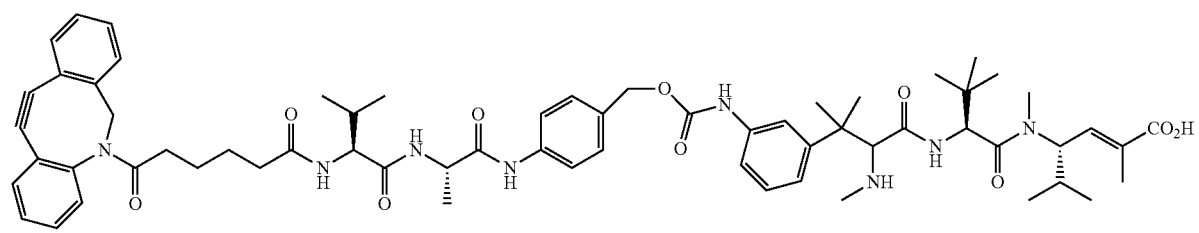
(J)

-continued
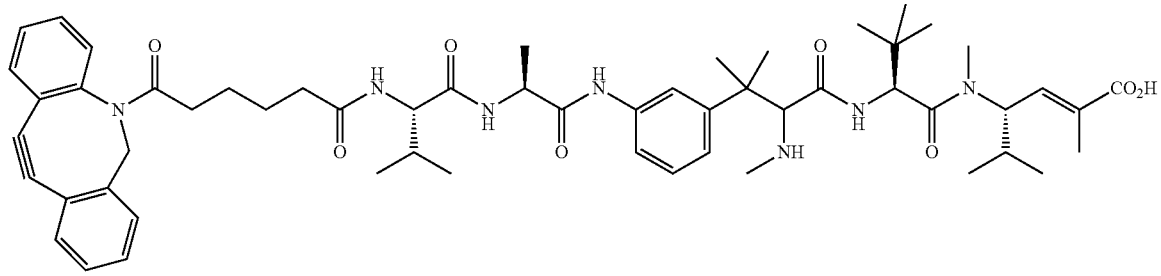
(K)
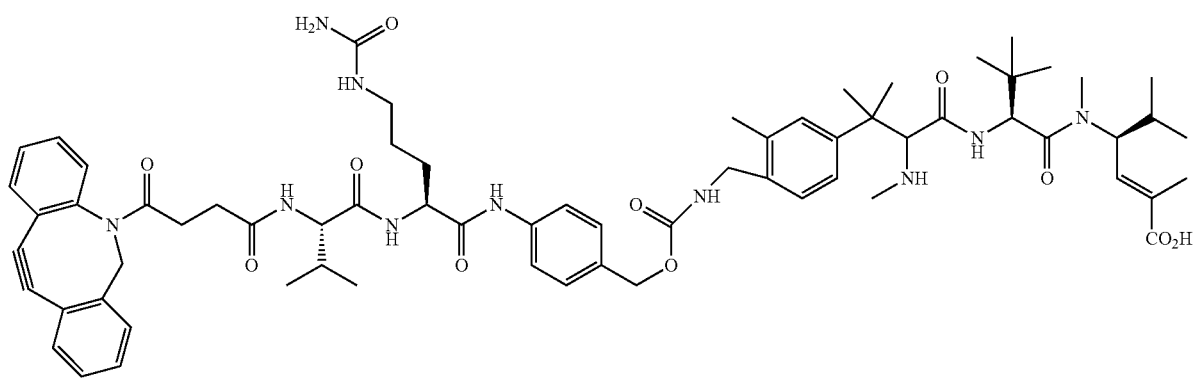
(L)
In some embodiments, the stereochemistry of the linker precursors identified as (A)-(L) is identified with R and S notation for each chiral center, from left to right as depicted in formulas (A1)-(L1) and (A2)-(L2) illustrated below:
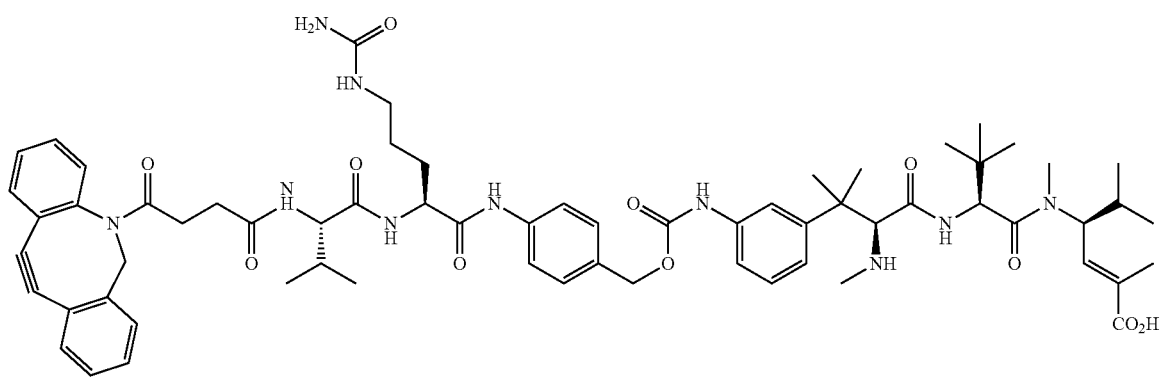
(A1)
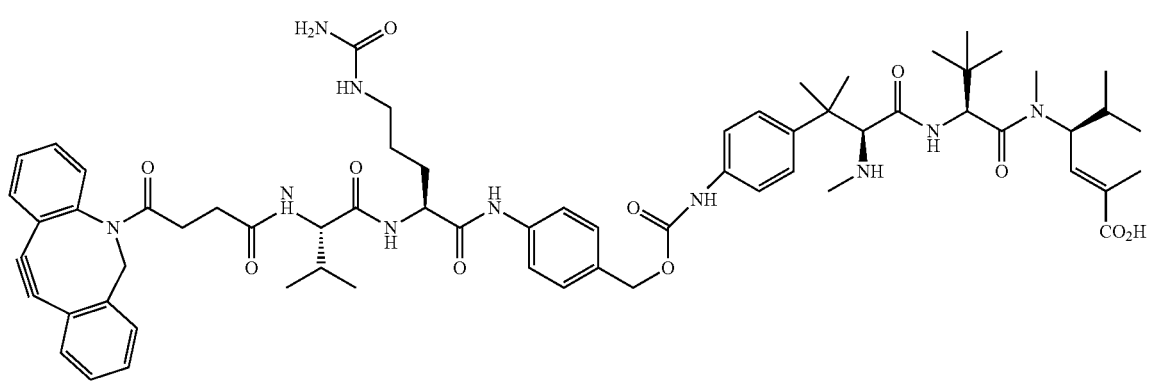
(B1)

-continued
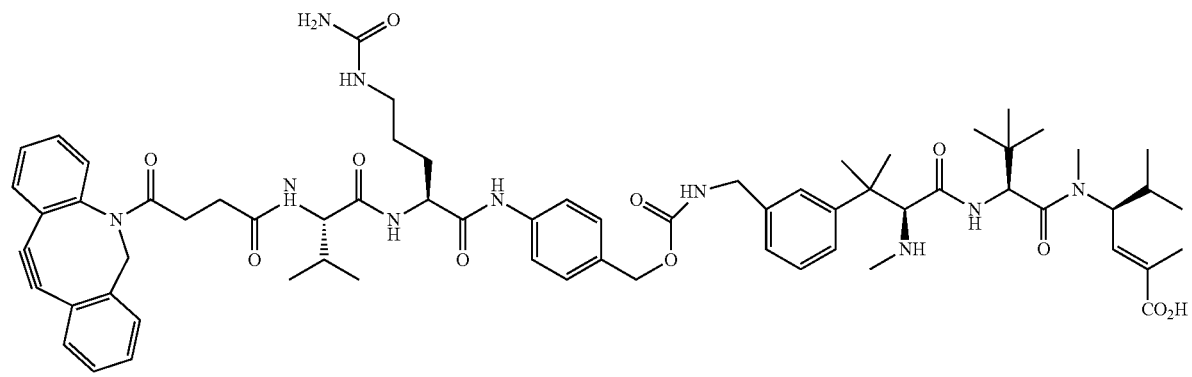
(C1)
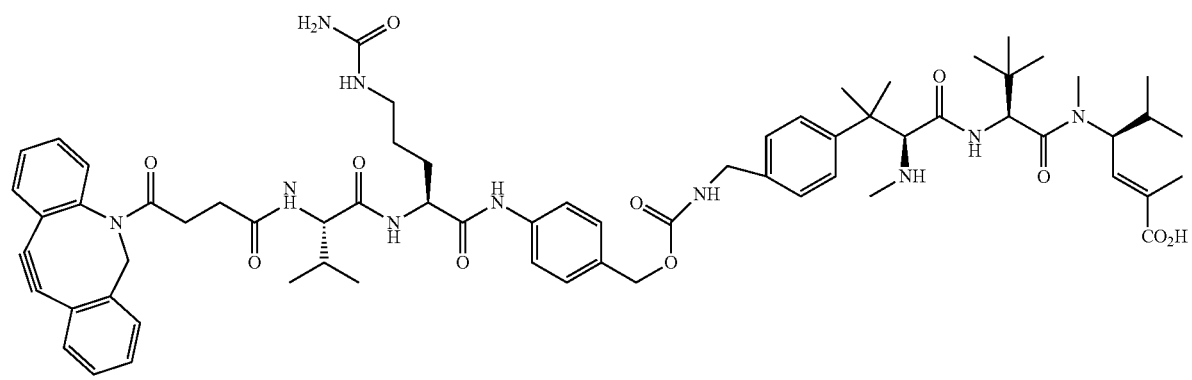
(D1)
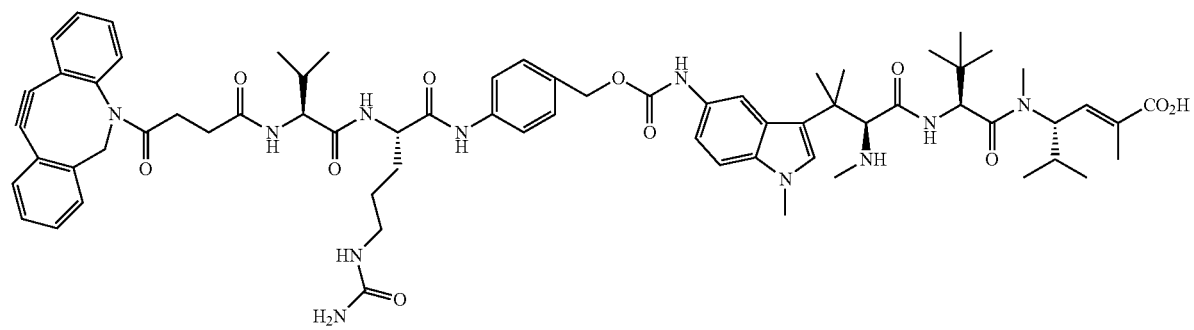
(E1)
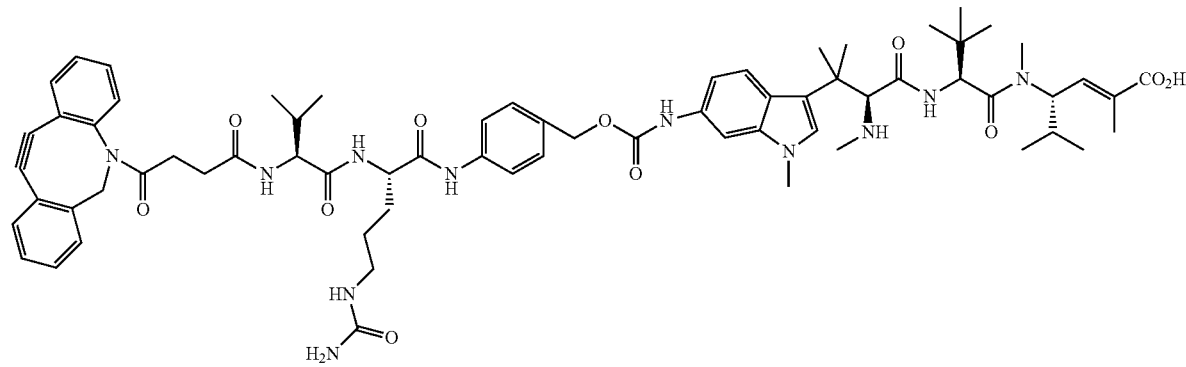
(F1)

-continued
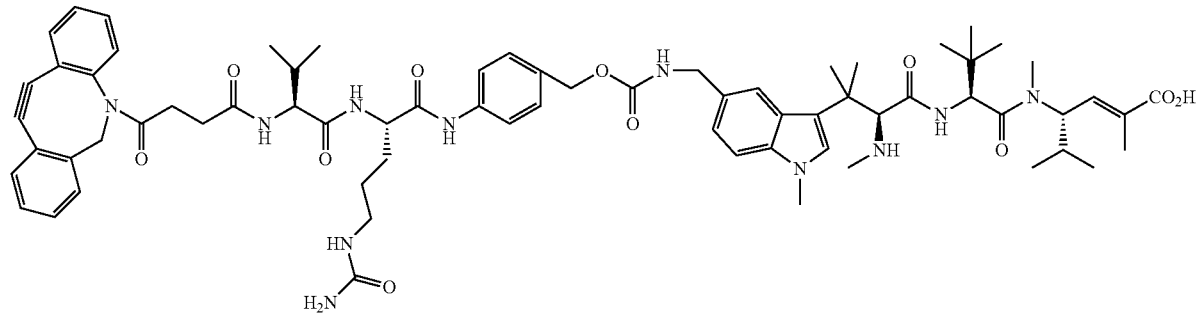
(G1)
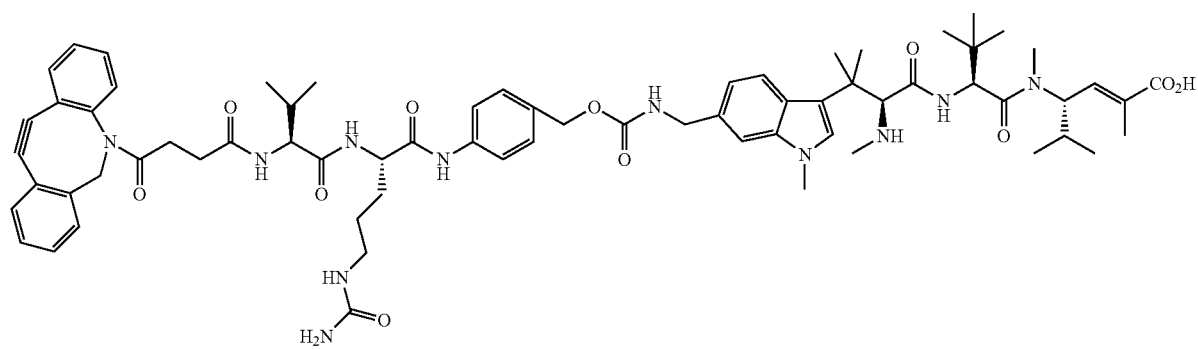
(H1)
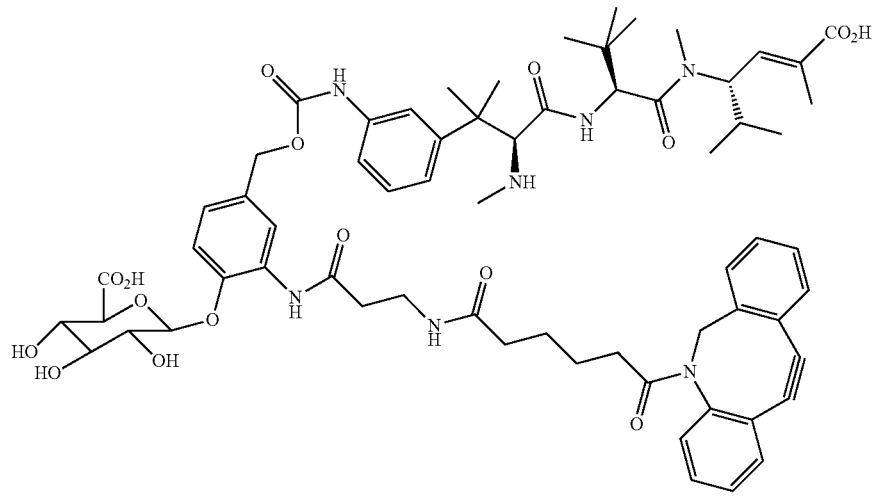
(I1)
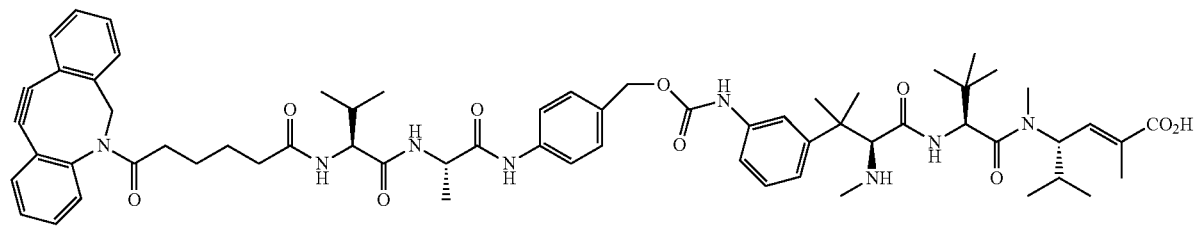
(J1)

-continued
(K1)
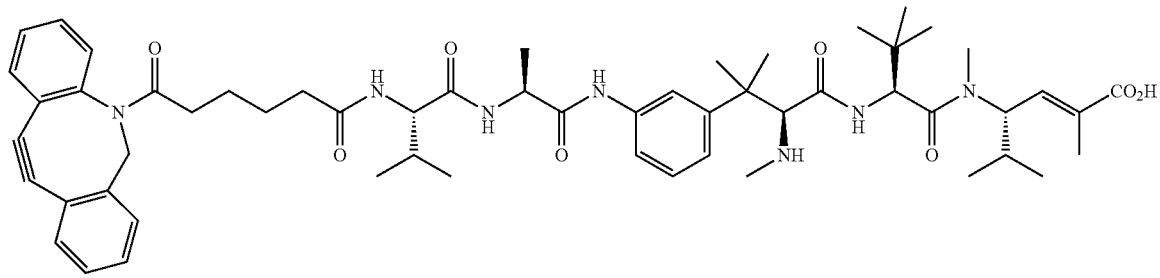
(L1)
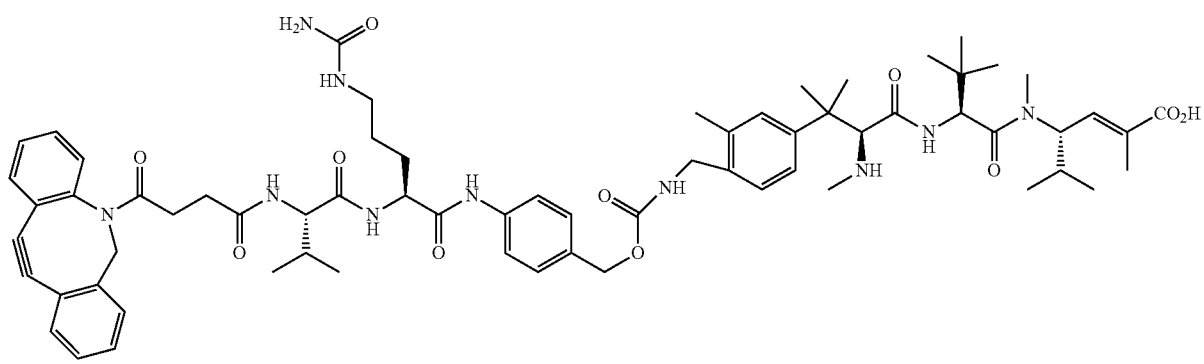
(A2)
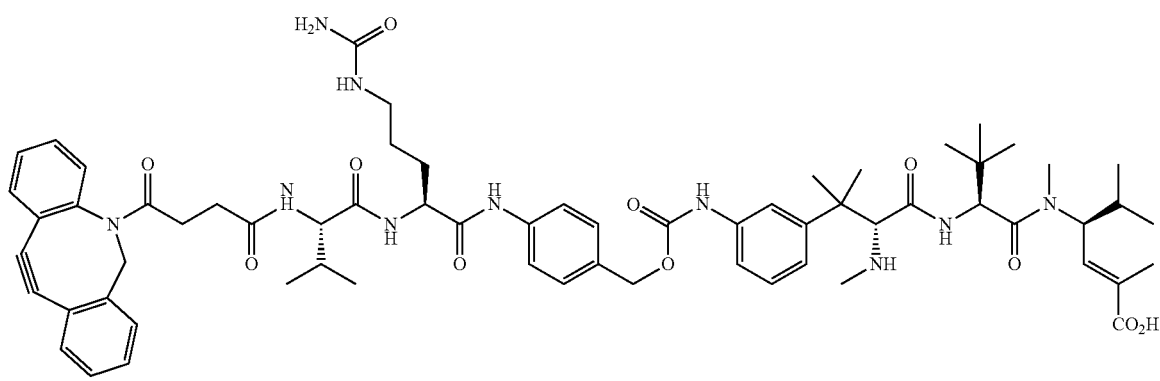
(B2)
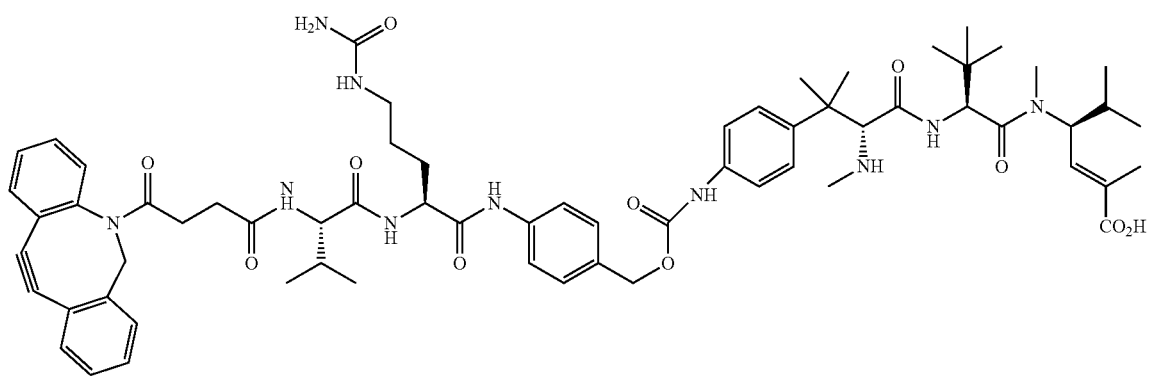

-continued
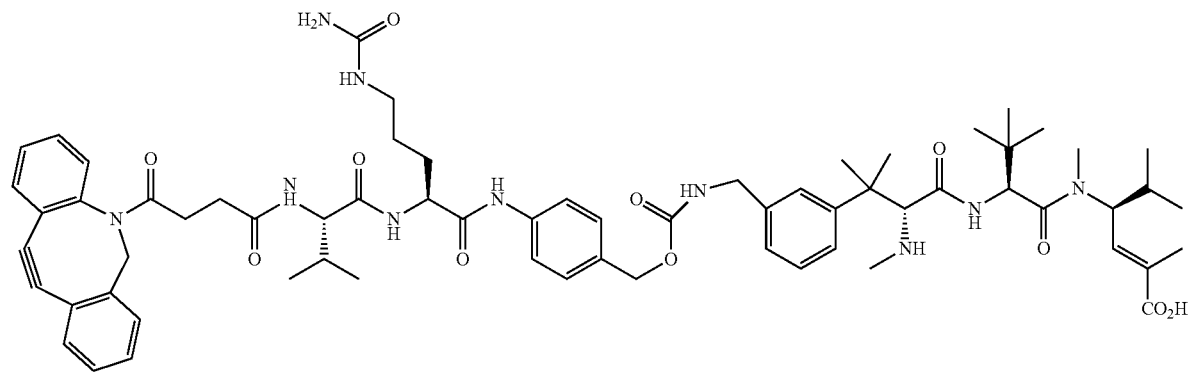
(C2)
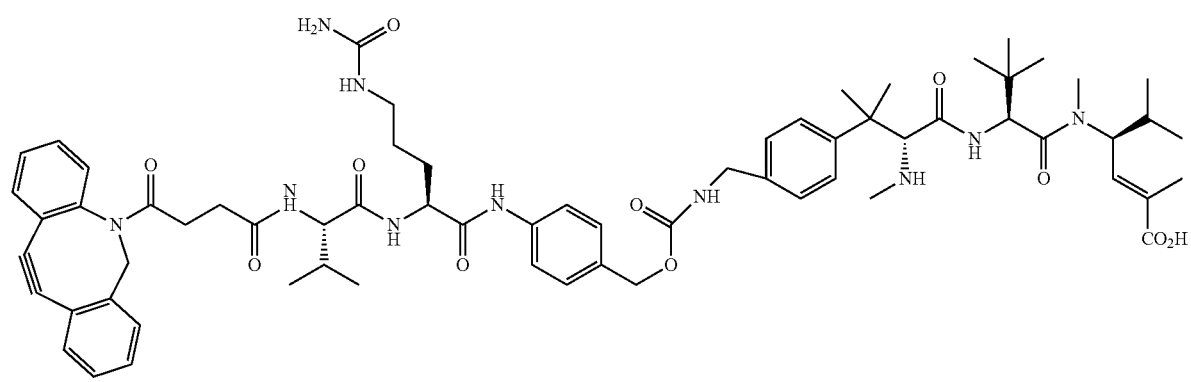
(D2)
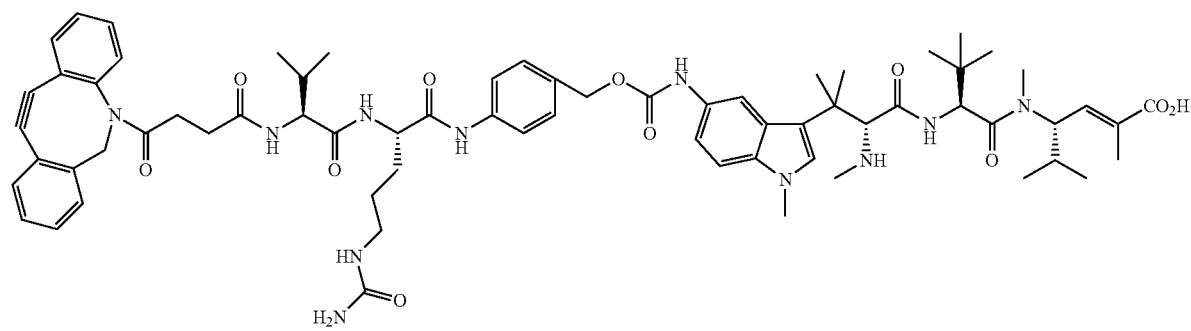
(E2)
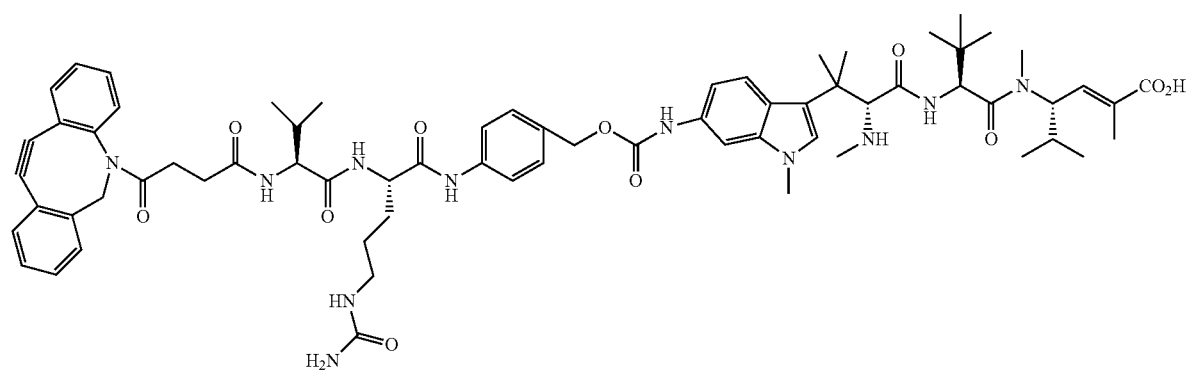
(F2)

-continued
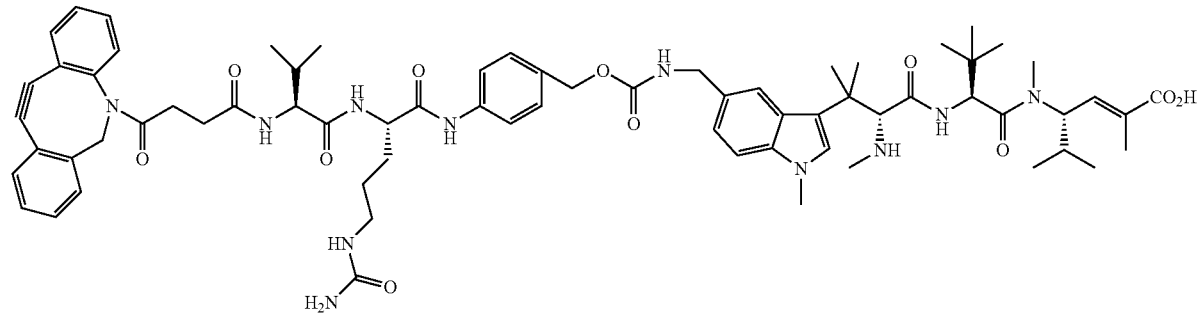
(G2)
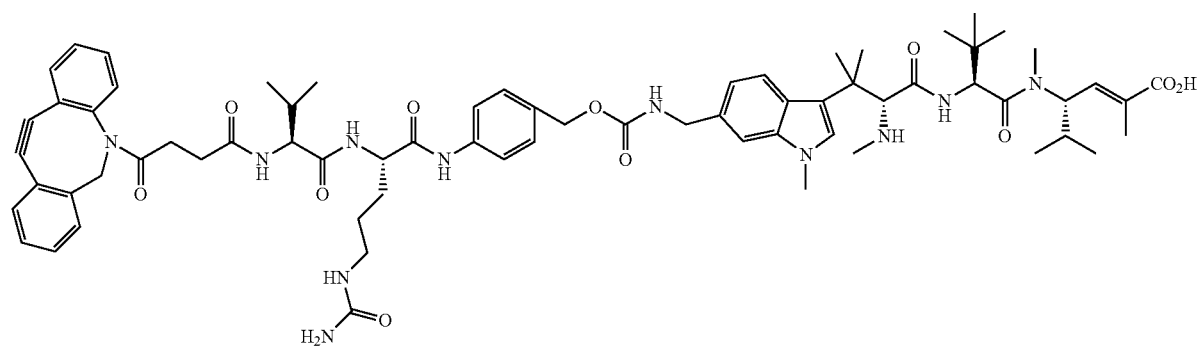
(H2)
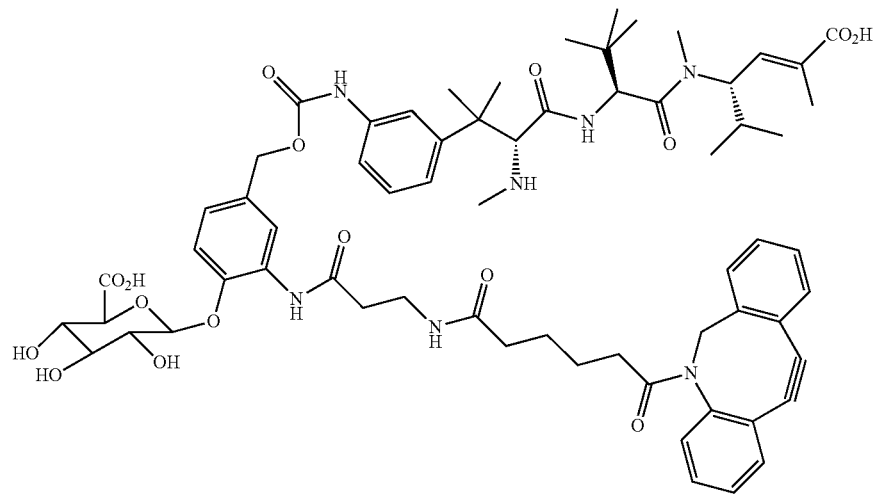
(I2)
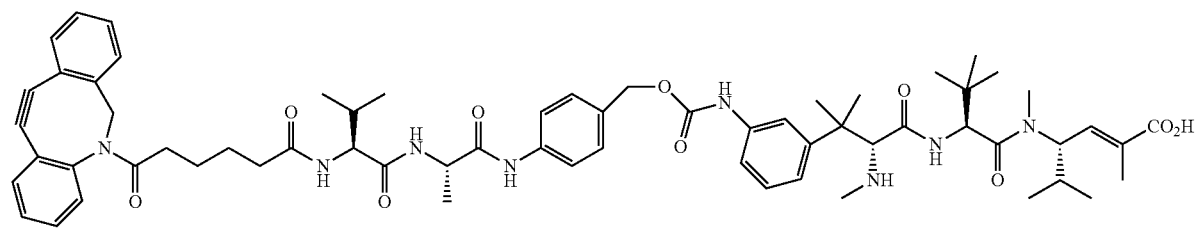
(J2)

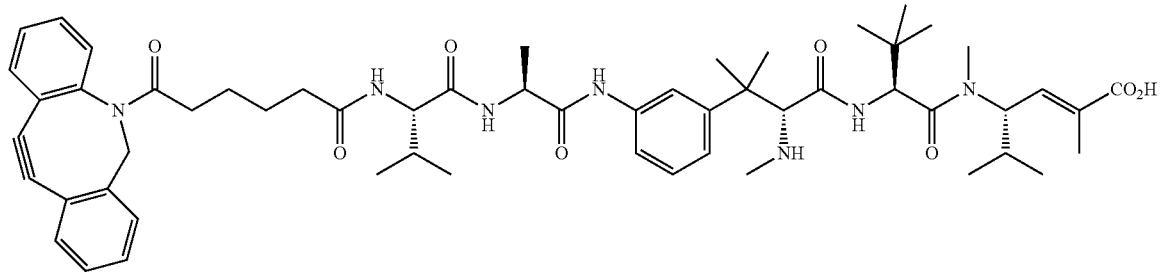

(K2)

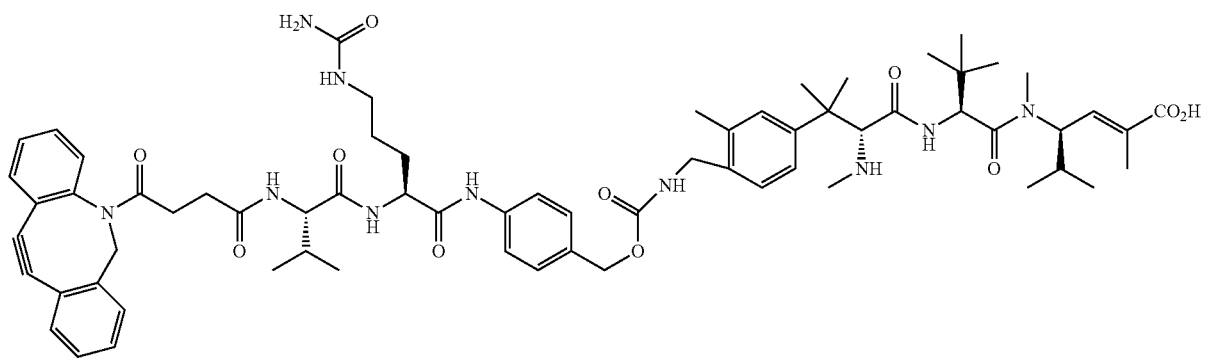

(L2)

13. Vectors, Host Cells, and Recombinant Methods

Embodiments are also directed to the provision of isolated nucleic acids encoding anti-FOLR1 antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella, Bacilli* (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-FOLR1 antibody-encoding vectors. *Saccharomyces cerevisiae*, or common baker's yeast, is a commonly used lower eukaryotic host microorganism. However, a number of other genera, species, and strains are available and useful, such as *Spodoptera frugiperda* (e.g., SF9), *Schizosaccharomyces pombe, Kluyveromyces* (*K. lactis, K. fragilis, K. bulgaricus K. wickeramii, K. waltii, K. drosophilarum, K. thermotolerans,* and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium,* and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-FOLR1 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low. The antibodies produced in a cell-free system may be aglycosylated depending on the source of the cells.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

14. Pharmaceutical Compositions and Methods of Administration

The antibody conjugates provided herein can be formulated into pharmaceutical compositions using methods available in the art and those disclosed herein. Any of the antibody conjugates provided herein can be provided in the appropriate pharmaceutical composition and be administered by a suitable route of administration.

The methods provided herein encompass administering pharmaceutical compositions comprising at least one antibody conjugate provided herein and one or more compatible and pharmaceutically acceptable carriers. In this context, the term "pharmaceutically acceptable" means approved by a regulatory agency of the Federal or a state government or listed in the U.S.

Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions or antibody conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof.

In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethyl-hexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

14.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

14.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody conjugate or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody conjugate provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody conjugate outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody conjugate or composition provided herein followed by one or more maintenance doses.

In certain embodiments, a dose of an antibody conjugate or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

14.3. Combination Therapies and Formulations

In certain embodiments, provided are compositions and therapeutic formulations comprising any of the antibody conjugates provided herein in combination with one or more chemotherapeutic agents disclosed herein, and methods of treatment comprising administering such combinations to subjects in need thereof. Examples of chemotherapeutic agents include, but are not limited to, Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammaI1, and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

In certain embodiments, provided are compositions and therapeutic formulations comprising any of the antibody conjugates provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L1 pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMP-224 (GlaxoSmithKline), MEDI0680/AMP-514 (AstraZeneca), PDR001 (Novartis), cemiplimab, TSR-042 (Tesaro), Tizlelizumab/BGB-A317 (Beigene), CK-301 (Checkpoint Therapeutics), BMS-936559 (Bristol-Meyers Squibb), camrelizumab, sintilimab, toripalimab, genolimzumab, and A167 (Sichuan Kelun-Biotech Biopharmaceutical). In some embodiments, the one or more PD-1 or PD-L inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), (LLY) AM0001 (Armo Biosciences), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (Pieris Pharmaceuticals), ALPN-202 (Alpine Immune Science), TSR-075 (Tesaro/Anaptys Bio), MCLA-145 (Merus), MGD013 (Macrogenics), MGD019 (Macrogenics). In some embodiments, the one or more PD-1 or PD-L1 inhibitors are selected from an anti-PD1 monospecific or bi-specific antibody described in, for example, WO 2016/077397, WO 2018/156777, and International Application No. PCT/US2013/034213, filed May 23, 2018.

The agents administered in combination with the antibody conjugates disclosed herein can be administered just prior to, concurrent with, or shortly after the administration of the antibody conjugates. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents, PD-1 inhibitors, or PD-L1 inhibitors disclosed herein.

15. Therapeutic Applications

For therapeutic applications, the antibody conjugates provided herein can be administered to a mammal, generally a human, in a pharmaceutically acceptable dosage form such as those known in the art and those discussed above. For example, the antibody conjugates may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The antibody conjugates provided herein may be useful for the treatment of any disease or condition involving folate receptor alpha (FOLR1). In some embodiments, the disease or condition is a disease or condition that can be diagnosed by overexpression of folate receptor alpha. In some embodiments, the disease or condition is a disease or condition that can benefit from treatment with an anti-folate receptor alpha antibody. In some embodiments, the disease or condition is a cancer.

Any suitable cancer may be treated with the antibody conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer (including triple-negative breast cancer, or TNBC), bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fallopian tube carcinoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer (NSCLC), oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, primary peritoneal carcinoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibody conjugates provided herein is gastric cancer, colorectal cancer, renal cell carcinoma, cervical cancer, non-small cell lung carcinoma, ovarian cancer, uterine cancer, fallopian tube carcinoma, primary peritoneal carcinoma, uterine corpus carcinoma, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is triple-negative breast cancer (TNBC). In some embodiments, the disease is lung cancer. In some embodiments, the disease is non-small cell lung cancer (NSCLC). In some embodiments, the disease is head and neck cancer. In some embodiments, the disease is renal cell carcinoma. In some embodiments, the disease is brain carcinoma. In some embodiments, the disease is endometrial cancer.

16. Diagnostic Applications

In some embodiments, the antibody conjugates provided herein are used in diagnostic applications. For example, an anti-FOLR1 antibody conjugate may be useful in assays for FOLR1 protein. In some aspects the antibody conjugate can be used to detect the expression of FOLR1 in various cells and tissues. These assays may be useful, for example, in making a diagnosis and/or prognosis for a disease, such as a cancer.

In some diagnostic and prognostic applications, the antibody conjugate may be labeled with a detectable moiety. Suitable detectable moieties include, but are not limited to radioisotopes, fluorescent labels, and enzyme-substrate labels. In another embodiment, the anti-FOLR1 antibody conjugate need not be labeled, and the presence of the antibody conjugate can be detected using a labeled antibody which specifically binds to the anti-FOLR1 antibody conjugate.

17. Affinity Purification Reagents

The antibody conjugates provided herein may be used as affinity purification agents. In this process, the antibody conjugates may be immobilized on a solid phase such a resin or filter paper, using methods well known in the art. The immobilized antibody conjugate is contacted with a sample containing the folate receptor alpha protein (or fragment thereof) to be purified, and thereafter the support is washed with a suitable solvent that will remove substantially all the material in the sample except the folate receptor alpha protein, which is bound to the immobilized antibody. Finally, the support is washed with another suitable solvent, such as glycine buffer, pH 5.0 that will release the folate receptor alpha protein from the antibody.

18. Kits

In some embodiments, an anti-FOLR1 antibody conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-FOLR1 antibody conjugate. In some embodiments, the anti-FOLR1 antibody conjugate is provided in the form of a pharmaceutical composition.

EXAMPLES

Example 1

Generation and Primary Screening of Anti-FOLR1 Antibodies

Antibody Fab libraries were constructed using a standard overlap extension PCR protocol with mutagenic primers targeting complementary determining regions (CDRs). See Heckman and Pease, *Nat. Protoc.*, 2007, 2:924-932; Stafford et al., 2014, *Protein Eng. Des. Sel.* 27:97-109, both incorporated by reference in their entireties. Selections for novel antibodies were performed using standard ribosome display protocols. See Dreier and Plückthun, 2011, *Methods Mol Biol* 687:283-306, which is incorporated herein by reference in its entirety.

Initial antibody leads from ribosome display were derived from a naïve human library which was constructed by overlapping PCR using trastuzumab HC as the base template. CDRs H1 and H2 were randomized with the same design as described by Lee et al., *J. Mol. Biol.* 2004, 340:1073-1093 using oligonucleotides purchased from Integrated DNA Technologies. In this design, CDRs H1 and H2 closely match the observed amino acid distributions of natural human antibodies. CDR H3 was diversified using oligonucleotides incorporating trimer phosphoramidite mixtures (TRIMs) for amino acid randomization. The TRIM oligos were synthesized as described by Yagodkin A et al., *Nucleosides Nucleotides Nucleic Acids* 2007, 26:473-97. Specifically, six separate oligonucleotides containing TRIMs were used to make 6 separate H3 loop-lengths (13-18; as defined by Zemlin et al.) to match the most common loop lengths observed in the human repertoire. Together these loop lengths comprise approximately 54.5% of the naturally-occurring loop length variation in human IgGs as reported by Zemlin et al., *J. Mol. Biol.* 2003, 334:733-749. The frequency distribution of each amino acid was designed to closely match the observed distribution of amino acids in CDR H3 of human IgGs as reported by Zemlin et al. Altogether, the library closely matches natural human antibody variation which is known in the field to improve antibody stability and folding of antibodies as described by Zhai et al., *J Mol Biol.* 2011, 412:55-71. The heavy chain (HC) library was paired with a constant, unmodified trastuzumab light chain (LC) throughout the selection process as described by Stafford et al., *Protein Eng Des Sel* 2014, 27:97-109.

Affinity matured antibody leads (e.g., SRP 1848 antibodies, below) were derived from a focused library, biased towards two leads, which was constructed by overlapping PCR using "soft-randomized" oligonucleotides purchased from Eurofins MWG Operon. Soft-randomization is a process in which a biased distribution of nucleotides is used for each soft-randomized codon such that the parent amino acid sequence is coded more frequently than other amino acids ~30% of the time. Other amino acids are coded at each position but at a lower percentage. At each soft-randomized position, 70% of the parent nucleotide is mixed with 10% of the other three nucleotides. For the library, CDRs H1, H2, and H3 were soft-randomized simultaneously and selected by standard ribosome display protocols. As with the selection of initial leads, the affinity matured antibodies were paired with a constant, unmodified trastuzumab LC throughout the selection process as described by Stafford et al., *Protein Eng Des Sel* 2014, 27:97-109.

Selections for novel antibodies were performed using standard ribosome display protocols. See Dreier and Pluckthun, *Methods Mol. Biol.*, 2003, 687:283-306, Clifton, N.J., incorporated by reference in its entirety. Fab ribosome display selections were performed according to published protocols. See Stafford et al., 2014, *Protein Eng. Des. Sel.* 27:97-109; Hanes and Plückthun, *Proc. Natl. Acad. Sci. U.S.A.*, 1997, 94:4937-4942; both incorporated by reference in their entireties. After multiple rounds of selection, the DNA from RT-PCR output was cloned into an optimized vector for cell-free expression using standard molecular biology techniques. See Yin et al., mAbs, 2012, 4:217-225, incorporated by reference in its entirety. All constructs were HIS- and FLAG-tagged to streamline purification and testing during screening.

Libraries of antibody variants generated by selection workflow were transformed into *E. coli* and grown on agar plates with antibiotic (kanamycin). Individual colonies were grown in liquid broth (TB+kanamycin), and used as a template for DNA amplification via rolling circle amplification (RCA). The variants were then expressed in cell-free protein synthesis reactions as described in Yin et al., *mAbs*, 2012, 4:217-225.

Briefly, cell-free extracts were treated with 50 µM iodoacetamide for 30 min at room temperature (20° C.) and added to a premix containing cell-free components (see Cai et al., *Biotechnol Prg*, 2015, 3:823-831, incorporated by reference in its entirety) and 10% (v/v) RCA DNA template (approximately 10 µg/mL DNA) for HC variants, in addition to 2.5 ug/mL Trastuzumab LC which is present for antibody assembly but is not varied in the library. Sixty microliters of cell-free reactions were incubated at 30° C. for 12 hr on a shaker at 650 rpm in 96-well plates. Four hundred to one-thousand-five-hundred (400 to 1500) colonies were screened, depending on the predicted diversity of different selection campaigns.

Following synthesis, each reaction was diluted 1:50 into PBS (pH 7.4) with 3% fetal bovine serum (FBS), and expressed variants were tested for functional activity via cell-based ELISA binding to CHO-hFOLR1 cells (human FOLR1 expressed recombinantly in Chinese Hamster Ovary cells). Briefly, 384-well plates were seeded with CHO-control or CHO-hFOLR1 cells the day before the assay. On the day of the assay, cells were fixed with 20 uL of 4% paraformaldehyde in PBS for 15 minutes in the dark, washed with PBS, and then blocked with 30% FBS in PBS for 30 minutes at room temperature. Antibody variants of interest (1:50 diluted cell-free reaction) were allowed to bind to the fixed CHO-hFOLR1 cells, and detected with secondary antibodies (e.g. HRP-conjugated Anti-human Fc or anti-FLAG) and then detected with chemiluminescent substrate (Pierce ELISA SuperSignal™ Substrate). Chemiluminescence was quantified on a Molecular Devices SpectraMax® M5 plate reader. Top hits were selected based on cell-based ELISA signal/noise ratio, and their nucleotides were sequenced. Based on binding activity and sequence analysis, a subset of variants was selected for further scale-up and characterization.

The top leads from ELISA-based screening were cultured, and plasmid minipreps were performed using a QIAprep® 96 Turbo miniprep kit (Qiagen) according to the manufacturer's instructions. 10 µg/mL miniprepped DNA was added to 4 mL cell-free reactions and incubated overnight for 12 hr at 30° C., at 650 rpm. In the case of IgG variants with a common Trastuzumab LC, 7.5 ug/mL of the HC variant DNA and 2.5 ug/mL of the common Trastuzumab LC were added to the reaction.

Expressed variants from clarified cell-free reactions were purified via immobilized metal ion affinity chromatography (IMAC) purification using a semi-automated high throughput batch purification method. Briefly, purifications were performed in a 96-well plate format where 50 µL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 µL IMAC elution buffer (50 mM Tris pH 8.0, 300 mM NaCl, 500 mM imidazole) and buffer exchanged into PBS using a 96-well Zeba plate (7 kD MWCO, Thermo Fisher). Purified antibodies were quantified via high throughput capillary electrophoresis using the LabChip GXII (Perkin Elmer) against a Herceptin standard curve, according to the manufacturer's instructions.

Exemplary affinity-matured antibodies are reported in Table 5, below.

TABLE 5

Affinity Matured (SRP1848) Antibodies

| Antibody | VH | SEQ ID NO. | VL | SEQ ID NO. |
|---|---|---|---|---|
| 1 | SRP1848-A01 | 308 | Trastuzumab | 367 |
| 2 | SRP1848-A02 | 309 | Trastuzumab | 367 |
| 3 | SRP1848-A04 | 310 | Trastuzumab | 367 |
| 4 | SRP1848-A06 | 311 | Trastuzumab | 367 |
| 5 | SRP1848-A07 | 312 | Trastuzumab | 367 |
| 6 | SRP1848-A08 | 313 | Trastuzumab | 367 |
| 7 | SRP1848-A09 | 314 | Trastuzumab | 367 |
| 8 | SRP1848-A10 | 315 | Trastuzumab | 367 |
| 9 | SRP1848-B01 | 316 | Trastuzumab | 367 |
| 10 | SRP1848-B03 | 317 | Trastuzumab | 367 |
| 11 | SRP1848-B04 | 318 | Trastuzumab | 367 |
| 12 | SRP1848-B05 | 319 | Trastuzumab | 367 |
| 13 | SRP1848-B06 | 320 | Trastuzumab | 367 |
| 14 | SRP1848-B07 | 321 | Trastuzumab | 367 |
| 15 | SRP1848-B09 | 322 | Trastuzumab | 367 |
| 16 | SRP1848-B10 | 323 | Trastuzumab | 367 |
| 17 | SRP1848-B11 | 324 | Trastuzumab | 367 |
| 18 | SRP1848-C01 | 325 | Trastuzumab | 367 |
| 19 | SRP1848-C03 | 326 | Trastuzumab | 367 |
| 20 | SRP1848-C04 | 327 | Trastuzumab | 367 |
| 21 | SRP1848-C05 | 328 | Trastuzumab | 367 |
| 22 | SRP1848-C07 | 329 | Trastuzumab | 367 |
| 23 | SRP1848-C10 | 330 | Trastuzumab | 367 |
| 24 | SRP1848-D02 | 331 | Trastuzumab | 367 |
| 25 | SRP1848-D03 | 332 | Trastuzumab | 367 |
| 26 | SRP1848-D04 | 333 | Trastuzumab | 367 |
| 27 | SRP1848-D05 | 334 | Trastuzumab | 367 |
| 28 | SRP1848-D07 | 335 | Trastuzumab | 367 |
| 29 | SRP1848-D09 | 336 | Trastuzumab | 367 |
| 30 | SRP1848-D10 | 337 | Trastuzumab | 367 |
| 31 | SRP1848-E01 | 338 | Trastuzumab | 367 |
| 32 | SRP1848-E02 | 339 | Trastuzumab | 367 |
| 33 | SRP1848-E03 | 340 | Trastuzumab | 367 |
| 34 | SRP1848-E05 | 341 | Trastuzumab | 367 |
| 35 | SRP1848-E06 | 342 | Trastuzumab | 367 |
| 36 | SRP1848-E07 | 343 | Trastuzumab | 367 |
| 37 | SRP1848-F01 | 344 | Trastuzumab | 367 |
| 38 | SRP1848-F02 | 345 | Trastuzumab | 367 |
| 39 | SRP1848-F04 | 346 | Trastuzumab | 367 |
| 40 | SRP1848-F05 | 347 | Trastuzumab | 367 |
| 41 | SRP1848-F06 | 348 | Trastuzumab | 367 |
| 42 | SRP1848-F07 | 349 | Trastuzumab | 367 |
| 43 | SRP1848-F08 | 350 | Trastuzumab | 367 |
| 44 | SRP1848-F09 | 351 | Trastuzumab | 367 |
| 45 | SRP1848-F10 | 352 | Trastuzumab | 367 |
| 46 | SRP1848-F11 | 353 | Trastuzumab | 367 |
| 47 | SRP1848-G01 | 354 | Trastuzumab | 367 |
| 48 | SRP1848-G03 | 355 | Trastuzumab | 367 |
| 49 | SRP1848-G04 | 356 | Trastuzumab | 367 |
| 50 | SRP1848-G06 | 357 | Trastuzumab | 367 |
| 51 | SRP1848-G07 | 358 | Trastuzumab | 367 |
| 52 | SRP1848-G09 | 359 | Trastuzumab | 367 |
| 53 | SRP1848-G10 | 360 | Trastuzumab | 367 |
| 54 | SRP1848-G11 | 361 | Trastuzumab | 367 |
| 55 | SRP1848-H01 | 362 | Trastuzumab | 367 |

Example 2

Preparation of SCFVS

A single-chain antibody is made in either the $V_H V_L$ or $V_L V_H$ orientation with a linker sequence between the $V_H$ and $V_L$ domains. Typically scFv linkers are composed of (GGGGS)n repeats where n=3, 4, 5, or 6 for linkers of 15, 20, 25, or 30 residues respectively. For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 378). C-terminal affinity tags can optionally be added to facilitate purification and assay development. An exemplary affinity tag is a C-terminal FlagHis tag GSGDYKDDDDKGSGHHHHHH (SEQ ID NO: 376). A stop codon is typically inserted at the end of the sequence. An exemplary scFv can include an N-terminal Met residue, a $V_H$ domain, a GGGGSGGGGSGGGGS (SEQ ID NO: 377) linker, a $V_L$ domain, an AAGSDQEPKSS (SEQ ID NO: 378) linker, an Fc domain, a FlagHis tag, and a stop codon.

Example 3

Affinity and Kinetic Binding Analyses

Anti-Fc polyclonal antibodies were immobilized onto a CM5 chip (GE Life Sciences) using amine coupling chemistry (from Amine Coupling Kit, GE Life Sciences). The immobilization steps were carried out at a flow rate of 25 µL/min in 1×HBS-EP+ buffer (GE Life Sciences; 10× Stock diluted before use). The sensor surfaces were activated for 7 min with a mixture of N-hydroxysuccinimide (NHS, 0.05 M) and 1-ethyl-3-(3-dimethylaminopropyl)-carbodiimide (EDC, 0.2 M). The anti-Fc polyclonal antibodies were injected over all 4 flow cells at a concentration of 25 gig/mL in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1×HBS-EP+ buffer. Test and control antibodies were injected over the anti-Fc surface at concentrations of 5-10 µg/mL for 12 seconds at a flow rate of 10 µL/min on flow cells 2, 3 and 4, followed by a buffer wash for 30 seconds at the same flow rate. Kinetic characterization of antibody samples was carried out with a single concentration of antigen (for off-rate ranking) or a 1:2 dilution series of antigen (for kinetic characterization) and 1 injection of 0 nM antigen. After capturing ligand (antibody) on the anti-Fc surface, the analyte (human FOLR1-HIS) was bound at 50, 25, 12.5, 6.25 and 0 nM for 180 seconds, followed by a 600 second dissociation phase at a flow rate of 50 µL/min. Between each ligand capture and analyte binding cycle, regeneration was carried out using 2 injections of 10 mM glycine pH 2.0 for 30 seconds at 30 µL/min, followed by a 30 second buffer wash step.

The data were fit with the Biacore T200 Evaluation software, using a 1:1 Langmuir binding model. $K_D$ (affinity, nM) was determined as a ratio of the kinetic rate constants calculated from the fits of the association and dissociation phases.

Example 4

Flow Cytometry-Based Cell Binding Assay

Variants with expression levels >250 nM were tested in a fluorescence-activated cell sorting (FACS) cell-binding assay. CHO cells were transfected to stably express human (CHO-hFOLR1), cynomolgus (CHO-cFOLR1), or mouse (CHO-mFOLR1) target molecule FOLR1 on the cell surface. Parental CHO cells were used as a negative control to determine background binding levels. Parental CHO and stably transfected CHO-hFOLR1, CHO-cFOLR1, and CHO-mFOLR1 cells were cultured in Ham's F-12: high glucose DMEM (50:50) (Corning, Cellgro-Mediatech) supplemented with 10% heat-inactivated fetal bovine serum (Corning, Cellgro-Mediatech), 1% Penicillin/Streptomycin (Corning, Cellgro-Mediatech) and 2 mmol/L-glutamax (Life Technology).

A mixture of fluoresecent-labeled parental CHO cells and unlabeled CHO-hFOLR1 cells were prepared as follows. Parental CHO cells were washed twice in PBS and incubated in PBS containing with 1 nM CellTrace™ Oregon Green488® (Life Technologies) at 37° C. for 30 minutes. Labeled parental CHO cells were then washed 2× with Ham's F-12 media and 2× with FACS buffer (PBS with 1% bovine serum albumin). Unlabeled CHO-hFOLR1 cells were similarly washed and prepared. Labeled parental CHO and unlabeled CHO-hFOLR1 cells were combined at 1:1 ratio and seeded at 50 µL per well (200,000 cells per well) in 96 well polypropylene plates. Cells were mixed with 50 µL of test antibodies (i.e., anti-FOLR1 variants) serially diluted in FACS buffer and incubated on ice for 60 mins. Cells were washed with FACS buffer and incubated on ice for 60 mins with 100 µL FACS buffer containing 2.5 µg/mL R-Phycoerythrin-conjugated goat anti-Human IgG (Jackson ImmunoResearch Laboratories, West Grove, Pa.). Cells were washed twice with FACS buffer, fixed in 2% paraformaldehyde in PBS (Santa Cruz Biotechnology; Dallas, Tex.) for 10 mins on ice in the dark, and analyzed using the BD LSR II Flow Cytometer (BD Biosciences; San Jose, Calif.). Data were analyzed using FlowJo® software (FlowJo, LLC; Ashland, Oreg.) to determine mean fluorescence intensities. Binding constants were calculated using the statistical software, GraphPad Prism (GraphPad Software; La Jolla, Calif.) using the nonlinear regression equation, one site-specific binding with Hill slope. Secondary antibody alone was used as a control, in addition to measuring non-specific antibody binding to CHO parental cells.

This procedure was repeated to assess cell binding in CHO-cFOLR1 and CHO-mFOLR1 cells.

Example 5

Cell-Killing Analysis

The internalization of the antibodies was evaluated by a secondary antibody cell killing assay on target positive cells. FOLR1-positive KB cells were obtained from ATCC, and FOLR1-positive Igrov1 cells were obtained from NIH. The cells were maintained in Ham's F-12: high glucose DMEM (50:50) (Corning, Cellgro-Mediatech) supplemented with 10% heat-inactivated fetal bovine serum (Corning, Cellgro-Mediatech, Manassas, Va.), 1% Penicillin/Streptomycin (Corning, Cellgro-Mediatech, Manassas, Va.) and 2 mmol/ L-glutamax (Thermo Fisher Scientific, Waltham, Mass.). Adherent cells were washed twice with calcium and magnesium-free Hanks Balanced Salt Solution (HBSS), harvested with HYQ® TASE™ (Hyclone; Thermo Fisher Scientific, Waltham, Mass.) and counted by the Vi-CELL Cell Viability Analyzers (Beckman Coulter, Indianapolis, Ind.). A total of 625 cells were seeded in each well of a 384-well flat bottom white polystyrene plate. Lead antibodies were formulated at 4-fold starting concentration in the cell culture medium and filtered through MultiScreenHTS 96-Well Filter Plates (Millipore; Billerica, Mass.). Serial dilutions of test antibody (1:3 serial dilution starting from 200 nM) was added into treatment wells, and an anti-human Fc nanobody conjugated to hemiasterlin via a cleavable linker was then added into each well at a fixed final concentration of 20 nM. Assay plates were cultured at 37° C. in a $CO_2$ incubator for 120 hrs before assay. For cell viability measurement, 30 µL of Cell Titer-Glo® reagent (Promega Corp. Madison, Wis.) was added into each well, and plates were processed as per product instructions. Relative luminescence was measured on an ENVISION® plate reader (Perkin-Elmer; Waltham, Mass.). Relative luminescence readings were converted to percent viability using untreated cells as controls. Data was fitted with non-linear regression analysis, using a log(inhibitor) vs. response-variable slope, 4 parameter fit with GraphPad Prism (GraphPad v 5.0, Software; San Diego, Calif.). Data was expressed as relative cell viability (ATP content) % vs. dose of antibody.

Example 6

Generation of Hybridoma

Immunocompetent mice (C57BL/6) were immunized with mouse MC38 cells overexpressing human FOLR1. FOLR1-specific antibodies were detected in the sera, and the spleen was harvested and fused with P3X cells to generate the hybridomas (Aragen Biosciences, Morgan Hill, Calif.), similar to what has been previously described. See *Chronopoulou*, et al., 2014, *Methods Mol Biol* 1131:47-70, and Kim, et al., 2014, *Methods Mol Biol* 1131:31-45, each of which is incorporated herein by reference in its entirety. Total RNA was extracted from hybridoma cells using QIAGEN RNeasy Mini Kit (Cat No. 74104) and converted to cDNA using a Clontech SMARTer RACE cDNA Amplification Kit (Cat. No. 634923) (Lake Pharma, Belmont, Calif.). Positive clones were identified by gel electrophoresis, cloned using an Invitrogen TOPO kit, and sequenced using standard Sanger methods. The CDRs for m6D1 were grafted onto human antibody frameworks VH1-18, VH3-33, VH2-5, VH2-70, VH4-30-4, Vk1-5, Vk3-11, Vk2-30, Vk1-33, and Vk1-16 by standard methodology to yield humanized antibodies. See Kuramochi, et al., 2014, *Methods Mol Biol* 1060:123-137, which is incorporated herein by reference in its entirety. Of these grafts, the h6D1-HC3/LC4 (VH3-33/Vk3-11 grafts) and h6D1-HC3/LC5 (VH3-33/ Vk1-5 grafts) IgGs gave the best yield when expressed in cell-free and maintained the highest affinity. Both HC3/LC4 and HC3/LC5 humanized variants were progressed into affinity maturation by Fab-based ribosome display (as described above) targeting the heavy chain CDRs by soft-randomization leaving the light-chain constant, as described in Stafford, et al., 2014, *Protein Eng Des Sel* 4:97-109, which is incorporated herein by reference in its entirety.

Certain antibodies were generated by affinity maturation of humanized mouse antibodies. Exemplary antibody candidates are reported in Table 6, below.

TABLE 6

| Affinity-matured humanized antibodies (SRP2060). | | | | |
|---|---|---|---|---|
| Antibody | VH | SEQ ID NO. | VL | SEQ ID NO. |
| 56 | SRP2060-E10 | 363 | H6D1-LC4 | 368 |
| 57 | SRP2060-E05 | 364 | H6D1-LC4 | 368 |
| 58 | SRP2060-B01 | 365 | H6D1-LC5 | 369 |
| 59 | SRP2060-A06 | 366 | H6D1-LC5 | 369 |

Example 7

Characteristics of Illustrative Anti-FOLR1 Antibodies

Tables 7 through 9 show results obtained using the illustrative antibodies described herein.

Table 7 shows results obtained with antibodies isolated from affinity-maturation of initial antibody leads obtained from a naïve Fab TRiM ribosome display library, constructed on a Trastuzumab heavy chain (HC) framework.

Table 8 shows kinetic binding results obtained for the same antibodies listed in Table 7.

Table 9 shows results obtained from antibodies isolated from humanized mouse clone candidates.

TABLE 7

Affinity-matured antibodies from initial leads (Trastuzumab HC framework).

| Fab-HC Variant ID | KB, 2° Antibody Cell Killing, Nb-239 | | Igrov, 2° Antibody Cell Killing, Nb-SC239 | | CHO-human FolR1 | | CHO-cyno FolR1 | | CHO-mouse FolR1 | |
|---|---|---|---|---|---|---|---|---|---|---|
| | EC50 (nM) | Span (%) | EC50 (nM) | Span (%) | Bmax (MFI) | $K_D$ (nM) | Bmax (MFI) | $K_D$ (nM) | Bmax (MFI) | $K_D$ (nM) |
| SRP1848-A01 | 0.064 | 94 | 0.015 | 71 | 25899 | 0.39 | 22552 | 0.44 | 16475 | 0.8 |
| SRP1848-A02 | 0.028 | 94 | 0.039 | 71 | 24710 | 0.64 | 18500 | 0.50 | 18569 | 2.4 |
| SRP1848-A07 | 0.062 | 95 | 0.029 | 68 | 29182 | 0.61 | 23643 | 0.43 | 9646 | 0.9 |
| SRP1848-C03 | 0.074 | 93 | 0.035 | 72 | 29143 | 0.51 | 25148 | 0.50 | 3310 | 3.0 |
| SRP1848-F04 | 0.096 | 93 | 0.015 | 73 | 26867 | 0.73 | 26353 | 0.55 | 2741 | 11.0 |
| SRP1848-B04 | 0.035 | 94 | 0.018 | 70 | 27818 | 0.72 | 27796 | 0.65 | 2187 | 17.9 |
| SRP1848-B11 | 0.058 | 93 | 0.026 | 74 | 28394 | 0.56 | 22885 | 0.34 | 1632 | 3.9 |
| SRP1848-F07 | 0.057 | 92 | 0.018 | 71 | 27371 | 0.58 | 18662 | 0.56 | 1387 | 8.8 |
| SRP1848-E06 | 0.060 | 93 | 0.025 | 74 | 25611 | 0.48 | 15755 | 0.26 | 2349 | 1.2 |
| SRP1848-A09 | 0.060 | 93 | 0.026 | 71 | 28910 | 0.61 | 20248 | 0.31 | 7990 | 1.0 |
| SRP1848-E07 | 0.059 | 94 | 0.013 | 73 | 27284 | 0.54 | 20381 | 0.23 | 11837 | 1.2 |
| SRP1848-G03 | 0.064 | 91 | 0.021 | 76 | 26424 | 0.82 | 19238 | 0.44 | 2220 | 2.4 |
| SRP1848-A04 | 0.052 | 92 | 0.015 | 64 | 26810 | 0.43 | 23055 | 0.30 | 3888 | 2.0 |
| SRP1848-H01 | 0.049 | 96 | 0.016 | 67 | 26985 | 0.59 | 17227 | 0.28 | 3950 | 33.8 |
| SRP1848-B10 | 0.040 | 97 | 0.020 | 71 | 28186 | 0.83 | 21268 | 0.44 | 2455 | 7.3 |
| SRP1848-C07 | 0.065 | 93 | 0.013 | 67 | 28757 | 0.62 | 18136 | 0.23 | 3170 | 1.4 |
| SRP1848-F05 | 0.061 | 94 | 0.015 | 74 | 27155 | 0.72 | 24731 | 0.61 | 5100 | 18.0 |
| SRP1848-D02 | 0.034 | 93 | 0.027 | 71 | 28804 | 0.60 | 27973 | 0.61 | 916 | 87.0 |
| SRP1848-A08 | 0.039 | 93 | 0.013 | 65 | 28554 | 0.62 | 26197 | 0.45 | 3202 | 2.5 |
| SRP1848-E03 | 0.057 | 94 | 0.027 | 73 | 26694 | 0.76 | 17427 | 0.43 | 5939 | 0.5 |
| SRP1848-A10 | 0.033 | 96 | 0.027 | 75 | 27097 | 0.66 | 14816 | 0.47 | 10167 | 1.2 |
| SRP1848-F10 | 0.038 | 94 | 0.009 | 68 | 25554 | 0.36 | 20700 | 0.40 | 1742 | 6.9 |
| SRP1848-D05 | 0.055 | 92 | 0.030 | 73 | 26748 | 0.57 | 22202 | 0.45 | 1360 | 14.0 |
| SRP1848-C01 | 0.060 | 90 | 0.023 | 68 | 28527 | 0.66 | 25941 | 0.60 | 1369 | 26.0 |
| SRP1848-F01 | 0.047 | 91 | 0.018 | 69 | 25240 | 0.56 | 21491 | 0.43 | 3750 | 1.8 |
| SRP1848-D04 | 0.380 | 97 | 0.068 | 77 | 29297 | 2.21 | 25737 | 2.84 | NB | NB |
| SRP1848-E05 | 0.071 | 95 | 0.027 | 78 | 27306 | 0.46 | 28170 | 0.55 | NB | NB |
| SRP1848-A06 | 0.046 | 93 | 0.020 | 72 | 24521 | 0.47 | 20170 | 0.30 | 2767 | 2.4 |
| SRP1848-B01 | 0.064 | 95 | 0.031 | 82 | 26634 | 1.06 | 23881 | 0.83 | 3404 | 16.4 |
| SRP1848-C04 | 0.006 | 94 | 0.016 | 68 | 26269 | 0.44 | 22014 | 0.86 | 2506 | 62.0 |
| SRP1848-C10 | 0.057 | 96 | 0.036 | 75 | 27465 | 0.91 | 15966 | 0.27 | 2326 | 5.6 |
| SRP1848-B09 | 0.073 | 97 | 0.027 | 74 | 25152 | 0.46 | 25213 | 0.99 | 1424 | 78.0 |
| SRP1848-C05 | 0.073 | 92 | 0.021 | 62 | 26836 | 0.52 | 15199 | 0.35 | 4134 | 4.8 |
| SRP1848-F02 | 0.054 | 92 | 0.009 | 54 | 25714 | 0.62 | 14911 | 0.19 | 2741 | 2.6 |
| SRP1848-F08 | 0.061 | 94 | 0.024 | 77 | 26483 | 0.91 | 21024 | 1.07 | NB | NB |
| SRP1848-D07 | 0.075 | 94 | 0.032 | 71 | 25738 | 0.77 | 24272 | 0.92 | NB | NB |
| SRP1848-F11 | 0.054 | 91 | 0.017 | 70 | 26774 | 0.75 | 21790 | 0.47 | 1762 | 4.6 |
| SRP1848-F09 | 0.056 | 93 | 0.050 | 79 | 23816 | 0.36 | 24178 | 0.75 | 1671 | 90.7 |
| SRP1848-D10 | 0.016 | 90 | 0.012 | 54 | 26468 | 0.48 | 20578 | 0.52 | 1859 | 13.0 |
| SRP1848-G01 | 0.070 | 91 | 0.022 | 66 | 27406 | 0.98 | 20913 | 0.56 | 1993 | 4.6 |
| SRP1848-B06 | 0.058 | 95 | 0.022 | 72 | 25070 | 0.67 | 26767 | 1.21 | NB | NB |
| SRP1848-D03 | 0.160 | 98 | 0.038 | 76 | 25977 | 1.90 | 14130 | 0.58 | 3170 | 9.5 |
| SRP1848-B07 | 0.079 | 96 | 0.038 | 73 | 25612 | 0.66 | 25491 | 1.05 | NB | NB |
| SRP1848-E02 | 0.046 | 93 | 0.025 | 71 | 23847 | 0.53 | 18717 | 0.59 | 1473 | 21.0 |
| SRP1848-B03 | 0.050 | 94 | 0.028 | 66 | 26338 | 0.82 | 17228 | 0.41 | 2722 | 6.4 |
| SRP1848-E01 | 0.088 | 92 | 0.029 | 72 | 26430 | 1.01 | 22420 | 0.96 | NB | NB |
| SRP1848-B05 | 0.065 | 94 | 0.040 | 72 | 24536 | 0.65 | 21871 | 0.64 | NB | NB |
| SRP1848-D09 | 0.042 | 91 | 0.023 | 70 | 24966 | 0.46 | 21306 | 0.65 | NB | NB |
| SRP1848-F06 | 0.066 | 94 | 0.032 | 77 | 25598 | 0.87 | 26528 | 0.86 | NB | NB |
| SRP1848-G10 | 0.046 | 97 | 0.019 | 79 | 25269 | 0.49 | 14163 | 0.24 | 2891 | 4.3 |
| SRP1848-G04 | 0.051 | 92 | 0.016 | 75 | 25156 | 0.76 | 12538 | 0.25 | 1999 | 2.5 |
| SRP1848-G06 | 0.057 | 96 | 0.026 | 81 | 25838 | 0.63 | 12830 | 0.31 | 1857 | 11.1 |
| SRP1848-G07 | 0.058 | 94 | 0.038 | 78 | 24939 | 0.78 | 13668 | 0.35 | 1978 | 2.9 |
| SRP1848-G09 | 0.073 | 97 | 0.036 | 83 | 25066 | 0.59 | 17685 | 0.35 | 2184 | 6.4 |
| SRP1848-G11 | 0.040 | 97 | 0.023 | 84 | 27191 | 0.68 | 11837 | 0.26 | 2744 | 7.6 |

TABLE 8

Affinity-matured antibodies from initial leads
(Trastuzumab HC framework): Kinetic binding results

| | Biacore Kinetics | | |
|---|---|---|---|
| Variant ID | ka (1/Ms) | kd (1/s) | $K_D$ (M) |
| SRP1848-A01 | 8.29E+05 | 1.55E−03 | 1.87E−09 |
| SRP1848-A02 | 5.25E+05 | 8.82E−03 | 1.68E−08 |
| SRP1848-A07 | 1.01E+06 | 8.66E−04 | 8.55E−10 |
| SRP1848-C03 | 1.36E+06 | 1.52E−03 | 1.11E−09 |
| SRP1848-F04 | 8.15E+05 | 1.08E−03 | 1.32E−09 |
| SRP1848-B04 | 7.80E+05 | 1.17E−03 | 1.50E−09 |
| SRP1848-B11 | 1.22E+06 | 1.86E−03 | 1.52E−09 |
| SRP1848-F07 | 1.60E+06 | 2.49E−03 | 1.56E−09 |
| SRP1848-E06 | 9.44E+05 | 1.54E−03 | 1.63E−09 |
| SRP1848-A09 | 7.30E+05 | 1.33E−03 | 1.82E−09 |
| SRP1848-E07 | 1.25E+06 | 2.40E−03 | 1.91E−09 |
| SRP1848-G03 | 9.90E+05 | 1.97E−03 | 1.99E−09 |
| SRP1848-A04 | 1.61E+06 | 3.26E−03 | 2.03E−09 |
| SRP1848-H01 | 6.59E+05 | 1.39E−03 | 2.11E−09 |
| SRP1848-B10 | 6.81E+05 | 1.48E−03 | 2.18E−09 |
| SRP1848-C07 | 8.56E+05 | 1.89E−03 | 2.21E−09 |
| SRP1848-F05 | 6.56E+05 | 1.57E−03 | 2.40E−09 |
| SRP1848-D02 | 8.51E+05 | 2.05E−03 | 2.41E−09 |
| SRP1848-A08 | 4.93E+05 | 1.19E−03 | 2.42E−09 |
| SRP1848-E03 | 6.88E+05 | 1.83E−03 | 2.67E−09 |
| SRP1848-A10 | 1.20E+06 | 3.30E−03 | 2.74E−09 |
| SRP1848-F10 | 8.72E+05 | 2.47E−03 | 2.83E−09 |
| SRP1848-D05 | 6.75E+05 | 1.98E−03 | 2.93E−09 |
| SRP1848-C01 | 7.30E+05 | 2.23E−03 | 3.05E−09 |
| SRP1848-F01 | 1.14E+06 | 3.62E−03 | 3.18E−09 |
| SRP1848-D04 | 4.97E+05 | 1.73E−03 | 3.48E−09 |
| SRP1848-E05 | 7.16E+05 | 2.51E−03 | 3.51E−09 |
| SRP1848-A06 | 1.37E+06 | 4.83E−03 | 3.51E−09 |
| SRP1848-B01 | 1.13E+06 | 4.16E−03 | 3.67E−09 |
| SRP1848-C04 | 1.29E+06 | 4.99E−03 | 3.86E−09 |
| SRP1848-C10 | 8.99E+05 | 3.63E−03 | 4.03E−09 |
| SRP1848-B09 | 1.55E+06 | 6.61E−03 | 4.26E−09 |
| SRP1848-C05 | 1.06E+06 | 4.54E−03 | 4.29E−09 |
| SRP1848-F02 | 1.42E+06 | 6.37E−03 | 4.49E−09 |
| SRP1848-F08 | 5.94E+05 | 2.72E−03 | 4.58E−09 |
| SRP1848-D07 | 1.09E+06 | 5.11E−03 | 4.70E−09 |
| SRP1848-F11 | 8.28E+05 | 3.90E−03 | 4.71E−09 |
| SRP1848-F09 | 1.40E+06 | 6.79E−03 | 4.85E−09 |
| SRP1848-D10 | 1.13E+06 | 5.58E−03 | 4.95E−09 |
| SRP1848-G01 | 4.44E+05 | 2.26E−03 | 5.09E−09 |
| SRP1848-B06 | 6.20E+05 | 3.17E−03 | 5.10E−09 |
| SRP1848-D03 | 1.03E+06 | 5.35E−03 | 5.19E−09 |
| SRP1848-B07 | 7.06E+05 | 3.78E−03 | 5.35E−09 |
| SRP1848-E02 | 1.14E+06 | 7.07E−03 | 6.21E−09 |
| SRP1848-B03 | 1.13E+06 | 8.59E−03 | 7.63E−09 |
| SRP1848-E01 | 6.64E+05 | 5.22E−03 | 7.87E−09 |
| SRP1848-B05 | 9.76E+05 | 8.85E−03 | 9.07E−09 |
| SRP1848-D09 | 1.07E+06 | 1.08E−02 | 1.01E−08 |
| SRP1848-F06 | 4.56E+05 | 7.75E−03 | 1.70E−08 |
| SRP1848-G10 | 7.58E+05 | 3.45E−03 | 4.55E−09 |
| SRP1848-G04 | 5.91E+05 | 3.79E−03 | 6.40E−09 |
| SRP1848-G06 | 5.69E+05 | 3.81E−03 | 6.70E−09 |
| SRP1848-G07 | 6.05E+05 | 4.51E−03 | 7.45E−09 |
| SRP1848-G09 | 8.56E+05 | 6.46E−03 | 7.56E−09 |
| SRP1848-G11 | 6.96E+05 | 6.37E−03 | 9.14E−09 |

TABLE 9

Results obtained with humanized 6D1 (2060) antibodies.

| | Biacore kinetics | | | Igrov 2° AntibodyCell Killing, Nb-SC239 | |
|---|---|---|---|---|---|
| SRP | ka (1/Ms) | kd (1/s) | $K_D$ (M) | EC50 (nM) | span (%) |
| SRP2060-E10 | 5.82E+05 | 1.20E−03 | 2.06E−09 | 0.061 | 68 |
| SRP2060-E05 | 5.41E+05 | 1.58E−03 | 2.92E−09 | 0.22 | 71 |
| SRP2060-B01 | 5.61E+05 | 1.47E−03 | 2.62E−09 | 0.045 | 76 |
| SRP2060-A06 | 5.47E+05 | 7.29E−03 | 1.33E−08 | 0.013 | 66 |

Example 8

FOLR1 Expression in Ovarian, Endometrial Cancer, NSCLC, and TNBC Cell Lines

High levels of FolRα have been found in ovarian and endometrial cancers, triple-negative breast cancer (TNBC) and non-small cell lung carcinoma (NSCLC). Based on reported FolRα mRNA expression levels, a panel of ovarian cancer, endometrial cancer, TNBC, and NSCLC cell lines were selected for in vitro testing of candidate ADC molecules. To measure the number of FolRα receptors expressed on the cell surface, Alexa647-conjugated antibody 1848-H01 (Y180/F404) was used in a FACS cell binding assay and FolRα copy number was determined based on Antibody Binding Capacity (ABC) of the conjugated antibody measured by quantitation beads (Simply Cellular anti-human IgG beads from Bangs Laboratories). As shown in Table 10, FolRα copy number on ovarian cancer, endometrial cancer, TNBC, and NSCLC cells ranged from 35,000 to 4,000,000 receptors per cell.

TABLE 10

FolRα copy numbers in various cell lines

| Disease Indication | Cell Line | FolRα Copy # per Cell |
|---|---|---|
| Ovarian Cancer | OVKATE | 3,590,356 |
| | Igrov1 | 1,375,828 |
| | OVMANA | 1,224,753 |
| | OVSAHO | 842,703 |
| | OVISE | 678,472 |
| | CAOV3 | 336,900 |
| | OVCAR3 | 196,426 |
| | OV90 | 97,717 |
| Endometrial Cancer | MFE-280 | 434,941 |
| | HEC-1-A | 220,690 |
| | EFE-184 | 128,166 |
| | HEC-1-B | 176,400 |
| | Ishikawa | 194,128 |
| | SNG-M | 61,961 |
| | NUGC-4 | 35,395 |
| Lung Cancer | H2342 | 1,419,355 |
| | H1651 | 918,800 |
| | H2110 | 347,447 |
| | H441 | 251,390 |
| | H226 | 85,164 |
| | H2405 | 68,182 |
| | H358 | 40,058 |
| | H2052 | 37,677 |
| | A549 | 35,078 |
| | H1770 | 33,781 |
| TNBC | HCC1143 | 255,813 |
| | HEC-251 | 113,270 |
| | HCC1599 | 65,624 |
| | MDA-MB-468 | 61,588 |
| | MDA-MB-231 | 50,005 |
| | HCC38 | 40,712 |

TABLE 10-continued

FolRα copy numbers in various cell lines

| Disease Indication | Cell Line | FolRα Copy # per Cell |
|---|---|---|
| | HCC1187 | 34,936 |
| | HCC1937 | 23,097 |

Example 9

FOLR1 Expression in Ovarian and Endometrial Cancer, TNBC and NSCLC Tissues

To determine prevalence of FolRα expression in patient samples representative of ovarian and endometrial cancers, TNBC and NSCLC, immunohistochemistry (IHC) staining was performed on commercially available tissue microarrays (TMAs) containing patient samples for the four indications. The TMAs (Biomax; Biomax; Cat # BC11115b, EMC1021, BR1001, and BC041115c) were stained for FolRα expression using a commercial FolRα IHC assay kit (Biocare; Cat. #IPI4006K G10) with the manufacturer's recommended protocol. Slides were imaged and stained tumor cores were scored for staining. Positive staining for FolRα was observed in ~80% of ovarian cancer, ~60% of endometrial cancer samples, ~30% of TNBC samples and ~50% of NSCLC samples; suggesting that these may be suitable indications for a FolRα-targeting therapeutic agent. The relative levels of expression of FolRα in ovarian and endometrial samples is summarized in Table 11.

TABLE 11

Summary of FolRα Expression Levels in Ovarian and Endometrial Cancer Samples

| Indication/Cat# of Slide (Biomax US) | Total # of disease cores | Staining intensity | | | |
|---|---|---|---|---|---|
| | | 0 | 1+ | 2+ | 3+ |
| Ovarian Cancer tissue microarray with adjacent normal tissue, 100 cases/100 cores (BC11115b) | 97 | 21 | 19 | 29 | 25 |
| Endometrial Cancer tissue microarray, 102 cases/102 cores (EMC1021) | 90 | 26 | 37 | 15 | 12 |

Example 10

Antibody-Drug Conjugate (ADC) Evaluation

Based on biacore affinity to the extracellular domain of FOLR1 (or "FolRα-ECD"), nine antibodies were selected for scale-up with para-azidomethyl-L-phenylalanine (pAMF) incorporated at the HC F404 site. The nine antibodies selected for testing were: 1848-A01, 1848-H01, 1848-A08, 1848-B04, 1848-D02, 1848-A07, 1848-B10, 1848-G10, and 1848-G04). Antibody 1848-D02 did not express well and was consequently not used for further investigation. The remaining eight antibodies were conjugated to a non-cleavable maytansine to form antibody-drug conjugates (ADCs) having the structure of Conjugate M, below:

Conjugate M

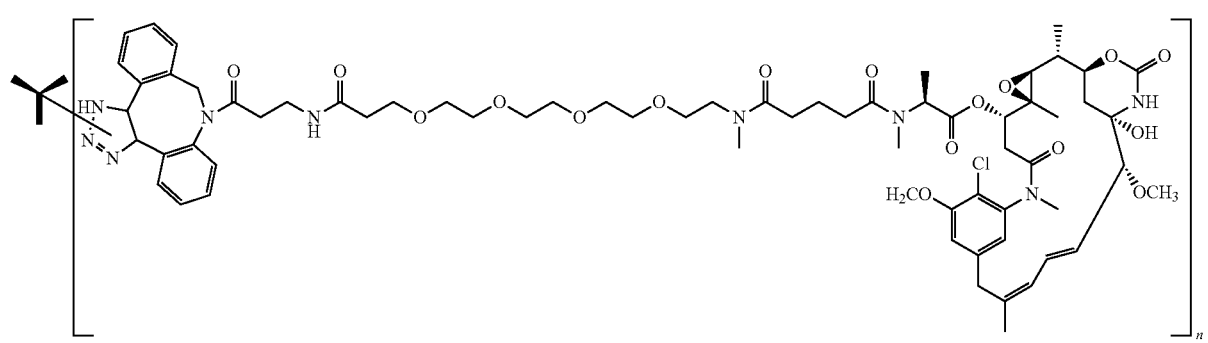

The candidate antibody-drug conjugates were tested in cell killing on FolRα-expressing cells, including KB, Igrov1, HeLa and JEG3. Table 12 provides a summary of the in vitro cytotoxic activity of the candidate conjugates on KB and JEG3 cells.

TABLE 12

In vitro cytotoxic activity of anti-FOLR1 antibody-drug conjugates

| | | Killing in KB cells | | Killing in JEG3 cells | |
|---|---|---|---|---|---|
| Antibody | [IgG], μg/mL | EC50 (nM) | Span (%) | EC50 (nM) | Span (%) |
| 1848-A01 | 1100 | 0.16 | 96 | 83* | 94* |
| 1848-A07 | 1021 | 0.17 | 96 | 80* | 96* |
| 1848-A08 | 1358 | 0.17 | 95 | 74* | 95* |
| 1848-B04 | 1257 | 0.3 | 98 | 113* | 85* |
| 1848-B10 | 802 | 0.23 | 98 | 43* | 82* |
| 1848-D02 | 1208 | Not tested | Not tested | Not tested | Not tested |
| 1848-G04 | 1415 | 0.31 | 94 | 38* | 93* |
| 1848-G10 | 1746 | 0.26 | 92 | NC | NC |
| 1848-H01 | 1723 | 0.24 | 93 | NC | NC |

*Estimated
NC = Not calculable

There was no significant difference between ADCs in cell killing activity on KB and JEG3 cells, Table 12. Accordingly, four leads (1848-A01, 1848-A07, 1848-B04, 1848-G10) conjugated to the non-cleavable maytansine to form structures of Conjugate M at a drug-antibody ratio of two (DAR2) were selected for an in vivo study based on Biacore affinity (Table 8) and maximizing sequence diversity. Additionally, there was weak cytotoxic activity on JEG3 cells with the ADCs having DAR2.

To study the effect of drug-antibody ratio (DAR) on the cell killing activity of anti-FolRα leads, the ADCs having DAR2 were also combined with a secondary DAR2 anti-human IgG nanobody conjugated to non-cleavable maytansine to approximate a DAR 4 ADC in cell killing assays. In this assay, 1848-B10 ADC showed the best cell killing activity when combined with the secondary nanobody on JEG3 and Igrov1 cells (data not shown). Based on this result, 1848-B10 ADC at DAR2 was added to an in vivo study to evaluate ADC candidates in addition to the other four leads (1848-A01, 1848-A07, 1848-B04, 1848-G10). Results from the in vivo efficacy study testing revealed that only 1848-B10 ADC at DAR2 showed weak tumor inhibition in the KB model (data not shown).

As a result, 1848-B10 was selected as one of the lead antibodies for further ADC studies.

Example 11

Efficacy Screening of Top FOLR1 Antibody Leads

The ADCs containing Conjugate M at DAR2 had potent in vitro activity against KB cells, which express high levels of FolRα. However, the ADCs had poor in vitro activity in JEG3 and Igrov1 cells, which express more moderate levels of FolRα, and low in vivo activity in the KB model. The pattern and levels of FolRα expression in JEG3 and Igrov1 cells is more representative of expression in patient tumors, while evaluation of ADC leads in KB cells do not appear to differentiate between the properties of the different leads. FolRα undergoes rapid internalization and recycling without reaching the lysosome; therefore, in order to improve activity of an ADC that targets FolRα, it would be useful to have a linker that can release the drug in the endosomal compartment. Additionally, FolRα expression in primary ovarian tumors and Igrov1 xenografts is heterogenous (Ab et al. 2015. Molecular Cancer Therapeutics 14(7): 1605-1613) suggesting that an ADC with bystander activity could potentially have higher activity in these tumors. To tailor the design of a FolRα-targeting ADC to the biology of the target as well as the expression level and pattern in ovarian cancer, several changes were implemented in the screening strategy. The KB model was used for primary screening, and the activity of leads was tested on Igrov1 cells in vitro and in vivo to evaluate and compare the different leads.

Initial screening of FolRα ADC variants was conducted in KB tumors which express high levels of FolRα. This study sought to evaluate the anti-tumor effects of four different anti-FolRα antibodies conjugated to the same linker-warhead (Conjugate P, below) and conjugation sites (Y180/F404). KB cervical carcinoma cells were implanted subcutaneously into athymic nude mice and treated with a single dose of 2.5 mg/kg FolRα ADC variants listed in Table 13. ADC variants were administered when tumors reached ~150 mm³.

Conjugate P

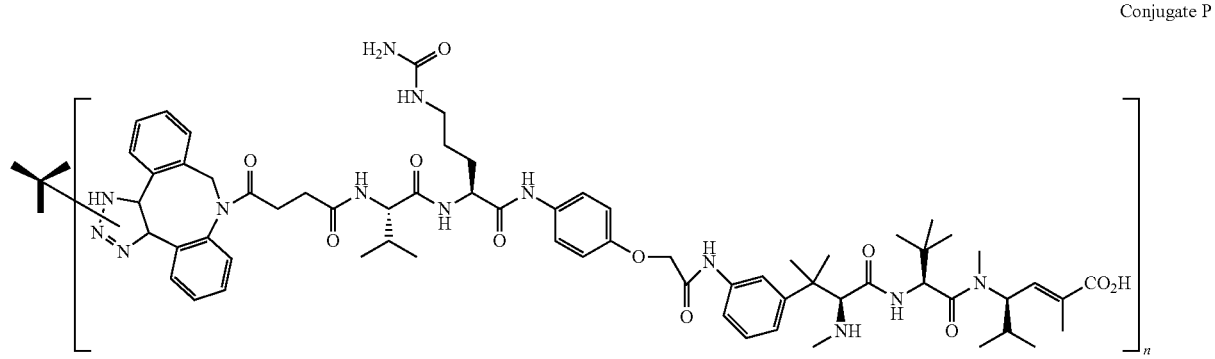

TABLE 13

| ADC Molecule | Antibody | Conjugation Sites | Conjugate Form | DAR |
|---|---|---|---|---|
| Vehicle (PBS Only) | — | — | — | NA |
| 1 | 1848-B10 | HC-Y180, F404 | P | 3.8 |
| 2 | 1848-A07 | HC-Y180, F404 | P | 3.9 |
| 3 | 1848-B04 | HC-Y180, F404 | P | 3.8 |
| 4 | 1848-H01 | HC-Y180, F404 | P | 3.8 |

Tested ADC variants

Figure 6:
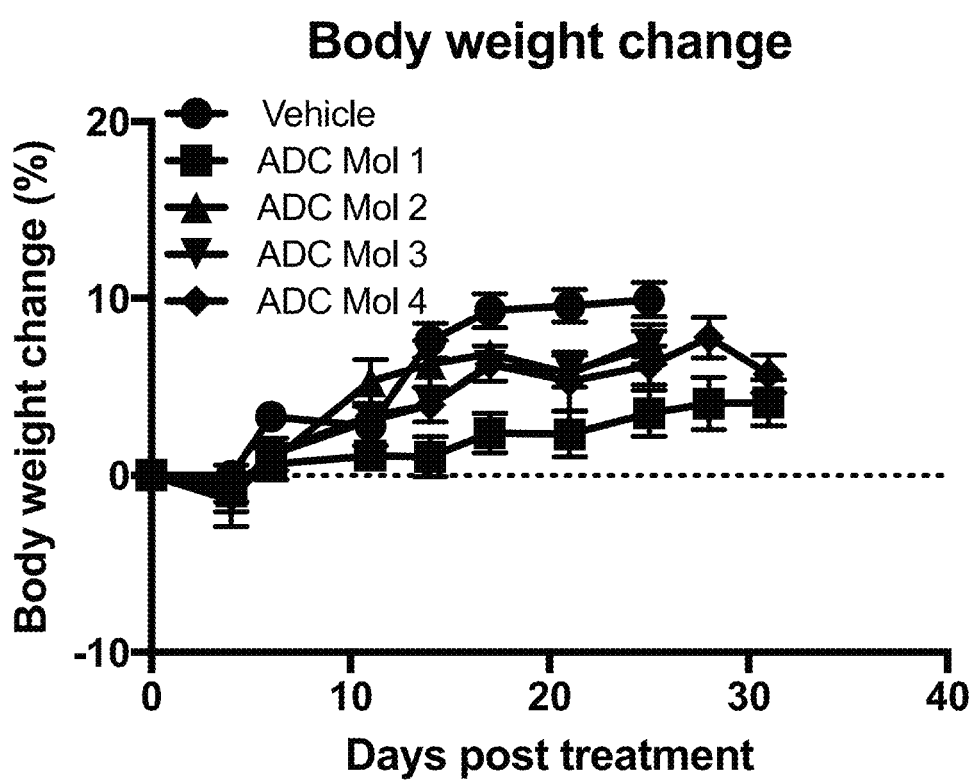
FIG. 6 is a graph illustrating body weight change in mice implanted with KB cervical carcinoma cells after being administered a single dose of different FOLR1 antibody-drug conjugates as disclosed herein.
Figure 7A:
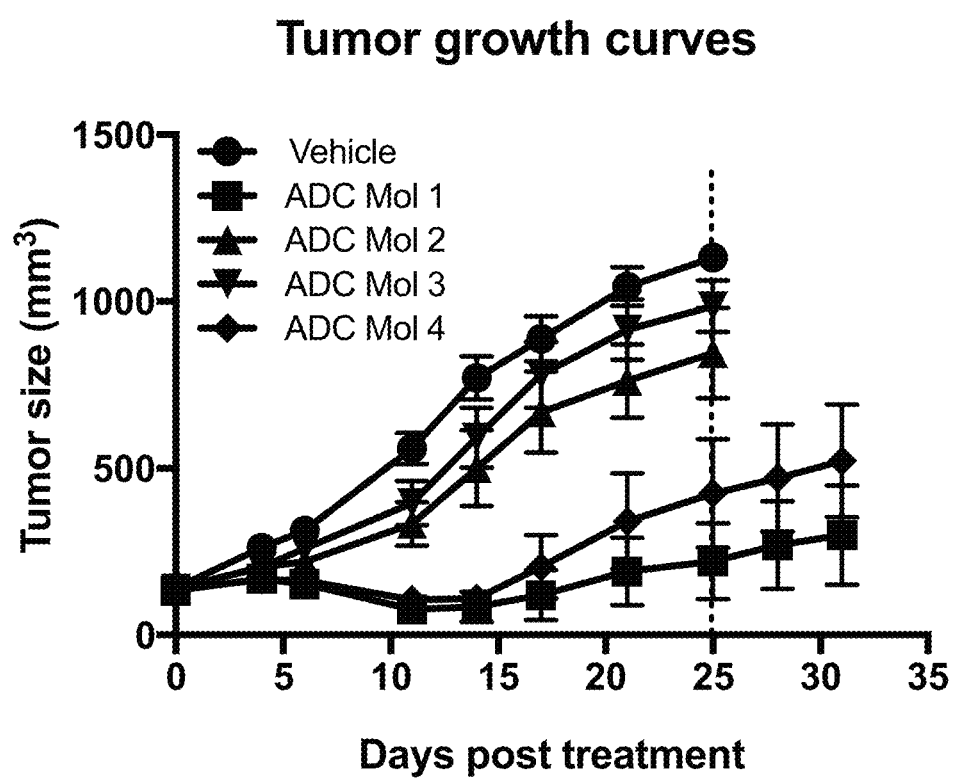
FIG. 7 (A, B) are graphs illustrating tumor growth curves and tumor size at day 25 in mice implanted with KB cervical carcinoma cells after being administered a single dose of different FOLR1 antibody-drug conjugates as disclosed herein.
Figure 7B:
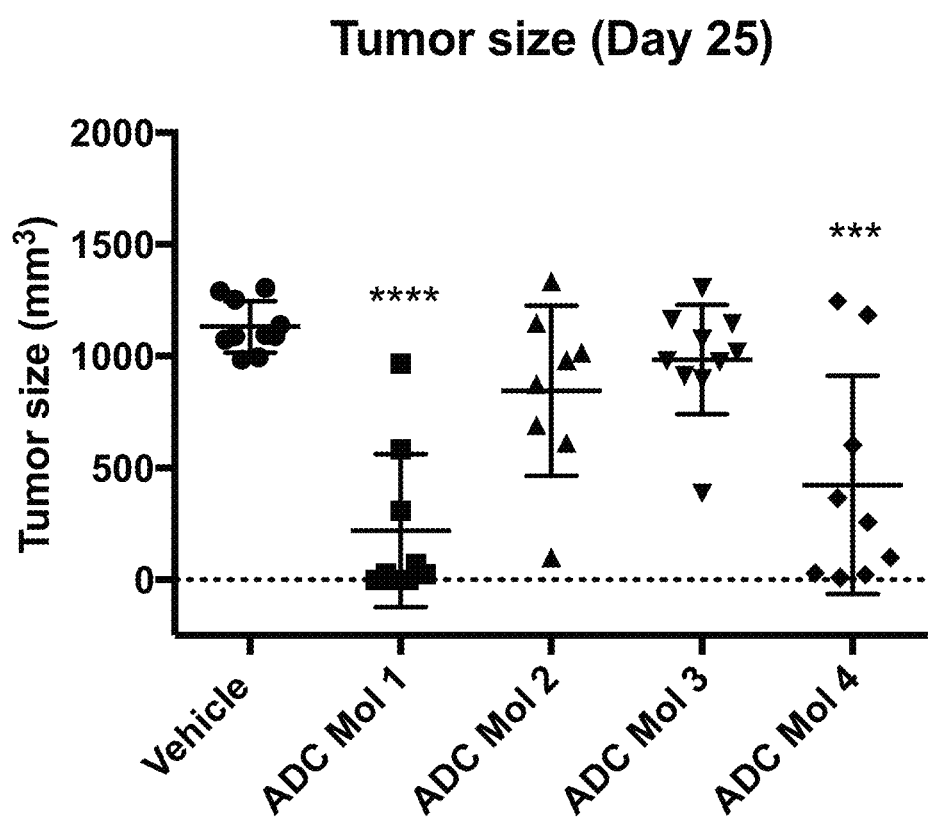
Figure 8:
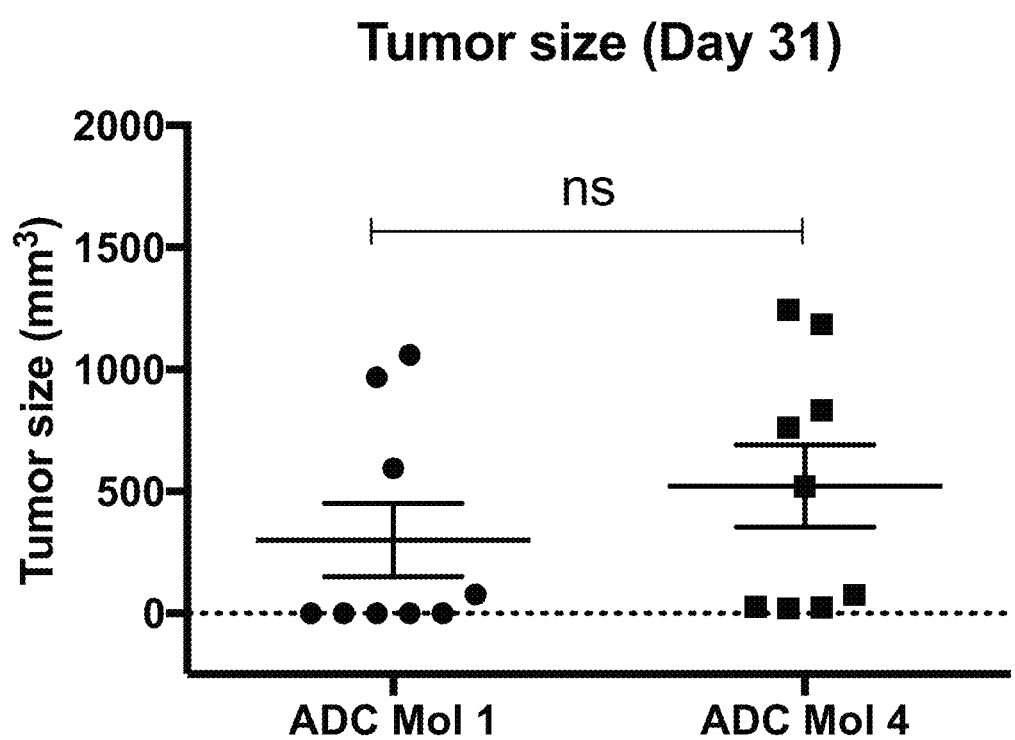
FIG. 8 is a scatter plot illustrating final tumor size at day 31 in mice implanted with KB cervical carcinoma cells after single-dose treatment with two different FOLR1 antibody-drug conjugates disclosed herein.

No toxicity was observed with any test article as evidenced by the absence of any significant weight loss, defined as >20% decrease in animal weight (FIG. 6). FIGS. 7 (A, B) illustrate the effects of treatment on KB tumor growth and tumor size on day 25 when the vehicle control group reached the study endpoint (>1000 mm³). Results show that ADC Molecule 1 (1848-B10 FolRα antibody, Y180/F404, Conjugate P) and ADC Molecule 4 (1848-H01 FolRα antibody, Y180/F404, Conjugate P) significantly inhibited KB tumor growth compared to control, while the other two ADC variants did not exhibit any anti-tumor activity. By the end of the study on day 31, there was no significant difference between ADC Molecules 1 and 4 (FIG. 8). Therefore, ADCs containing 1848-B10 and 1848-H01 anti-FolRα antibodies were investigated for further characterization and testing.

Example 12

Drug-Antibody Ratio for Antibody-Drug Conjugates

ADCs with increasing DAR (2-6) and with a cleavable linker were evaluated to determine whether varying these features would improve activity of the molecule. To increase the in vivo potency of the FolRα targeting ADCs, 1848-B10 antibodies was expressed with 2, 4, or 6 para-azidomethyl-phenylalanine (pAMF) residues incorporated on each antibody and conjugated to non-cleavable maytansine (Conjugate M, Example 10) and cleavable hemiasterlin (Conjugate P, Example 11) to generate ADCs with DAR=2, 4 or 6.

In vitro cell killing on FolRα-positive cells (KB, Igrov1, and JEG3) showed that antibody 1848-B10 conjugates of Conjugate P were more potent than 1848-B10 conjugates of Conjugate M on Igrov1 cells, which have moderate levels of FolRα expression (Table 14). Additionally, increasing the DAR to 4 resulted in ADCs with greatly improved potency compared to the DAR2 versions, while DAR6 ADCs further improved the cell killing activity only marginally over DAR4. Based on these data, the cleavable hemiasterlin conjugates (Conjugate P) at DAR4 was determined to be the optimal conjugate format for the FolRα ADC.

Figure 9:
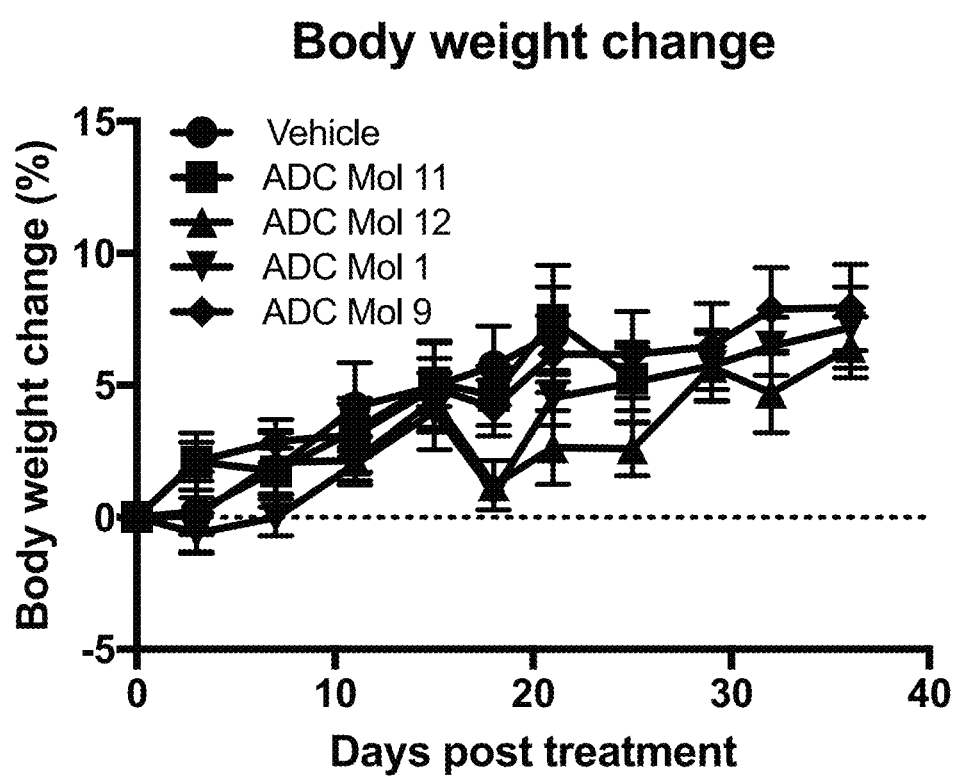
FIG. 9 is a graph illustrating body weight change in mice implanted with KB cervical carcinoma cells after being administered a single dose of different FOLR1 antibody-drug conjugates as disclosed herein.
Figure 10A:
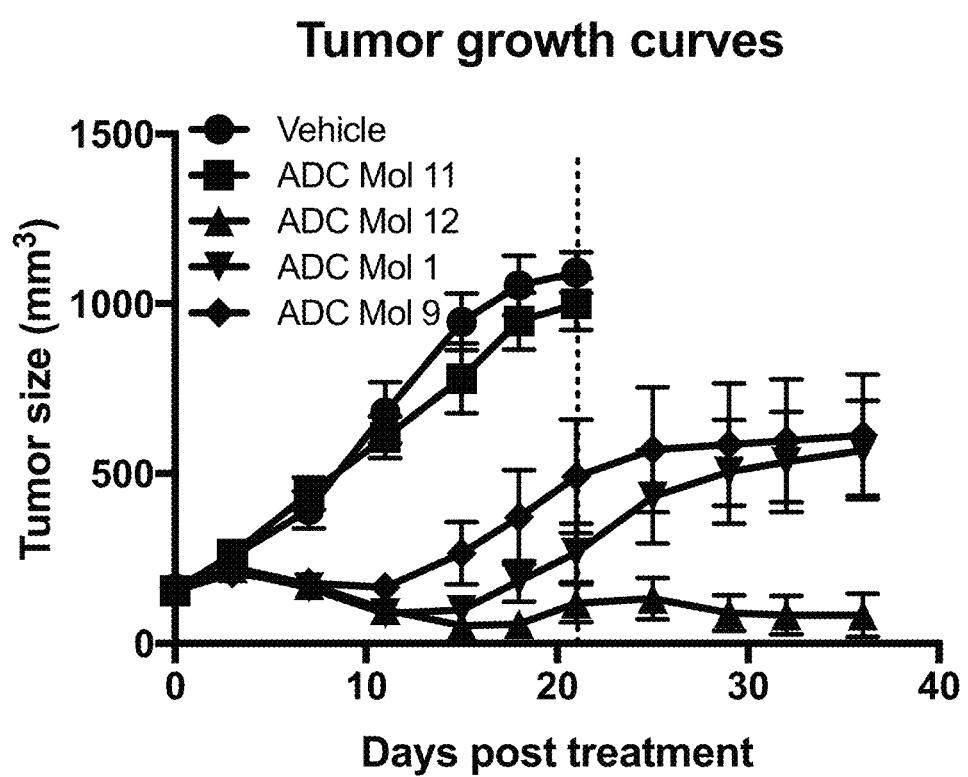
FIG. 10 (A, B) are graphs illustrating tumor growth curves and tumor size at day 21 in mice implanted with KB cervical carcinoma cells after being administered a single dose of different FOLR1 antibody-drug conjugates as disclosed herein.
Figure 10B:
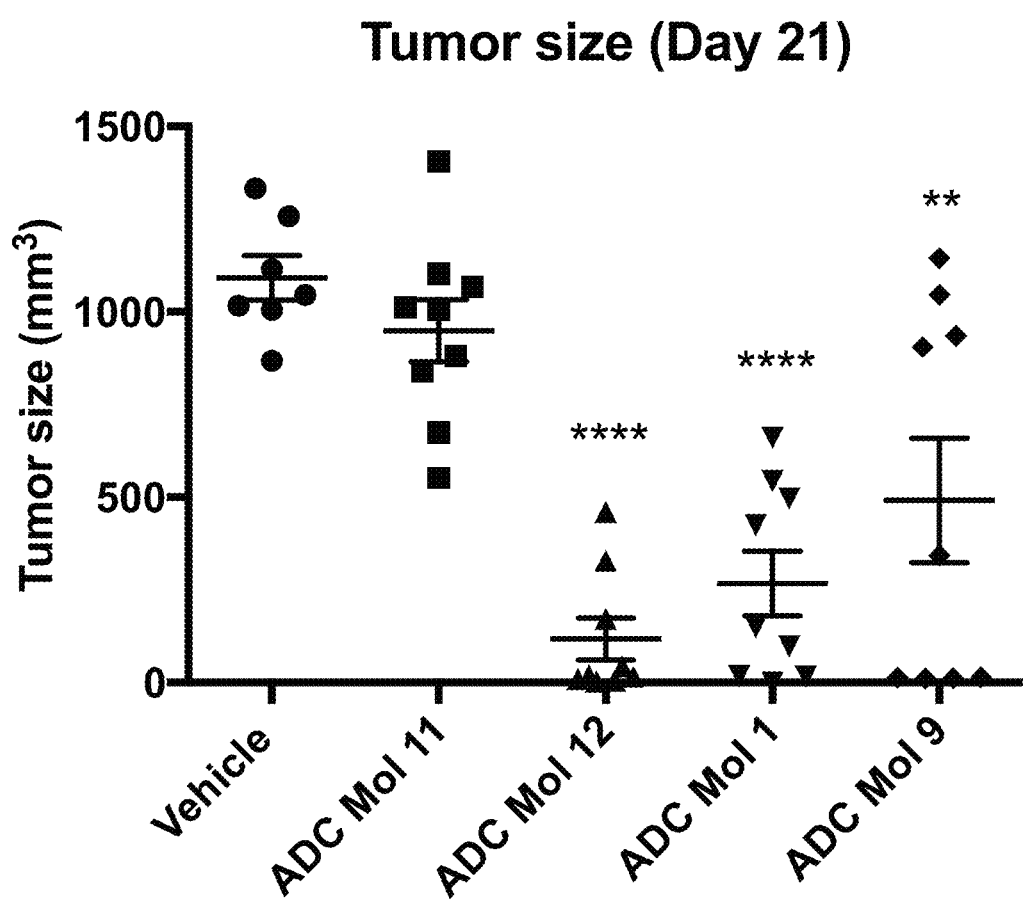
Figure 11:
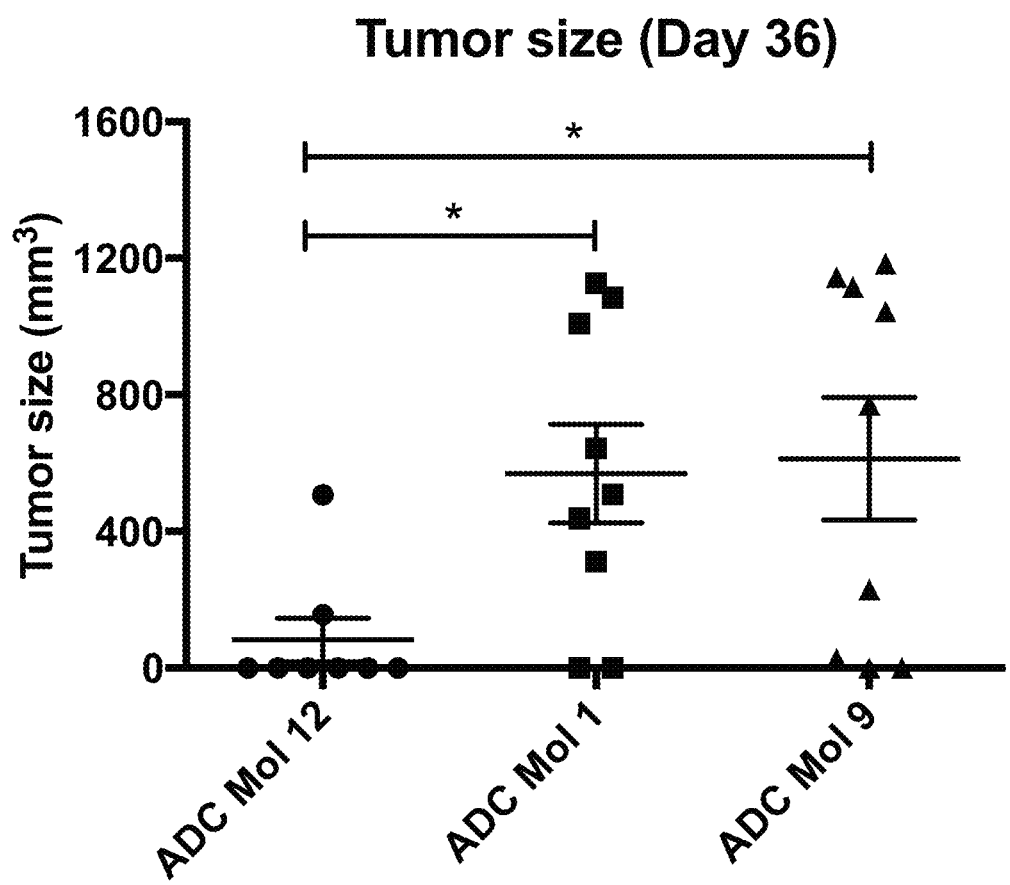
FIG. 11 is a scatter plot illustrating final tumor size at day 36 in mice implanted with KB cervical carcinoma cells after single-dose treatment with three different FOLR1 antibody-drug conjugates disclosed herein.

For in vivo efficacy testing, KB cervical carcinoma cells were implanted subcutaneously into athymic nude mice and treated with a single dose of 2.5 mg/kg FolRα ADC variants listed in Table 15. ADCs were administered when tumors reached ~150 mm$^3$. No toxicity was observed with any test article as evidenced by the absence of any significant weight loss, defined as >20% decrease in animal weight (FIG. 9). FIGS. 10 (A, B) illustrate the effect of treatment on KB tumor growth and tumor size on day 21 when the vehicle treated tumors reached the study endpoint (>1000 mm$^3$), after which the study was terminated. Results show that all three FolRα ADC variants (ADC Molecules 1, 12, and 9) with different conjugation sites initially induced tumor regression and significantly delayed tumor growth compared to the vehicle control, while control anti-GFP ADC (ADC Molecule 11) behaved similarly to vehicle (FIGS. 10A and 10B). By the end of study on day 36, ADC Molecule 12 exhibited the best duration of response with most tumors in this group remaining growth inhibited, while tumor re-growth was observed for ADC Molecules 1 and 9 (FIG. 10A). Statistical analysis showed that ADC Molecule 12 was significantly more efficacious compared to ADC Molecule 9 (p=0.0297) and ADC Molecule 1 (p=0.0470) (FIG. 11). In conclusion, the Y180/K42 conjugation site resulted in the best potency and duration of response in KB tumors.

TABLE 14

Comparison of in vitro cytotoxic activity of 1848-B10 ADCs

| ADC Molecule | Sites of Conjugation | Linker drug/ Conjugate | Expected DAR | Measured DAR | KB (+++) EC50 (nM) | KB (+++) Span (%) | Igrov (++) EC50 (nM) | Igrov (++) Span (%) | A549 (−) EC50 (nM) | A549 (−) Span (%) |
|---|---|---|---|---|---|---|---|---|---|---|
| 5 | F404 | Conjugate M | 2 | 1.94 | 0.74 | 87 | NC | NC | NK | NK |
| 6 | K42/F404 | Conjugate M | 4 | 3.86 | 0.42 | 94 | NC | NC | NK | NK |
| 7 | K42/Y180/F404 | Conjugate M | 6 | 5.54 | 0.2 | 96 | NC | NC | NK | NK |
| 8 | F404 | Conjugate P | 2 | 1.89 | 0.81 | 80 | 0.55 | 56 | NK | NK |
| 9 | K42/F404 | Conjugate P | 4 | 3.69 | 0.35 | 94 | 0.17 | 62 | NK | NK |
| 10 | K42/Y180/F404 | Conjugate P | 6 | 5.28 | 0.21 | 97 | 0.14 | 69 | NK | NK |

NC = Not calculable
NK = No killing

Example 13

Study to Compare Activity of Different Site Pairs in ADCs

This study sought to compare the anti-tumor effects of three different conjugation site pairs (Y180/F404, Y180/K42, and F404/K42) using the same FolRα antibody (1848-B10) and linker-warhead (Conjugate P). The in vitro cell killing activity of the three ADCs were very similar on KB and Igrov1 cells (Table 15).

TABLE 15

In vitro cell killing activity of tested ADCs (Conjugate P)

| ADC Molecule | Antibody | Conjugation Sites | Conjugate Form | DAR | EC50 on KB cells (nM) | EC50 on Igrov1 cells (nM) |
|---|---|---|---|---|---|---|
| 11 | α-GFP | HC-Y180, F404 | P | 3.58 | NK | NK |
| 12 | 1848-B10 | HC-Y180, LC-K42 | P | 3.93 | 0.21 | 0.085 |
| 1 | 1848-B10 | HC-Y180, F404 | P | 3.82 | 0.21 | 0.083 |
| 9 | 1848-B10 | HC-F404, LC-K42 | P | 3.90 | 0.19 | 0.061 |

Example 14

Study for Selection of Lead Anti-FOLR1 Antibodies for ADC Design

To assess potential lead antibodies for anti-FolRα ADCs, a selection of FolRα top leads that were conjugated to form Conjugate P with DAR4 were screened in vitro. In vitro cell killing activity for the top antibody leads are very similar on KB and Igrov1 cells and, the result is summarized in Table 16.

TABLE 16

In vitro cell killing activity of lead ADCs (Conjugate P)

| ADC Molecule | Sample | Sites of Conjugation | DAR | KB EC50 (nM) | KB Span (%) | Igrov1 EC50 (nM) | Igrov1 Span (%) | A549 EC50 (nM) | A549 Span (%) |
|---|---|---|---|---|---|---|---|---|---|
| 1 | 1848-B10 | Y180/F404 | 3.82 | 0.21 | 98 | 0.083 | 76 | NK | NK |
| 2 | 1848-A07 | Y180/F404 | 3.76 | 0.18 | 97 | 0.084 | 61 | NK | NK |
| 3 | 1848-B04 | Y180/F404 | 3.84 | 0.16 | 97 | 0.081 | 68 | NK | NK |
| 4 | 1848-H01 | Y180/F404 | 3.84 | 0.12 | 96 | 0.028 | 76 | NK | NK |

The same Conjugate P with DAR4 for the four top lead antibodies were screened in an in vivo efficacy study in the KB model (FIGS. 7, 8). Based on results in these studies, 1848-B10 and 1848-H01 were picked as the top antibody leads for further characterization. The sequences of 1848-B10 and 1848-H01, as well as the corresponding CDRs, is shown in Table 32. Additional properties for the top antibody leads are summarized in Table 17.

TABLE 17

Properties of lead antibodies

| Property | 1848-B10, Y180/F404 | 1848-H01, Y180/F404 |
|---|---|---|
| $K_D$ (Biacore) | 1.4 nM | 1 nM |
| $K_D$ (FACS cell binding, (CHO-h-FOLRα) | 4.5 nM | 3.7 nM |
| Cross-reactivity, Cyno (CHO-c-FOLRα) | 3.3 nM | 3.8 nM |
| Thermostability (DSC) | 66.6° C., 85.9° C. | 66.8° C., 83.4° C. |
| Mouse PK (ADC, no DAR analysis)* | 11.2 days; 6.94 mL/kg/day | 14.3 days; 5.46 mL/kg/day |
| Cyno PK (naked antibody)* | comparable to most antibodies; $T_{1/2}$ = 13.6 days | comparable to most antibodies; $T_{1/2}$ = 8.5 days |
| ADA in Cyno (naked antibody)* | Very low ADA response | ADA response observed in all animals, affected $T_{1/2}$, no AUC post second dose in one animal |
| ADC cell killing (Igrov1), Conjugate = P | 0.26 nM, 63% span | EC50 < 0.09 nM, span > 70% (averaged across 10 independent experiments) |
| ADC cell killing (OVCAR3), Conjugate = P | | EC50 = 0.03 nM, Span = 71% |
| Efficacy of multiple leads in KB model and clinical Igrov1 model | Weak tumor inhibition compared to vehicle group (E4) | Significant tumor inhibition compared to vehicle group (E4) |

DSC: Differential Scanning Calorimetry
*Surrogate ADCs: (1) 1848-B10, Y180/K42, (2) 1848-H01, Y180/K42

Example 15

Selection of Optimal Linker for Cleavable Hemiasterlin

Hemiasterlin with multiple linkers having different cleavage properties were generated. The antibody 1848-B10 was conjugated to several of the candidate linker variants, and the resulting ADCs were tested in in vitro cytotoxicity assays (Table 18). Among the candidate linker variants, an alternative of Conjugate P, having a proteolytic sequence of ValAla in place of ValCit, showed good cell killing activity (Conjugate Q, below) and afforded a potential advantage in scalability and synthetic efficiency.

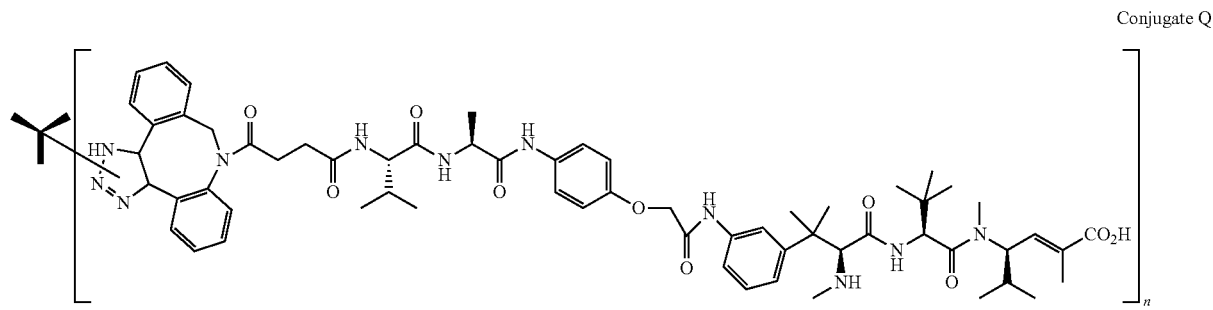

Conjugate Q

TABLE 18

Comparison of in vitro cytotoxity of cleavable hemiasterlin linker-drug variants

| ADC Molecule | Antibody | Conjugate Form | DAR | Igrov1 EC50 (nM) | Igrov1 Span (%) | A549 EC50 (nM) | A549 Span (%) |
|---|---|---|---|---|---|---|---|
| 12 | 1848-B10, Y180/K42 | P | 3.74 | 0.12 | 78 | NK | NK |
| 16 | 1848-B10, Y180/K42 | Q | 3.6 | 0.32 | 66 | NK | NK |

The in vitro cytotoxic activity of multiple lots of candidate ADC variants are summarized in Table 19. ADC Molecule 4 showed consistent cell killing with an EC50 ranging from 0.03-0.66 nM and a span ranging from 69-96% across different experiments.

TABLE 19

Summary of in vitro cytotoxicity studies in KB and Igrov1 cell lines

| Cell Line | 1848-H01, Y180/F404, Conjugate P (ADC Molecule 4) | | 1848-H01, Y180/F404, Conjugate Q (ADC Molecule 20) | | 1848-B10, Y180/F404, Conjugate P (ADC Molecule 1) | | 1848-B10, Y180/F404, Conjugate Q (ADC Molecule 17) | |
|---|---|---|---|---|---|---|---|---|
| | EC50 (nM) | Span (%) | EC50 (nM) | Span (%) | EC50 (nM) | Span (%) | EC50 (nM) | Span (%) |
| KB | 0.66 | 78 | | | 0.45 | 83 | | |
| | 0.12 | 96 | | | 0.21 | 98 | | |
| Igrov1 | 0.11 | 69 | | | 0.26 | 63 | | |
| | 0.03 | 76 | | | 0.08 | 76 | | |
| | | | 0.31 | 72 | | | 0.21 | 71 |
| | 0.16 | 62 | 0.24 | 42 | | | | |
| | 0.12 | 68 | 0.21 | 53 | | | | |
| | 0.06 | 70 | 0.13 | 54 | | | | |
| | 0.08 | 80 | 0.13 | 70 | | | | |
| | | | | | 0.09 | 81 | 0.23 | 70 |
| | | | | | 0.02 | 74 | 0.11 | 73 |

In addition, in a separate study, an antibody-drug conjugate was synthesized using antibody 1848-B10 Y180/F404 and Conjugate R (below):

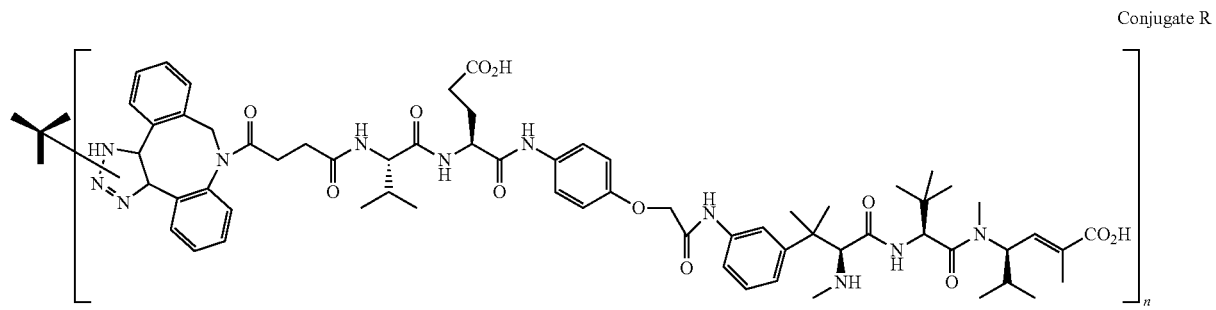

Conjugate R

Figure 14A:
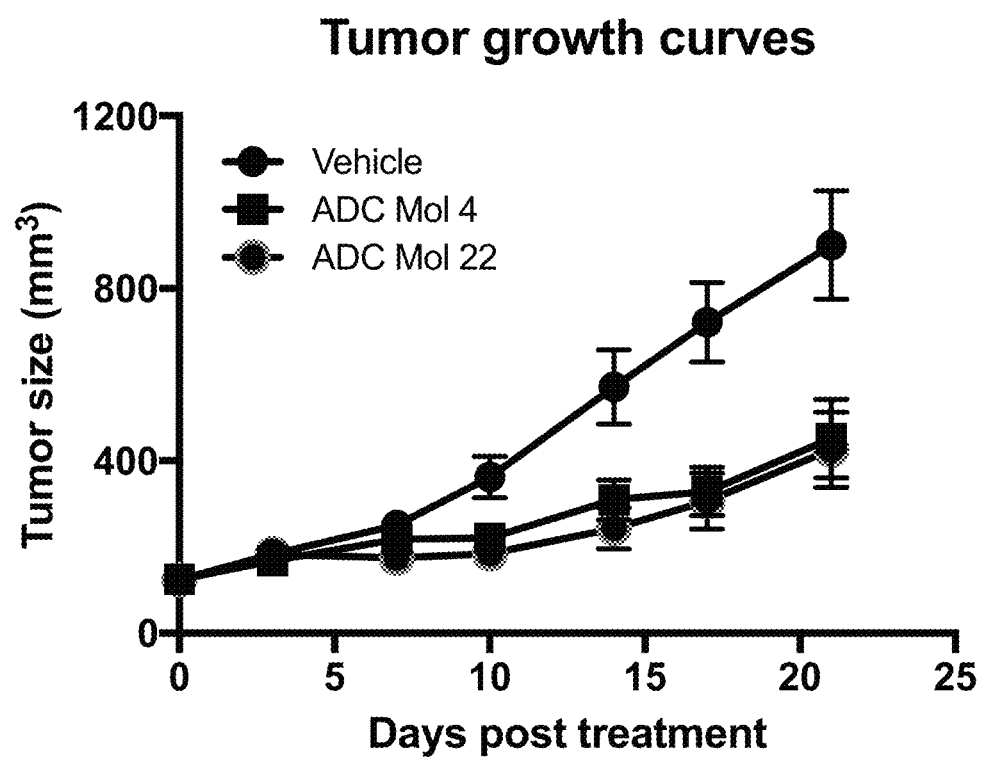
FIG. 14A is a graph illustrating tumor growth curves in mice implanted with Igrov1 ovarian cancer cells after being administered a single dose of different FOLR1 antibody-drug conjugates as disclosed herein.
Figure 14B:
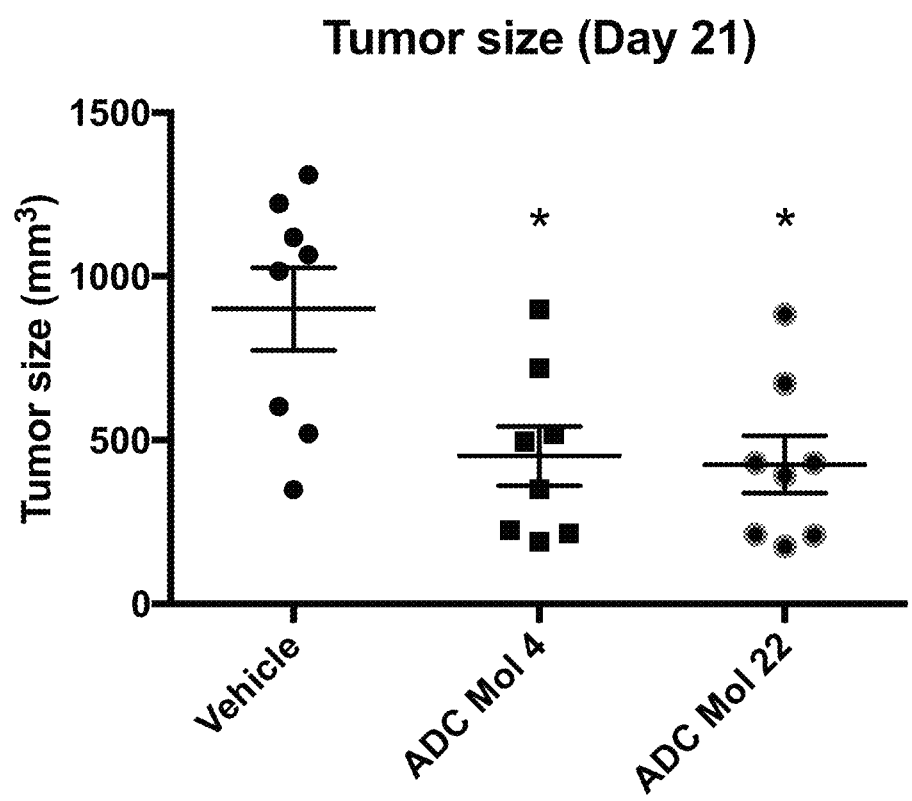
FIG. 14B is a scatter plot illustrating tumor size at day 21 in mice implanted with Igrov1 ovarian cancer cells after single-dose treatment with different FOLR1 antibody-drug conjugates disclosed herein.

Conjugate R includes DBCO adipoyl ValGlu linked to a hemiasterlin warhead. The ADC comprising 1848-H01 HC-Y180/F404 with Conjugate R (ADC Molecule 22) showed comparable in vitro cell-killing activity to ADC Molecule 4 (data not shown) as well as comparable in vivo activity in the Igrov1 model (FIGS. 14A, 14B). Accordingly, these results indicate that antibody 1848-B10 HC-Y180/F404 can be used with alternative linker warheads in ADCs targeting FolRα.

Example 16

Selection of an Optimal ADC Lead

This study sought to assess different aspects of the FolRα ADC molecule including the antibody, conjugation sites, and linker warhead. Igrov1 ovarian cancer cells were implanted subcutaneously into SCID Beige mice and treated with a single dose of 2.5 mg/kg FolRα ADC variants listed in Table 20. ADCs were administered when tumors reached ~150 mm$^3$.

TABLE 20

ADCs tested in the efficacy screening

| ADC Molecule | Antibody | Conjugation Sites | Conjugate Form | DAR | Igrov1 Cell Killing EC50 (nM) | Span (%) |
|---|---|---|---|---|---|---|
| 1 | 1848-B10 | Y180/F404 | P | 3.82 | 0.09 | 76 |
| 17 | 1848-B10 | Y180/F404 | Q | 3.74 | 0.21 | 71 |
| 12 | 1848-B10 | K42/Y180 | P | 3.72 | 0.12 | 78 |
| 16 | 1848-B10 | K42/Y180 | Q | 3.6 | 0.32 | 66 |
| 4 | 1848-H01 | Y180/F404 | P | 3.84 | 0.03 | 76 |
| 18 | 1848-H01 | K42/Y180 | P | 3.87 | 0.14 | 70 |
| 19 | 1848-H01 | K42/Y180 | Q | 3.61 | 0.23 | 52 |

Figure 12:
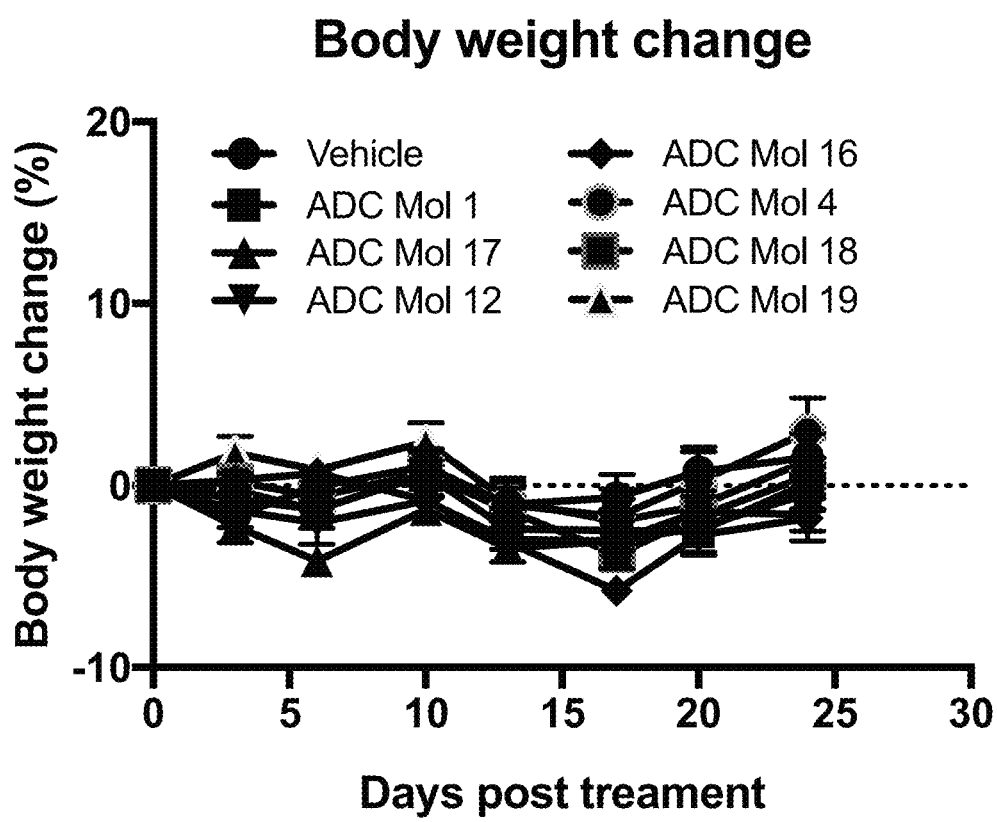
FIG. 12 is a graph illustrating body weight change in mice implanted with Igrov1 ovarian cancer cells after being administered a single dose of different FOLR1 antibody-drug conjugates as disclosed herein.
Figure 13A:
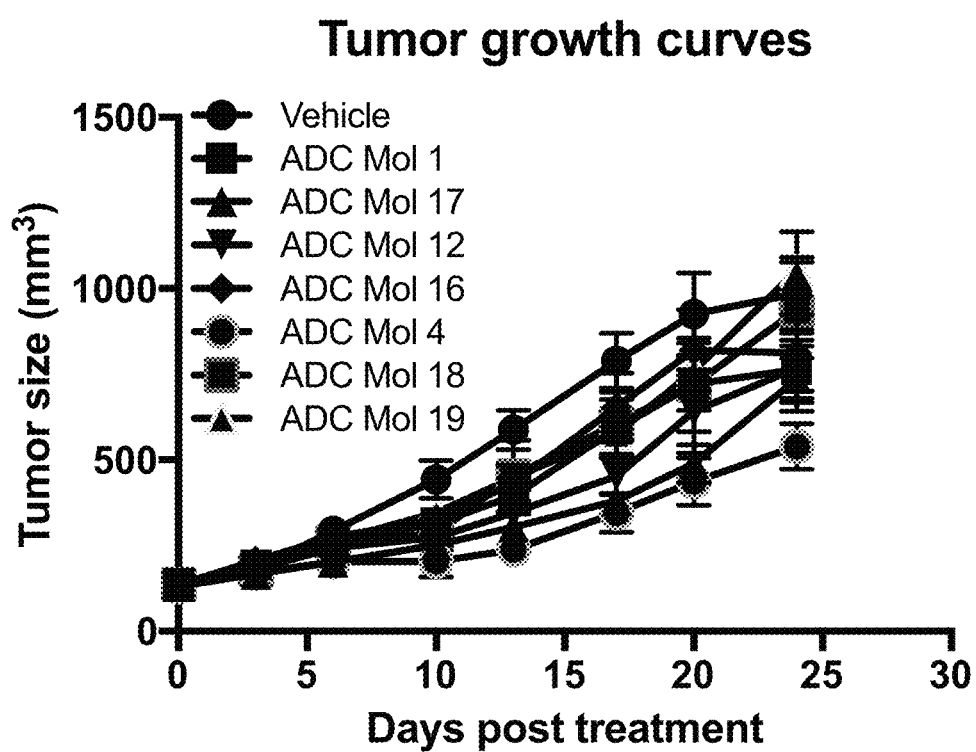
FIG. 13 (A, B) are graphs illustrating tumor growth curves and tumor size at day 24 in mice implanted with Igrov1 ovarian cancer cells after being administered a single dose of different FOLR1 antibody-drug conjugates as disclosed herein.
Figure 13B:
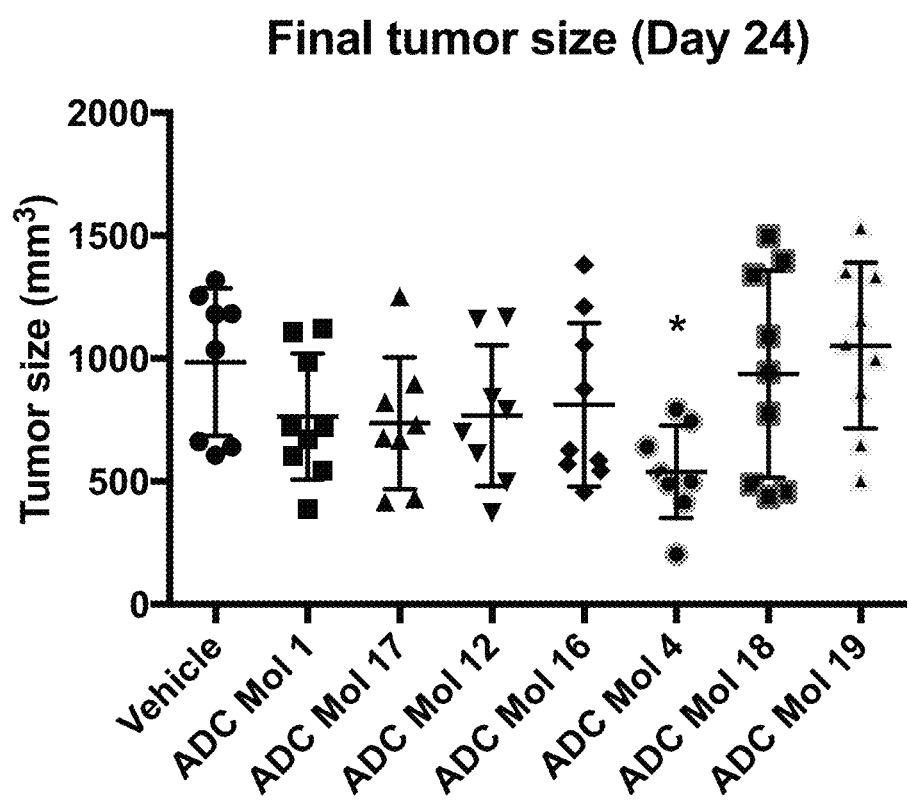

No toxicity was observed with any test article as evidenced by the absence of any significant weight loss, defined as >20% decrease in animal weight (FIG. 12). FIG. 13 (A, B) illustrates the effects of treatment on Igrov1 tumor growth and final tumor size on post treatment day 24 when the vehicle control treated tumors reached the study endpoint (~1000 mm$^3$). Out of seven FolRα ADC variants tested, ADC Molecule 4 significantly inhibited tumor growth compared to the vehicle control (FIGS. 13A,13B). This result identifies 1848-H01, Y180/F404, and SC239 as an optimal combination of anti-FolRα antibody, conjugation sites, and linker warhead, respectively, in Igrov-1 tumors.

Example 17

Cross-Reactivity of ADC Variants to FOLR Isoforms

The folate receptor has three isoforms in humans, termed hFolRα, hFolRβ, and hFolRγ (also FOLR1, FOLR2, and FOLR3, respectively). hFolRα and hFolRβ are expressed at the plasma membrane via a GPI anchor, whereas FolRγ is secreted. In normal tissues FolRα is generally expressed on the apical surface of polarized epithelial cells, while hFolRβ is expressed in latter stages of normal myelopoiesis and in the placenta, spleen, and thymus. In the normal development of the myelomonocytic lineage, hFolRβ is seen as a differentiation marker coexpressed with CD14 at relatively low levels in monocytes but not in CD34+ normal hematopoietic progenitors. hFolRγ is secreted at low levels from lymphoid cells in the spleen, thymus, and bone marrow. The three FR isoforms have a high degree of homology with FolRα, sharing 72% and 71% sequence identity with FolRβ and FolRγ respectively. Therefore, it is useful to determine the specificity of lead antibodies 1848-B10 and 1848-H01 for FolRα, and the extent of cross reactivity with cells expressing FolRβ and FolRγ.

Figure 15:
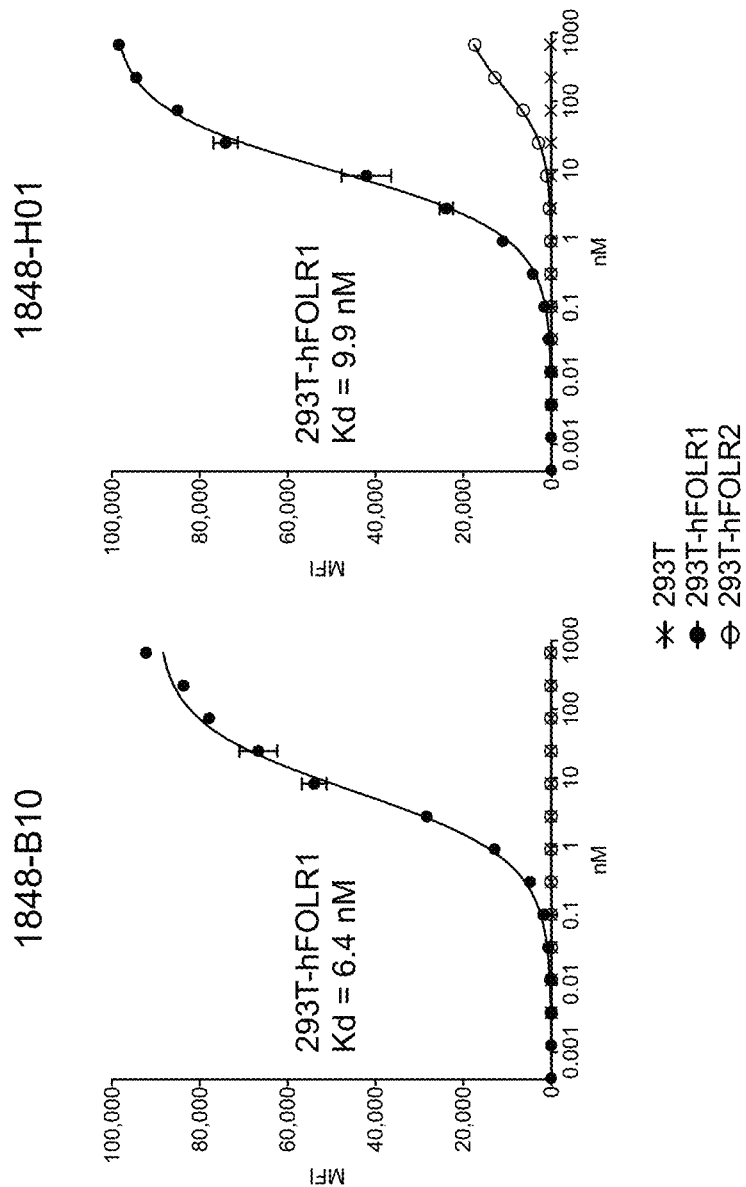
FIG. 15 includes plots illustrating binding of different FOLR1 antibodies to 293T transformed cells stably expressing different folate receptor isoforms (hFOLR1, hFOLR2).
Figure 16:
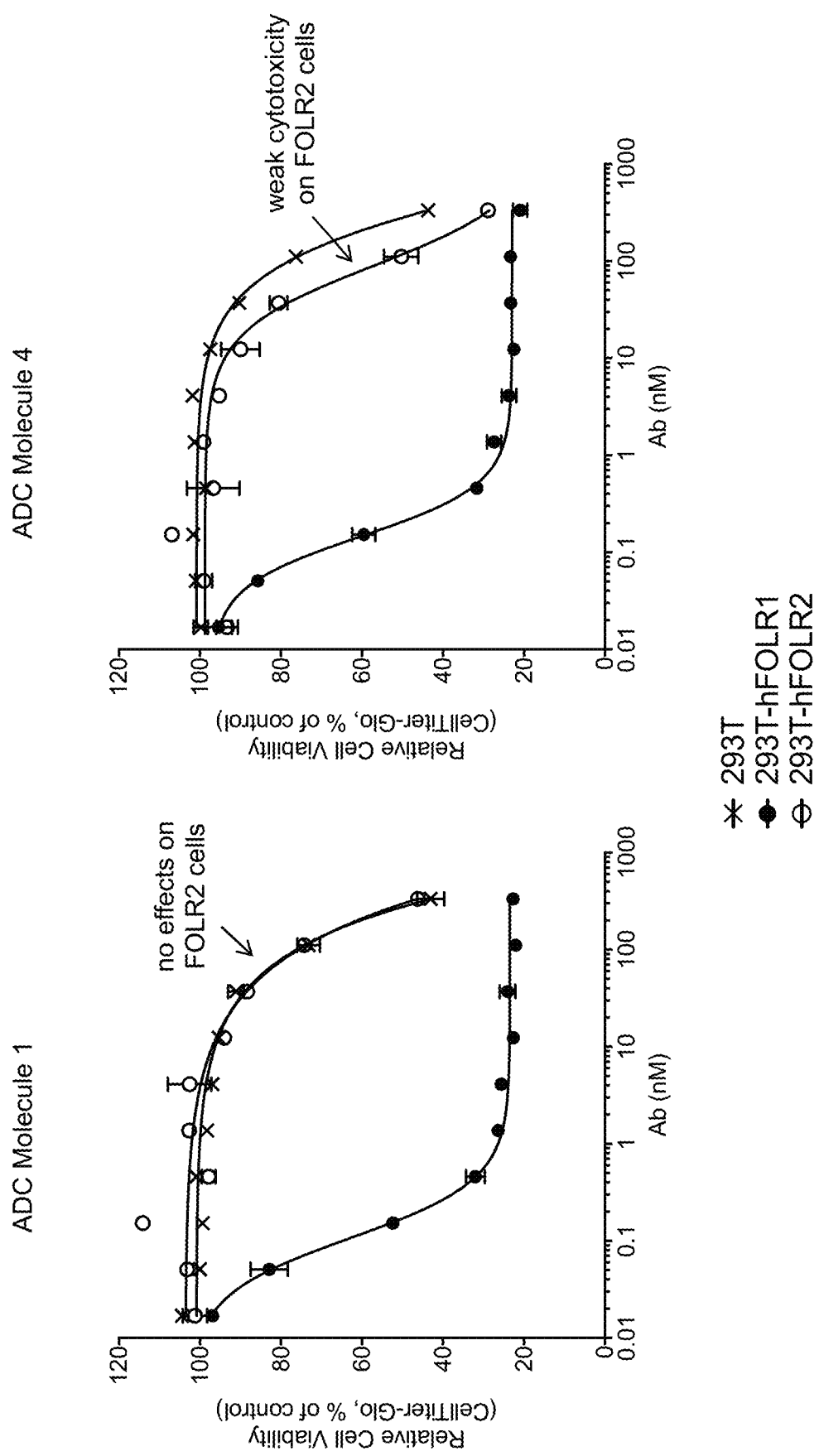
FIG. 16 includes plots illustrating the cytotoxic activity of different FOLR1 antibody-drug conjugates on 293T transformed cells stably expressing different folate receptor isoforms (hFOLR1, hFOLR2).

293T cells stably expressing the three folate receptor isoforms (hFolRα, hFolRβ, and hFolRγ) were generated and tested for binding to antibodies 1848-B10 and 1848-H01 in a FACS assay. In this assay, 1848-H01 but not 1848-B10 showed very weak binding to FolRβ (FIG. 15) but not to FolRγ (not shown). The 1848-H01 binding to FolRβ expressing cells had an affinity of 156 nM, with a B$_{max}$ that was only 20% compared to the B$_{max}$ for FolRα. Assessment of the cytotoxic activity of the corresponding ADC Molecules 4 and 1 on 293T cells expressing the FolRα and FolRβ isoforms showed that ADC Molecule 4 had a weak but specific cytotoxic effect on cells expressing FolRβ at concentrations above 10 nM, with an EC50 of ~100 nM compared to an EC50 of <10 nM for FolRα expressing cells (FIG. 16).

Example 18

Binding and Cytotoxic Activity of ADC Variants in Hematopoietic Cells

To determine if ADC Molecules 1 and 4 have an effect on viability of hematopoietic cells, FolR expression was determined in T cells, B cells and monocytes in isolated PBMCs (n=4 donors) and the extent of antibody 1848-H01 and 1848-B10 binding to FolRβ on immune cells was assessed. Heterogenous (donor variable) FolRα expression was detected in monocytes but this expression was transient and disappeared after 1 day in culture (data not shown), whereas FolRβ was consistently expressed in a subpopulation of monocytes (data not shown). Neither antibody 1848-B10 nor 1848-H01 was observed to bind monocytes, although FolRβ expression was detectable on these cells (data not shown). Further, CD14 monocytes were assayed for viability following treatment with ADC Molecules 1 and 4 and to address potential cytotoxicity. In correlation with negative cell binding, the ADC variants did not affect viability of monocytes/macrophages, suggesting no clinical impact on PB monocytes in humans (data not shown).

FolRβ is weakly expressed on M1 macrophages, and highly expressed on M2 macrophages and their subsets. Antibodies 1848-H01 and 1848-B10 were therefore assessed for their ability to bind isolated macrophages. However, neither antibody showed any binding to M1 or M2 macrophages although FolRβ expression was confirmed in these cells. To confirm this lack of interaction, the corresponding ADC molecules (1, 4) were assessed for cell killing activities on polarized macrophages (10,000 cells, incubation period=3 days). Consistent with the lack of binding, neither ADC variant showed any cytotoxic activity on the macrophages from multiple donors (data not shown).

Accordingly, the ADC variants were demonstrated to have minimum binding and cytotoxic impact on monocytes and macrophages isolated from human donors.

Example 19

Additional Characterization of Antibody-Drug Conjugates

Lead antibody-drug conjugates (ADCs) comprising an anti-FolRα antibody were evaluated and characterized. The characteristics that were measured and analyzed included expression and purification profiles of the lead ADCs, conjugation efficiency and in vitro and in vivo activity of the ADC in clinically relevant models. The properties of the anti-FolRα lead ADCs are summarized in Table 21.

TABLE 21

Properties of lead anti-FolRα ADCs

| Property | ADC Molecule 4 | ADC Molecule 20 |
| --- | --- | --- |
| DAR by MALDI | 3.73 | 3.81 |
| Conjugation Efficiency | 93% | 95% |
| ADC cell killing | Igrov1: EC50 = 0.08 nM. span = 80% | Igrov1: EC50 = 0.13 nM, span = 70% |
| Preclinical in vivo efficacy | Complete tumor growh inhibition at 5 mpk dose and above | Complete tumor inhibition at 10 and 15 mpk, weak tumor inhibition at 5 mpk |

Example 20

Dose Ranging Efficacy Study

The dose-response relationship of ADC Molecules 4 and 20 was evaluated in Igrov-1 tumors. This study sought to: (1) assess which FolRα ADC variant conjugated to hemiaster-lin-based linker warheads (Conjugates P, Q) was superior; (2) compare the anti-tumor activity of these FolRα ADC variants to a comparator molecule (ADC Molecule 21), and (3) determine the minimum and maximum efficacious dose of the more efficacious FolRα ADC variant identified.

All test articles are described in Table 22.

TABLE 22

ADCs tested in the dose range study

| ADC Molecule | Antibody | Conjugation Sites | Conjugate Form | DAR |
| --- | --- | --- | --- | --- |
| Vehicle (PBS Only) | NA | NA | NA | NA |
| 4 | 1848-H01 | Y180/F404 | P | 3.73 |
| 20 | 1848-H01 | Y180/F404 | Q | 3.76 |
| 21 | | Mov19-sulfo-SPDB-DM4 | | 3.3 |

Figure 17:
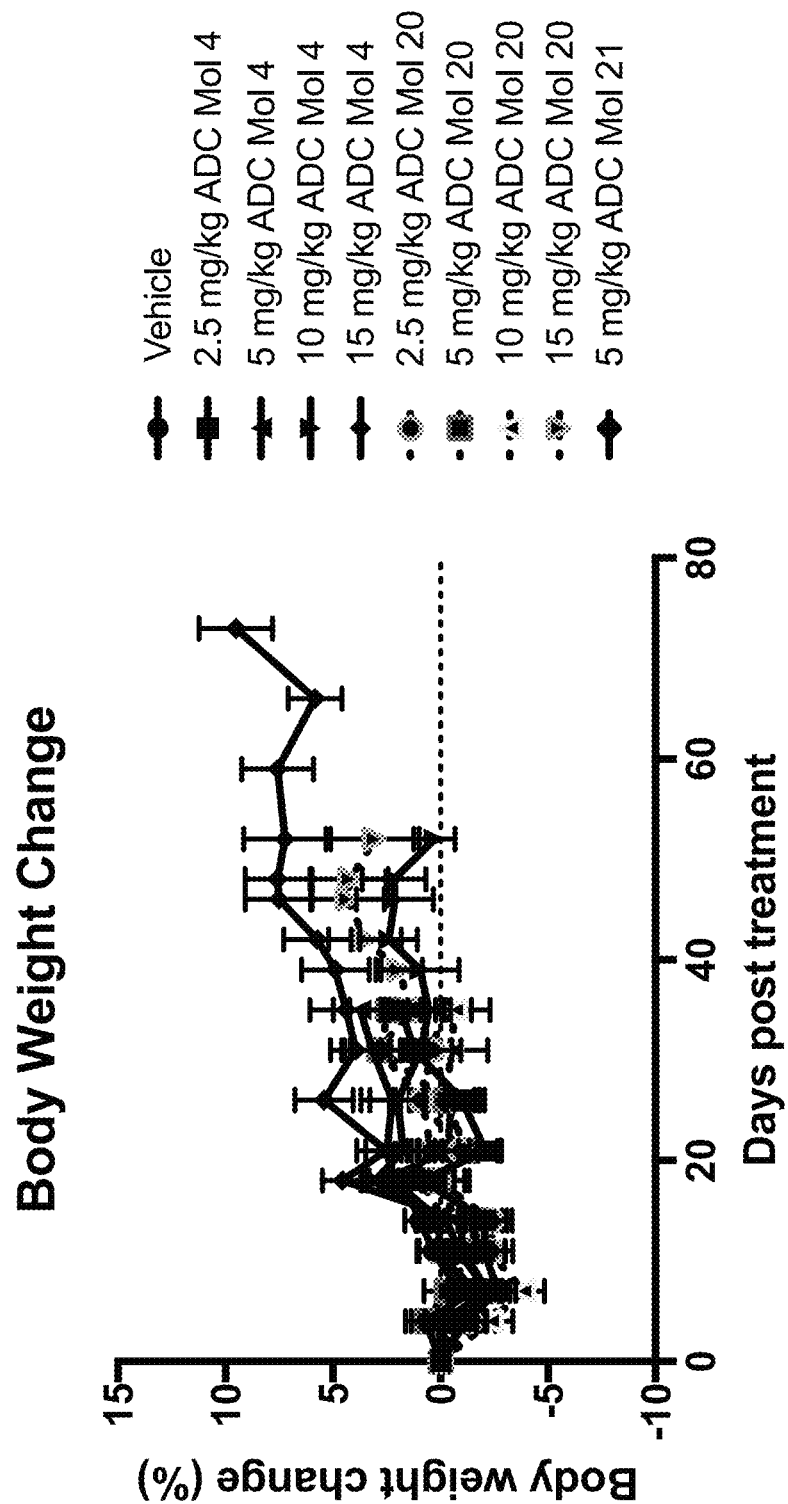
FIG. 17 is a graph illustrating body weight change in mice implanted with Igrov1 ovarian cancer cells after being administered various doses of different FOLR1 antibody-drug conjugates as disclosed herein.
Figure 18A:
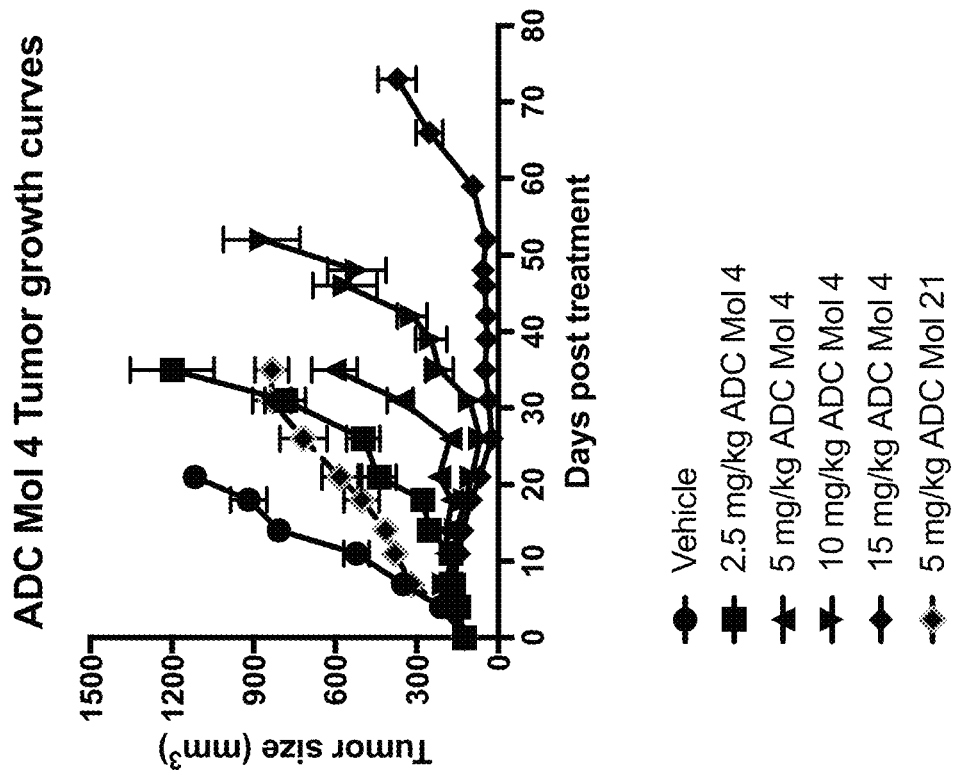
FIG. 18 (A, B, C) includes tumor growth curves and scatter plot with tumor size at day 21 in mice implanted with Igrov1 ovarian cancer cells after being administered various doses of different FOLR1 antibody-drug conjugates as disclosed herein.
Figure 18B:
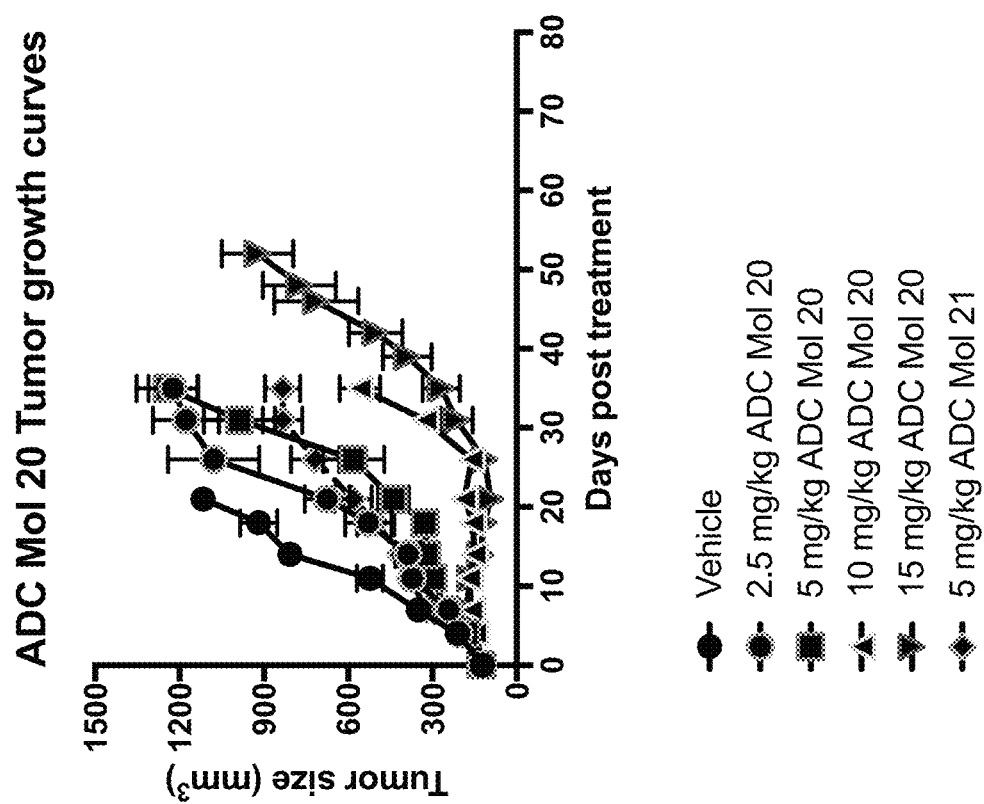
Figure 18C:
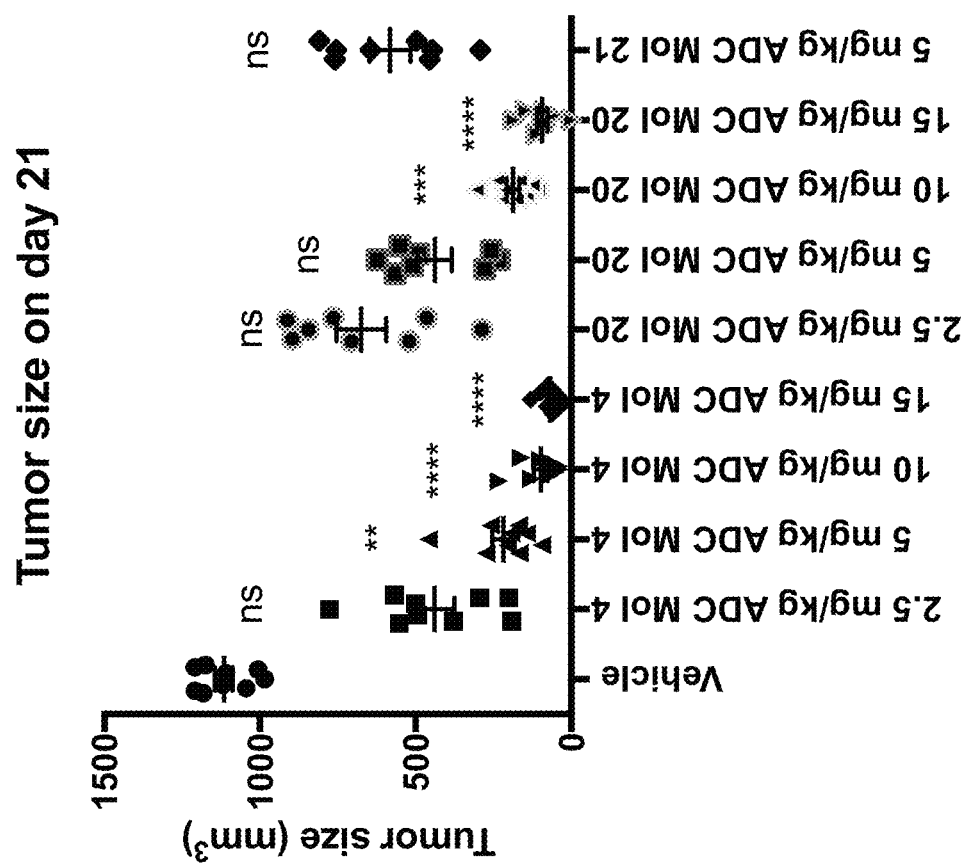
Figure 19A:
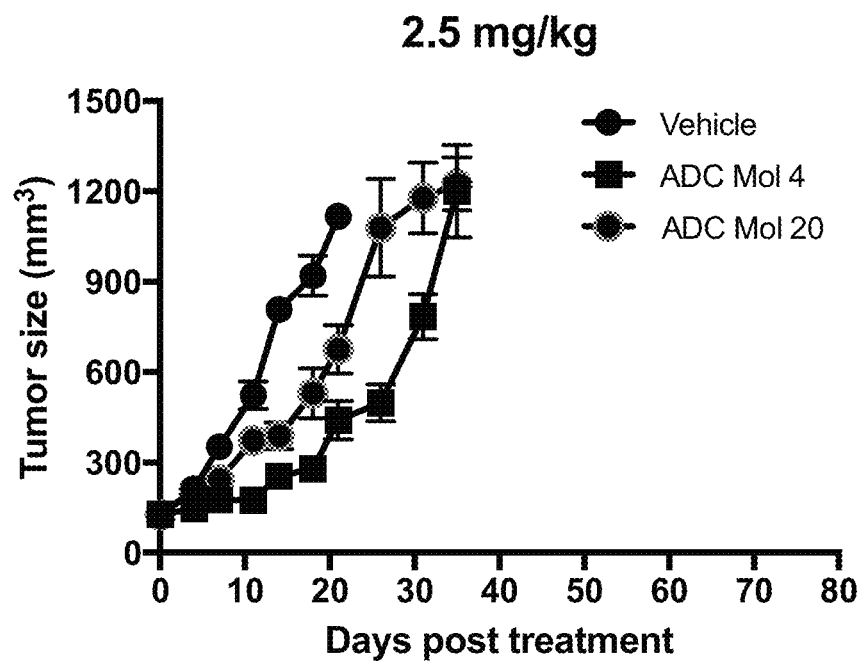
FIG. 19 (A, B, C, D) includes graphs illustrating tumor size in mice implanted with Igrov1 ovarian cancer cells after being administered various doses of different FOLR1 antibody-drug conjugates as disclosed herein.
Figure 19B:
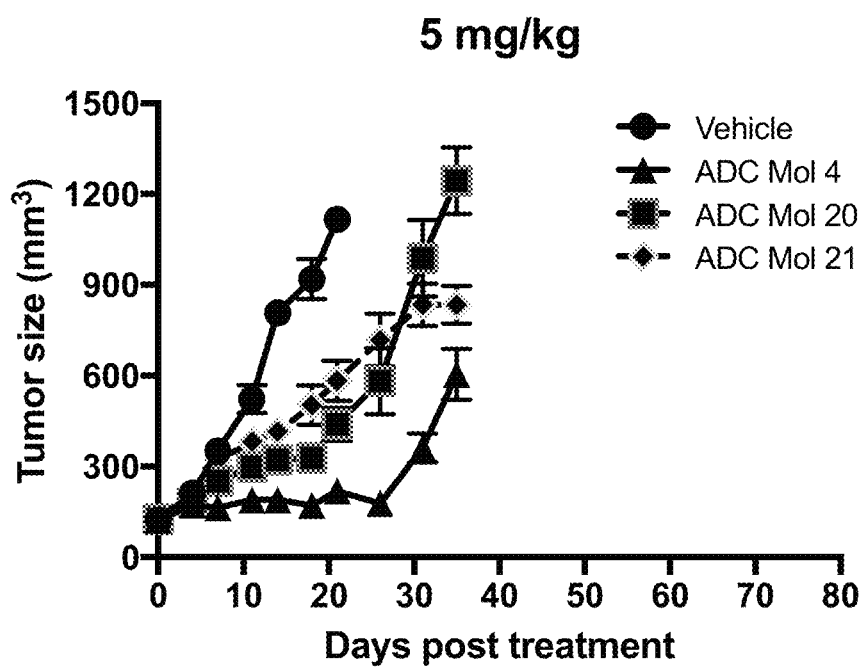
Figure 19C:
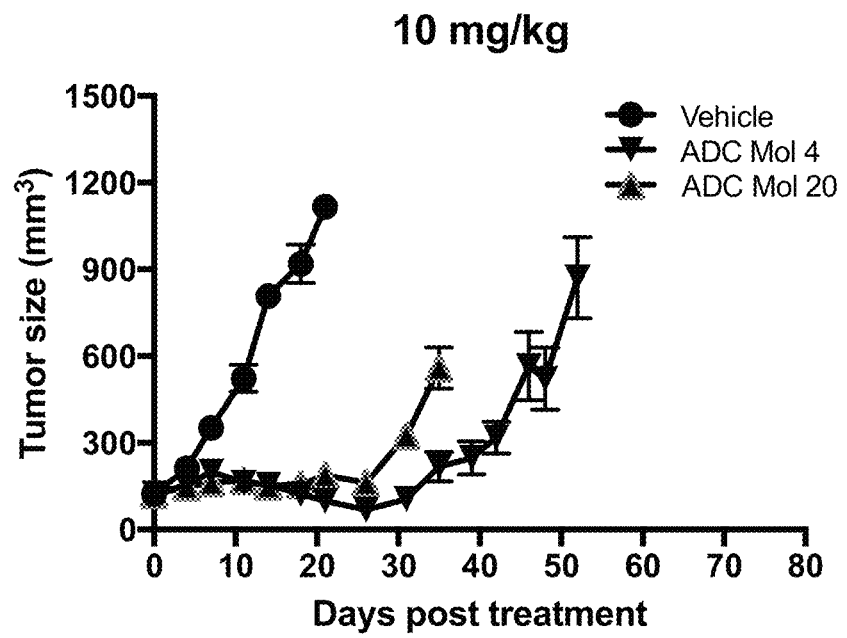
Figure 19D:
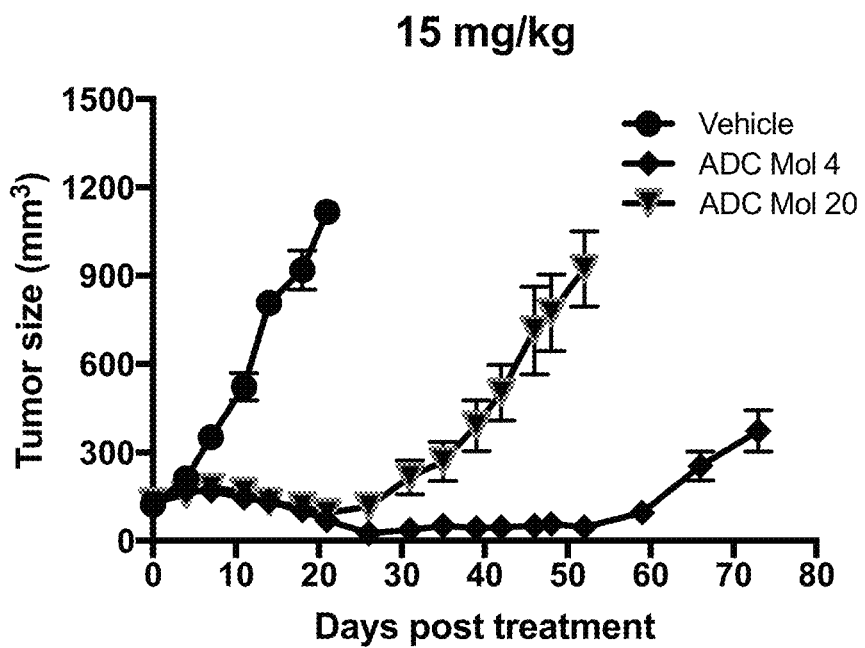
Figure 20:
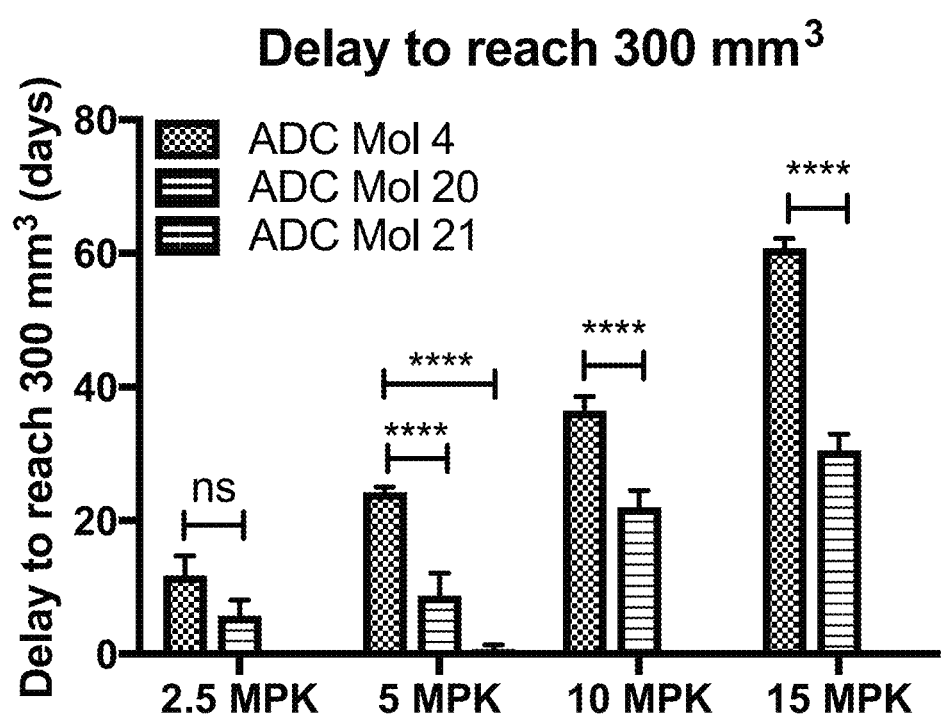
FIG. 20 is a chart illustrating the delay of tumor growth in mice implanted with Igrov1 ovarian cancer cells after being administered various doses of different FOLR1 antibody-drug conjugates as disclosed herein.

SCID Beige mice with established Igrov1 ovarian tumors were treated once with 4 doses of ADC Molecule 4 or 20, with the dosage ranging from 2.5 mg/kg to 15 mg/kg. For comparison, the benchmark group was treated once with 5 mg/kg of a comparator ADC molecule (ADC Molecule 21). No toxicity was observed with any test article as evidenced by the absence of significant weight loss (defined as >20% decrease in animal weight) (FIG. 17). FIG. 18 (A, B, C) illustrates the effects of treatment on Igrov1 tumor growth and the individual tumor sizes until post treatment day 21 when the vehicle control treated tumors reached the study endpoint (>1000 mm$^3$). Comparison of tumor size on day 21 (versus vehicle control) indicates that 5 mg/kg and 10 mg/kg doses of ADC Molecule 4 are more efficacious than equivalent doses of ADC Molecule 20 or comparator ADC Molecule 21 based on lower p values (FIG. 18C). At the highest dose (15 mg/kg), both ADC Molecules 4 and 20 demonstrated potent anti-tumor activity with similar p values compared to vehicle control (FIG. 18C). Side by side comparison of tumor growth curves sorted by dose revealed that ADC Molecule 4 was more potent than ADC Molecule 20 based on superior activity of ADC Molecule 4 at lower doses (FIG. 19, A-D). Tumor stasis was observed until day 26 post treatment at 5 mg/kg ADC Molecule 4 versus at 10 mg/kg ADC Molecule 20 (FIGS. 19B, 19C). Tumor regression was induced starting at 10 mg/kg ADC Molecule 4 versus 15 mg/kg ADC Molecule 20 (FIGS. 19C, 19D). In addition, ADC Molecule 4 significantly delayed tumor growth to reach 300 mm$^3$ compared to ADC Molecule 20 at 5, 10 and 15 mg/kg and comparator ADC Molecule 21 at 5 mg/kg (FIG. 20).

Cumulatively, these results demonstrate that ADC Molecule 4 is significantly more more efficacious than ADC Molecule 20 and ADC Molecule 21 in Igrov1 tumors. The minimum efficacious dose of ADC Molecule 4 was observed at 5 mg/kg, while 15 mg/kg was the maximum efficacious dose with longest duration of response.

Example 21

Efficacy of ADC Variants in Combination Treatment with Carboplatin

Figure 21A:
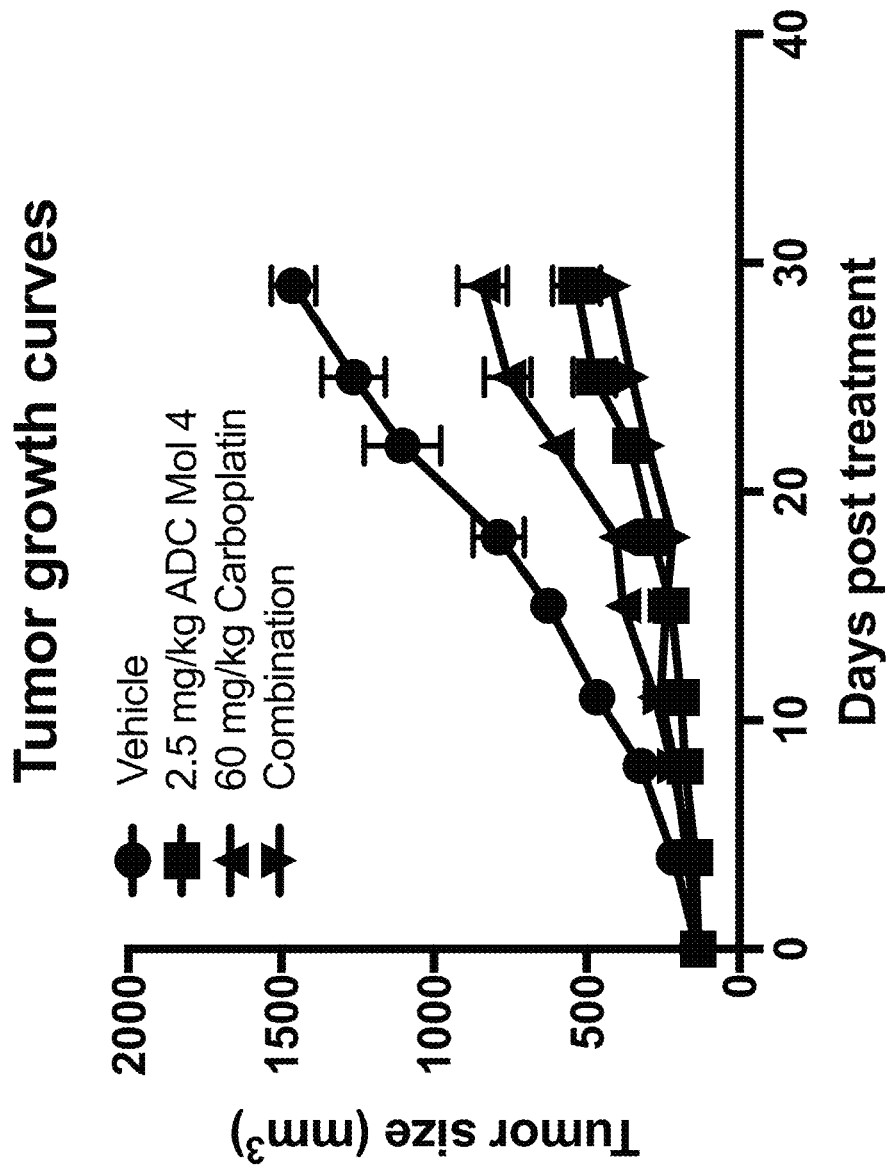
FIG. 21 (A, B, C) includes tumor growth charts, a scatter plot illustrating tumor size at day 29, and a chart illustrating tumor growth inhibition at day 29 in animals bearing established Igrov1 tumors treated with a single dose of an exemplary FOLR-1 antibody-drug conjugate with or without carboplatin.
Figure 21B:
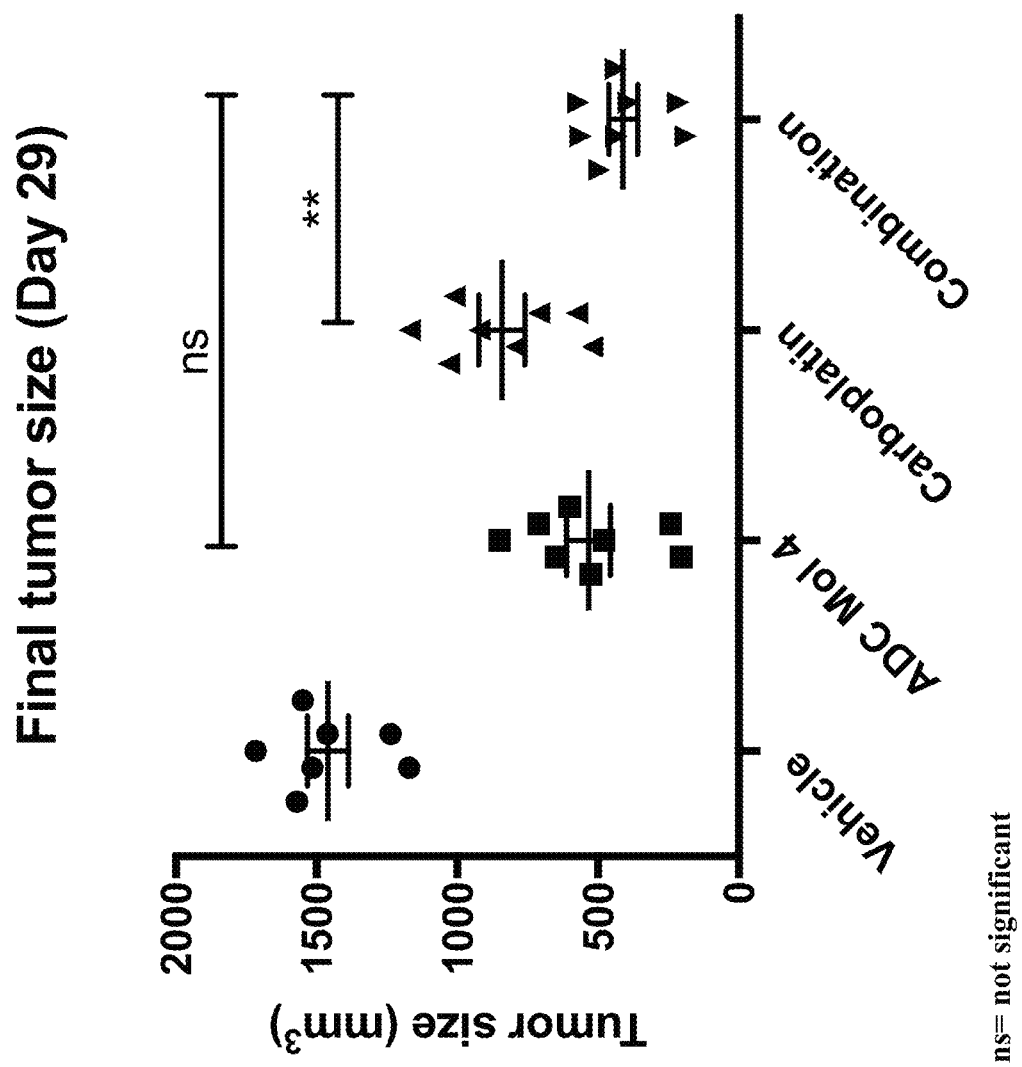
Figure 21C:
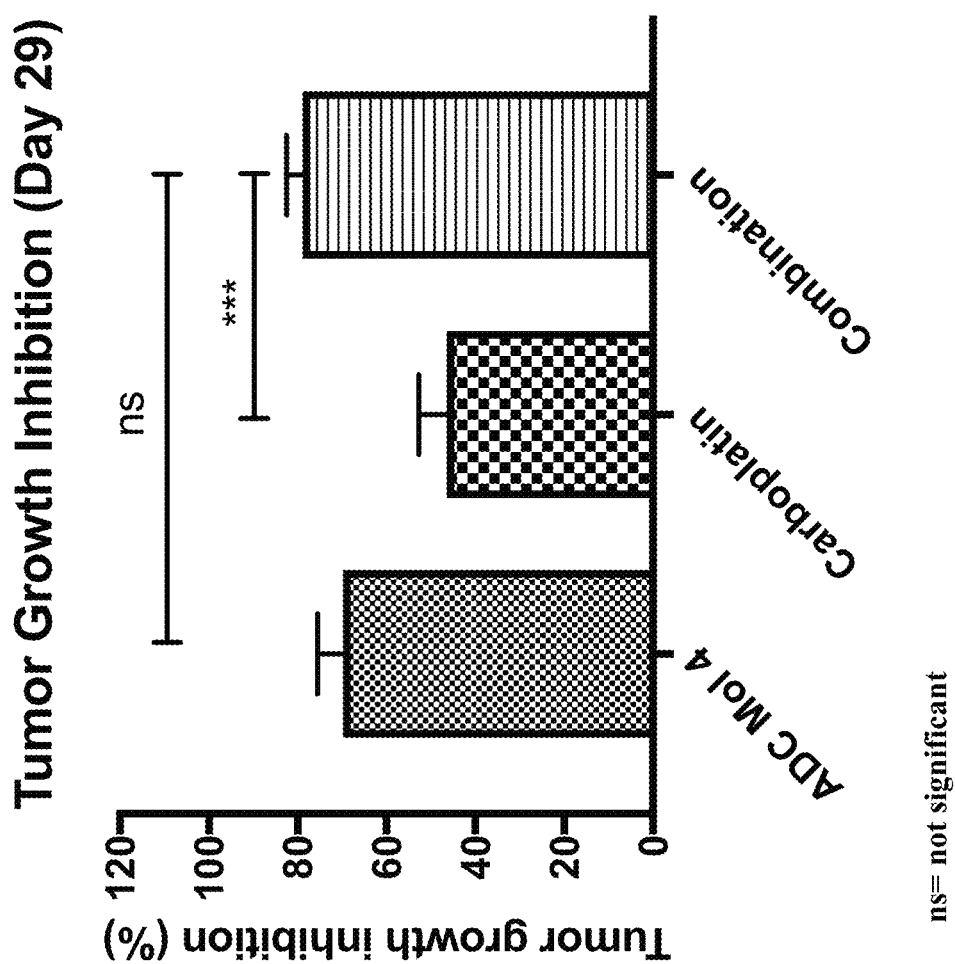

The efficacy of ADC Molecule 4 in combination with a standard chemotherapeutic agent for ovarian cancer, carboplatin, was evaluated in Igrov1 tumors. Animals bearing established Igrov1 tumors (average tumor size 150 mm$^3$) were treated with a single dose of 2.5 mg/kg ADC Molecule 4 with or without 60 mg/kg carboplatin every 7 days, for two treatments (q7dx2). FIG. 21A illustrates the effects of treatment on Igrov1 tumor growth until post treatment day 29 when the mean of vehicle control treated tumors reached the study endpoint (~1200 mm$^3$). Analysis of final tumor size and tumor growth inhibition (TGI) on day 29 showed that single agent ADC Molecule 4 and carboplatin exhibited moderate activity compared to vehicle control with TGI ranging from 50% and 70%, respectively (FIGS. 21B and 21C). The combination of ADC Molecule 4 with carboplatin significantly improved efficacy compared to carboplatin alone, but the combination was not significantly different compared to the single agent ADC Molecule 4 (FIG. 21A). The final mean tumor size in combination treated animals was significantly smaller compared to single agent carboplatin treated animals (414 mm$^3$ vs. 842 mm$^3$, p=0.0011) (FIG. 21B). In addition, TGI in combination treated group was higher at 79% vs. 47% for single agent carboplatin group (p=0.0008) (FIG. 21C).

In conclusion, significant added benefit was observed when ADC Molecule 4 was combined with carboplatin compared to single agent carboplatin. This observation was consistently reproduced in two additional independent studies using the same model dosed with similar doses of ADC Molecule 4 and carboplatin (data not shown).

Example 22

Efficacy of ADC Variants in Ovarian Tumor Models

Figure 22A:
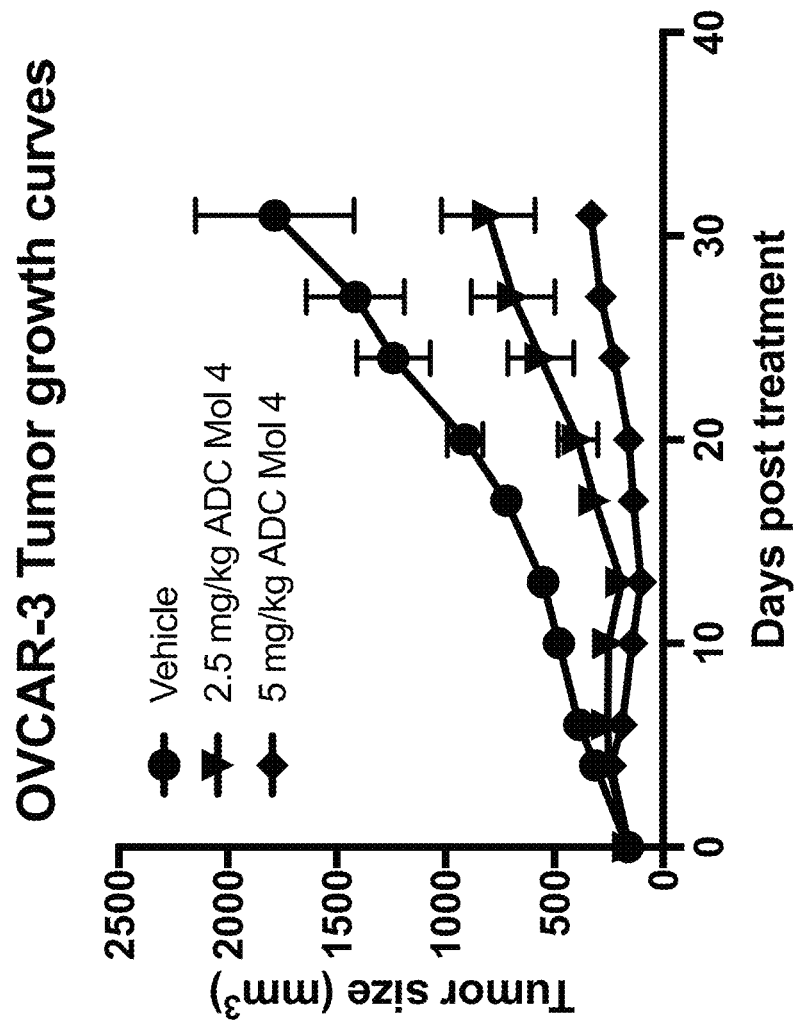
FIG. 22 (A, B) includes a tumor growth chart and a scatter plot illustrating tumor size at day 31 in animals bearing established OVCAR3 tumors.
Figure 22B:
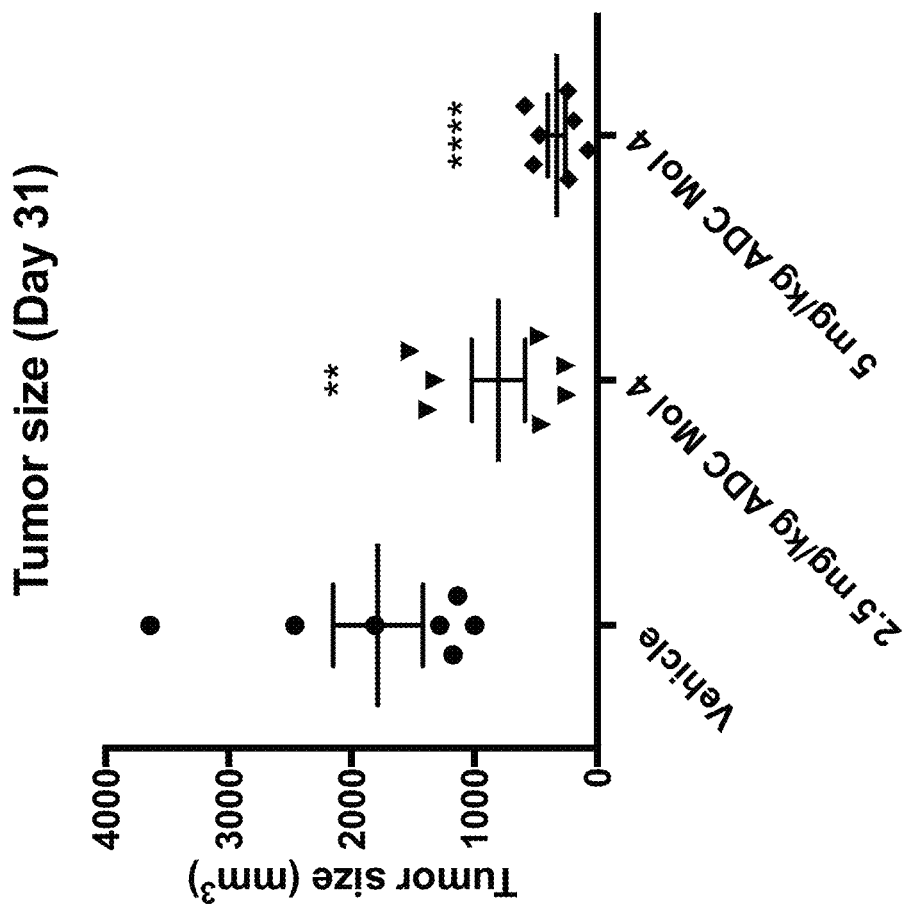
Figure 23A:
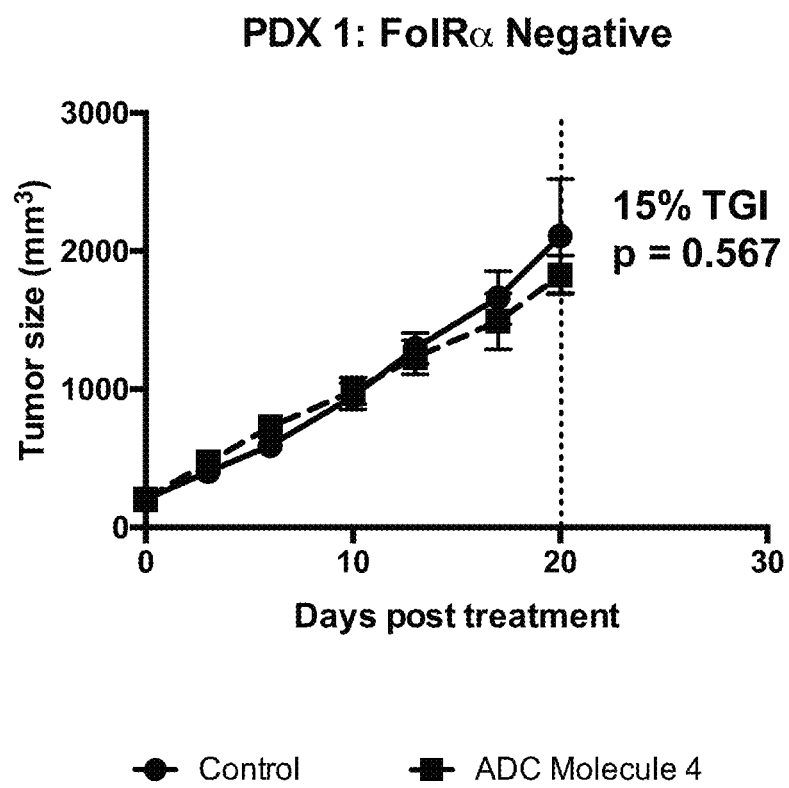
FIG. 23 (A-F) includes tumor growth curves of various endometrium patient derived xenograft models to which an exemplary FOLR1 antibody-drug conjugate was administered.
Figure 23B:
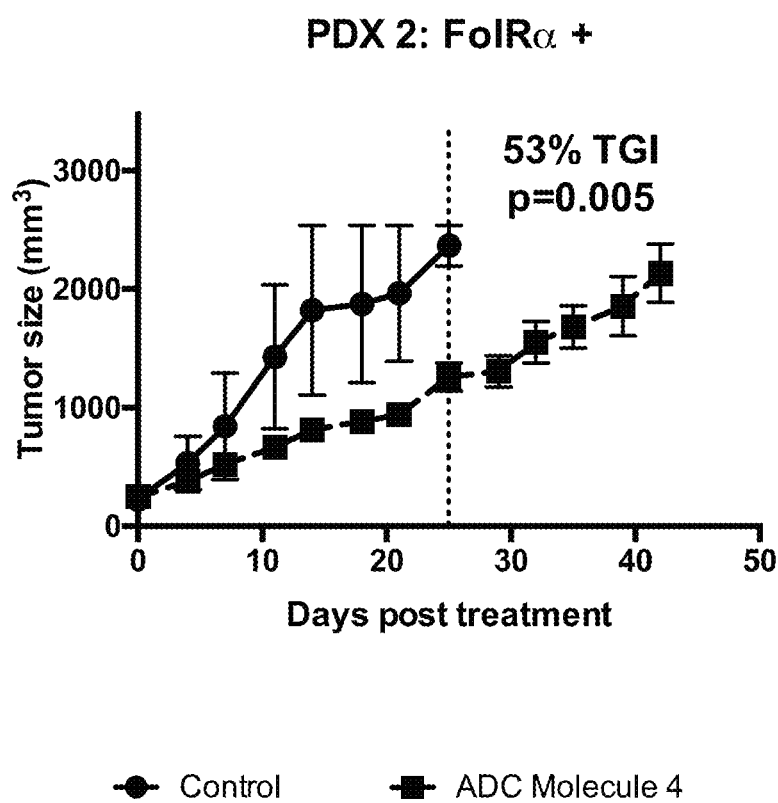
Figure 23C:
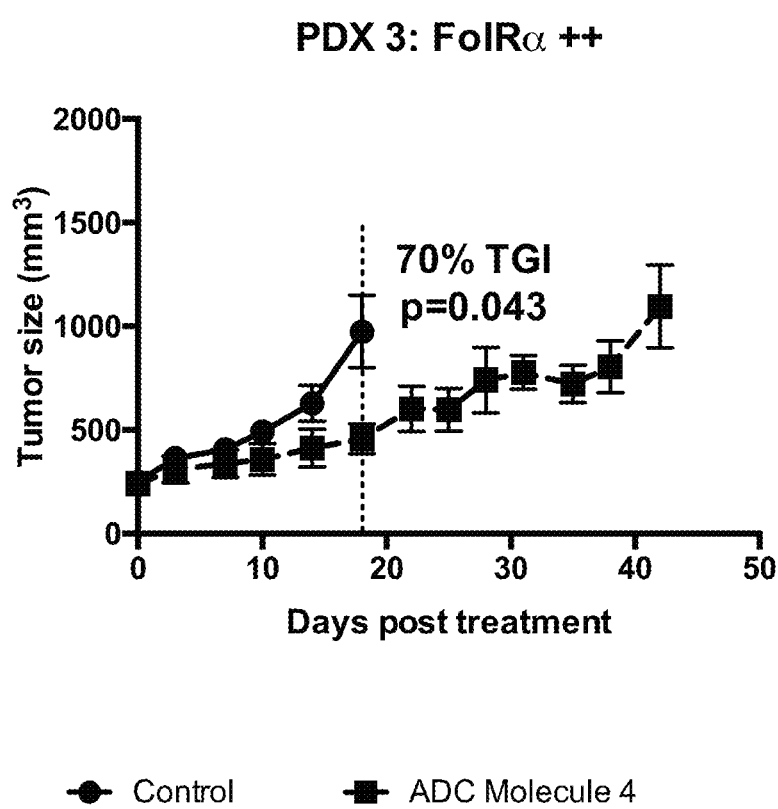
Figure 23D:
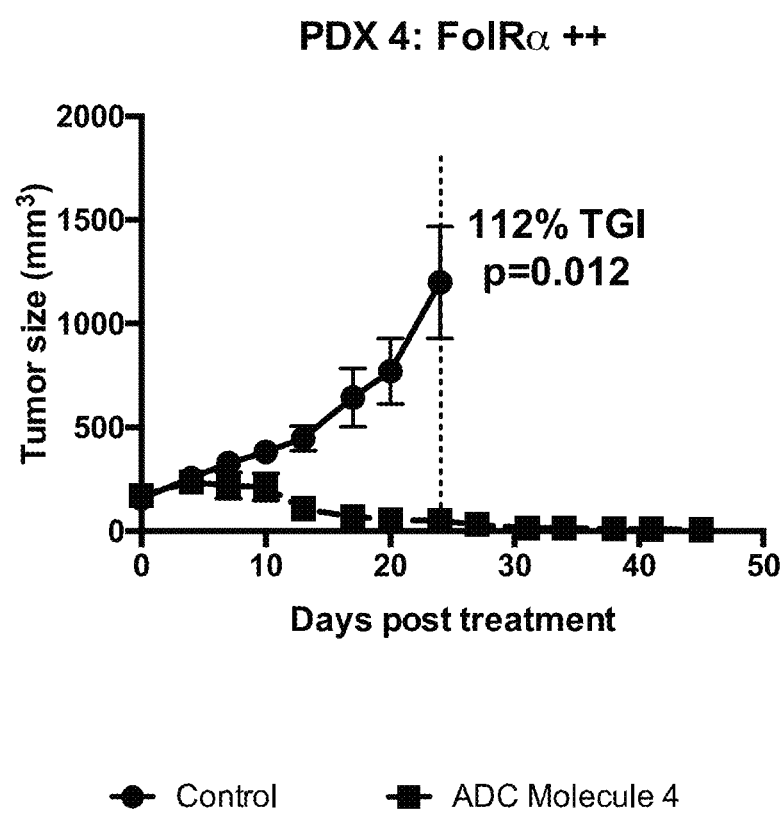
Figure 23E:
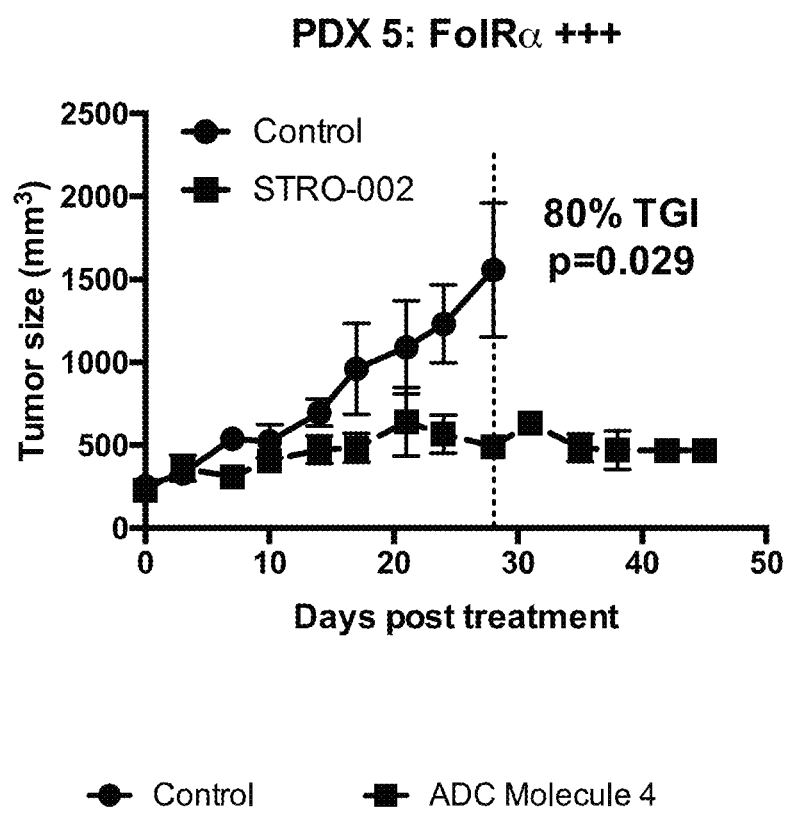
Figure 23F:
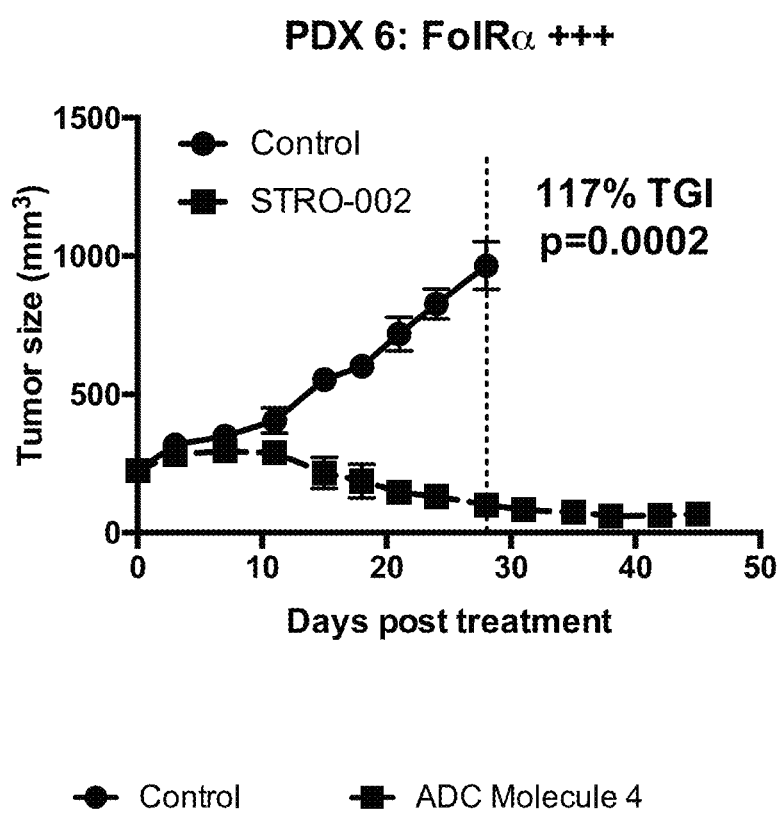

The efficacy of ADC Molecule 4 was evaluated in human ovarian cell line OVCAR3 tumor models. Animals bearing established OVCAR3 tumors ranging from 100-200 mm$^3$ were treated with a single dose of 2.5 or 5 mg/kg of ADC Molecule 4. FIG. 22 (A, B) illustrates the effects of treatment on OVCAR3 tumor growth and final tumor size on post treatment day 31 when the mean of vehicle control treated tumors reached >1500 mm$^3$. Treatment with 2.5 mg/kg ADC Molecule 4 resulted in tumor stasis until around 12 days post treatment, while 5 mg/kg ADC Molecule 4 induced tumor regression with regrowth observed around day 20 post treatment (FIG. 22A). Analysis of final tumor size on day 31 showed that treatment with 2.5 and 5 mg/kg of ADC Molecule 4 were both significantly efficacious compared to vehicle control exhibiting 60% and 89% tumor growth inhibition (TGI), respectively (FIG. 22B).

Example 23

Efficacy of ADC Variants in Endometrium Patient Derived Xenograft Models

Endometrium cancer patient derived xenograft (PDX) models were assessed for FolRα expression levels by immunohistochemistry analysis of xenograft tissue using a biotinylated mouse monoclonal antibody against FolRα. The efficacy of ADC Molecule 4 was assessed in a subset of these PDX models and included models with negative, low (+), medium (++) and high (+++) FolRα expression. Animals bearing established (~100-200 mm$^3$) PDX tumors received 10 mg/kg ADC Molecule 4 weekly via intravenous (IV) injection (n=3) or no treatment (control, n=2-3) until the group mean was >1,000 mm$^3$ or until day 45 post treatment. If the tumors reached 1,000 mm$^3$ before Day 14 post treatment, the endpoint was extended to 2,000 mm$^3$.

Statistically significant efficacy was observed in about 50% of the FolRα positive models tested, with tumor growth inhibition (TGI) ranging from approximately 50% to greater than 100% (indicating regression below the tumor size at the start of treatment). Meanwhile, no significant activity was observed in all PDX models with negative FolRα expression. The degree of anti-tumor activity of ADC Molecule 4 appeared to positively correlate with FolRα expression levels (e.g. PDX tumors with higher levels of FolRα exhibited higher TGI in response to treatment with ADC Molecule 4). The data shown (FIG. 23) is a representation of some of the models that exhibited efficacy: (A) PDX model with FolRα-negative expression; (B) PDX model with FolRα+ expression; (C, D) PDX models with FolRα++ expression; (E, F) PDX models with FolRα+++ expression. Percent TGI (determined on the last day of control tumors) and corresponding p values are indicated on the graphs. Statistical analysis of TGI was performed using an unpaired t test. A probability of less than 5% (p<0.05) was considered as significant. All graphs are presented as mean±SEM.

Example 24

Efficacy of ADC Variants in Combination Treatment with Avelumab

Figure 24A:
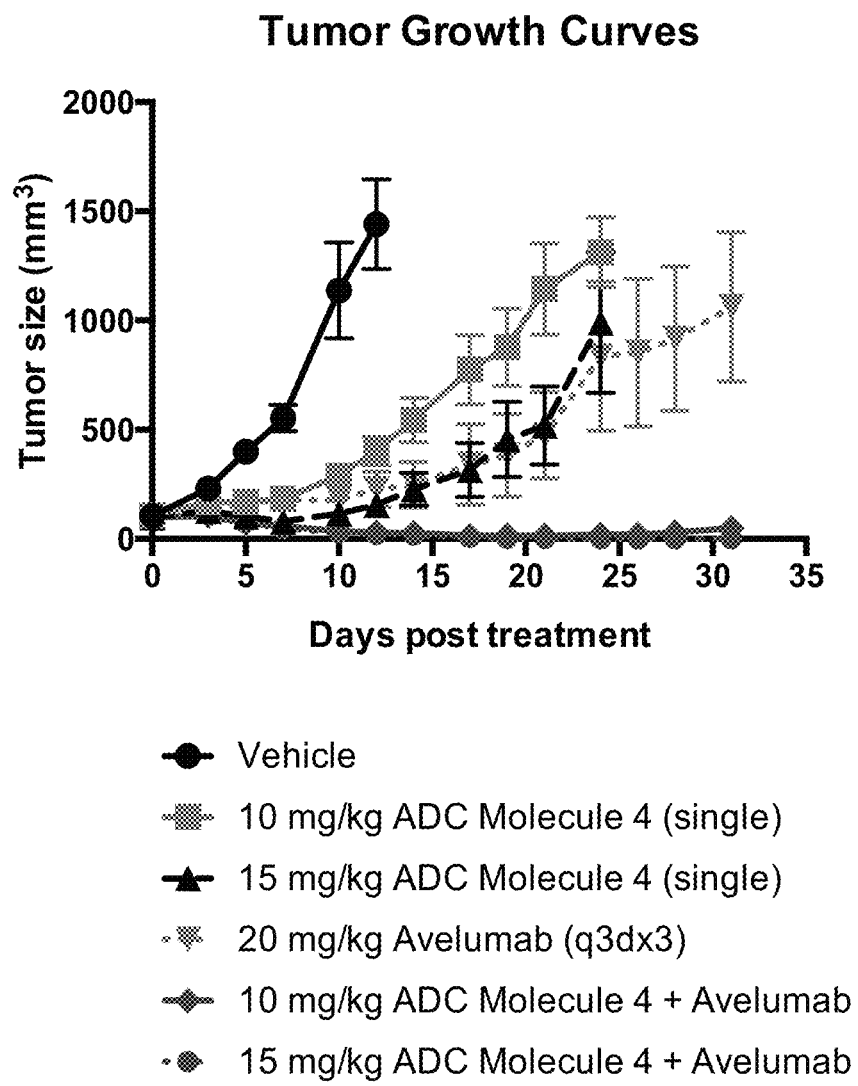
FIG. 24 (A, B) includes tumor growth curves and a tumor size scatter plot of animals with MC38-hFOLR1 tumors in response to treatment with an exemplary FOLR1 antibody-drug conjugate, Avelumab, or a combination of both.
Figure 24B:
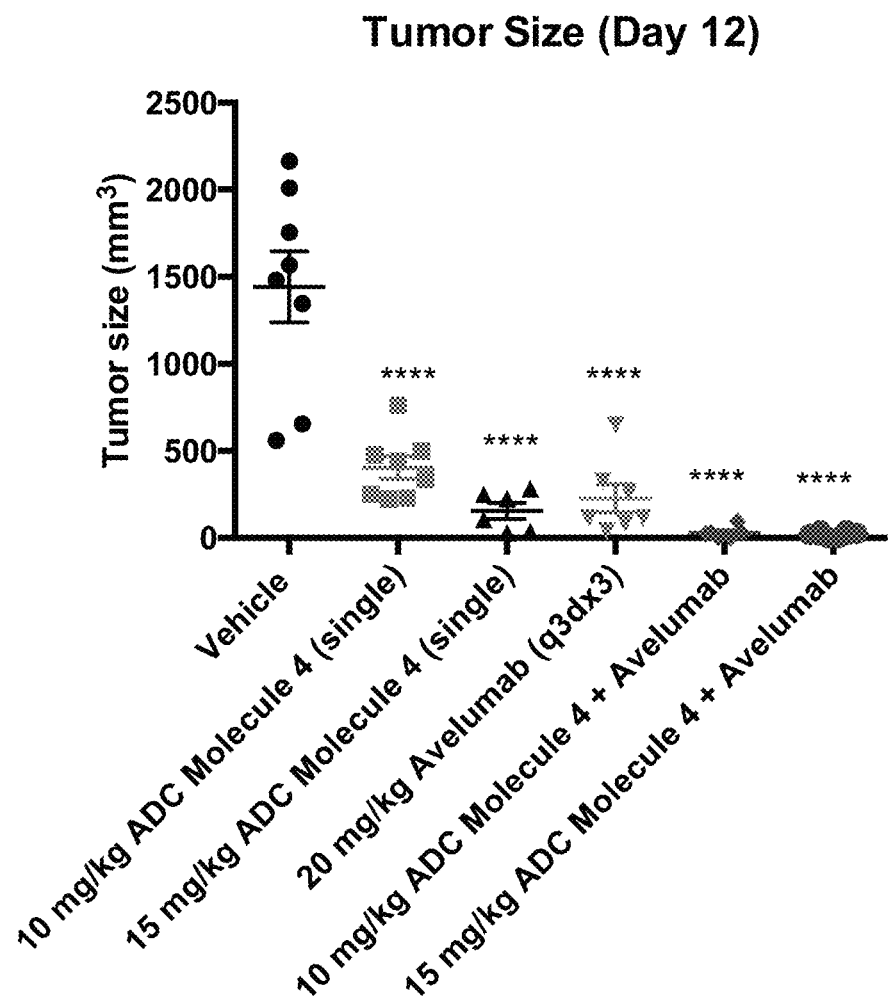
Figure 25A:
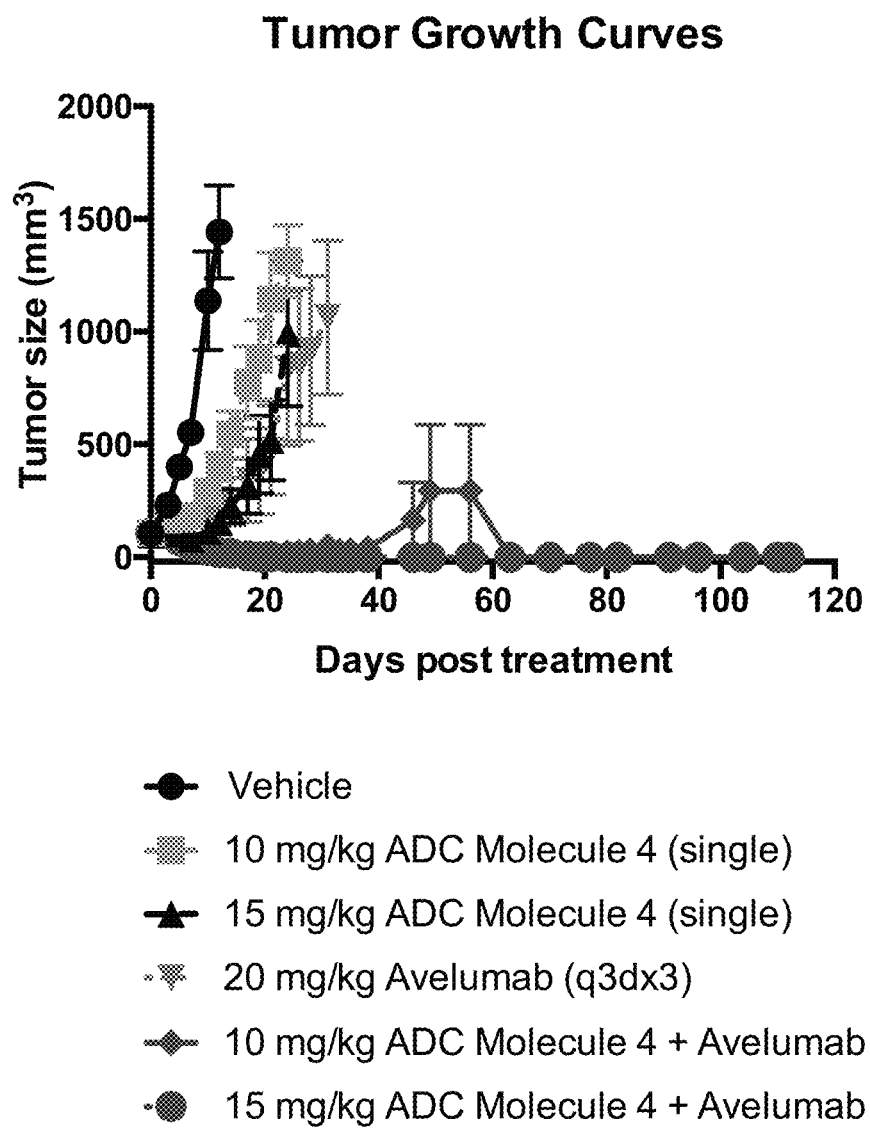
FIG. 25 (A, B) includes tumor growth curves and a Kaplan-Meier survival plot of animals with MC38-hFOLR1 tumors in response to treatment with an exemplary FOLR1 antibody-drug conjugate, Avelumab, or a combination of both.
Figure 25B:
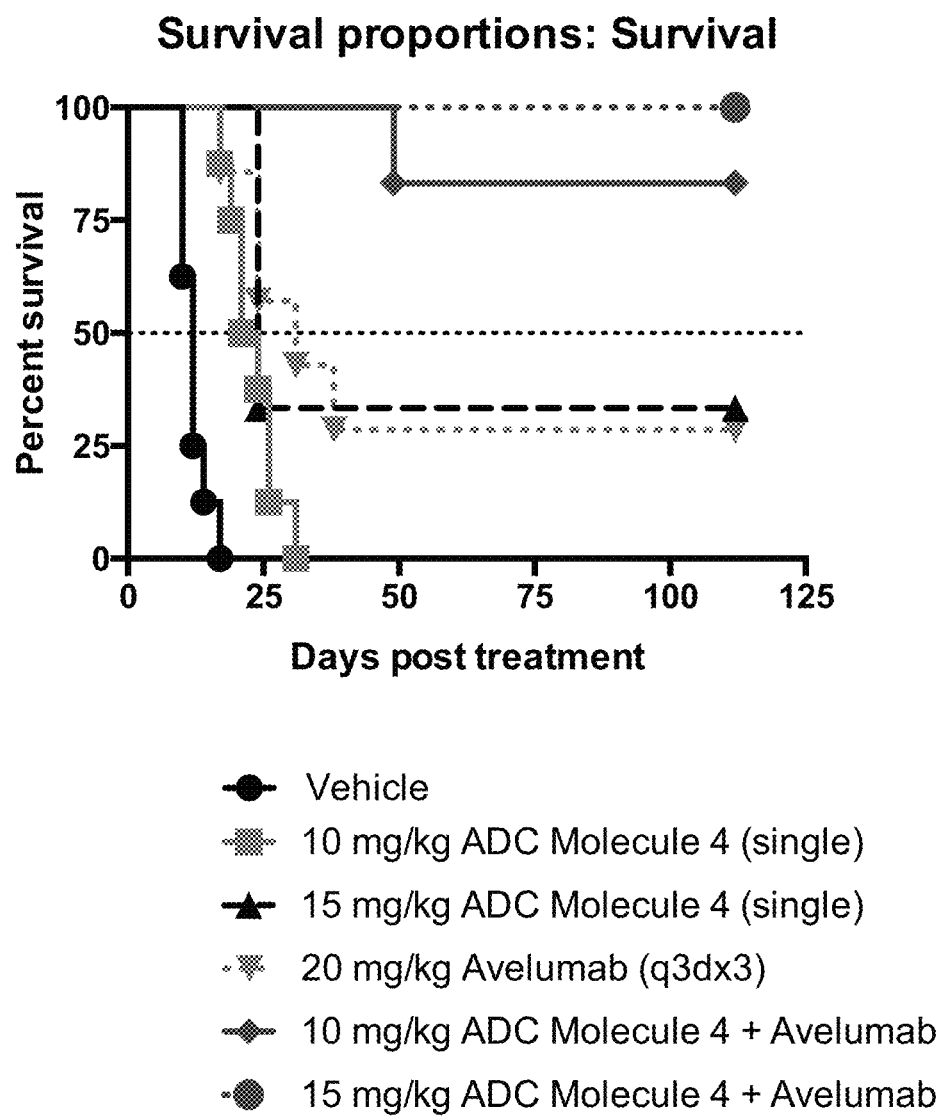

The efficacy of ADC Molecule 4 in combination with PD-L1 inhibitor Avelumab (clinical grade) was evaluated in animals bearing established MC38-FolRα tumors. Results are illustrated in FIGS. 24 and 25. FIGS. 24A and 25A illustrate MC38-hFolRα tumor growth curves in response to indicated doses of ADC Molecule 4, Avelumab, or a combination of both. Growth curves are shown until >50% of animals in the single agent treatment groups were euthanized due to reaching tumor size limit based on 1ACUC protocol. FIG. 24B is a scatter plot of individual tumor size on day 12 when mean of control tumors was >1,200 mm$^3$. Statistical analysis for comparison to vehicle control was performed using one-way ANOVA with Dunnett's multiple comparisons test. A probability of less than 5% (p<0.05) was considered as significant. FIG. 25B is a Kaplan-Meier curve that shows the fraction of animals that survive in response to treatment with indicated doses of ADC Molecule 4, Avelumab or combination of both. All graphs are presented as mean or individual values±SEM.

As illustrated in FIG. 24, single agent ADC Molecule 4 at either dose (10 mg/kg or 15 mg/kg once via IV injection) or Avelumab (administered q3dx3 intraperotineally) initially resulted in tumor stasis until approximately day 7, while combination treatment induced tumor regression (FIG. 24A). Analysis of tumor size on day 12 showed significant inhibition of tumor growth in all treatment groups compared to vehicle control (FIG. 24B). Continued monitoring revealed that ADC Molecule 4 in combination with Avelumab markedly enhanced anti-tumor activity compared to either single agent alone as evidenced by complete regression (e.g. no palpable tumors) in 14 out of 15 animals (FIG. 24B).

As illustrated in FIG. 25, tumor re-growth was observed in one animal in the 10 mg/kg ADC Molecule 4+ Avelumab group and was euthanized on day 59 due to reaching the maximum tumor size (FIG. 25A). Furthermore, combination treatment demonstrated curative effects or complete remission based on significantly prolonged survival of healthy animals with normal body weight gain and no tumor regrowth up to 112 days post-treatment which is 3-4 fold longer median survival than single agents (FIG. 25B).

Example 25

Pharmacokinetic Properties of ADC Variants in SCID Beige Mice

The non-compartmental pharmacokinetic parameters of candidate FolRα ADC variants that demonstrated good efficacy in the KB and Igrov1 tumor models were evaluated in non-tumor bearing SCID Beige mice. A single 5 mg/kg IV bolus was administered, sampled and pooled from different mice to obtain time-points for pharmacokinetic (PK) parameters. FolRα ADC variants do not bind murine FolRα, therefore, antigen-mediated PK effects are not expected. A list of tested articles and summary of the results are presented in Table 23.

TABLE 23

Pharmacokinetic parameters of FolRα ADC variants in SCID Beige mice

| Parameters | Units | ADC Molecule 4 | ADC Molecule 20 | ADC Molecule 21 |
|---|---|---|---|---|
| Dose | mg/kg | 5 | 5 | 5 |
| Study length | Days | 21 | 21 | 21 |
| $T_{1/2}$ | Days | 6.36 | 5.48 | 7.59 |
| $C_0$ | ug/mL | 122 | 125 | 115 |
| Cmax ± SE | µg/mL | 118 ± 5 | 123 ± 10 | 113 ± 4 |
| $AUC_{(0\text{-}all)}$ ± SEM | day* µg/mL | 476 ± 22 | 543 ± 22 | 447 ± 8 |
| $AUC_{(0\text{-}\infty)}$ | day* µg/mL | 523 | 580 | 510 |
| CL | mL/day/kg | 9.57 | 8.63 | 9.8 |
| $V_{SS}$ | mL/kg | 79.7 | 62.2 | 95.2 |

The elimination half-life ($T_1/2$) was determined from a regression analysis of the log-linear plot of the concentration-time curves. Specifically, $T_{1/2}$, CL and Vss of ADC Molecule 4 were 6.36, 9.57 and 79.7, respectively. In addition, the $C_{max}$ for ADC Molecule 4 was determined to be 118±5 µg/mL.

Figure 26:
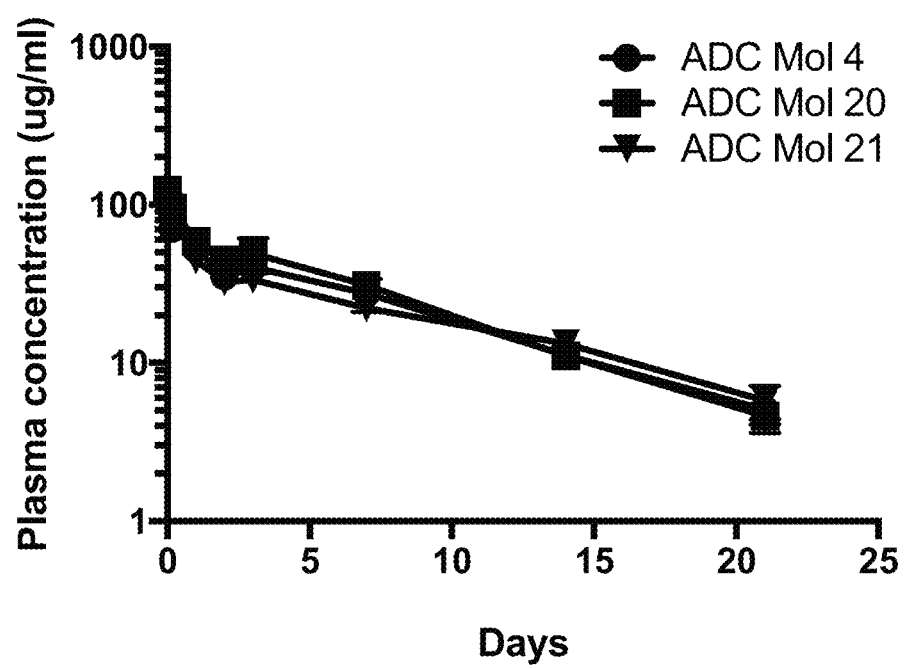
FIG. 26 is a graph illustrating the pharmacokinetic plasma profile of different FOLR1 antibody-drug conjugates in SCID Beige mice.

In general, the pharmacokinetic properties of all FolRα ADC variants tested were comparable and exhibited similar PK profiles values (FIG. 26). In addition, the murine pharmacokinetic profile of all test articles exhibited PK profiles that are similar those of other FDA-approved monoclonal IgG antibodies.

Example 26

Pharmacokinetic Properties of ADC Lead Antibodies in Cynomolgous Monkeys

The non-compartmental pharmacokinetic (PK) parameters of antibodies 1848-1310 and 1848-H01 with K42/Y180 conjugation sites was assessed in cynomologous monkeys (n=3 for each antibody dose) in a repeat dose study. Two 10 mg/kg IV doses were administered on day 1 and day 15, and samples analyzed to determine PK parameters and anti-drug antibody (ADA) response. The two antibodies bind cyno FolRα with comparable affinity to the human target, therefore, antigen-mediated PK effects would be expected. As summarized in Table 24, PK profiles for both antibodies are similar.

TABLE 24

Pharmacokinetic parameters of lead anti-FolRα antibodies in cynomolgous monkeys

| Treatment | | Terminal $t_{1/2}$ (day) | $C_0$ (µg/mL) | $AUC_{(0\text{-}last)}$ (day*µg/mL) | $AUC_{(0\text{-}\infty)}$ (day*µg/mL) | Clearance (mL/day/kg) | $V_{SS}$ (mL/kg) |
|---|---|---|---|---|---|---|---|
| 1848-B10, K42/Y180 (dose 1) | Mean SE | 9.73 1.01 | 263 8 | 1100 95 | 1700 171 | 6.02 0.59 | 78.8 8.4 |
| 1848-B10, K42/Y180 (dose 2) | Mean SE | 13.1 2.3 | 241 14 | 1670 120 | 2110 40 | 4.74 0.09 | 83.2 15.5 |
| 1848-H01, K42/Y180 (dose 1) | Mean SE | 6.54 0.51 | 267 8 | 1010 60 | 1310 130 | 7.83 0.83 | 67.3 2.0 |
| 1848-H01, K42/Y180 (dose 2) | Mean SE | 8.08 2.51 | 220 25 | 1370 30 | 1530 110 | 6.60 0.47 | 71.3 12.1 |

Mean pharmacokinetic parameters for antibody 1848-H01 (K42/Y180) were similar after Doses 1 and 2. Mean plasma clearance after Doses 1 and 2 was 7.83 and 6.60 mL/day/kg, respectively, and distribution volume was 67 and 71 mL/kg, respectively. Mean terminal half-life for Doses 1 and 2 was 6.5 and 8.0 days, respectively. Mean pharmacokinetic parameters for 1848-B10 (K42/Y180) were comparable after Dose 1 and Dose 2. Plasma clearances after Doses 1 and 2 was 6.02 and 4.74 mL/day/kg, respectively. Mean terminal half-life values for Doses 1 and 2 were 9.7 and 13 days, respectively. Distribution volume was approximately 80 mL/kg.

Serum samples from the treated animals were also analyzed for the development of anti-drug antibodies (data not shown). ADA analysis showed no significant response at day 15 (post 1st dose) for both antibodies, however ADA was detected in several animals at day 28 and 43 (post 2nd dose at day 15).

Example 27

Pharmacokinetic Evaluation of an ADC Candidate in Cynomolgous Monkeys

Female cynomolgus monkeys were administered IV slow bolus doses of vehicle control or ADC Molecule 4 at doses of 1, 3, 10 and 30 mg/kg on Days 1 and 22 (n=3/group) and were observed until day 43. Serum and plasma were collected at several time points from all groups for toxicokinetic profile evaluation (total antibody, ADC, and free drug (I) catabolite). Toxicokinetic analysis confirmed exposures of ADC Molecule 4 at all doses, assessed by evaluating circulating levels of the ADC, total antibody, and free drug (I). The mean $C_{max}$ and AUC values of ADC, total antibody, and free drug (I) increased with increases in dose levels of ADC Molecule 4 in an approximately dose proportional manner and were generally similar on Days 1 and 22. The half-life ($T_{1/2}$) of the ADC ranged from 1.7 to greater than 2 days, and $C_{max}$ ranged from 29-560 μg/mL depending on the dose administered.

Example 28

Identification of Catabolites Released from ADC Candidates

The anti-FolRα t ADCs described here are predicted to be processed within the endosome or lysosome resulting in release of the metabolite, free drug (I), that may permeate surrounding cells and can cause bystander activity. The free drug released from conjugates P and Q is predicted to be a compound of structure (I), which is illustrated below:

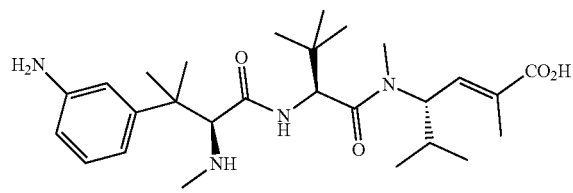

(I)

Figure 27:
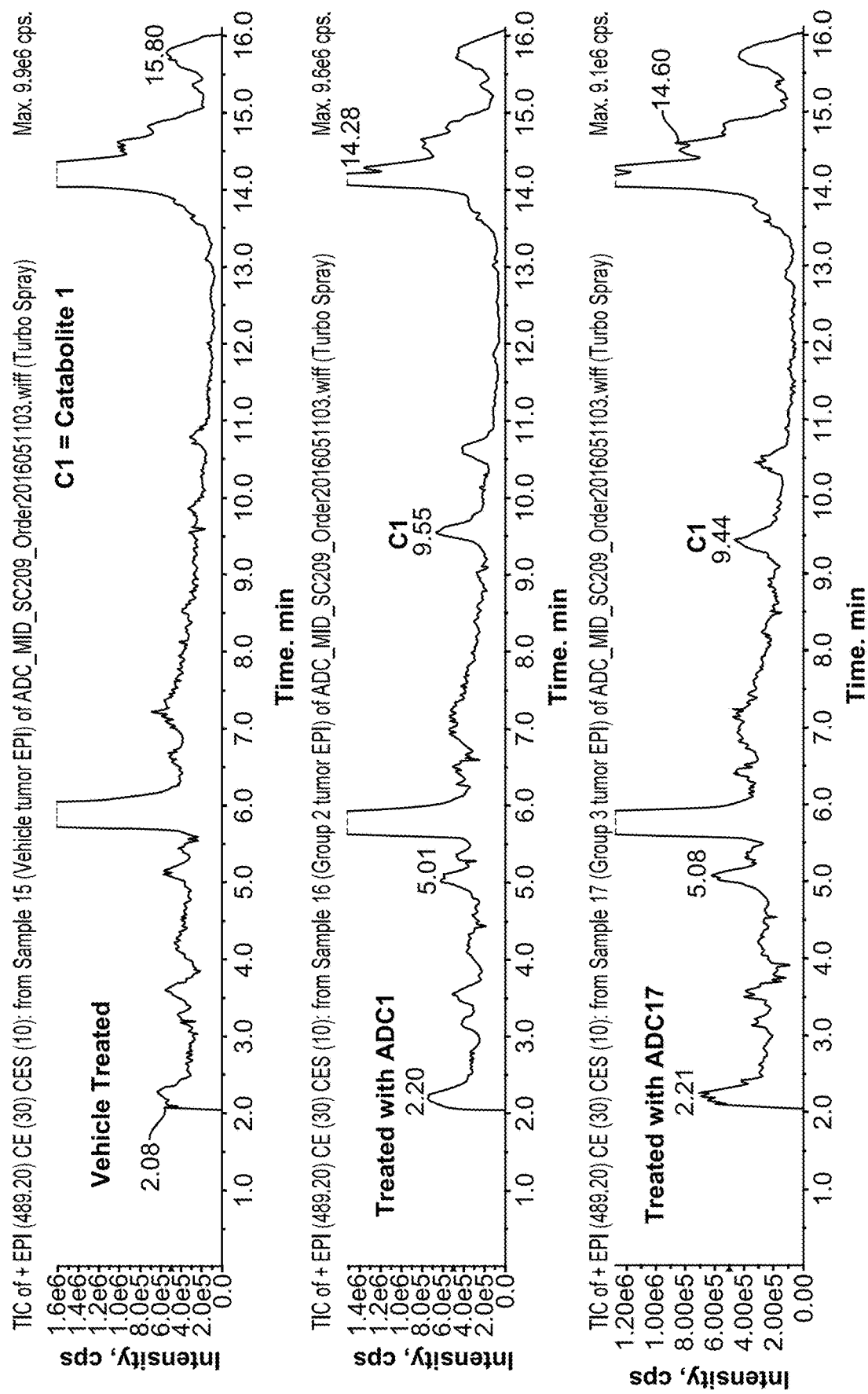
FIG. 27 is an LC/MS trace of small molecules detected in the plasma of mice treated with vehicle or with ADC Molecules 1 or 17.

The generation of free drug (I) was confirmed in cultured cells (not shown) and Igrov1 tumors treated with ADC Molecule 1 and ADC Molecule 17 with tumors harvested at different timepoints post dosing. Tumors were homogenized and extracted in acetonitrile and the solvent extracted fraction was analyzed by LC/MS. In the animals treated with ADC Molecule 1 and ADC molecule 17, catabolite C1 was found in the tumor samples but not in the plasma of the treated mice (FIG. 27). The LC/MS profile of C1 matched that of the predicted catabolite free drug (I) and the structure was confirmed by mass spectrophotometric analysis (not shown). Free drug (I) was shown to have cytotoxic activity in vitro, with an $EC_{50}$ ranging from 0.5-20 nM depending on the cell line tested (Table 26, data for all cell lines not shown).

Example 29

In Vivo Stability of ADC Candidates

Figure 28:
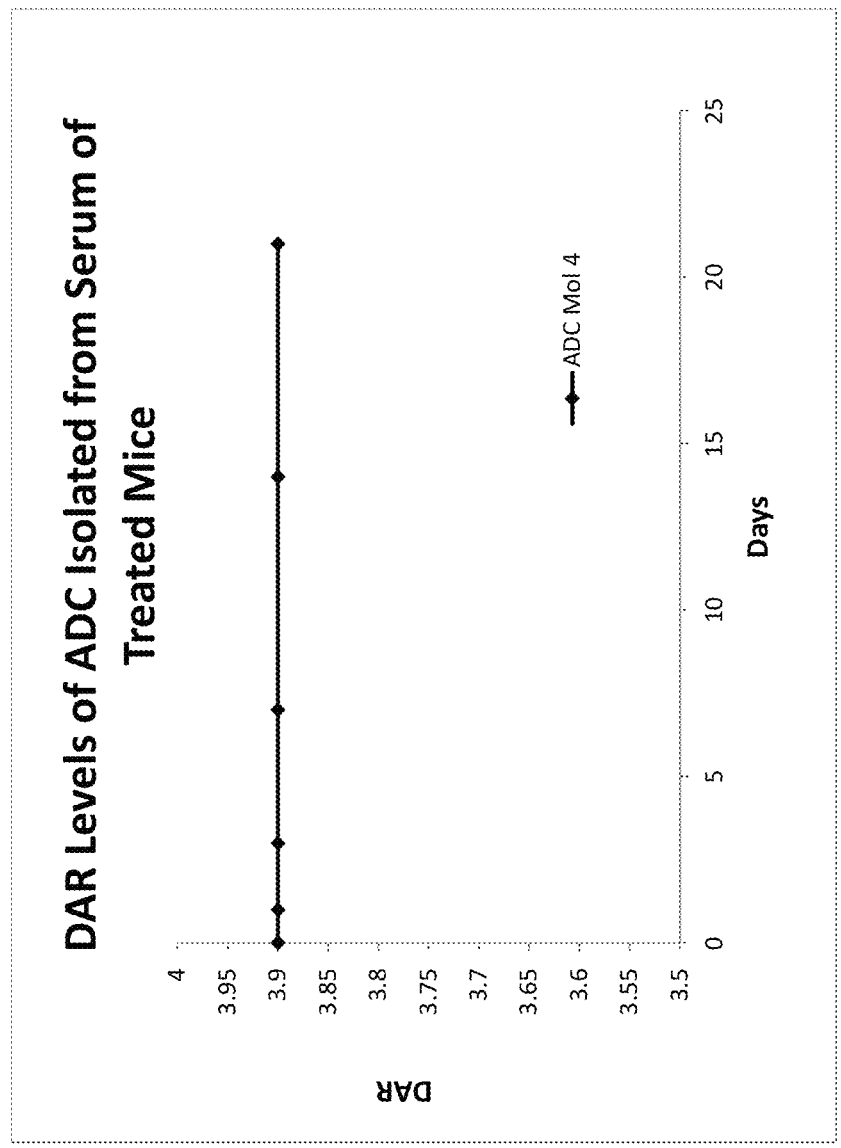
FIG. 28 includes a graph illustrating the plasma stability (as measured by drug-antibody ratio, or DAR) of a representative FOLR1 antibody-drug conjugate administered to SOD Beige mice.

The in vivo stability of ADC Molecule 4 was measured in nude strain of mice following a single dose of ADC at 5 mg/kg. Plasma was collected at various time points and analyzed for total IgG by ELISA. The DAR analysis of circulating ADC was measured by affinity capture followed by LC-MS. Data shows that the DAR value does not change over the course of the study FIG. 28. The observed degradation peak also does not change during the run and is present in a similar amount as see in the original stock.

Example 30

Stability of ADC Candidates in Plasma

Figure 29:
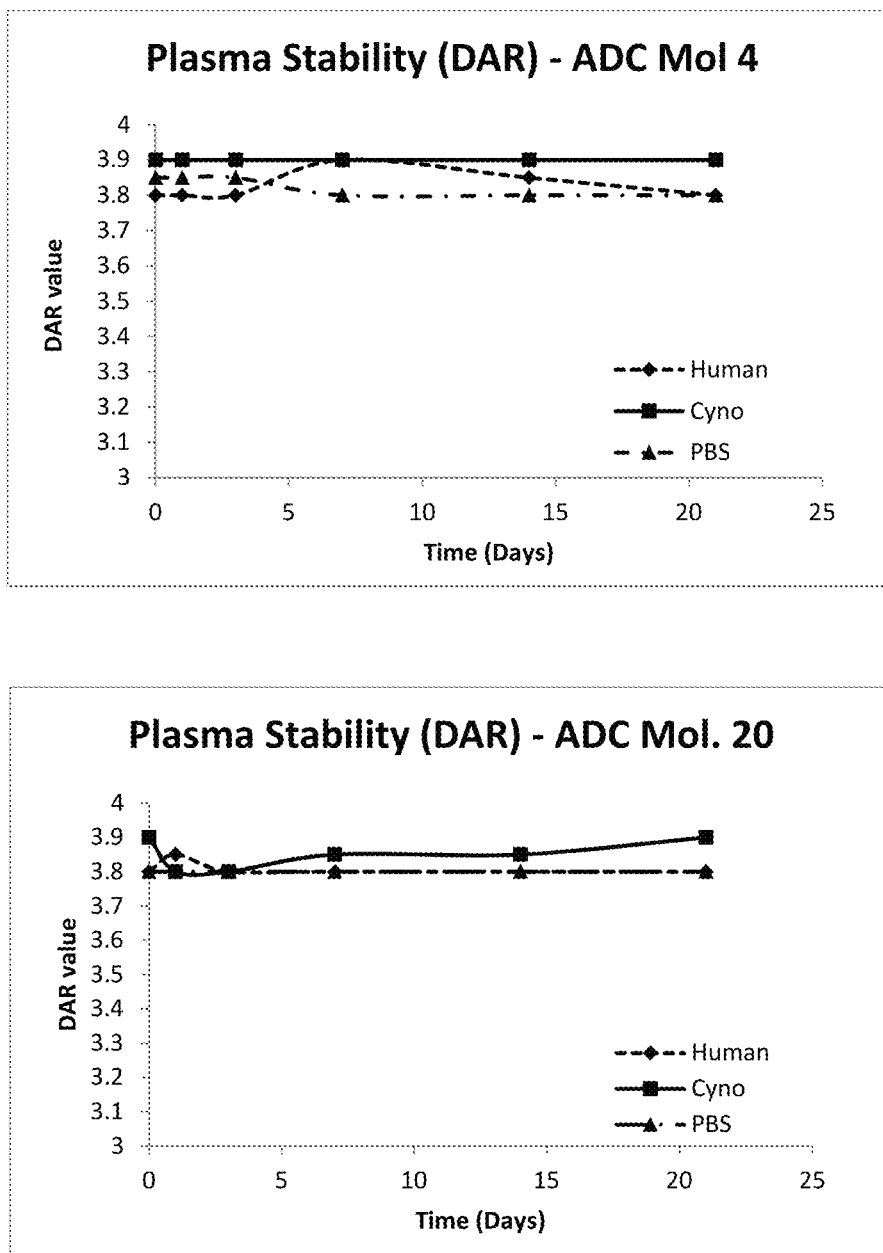
FIG. 29 includes graphs illustrating the plasma stability (as measured by drug-antibody ratio, or DAR) of various FOLR1 antibody-drug conjugates as tested in PBS, cynomolgous monkey plasma, or human plasma.

The stability of ADC Molecules 4 and 20 was tested in cynomolgous and human plasma to compare stability of the two linker-drugs, Conjugates P and Q. The ADCs were incubated in duplicate in PBS, human and cynomolgous plasma at 50 μg/mL. The samples were incubated for time points from 60 min, 1 day, 3 days, 7 days, 14 days, and 21 days. Total IgG by ELISA and DAR analysis of the ADC with affinity capture and LC-MS was used to assess the stability of the molecule. Data shown in FIG. 29 shows that the in vitro stability of ADC Molecules 4 and 20 was comparable in both human and cyno plasma, with DAR4 being retained until day 21. Both molecules also showed occurrence of clipping, likely in the C-terminal end of the antibody, which was observed starting at day 1 post incubation. This clipping is likely to be cleavage of the two lysine residues at the C-terminal end of the heavy chain and is unlikely to impact stability or activity of the molecule. Similar clipping is commonly observed during CHO production of IgG molecules.

Example 31

Comparison of ADC Candidate to a Comparator ADC

A comparator of the ADC candidates described herein is IMGN853. IMGN853 (mirvetuximab soravtansine) is an antibody-drug conjugate containing a FolRα-binding antibody linked to the tubulin-disrupting maytansinoid, DM4, via a cleavable (sulfo-SPDB) linker. The design of IMGN853, including selection of its antibody and linker components, was based on optimization of its antitumor activity in preclinical models having levels of FolRα expression representative of those in tumor samples from patients with ovarian and non-small cell lung cancer. Although IMGN853 looks promising in the clinic, based on its chemistry, it may have some potential liabilities that affect the stability, safety and activity of the molecule. Accordingly, assays to evaluate the properties and pre-clinical effects of an IMGN853 surrogate (ADC Molecule 21) and ADC Molecule 4 are described below.

Figure 30A:
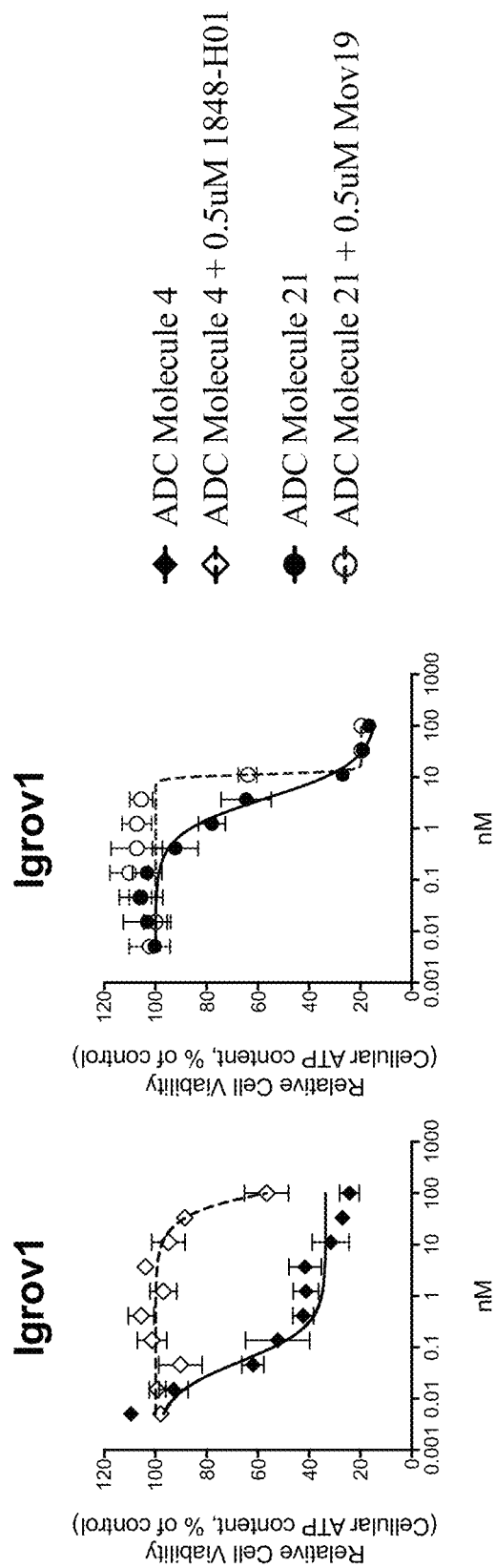
FIG. 30 (A-C) includes graphs illustrating the cytotoxic activity of ADC Molecule 4 and ADC Molecule 21 on various cells in the presence of the respective naked antibody as competitor.
Figure 30B:
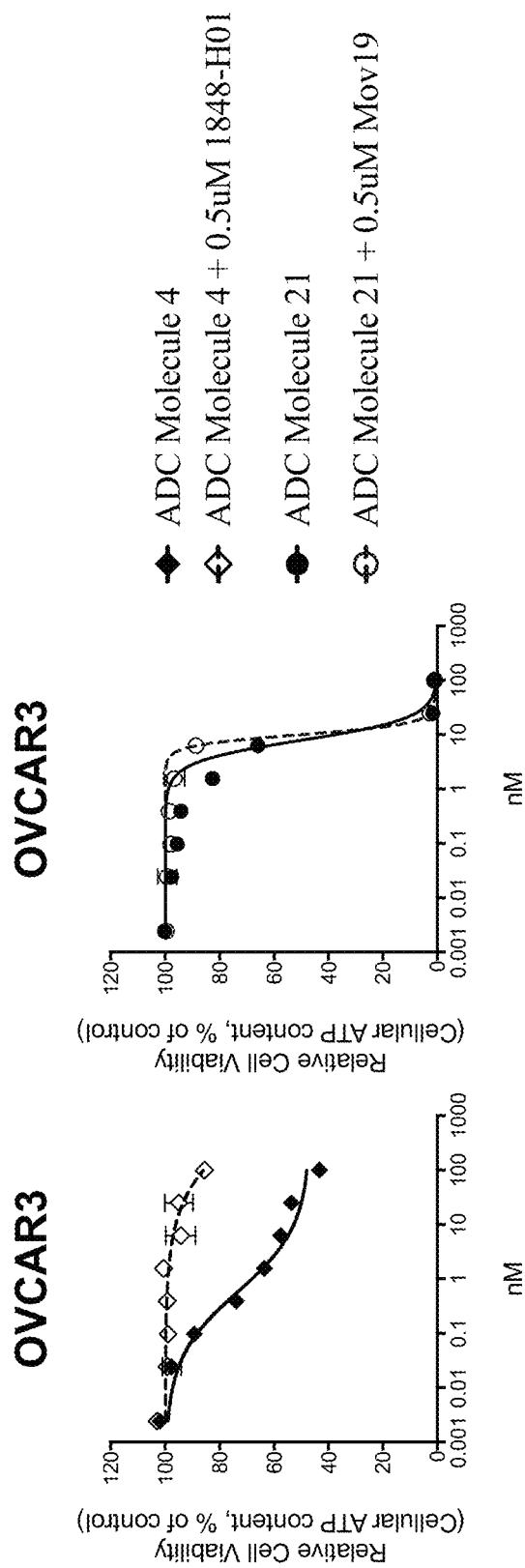
Figure 30C:
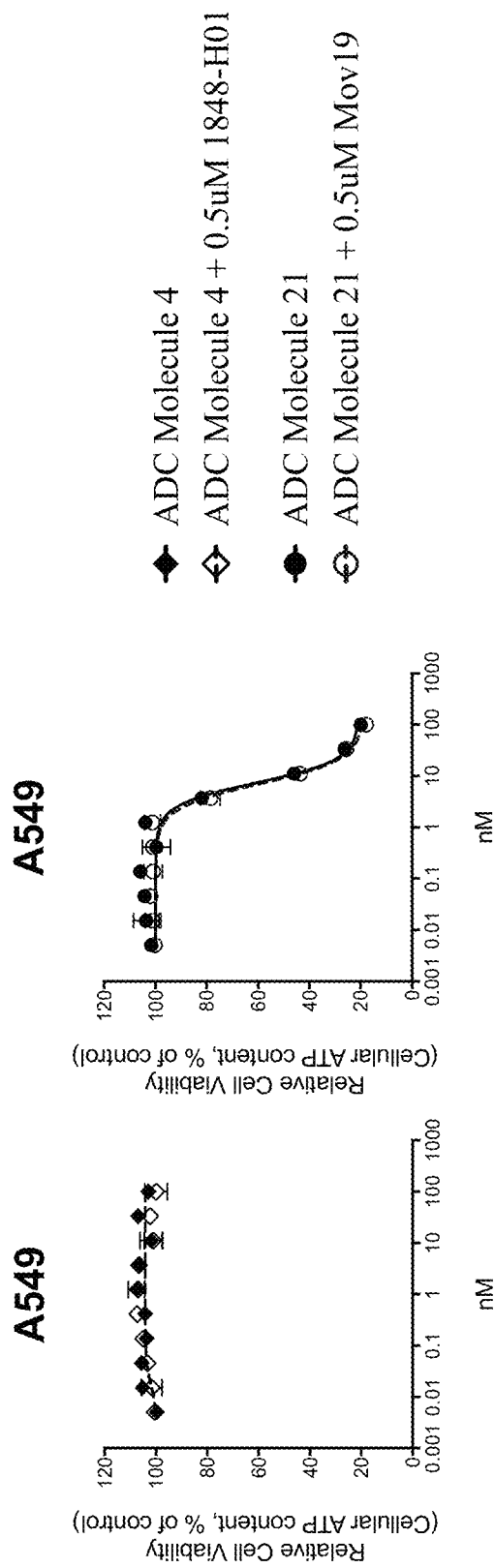

To assess the specificity of ADC Molecule 4 compared to that of IMGN853, the cytotoxic activities of ADC Molecule 4 was compared to a closely-approximating surrogate for IMGN853. The surrogate was expressed transiently in CHO cells and conjugated to sulfo-SPDB-DM4 to produce ADC Molecule 21. Cytotoxic activities of the two ADC molecules were compared in the presence of excess un-conjugated "naked" antibody as competitior, on cells that were positive FolRα expression (Igrov1 and OVCAR3) and on cells that were negative for FolRα expression (A549). For ADC Molecule 4, the cell killing activity on Igrov1 cells was reduced by about 800-fold in the presence of un-conjugated antibody (from an EC50 of 0.053 nM to an EC50 greater than 33 nM), indicating that the cell killing activity of ADC Molecule 4 is specific to the presence of FolRα antigen on the cell surface, since the naked antibody competes with the ADC for binding to the FolRα antigen. Cell killing activity of ADC Molecule 21 is not completely dependent on the presence of FolRα antigen on the cell surface since the addition of naked antibody only shifted the EC50 by about 3-fold on Igrov1 cells. Similar results were also observed on OVCAR3 cells (FIGS. 30A, 30B). On FolRα negative A549 cells, potent non-specific cell killing was observed for ADC Molecule 21, but non-specific cell killing was not observed for ADC Molecule 4 (FIG. 30C). Based on these data, it can be concluded that that ADC Molecule 4 shows potent and specific cell killing only on FolRα positive cells, while ADC Molecule 21 shows non-specific cell killing that is not related to ADC binding to FolRα antigen. The results are summarized in Table 25.

TABLE 25

Specific cytotoxic activities of ADC Molecule 4 and ADC Molecule 21 in FolRα positive and negative cells

| Sample Tested | Igrov1 | | OVCAR3 | | A549 | |
|---|---|---|---|---|---|---|
| | EC50 (nM) | Span (%) | EC50 (nM) | Span (%) | EC50 (nM) | Span (%) |
| ADC Molecule 4 | 0.053 | 66 | 0.58 | 53 | NK | NK |
| ADC Molecule 4 + 0.5 uM 1848-H01 | >33 | NC | >33 | NC | NK | NK |
| ADC Molecule 21 | 3.9 | 87 | 7.9 | 100 | 7.4 | 79 |
| ADC Molecule 21 + 0.5 uM Mov19 | ~11 | 80 | 10 | 99 | 7 | 81 |

NC = Not Calculable

NK = No Killing

ADC Molecule 4 had specific cell killing activity on FolRα-positive Igrov1 cells but did not have any activity on A549 FolRα-negative cells. In contrast, ADC Molecule 21 had cytotoxic activity on both negative- and positive-FolRα cell lines, suggesting a lack of specificity that can be attributed to the potential instability of the sulfo-SPDB linker under reducing conditions in culture and in vivo or due to pinocytosis of the ADC into the cells. The free drugs released from ADC Molecule 4 and ADC Molecule 21 are compounds of structure (I) and (II), respectively, which are illustrated below:

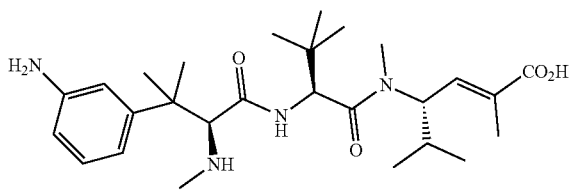

(I)

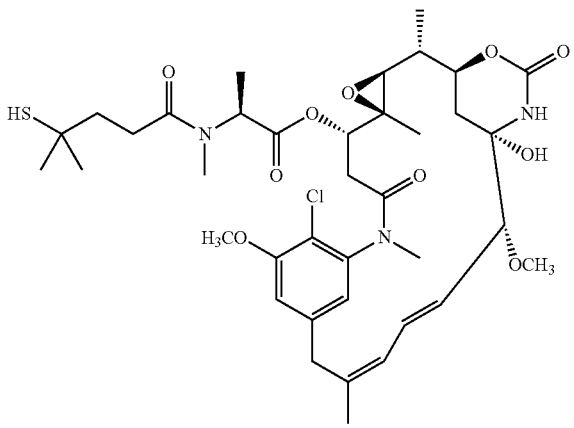

(II)

In in vitro cytotoxicity studies, the released free drugs (I) and (II) had comparable cytotoxic activity (Table 26). One key observation in this study is that ADC Molecule 4 is 10-fold more potent than the theoretical four free drug moieties (I) that it is conjugated to, indicating that the conjugate confers higher levels of specific killing to target cells than free drug (I).

TABLE 26

Cytotoxic activities in Igrov1 and A549 cells

| Molecule | Igrov1 | | A549 | |
|---|---|---|---|---|
| | EC50 (nM) | Span (%) | EC50 (nM) | Span (%) |
| ADC Molecule 4 | 0.06 | 70 | NK | NK |
| ADC Molecule 21 | 4.4* | 85 | 9* | 71 |
| Free drug (I) | 2.4 | 92 | 11 | 81 |
| Free drug (II) | 4.9 | 90 | 7.7 | 81 |

*estimated EC50 based on incomplete titration

NC = Not Calculable

NK = No Killing

Figure 31:
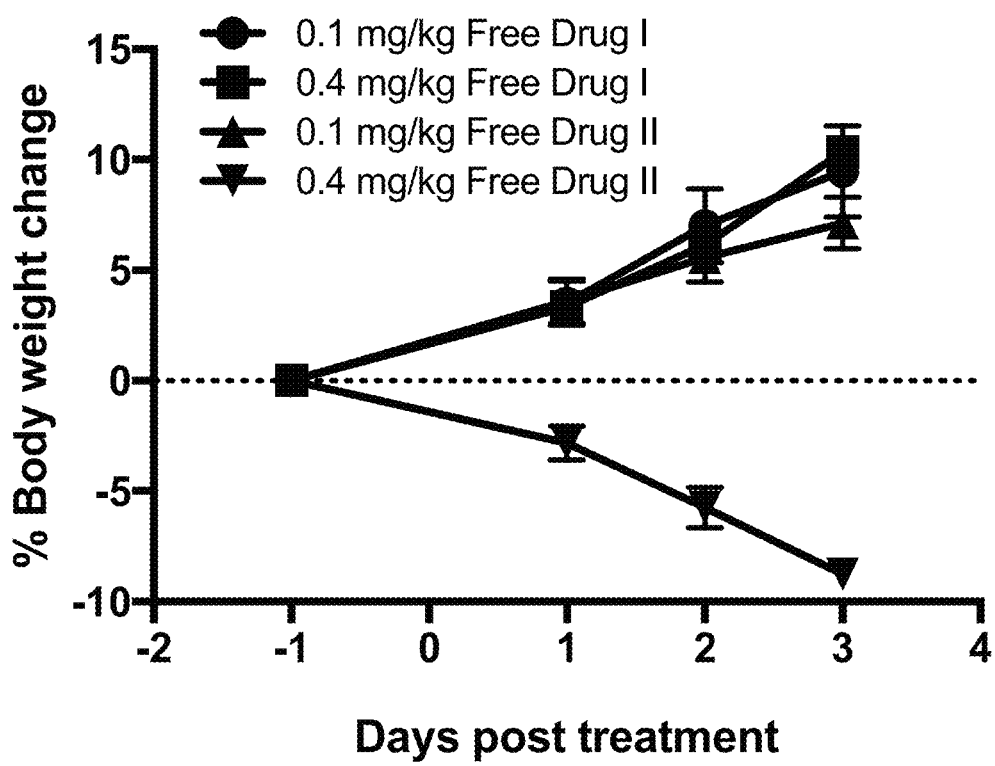
FIG. 31 is a graph illustrating the body weight change in rats that were administered various doses of the catabolites of FOLR1 antibody-drug conjugates disclosed herein.

To assess the pharmacokinetic profile of free drug (I), female Sprague-Dawley rats (mean body weight 250 g) were given either a 0.4 mg/kg or 1 mg/kg dose by IV bolus administration (N=three animal per dose level) via an indwelling jugular vein catheter. Blood samples were collected at 0, 0.83, 1, 2, 8, 24, 32, 48, and 72 hour post-dose. Levels of free drug (I) and (II) were measured by LC-MS/MS and non-compartmental pharmacokinetic analysis was conducted using Phoenix WinNonlin Version 6.4 (Pharsight Corporation). Table 27 provides the PK data collected from this study. The PK of free drug (I) could not be estimated due to the fact that concentrations of (I) increased from 2 to 8 hours and were undetectable thereafter. The results of this study suggest that clearance of free drug (I) is more rapid than that of free drug (II) since (I) is undetectable at 24 hours post dose (data not shown). In addition, administration of the two doses of free drug (I) did not have an effect on the body weight of the animals, while progressive body weight loss was observed upon treatment with 0.4 mg/kg of free drug (II) (FIG. 31).

TABLE 27

Pharmacokinetic data for free drugs (I) and (II)

| Compound ID | Dose Level | Terminal $t_{1/2}$ (hr) | $C_{max}$ ± SE (ng/mL) | $C_0$ (ng/mL) | $AUC_{0\text{-}last}$ ± SE (hr*ng/mL) | $AUC_{0\text{-}inf}$ (hr*ng/mL) | Clearance (L/hr/kg) | $V_{SS}$ (L/kg) |
|---|---|---|---|---|---|---|---|---|
| Free drug (I) | 0.1 mg/kg | Insuff. data | 5.82 ± 0.69 | 6.81 | 11.0 ± 2.1 | Insuff. data | Insuff. data | Insuff. data |
| Free drug (I) | 0.4 mg/kg | Insuff. Data | 12.8 ± 2.1 | 15.5 | 23.9 ± 2.6 | Insuff. data | Insuff. data | Insuff. data |
| Free drug (II) | 0.1 mg/kg | 22.4 | 9.31 ± 2.19 | 10.7 | 96.9 ± 11.0 | 129 | 0.775 | 15.8 |
| Free drug (II) | 0.4 mg/kg | 44.3 | 53.3 ± 19 | 62.5 | 211 ± 70 | 242 | 1.66 | 44.1 |

Table 28 is a summary of the properties of ADC Molecule 4 and its metabolite, free drug (I).

TABLE 28

Properties of ADC Molecule 4 and free drug (I)

| Property/Characteristic | Results for ADC Molecule 4 |
|---|---|
| PK of ADC Molecule 4 in mouse with DAR analysis | $T_{1/2}$: 6.38 days; Clearance rate~9.5 mL/kg/day; DAR4 retained to day 21 |
| Stability of ADC Molecule 4 in human and cyno plasma with DAR analysis | DAR4 retained to day 21 |
| PK of free drug (I) in rat vs. free drug (II) | Free drug (I) has faster clearance than (II) |
| Specificity of activity | ADC Molecule 4 is not active in cell lines that do not express FolRα |

Example 32

Comparison of Stability of Drug Linkage in ADC Candidate Vs. a Comparator ADC

Figure 32:
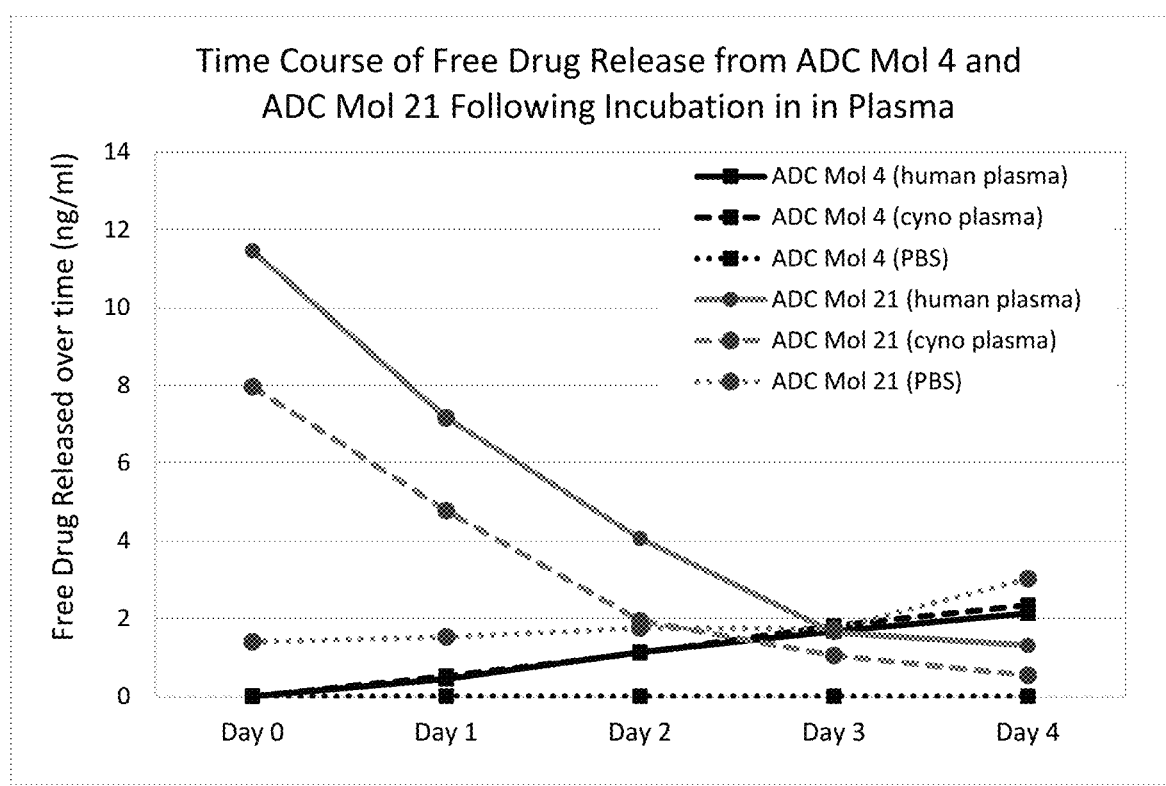
FIG. 32 is a graph illustrating the stability of a representative FOLR1 antibody-drug conjugate (ADC) compared to a comparator ADC as tested in cynomolgous monkey plasma, human plasma, and PBS.

The stability of ADC Molecule 4 and comparator ADC Molecule 21 was assessed in cynomolgous monkey and human plasma and PBS, followed by quantitation of the released catabolites, free drugs (I) and (II), respectively (see Example 29). Based on the data summarized in FIG. 32, the drug linkage for ADC Molecule 4 appears to be more stable than that for ADC Molecule 21. ADC Molecule 21 appears to be rapidly cleaved in human and cyno plasma, such that the free drug (II) is detected within 15-30 minutes of addition to plasma. Free drug (II) then appears to undergo further metabolism over time. In contrast, free drug (I) is not detected within 15-30 minutes of addition of ADC Molecule 4 to plasma. Levels of free drug (I) increase very slightly over 4 days of incubation in plasma but not in PBS; suggesting a more stable drug linkage in plasma.

Example 33

Comparison of ADC Catabolites for Efflux Pumps

Permeability glycoprotein 1 (PgP; also known as multidrug resistance protein 1 (MDR1)) is a cell membrane protein that pumps foreign substances out of cells, and reduces intracellular concentrations of a variety of cytotoxic drugs. PgP activity results in blunted chemotherapy-induced cytotoxicity in vitro and in vivo. Cancer cells frequently become resistant to drugs due to upregulation pf PgP, in some cases this upregulation is mediated by the drug itself. The assay comparing PgP sensitivity of free drugs (I) and (II) (Example 29) conducted in a cisplatin-resistant cell line model.

To evaluate if free drug (I) is specifically a substrate of P-glycoprotein (PgP), which is responsible for cisplatin-resistance in some of the ovarian cancer cell lines (Stordal et al. 2012. PLoS One 7(7)), the free drug cell killing activities were investigated on PgP over-expressing MES-SA/MX2 cell line and the parental MES-SA cells. The cell killing activity of free drug (I), free drug (II) and a control free drug (MMAE, designated "III") on the PgP-overexpressing MES-SA/MX2 cells were reduced by different levels compared to their activity on parental MES-SA cells. The MES-SA/MX2 cells were also treated with PgP inhibitor GF120918 (5 µM) to further investigate if the observed cell killing reduction is contributed by the presence of PgP on the cell surface. In the presence of PgP inhibitor, the cell killing activity of free drugs were reversed back to the same level as the parental MES-SA cell line, indicating that PgP overexpression in the MES-SA/MX2 cells were the main reason for the free drug resistance.

Figure 33:
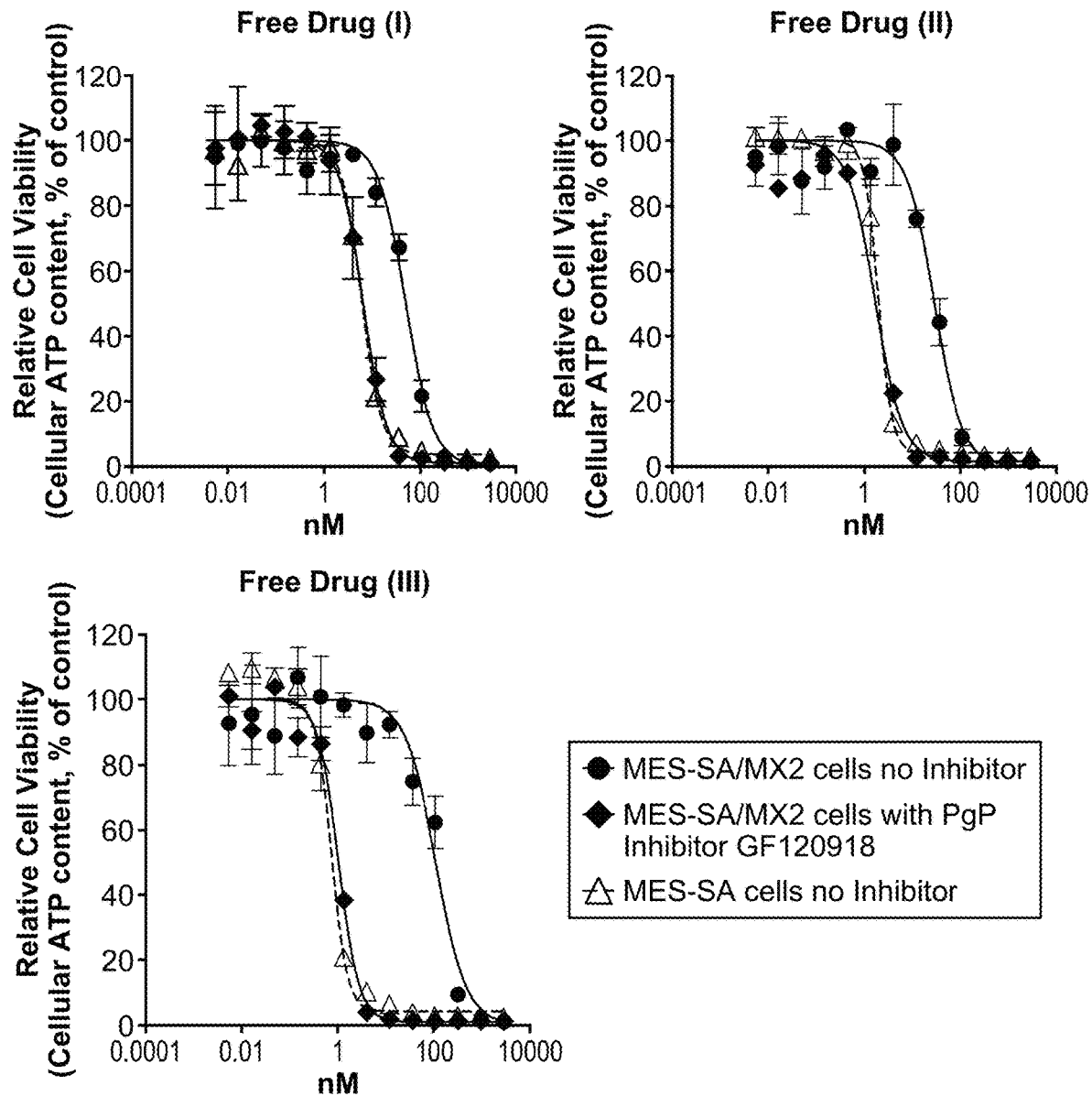
FIG. 33 includes graphs illustrating cytotoxic activity of the catabolites of a representative FOLR1 antibody-drug conjugate (ADC) disclosed herein compared to that of a comparator ADC in cells with varying levels of PgP and in the presence of a specific PgP inhibitor.

Cell killing EC50 of the positive control free drug (III) on MEA-SA/MX2 cells showed a 111-fold change in the presence and absence of PgP inhibitor GF120918, which indicated that free drug (III) is a very good substrate for PgP. Free drug (I) is a poor substrate for PgP based on the fact that only a 8-fold change in cell killing EC50 was observed in the presence and absence of PgP inhibitor on MEA-SA/MX2 cells. As a substrate for PgP, free drug (II) is also relatively poor but more susceptible to transport by efflux pumps compared to free drug (I) since a 17-fold change in cell killing EC50 was observed (Table 29, FIG. 33).

TABLE 29

Cytotoxic activities in Igrov1 and A549 cells

| | MEA-SA | | MEA-SA/MX2 | | | | |
|---|---|---|---|---|---|---|---|
| | No GF120918 | | No GF120918 | | GF120918 | | EC50 |
| Drug Tested | EC50 (nM) | Span (%) | EC50 (nM) | Span (%) | EC50 (nM) | Span(%) | shift |
| Free Drug (I) | 6 | 100 | 50 | 100 | 6.4 | 99 | 8 |
| Free Drug (II) | 1.9 | 100 | 28 | 100 | 1.7 | 98 | 17 |
| Free Drug (III) | 0.75 | 100 | 111 | 100 | 1 | 99 | 111 |

The data suggests that free drug (I) is a weaker substrate for active transport across the membrane by efflux pumps, compared to free drug (II). As a result, free drug (I) is less likely to be pumped out of cancer cells, which could lead to better cellular retention of the toxin and therefore improved cytotoxicity of ADC Molecule 4 compared to comparator ADC Molecule 21. PgP mediated drug efflux is a common resistance mechanism to ADCs, and in the clinic it is one of the key mechanisms of resistance to platinum agents and PARP inhibitors. The poor substrate capacity of free drug (I) for PgP thus makes it a promising warhead for targeting platinum-resistant and potential PARP-resistant cancers.

Example 34

Accumulation of Catabolites in Tumors and Plasma

Figure 34A:
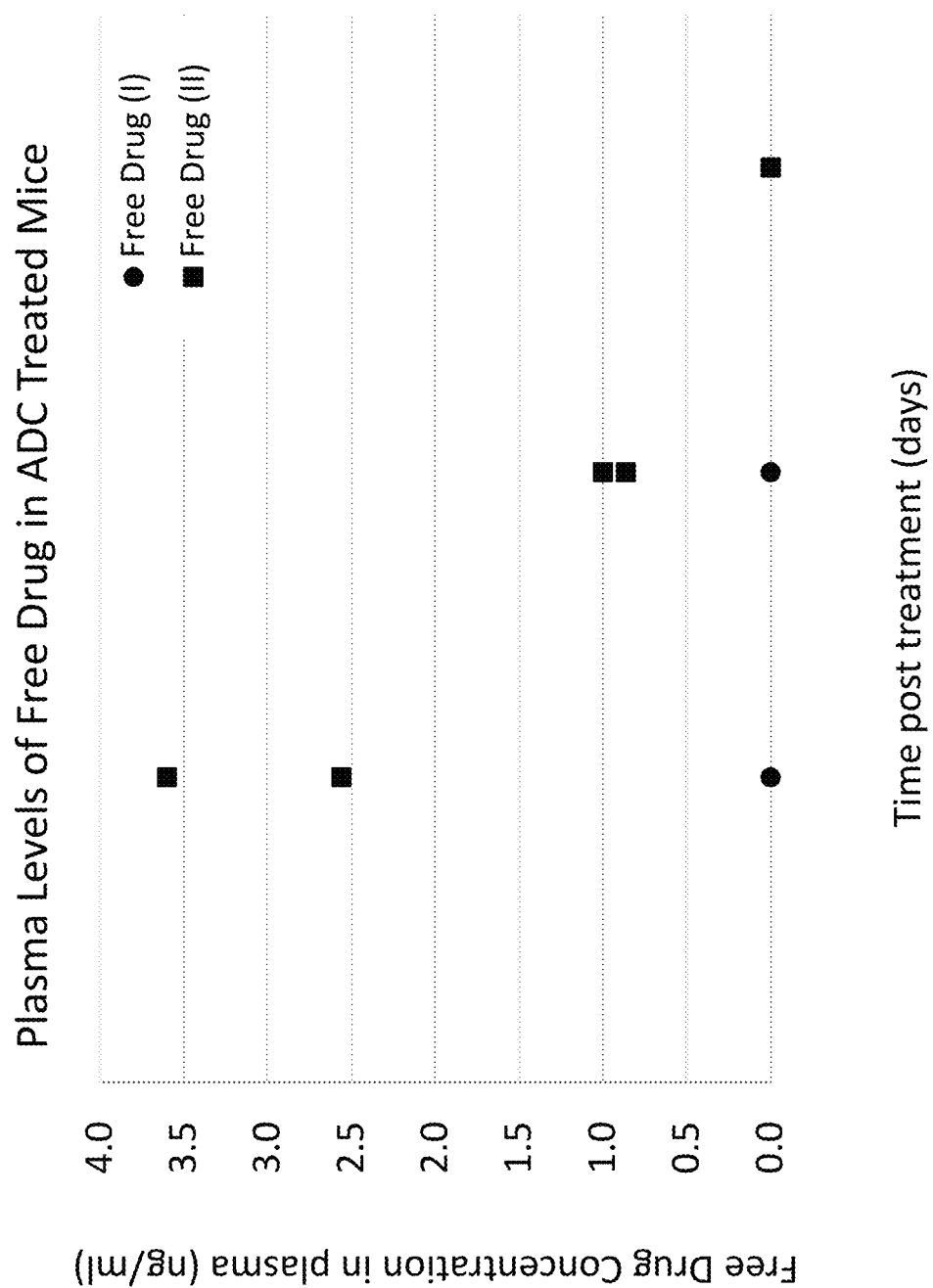
FIG. 34 (A, B) is a chart illustrating tumor and plasma levels of the catabolite of a representative FOLR1 antibody-drug conjugate (ADC) disclosed herein compared to that of a comparator ADC as measured in mice with established Igrov1 tumors.
Figure 34B:
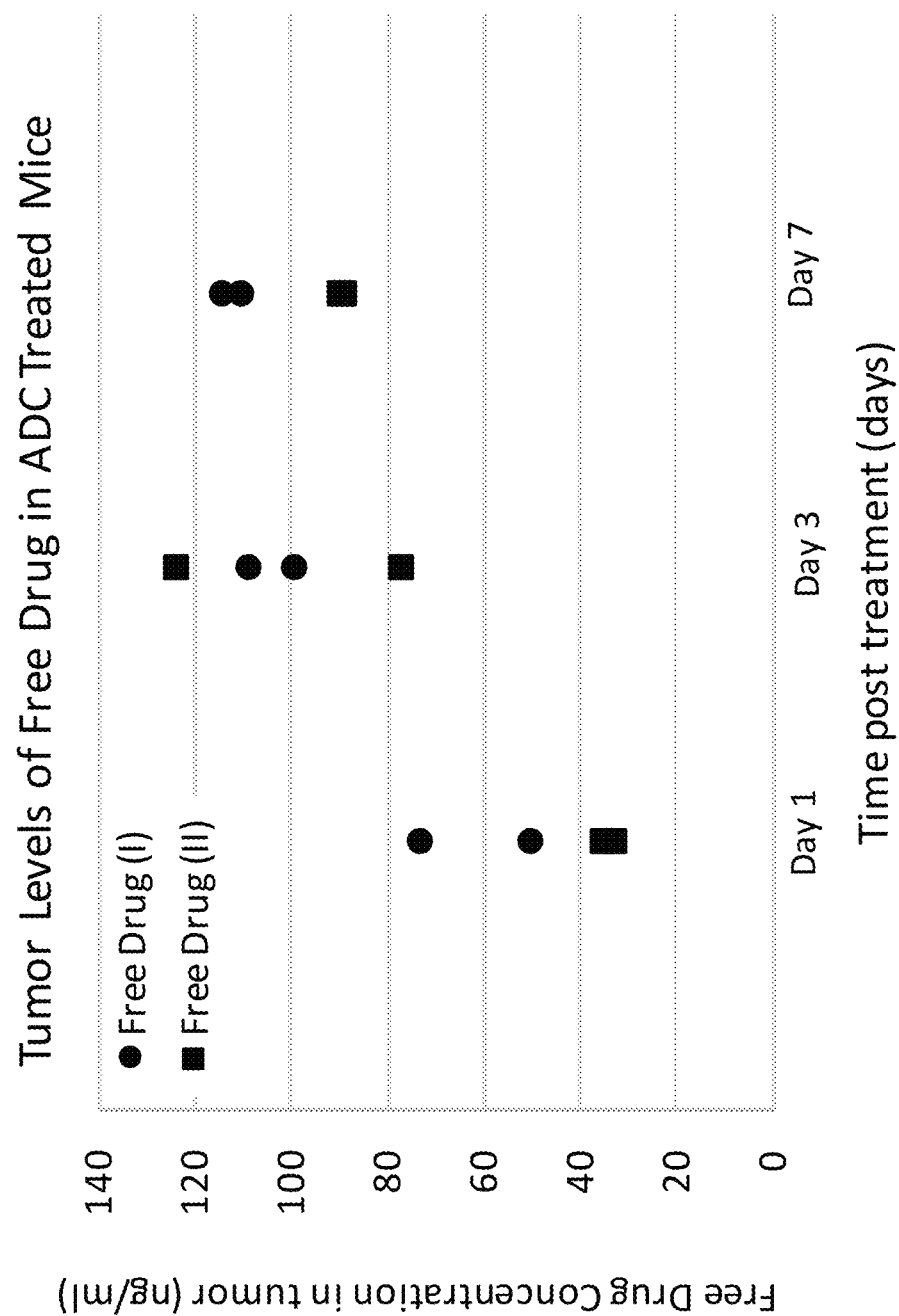

The drug-linkage of ADC Molecule 4 appears to be more stable than that of comparator ADC Molecule 21, however efficient release of free drug (I) from ADC Molecule 4 within the tumor cell is critical for its cytotoxicity. In order to assess warhead release from ADC Molecules 4 and 21, tumor and plasma levels of free drugs (I) and (II) were measured in mice bearing Igrov1 tumors treated with the two ADC molecules. As shown in FIG. 34, release and tumor accumulation of free drug (I) from ADC Molecule 4 was comparable or slightly better than that of free drug (II) from ADC Molecule 21. This data, taken together with the comparable cytotoxicity of the two warheads suggests that the cytotoxic activity of ADC Molecule 4 would be at least comparable to that of comparator ADC Molecule 21.

To summarize, the data described in Examples 29-32 suggests that a widened therapeutic index (TI) can result from both the attributes of the released warhead (free drug (I) versus free drug (II)) and the architecture of ADC Molecule 4 as a whole. Free drugs (I) and (II) are comparable in in vitro cytotoxic activity when administered as free drugs as well as comparable in their accumulation in tumors when administered as an ADC. The much weaker PgP substrate capability of free drug (I) versus free drug (II) predicts that as tumors develop resistance based on efflux, ADC Molecule 4 will retain most of its original activity. The protease-cleavable release mechanism of ADC Molecule 4 has greater stability, and tumor specificity, than the disulfide release mechanism of comparator ADC Molecule 21. This imparts concomitantly higher specificity for cells expressing FolRα. The greater stability of ADC Molecule 4 together with the faster clearance and higher tolerability of catabolite (I) also confers an improved safety profile for ADC Molecule 4. All of this indicates that ADC Molecule 4 could have a higher TI than comparator ADC IMGN853 as measured on surrogate ADC Molecule 21.

Example 35

Introduction of Mutations into Candidate Antibodies

A V262E mutation was introduced into antibody variant 1848-H01 (Y180/F404) to investigate whether this mutation would increase yields of the variant. Introduction of the V262E mutation resulted in about a 70% increase in yield post ProA purification (350 mg/L compared to parent titer of 170 mg/L) with no change in quality of purified protein (data not shown). The properties of the V262E mutated protein conjugated to Conjugate P (Example 11) and Conjugate Q (Example 15) was compared to the parental conjugate ADC Molecule 4 for conjugation efficiency and in vitro activity of the ADC. As seen in Table 30, introduction of the V262E mutation reduced the in vitro cytotoxic activity on Igrov1 cells of the P conjugate to a small extent and of the Q conjugate to a larger extent, although conjugation efficiency and DAR were comparable.

TABLE 30

Comparison of ADC molecules with or without V262E mutations

| ADC Molecule | Antibody | Conjugate | Conjugation Site(s) | DAR | % Conjugated | Cell Killing (Igrov1) EC50 (nM) | Span (%) |
|---|---|---|---|---|---|---|---|
| 4 | 1848-H01 | P | Y180/F404 | 3.73 | 93% | 0.083 | 80 |
| 20 | 1848-H01 | Q | Y180/F404 | 3.81 | 95% | 0.13 | 70 |
| 23 | 1848-H01 V262E | P | Y180/F404 | 3.57 | 89% | 0.088 | 72 |
| 24 | 1848-H01 V262E | Q | Y180/F404 | 3.76 | 94% | 0.19 | 56 |

Figure 35A:
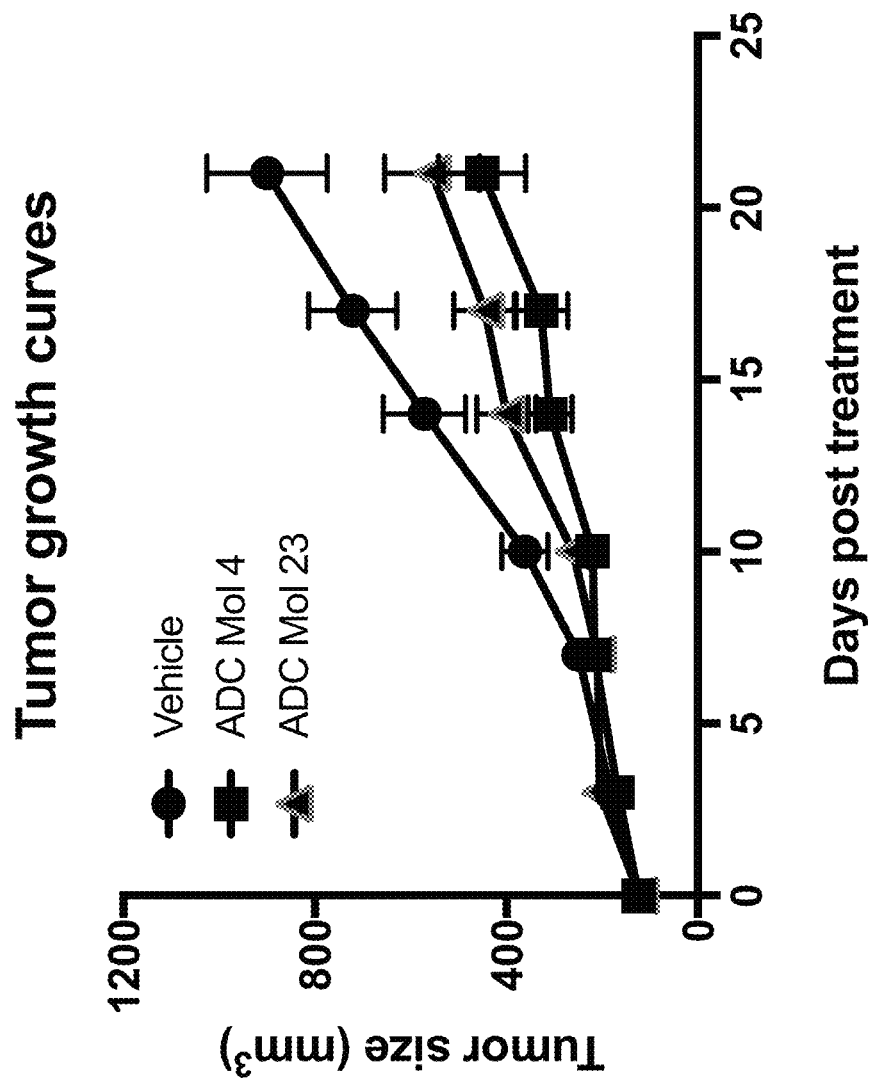
FIG. 35 (A, B) includes a tumor growth curve and a scatter plot illustrating tumor size at day 21 for different FOLR1 antibody-drug conjugates (ADC) as disclosed herein.
Figure 35B:
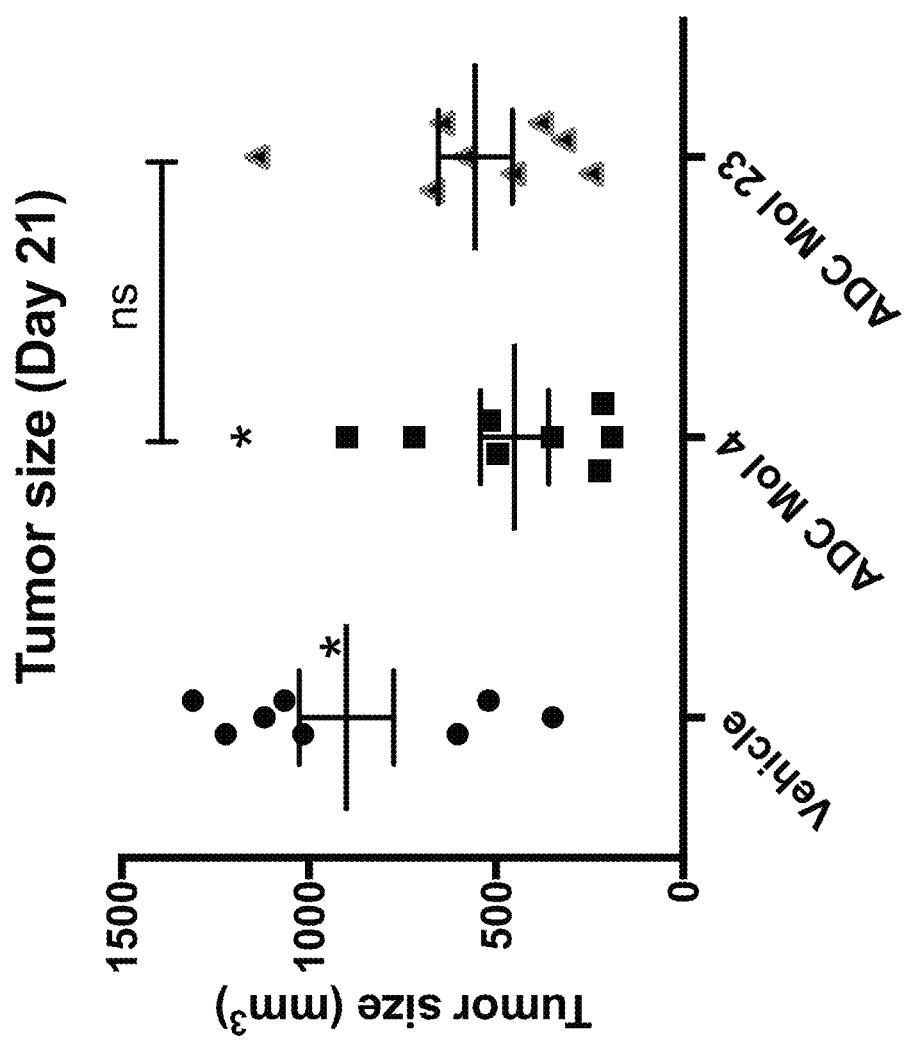
Figure 36:
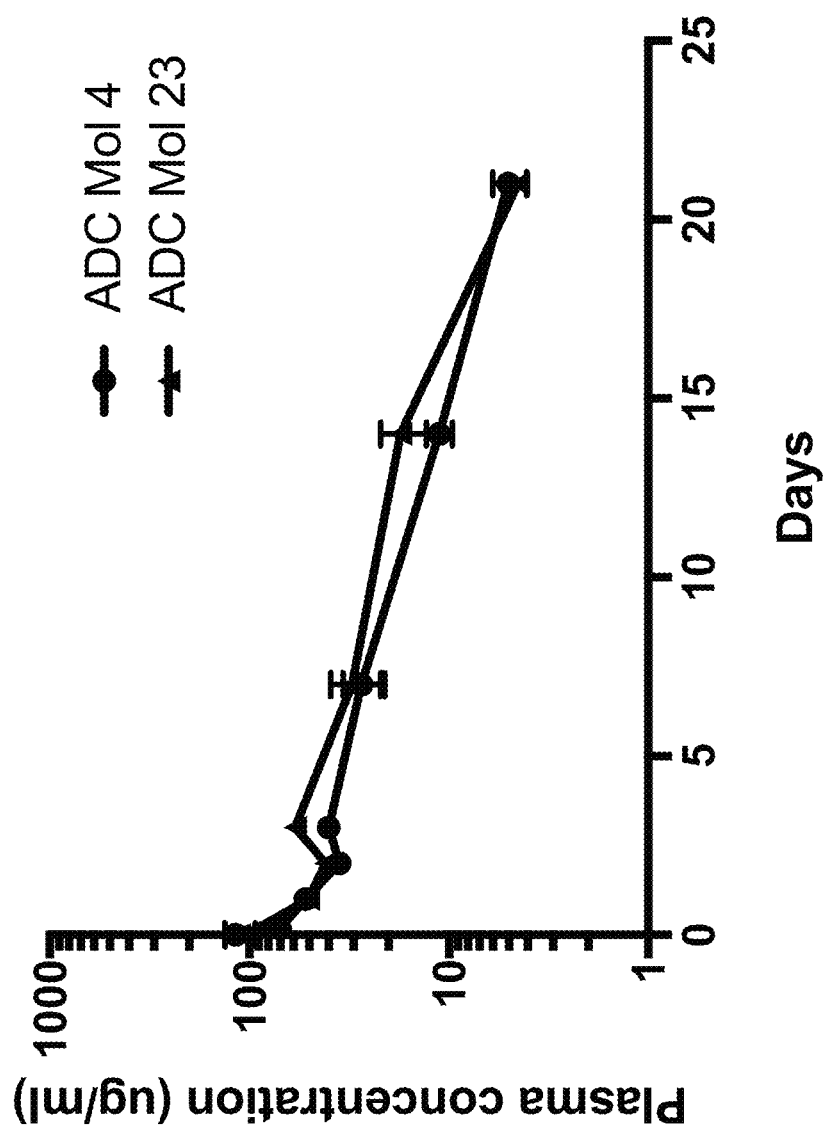
FIG. 36 is a graph illustrating the pharmacokinetic plasma profile of different FOLR1 antibody-drug conjugates in SCID Beige mice.

A comparison of the pharmacokinetic properties and in vivo stability and in vivo efficacy of the P conjugate to the ADC Molecule 4 showed that, while PK of the ADCs was comparable between the two versions (Table 31, FIG. 36), the in vivo activity of the mutated P conjugate (ADC Molecule 23) was marginally lower than that of ADC Molecule 4 (FIG. 35A). Statistical analysis of tumor size on day 21 showed that only treatment with ADC Molecule 4 resulted in significantly smaller tumors compared to vehicle, however tumor sizes in the ADC Molecule 4 and ADC Molecule 23 groups were not statistically different from each other (FIG. 35B). Based on this, ADC Molecule 23 is suitable as an alternative ADC for development and further investigation for targeting of FolRα.

TABLE 31

Pharmacokinetic properties of ADC molecules with or without V262E

| ADC Molecule | SP | Antibody | Conjugate | Conjugation Site(s) | Terminal $t_{1/2}$ (hr) | $C_0$ (µg/mL) | $C_{max} \pm$ SE (µg/mL) | $AUC_{0\text{-}last} \pm$ SE (day * µg/mL) | $AUC_{0\text{-}inf} \pm$ SE (day * µg/mL) | Clearance (mL/days/kg) | $V_{SS}$ (mL/kg) |
|---|---|---|---|---|---|---|---|---|---|---|---|
| 4 | 8193 | 1848-H01 | P | Y180/F404 | 6.36 | 122 | 118 ± 5 | 476 ± 22 | 523 | 9.57 | 79.7 |
| 23 | 8675 | 1848-H01 V262E | P | Y180/F404 | 5.70 | 115 | 113 ± 11 | 599 ± 34 | 636 | 7.87 | 60.5 |

Example 36

Sequences

Table 32 provides sequences referred to herein.

TABLE 32

Sequences

| SEQ ID NO: | Molecule | Region | Scheme | Sequence |
|---|---|---|---|---|
| 1 | Human folate receptor alpha (hFOLR1) | | | MAQRMTTQLLLLLVWVAVVGEAQTRIAW ARTELLNVCMNAKHHKEKPGPEDKLHEQ CRPWRKNACCSTNTSQEAHKDVSYLYRF NWNHCGEMAPACKRHFIQDTCLYECSPN LGPWIQQVDQSWRKERVLNVPLCKEDCE QWWEDCRTSYTCKSNWHKGWNWTSGFNK CAVGAACQPFHEYEPTPTVLCNEIWTHS YKVSNYSRGSGRCIQMWFDPAQGNPNEE VARFYAAAMSGAGPWAAWPFLLSLALML LWLLS |
| 2 | Cynomolgus folate receptor alpha | | | MAQRMTTQLLLLLVWVAVVGEAQTRTAR ARTELLNVCMNAKHHKEKPGPEDKLHEQ CRPWKKNACCSTNTSQEAHKDVSYLYRF NWNHCGEMAPACKRHFIQDTCLYECSPN LGPWIQQVDQSWRKERVLNVPLCKEDCE RWWEDCRTSYTCKSNWHKGWNWTSGFNK CPVGAACQPFHEYEPTPTVLCNEIWTYS YKVSNYSRGSGRCIQMWFDPAQGNPNEE VARFYAAAMSGAGPWAAMPLLLSLALTL LWLLS |
| 3 | Murine folate receptor alpha | | | MAHLMTVQLLLLLVMWMAECAQSRATRAR TELLNVCMDAKHHKEKPGPEDNLHDQCS PWKINSCCSINTSQEAHKDISYLYRENW NHCGTMTSECKRHFIQDTCLYECSPNLG PWIQQVDQSWRKERILDVPLCKEDCQQW WEDCQSSFTCKSNWHKGWNWSSGHNECP VGASCHPFTFYFPPTSAALCEEIWSHSYK LSNYSRGSGRCIQMWFDPAQGNPNEEVA REYAEAMSGAGEHGTWPLLCSLSLVLLW VIS |
| 4 | SRP1848-A01 | CDR-H1 | Chothia | GFNITRY |
| 5 | SRP1848-A02 | CDR-H1 | Chothia | GENTSGF |
| 6 | SRP1848-A04 | CDR-H1 | Chothia | GFNIDQS |
| 7 | SRP1848-A06 | CDR-H1 | Chothia | GFNIGNS |
| 8 | SRP1848-A07 | CDR-H1 | Chothia | GFNIGYH |
| 9 | SRP1848-A08 | CDR-H1 | Chothia | GSNIRKH |

TABLE 32-continued

Sequences

| SEQ ID NO: | Molecule | Region | Scheme | Sequence |
|---|---|---|---|---|
| 10 | SRP1848-A09 | CDR-H1 | Chothia | GFNIRKQ |
| 11 | SRP1848-A10 | CDR-H1 | Chothia | GFNIRKY |
| 12 | SRP1848-B01 | CDR-H1 | Chothia | GFNIRNY |
| 13 | SRP1848-B03 | CDR-H1 | Chothia | GFNISMK |
| 14 | SRP1848-B04 | CDR-H1 | Chothia | SFNISNH |
| 15 | SRP1848-B05 | CDR-H1 | Chothia | GFNISNY |
| 16 | SRP1848-B06 | CDR-H1 | Chothia | GFNISNY |
| 17 | SRP1848-B07 | CDR-H1 | Chothia | GFNISRF |
| 18 | SRP1848-B09 | CDR-H1 | Chothia | GFNITNY |
| 19 | SRP1848-B10 | CDR-H1 | Chothia | GFNTTTK |
| 20 | SRP1848-B11 | CDR-H1 | Chothia | GFNIGNN |
| 21 | SRP1848-C01 | CDR-H1 | Chothia | GFNIGNS |
| 22 | SRP1848-C03 | CDR-H1 | Chothia | GFNIGVY |
| 23 | SRP1848-C04 | CDR-H1 | Chothia | GFNIRHY |
| 24 | SRP1848-C05 | CDR-H1 | Chothia | GFNIRKY |
| 25 | SRP1848-C07 | CDR-H1 | Chothia | GFNIRKY |
| 26 | SRP1848-C10 | CDR-H1 | Chothia | GFNIRTY |
| 27 | SRP1848-D02 | CDR-H1 | Chothia | GFNISHN |
| 28 | SRP1848-D03 | CDR-H1 | Chothia | GFNIRYF |
| 29 | SRP1848-D04 | CDR-H1 | Chothia | GFNISHY |
| 30 | SRP1848-D05 | CDR-H1 | Chothia | GFNISIS |
| 31 | SRP1848-D07 | CDR-H1 | Chothia | GFNISKY |
| 32 | SRP1848-D09 | CDR-H1 | Chothia | GFNISNY |
| 33 | SRP1848-D10 | CDR-H1 | Chothia | GFNISRN |
| 34 | SRP1848-E01 | CDR-H1 | Chothia | GFNIINK |
| 35 | SRP1848-E02 | CDR-H1 | Chothia | GFNIGKY |
| 36 | SRP1848-E03 | CDR-H1 | Chothia | GFNIGNY |
| 37 | SRP1848-E05 | CDR-H1 | Chothia | GFNIGVY |
| 38 | SRP1848-E06 | CDR-H1 | Chothia | GFNINRY |
| 39 | SRP1848-E07 | CDR-H1 | Chothia | GFNIRKS |
| 40 | SRP1848-F01 | CDR-H1 | Chothia | GFNIRTY |
| 41 | SRP1848-F02 | CDR-H1 | Chothia | GFNIRTY |
| 42 | SRP1848-F04 | CDR-H1 | Chothia | GFNISNY |
| 43 | SRP1848-F05 | CDR-H1 | Chothia | GFNISKS |
| 44 | SRP1848-F06 | CDR-H1 | Chothia | GFNISLS |
| 45 | SRP1848-F07 | CDR-H1 | Chothia | GFNISNH |
| 46 | SRP1848-F08 | CDR-H1 | Chothia | GFNISNH |

TABLE 32-continued

Sequences

| SEQ ID NO: | Molecule | Region | Scheme | Sequence |
|---|---|---|---|---|
| 47 | SRP1848-F09 | CDR-H1 | Chothia | GFNISNH |
| 48 | SRP1848-F10 | CDR-H1 | Chothia | GFNISNN |
| 49 | SRP1848-F11 | CDR-H1 | Chothia | GFNISNN |
| 50 | SRP1848-G01 | CDR-H1 | Chothia | GFNISRH |
| 51 | SRP1848-G03 | CDR-H1 | Chothia | GFNISTY |
| 52 | SRP1848-G04 | CDR-H1 | Chothia | GFNIHST |
| 53 | SRP1848-G06 | CDR-H1 | Chothia | GFNIRST |
| 54 | SRP1848-G07 | CDR-H1 | Chothia | GFNIHST |
| 55 | SRP1848-G09 | CDR-H1 | Chothia | GFNIRGT |
| 56 | SRP1848-G10 | CDR-H1 | Chothia | GFNIRST |
| 57 | SRP1848-G11 | CDR-H1 | Chothia | GFNISST |
| 58 | SRP1848-H01 | CDR-H1 | Chothia | GFNIRTQ |
| 59 | SRP2060-E10 | CDR-H1 | Chothia | GFSLSTFGM |
| 60 | SRP2060-E05 | CDR-H1 | Chothia | GFSLSTFGM |
| 61 | SRP2060-B01 | CDR-H1 | Chothia | GFSLSTFGM |
| 62 | SRP2060-A06 | CDR-H1 | Chothia | GFSLSTFGM |
| 63 | SRP1848-A01 | CDR-H1 | Kabat | RYSIH |
| 64 | SRP1848-A02 | CDR-H1 | Kabat | GFRIH |
| 65 | SRP1848-A04 | CDR-H1 | Kabat | QSSIH |
| 66 | SRP1848-A06 | CDR-H1 | Kabat | NSYIH |
| 67 | SRP1848-A07 | CDR-H1 | Kabat | YHSIH |
| 68 | SRP1848-A08 | CDR-H1 | Kabat | KHSIH |
| 69 | SRP1848-A09 | CDR-H1 | Kabat | KQSIH |
| 70 | SRP1848-A10 | CDR-H1 | Kabat | KYSIH |
| 71 | SRP1848-B01 | CDR-H1 | Kabat | NYSIH |
| 72 | SRP1848-B03 | CDR-H1 | Kabat | MKYIH |
| 73 | SRP1848-B04 | CDR-H1 | Kabat | NHSIH |
| 74 | SRP1848-B05 | CDR-H1 | Kabat | NYYIH |
| 75 | SRP1848-B06 | CDR-H1 | Kabat | NYYIH |
| 76 | SRP1848-B07 | CDR-H1 | Kabat | RFYIH |
| 77 | SRP1848-B09 | CDR-H1 | Kabat | NYYIH |
| 78 | SRP1848-B10 | CDR-H1 | Kabat | TKSIH |
| 79 | SRP1848-B11 | CDR-H1 | Kabat | NNSIH |
| 80 | SRP1848-C01 | CDR-H1 | Kabat | NSYIH |
| 81 | SRP1848-C03 | CDR-H1 | Kabat | VYSIH |
| 82 | SRP1848-C04 | CDR-H1 | Kabat | HYSIH |
| 83 | SRP1848-C05 | CDR-H1 | Kabat | KYSIH |

TABLE 32-continued

Sequences

| SEQ ID NO: | Molecule | Region | Scheme | Sequence |
|---|---|---|---|---|
| 84 | SRP1848-C07 | CDR-H1 | Kabat | KYSIH |
| 85 | SRP1848-C10 | CDR-H1 | Kabat | TYYIH |
| 86 | SRP1848-D02 | CDR-H1 | Kabat | HNYIH |
| 87 | SRP1848-D03 | CDR-H1 | Kabat | YFSIH |
| 88 | SRP1848-D04 | CDR-H1 | Kabat | HYSIH |
| 89 | SRP1848-D05 | CDR-H1 | Kabat | ISYIH |
| 90 | SRP1848-D07 | CDR-H1 | Kabat | KYYIH |
| 91 | SRP1848-D09 | CDR-H1 | Kabat | NYYIH |
| 92 | SRP1848-D10 | CDR-H1 | Kabat | RNSIH |
| 93 | SRP1848-E01 | CDR-H1 | Kabat | NKYIH |
| 94 | SRP1848-E02 | CDR-H1 | Kabat | KYSIH |
| 95 | SRP1848-E03 | CDR-H1 | Kabat | NYYIH |
| 96 | SRP1848-E05 | CDR-H1 | Kabat | VYYIH |
| 97 | SRP1848-E06 | CDR-H1 | Kabat | RYYIH |
| 98 | SRP1848-E07 | CDR-H1 | Kabat | KSSIH |
| 99 | SRP1848-F01 | CDR-H1 | Kabat | TYSIH |
| 100 | SRP1848-F02 | CDR-H1 | Kabat | TYSIH |
| 101 | SRP1848-F04 | CDR-H1 | Kabat | NYSIH |
| 102 | SRP1848-F05 | CDR-H1 | Kabat | KSSIH |
| 103 | SRP1848-F06 | CDR-H1 | Kabat | LSYIH |
| 104 | SRP1848-F07 | CDR-H1 | Kabat | NHSIH |
| 105 | SRP1848-F08 | CDR-H1 | Kabat | NHSIH |
| 106 | SRP1848-F09 | CDR-H1 | Kabat | NHYIH |
| 107 | SRP1848-F10 | CDR-H1 | Kabat | NNSIH |
| 108 | SRP1848-F11 | CDR-H1 | Kabat | NNYIH |
| 109 | SRP1848-G01 | CDR-H1 | Kabat | RHSIH |
| 110 | SRP1848-G03 | CDR-H1 | Kabat | TYYIH |
| 111 | SRP1848-G04 | CDR-H1 | Kabat | STDIH |
| 112 | SRP1848-G06 | CDR-H1 | Kabat | STDIH |
| 113 | SRP1848-G07 | CDR-H1 | Kabat | STDIH |
| 114 | SRP1848-G09 | CDR-H1 | Kabat | GTDIH |
| 115 | SRP1848-G10 | CDR-H1 | Kabat | STDIH |
| 116 | SRP1848-G11 | CDR-H1 | Kabat | STDIH |
| 117 | SRP1848-H01 | CDR-H1 | Kabat | TQSIH |
| 118 | SRP2060-E10 | CDR-H1 | Kabat | TFGMGVG |
| 119 | SRP2060-E05 | CDR-H1 | Kabat | TFGMGVG |
| 120 | SRP2060-B01 | CDR-H1 | Kabat | TFGMGVG |

TABLE 32-continued

Sequences

| SEQ ID NO: | Molecule | Region | Scheme | Sequence |
|---|---|---|---|---|
| 121 | SRP2060-A06 | CDR-H1 | Kabat | TFGMGVG |
| 122 | SRP1848-A01 | CDR-H2 | Chothia | LPESGG |
| 123 | SRP1848-A02 | CDR-H2 | Chothia | YPESGA |
| 124 | SRP1848-A04 | CDR-H2 | Chothia | YPVDGT |
| 125 | SRP1848-A06 | CDR-H2 | Chothia | TPIDGN |
| 126 | SRP1848-A07 | CDR-H2 | Chothia | FPVDGT |
| 127 | SRP1848-A08 | CDR-H2 | Chothia | YPNDGT |
| 128 | SRP1848-A09 | CDR-H2 | Chothia | FPNDGT |
| 129 | SRP1848-A10 | CDR-H2 | Chothia | FPIDDI |
| 130 | SRP1848-B01 | CDR-H2 | Chothia | YPVDGI |
| 131 | SRP1848-B03 | CDR-H2 | Chothia | TPIDGM |
| 132 | SRP1848-B04 | CDR-H2 | Chothia | YPVDGI |
| 133 | SRP1848-B05 | CDR-H2 | Chothia | SPIDGY |
| 134 | SRP1848-B06 | CDR-H2 | Chothia | TPIDGY |
| 135 | SRP1848-B07 | CDR-H2 | Chothia | SPYDGF |
| 136 | SRP1848-B09 | CDR-H2 | Chothia | TPVDGY |
| 137 | SRP1848-B10 | CDR-H2 | Chothia | YPRDGI |
| 138 | SRP1848-B11 | CDR-H2 | Chothia | SPIDGF |
| 139 | SRP1848-C01 | CDR-H2 | Chothia | TPNDGY |
| 140 | SRP1848-C03 | CDR-H2 | Chothia | YPIDGN |
| 141 | SRP1848-C04 | CDR-H2 | Chothia | YPGPGN |
| 142 | SRP1848-C05 | CDR-H2 | Chothia | FPIDGI |
| 143 | SRP1848-C07 | CDR-H2 | Chothia | FPIDGI |
| 144 | SRP1848-C10 | CDR-H2 | Chothia | SPIDGY |
| 145 | SRP1848-D02 | CDR-H2 | Chothia | TPQDGY |
| 146 | SRP1848-D03 | CDR-H2 | Chothia | FPNDGS |
| 147 | SRP1848-D04 | CDR-H2 | Chothia | YPRDGI |
| 148 | SRP1848-D05 | CDR-H2 | Chothia | SPIDGY |
| 149 | SRP1848-D07 | CDR-H2 | Chothia | SPNDGY |
| 150 | SRP1848-D09 | CDR-H2 | Chothia | SPNDGY |
| 151 | SRP1848-D10 | CDR-H2 | Chothia | SPNDGT |
| 152 | SRP1848-E01 | CDR-H2 | Chothia | TPFDGF |
| 153 | SRP1848-E02 | CDR-H2 | Chothia | YPNDGN |
| 154 | SRP1848-E03 | CDR-H2 | Chothia | TPRDGF |
| 155 | SRP1848-E05 | CDR-H2 | Chothia | TPNDGY |
| 156 | SRP1848-E06 | CDR-H2 | Chothia | TPNDGY |
| 157 | SRP1848-E07 | CDR-H2 | Chothia | FPYDGS |

TABLE 32-continued

Sequences

| SEQ ID NO: | Molecule | Region | Scheme | Sequence |
|---|---|---|---|---|
| 158 | SRP1848-F01 | CDR-H2 | Chothia | FPNDGT |
| 159 | SRP1848-F02 | CDR-H2 | Chothia | FPNDGT |
| 160 | SRP1848-F04 | CDR-H2 | Chothia | YPIDGI |
| 161 | SRP1848-F05 | CDR-H2 | Chothia | YPNDGS |
| 162 | SRP1848-F06 | CDR-H2 | Chothia | SPIDGN |
| 163 | SRP1848-F07 | CDR-H2 | Chothia | YPNDGI |
| 164 | SRP1848-F08 | CDR-H2 | Chothia | YPVDGI |
| 165 | SRP1848-F09 | CDR-H2 | Chothia | SPLDGY |
| 166 | SRP1848-F10 | CDR-H2 | Chothia | FPNDGY |
| 167 | SRP1848-F11 | CDR-H2 | Chothia | TPIDGN |
| 168 | SRP1848-G01 | CDR-H2 | Chothia | APNDGS |
| 169 | SRP1848-G03 | CDR-H2 | Chothia | TPSDGF |
| 170 | SRP1848-G04 | CDR-H2 | Chothia | TPAGGA |
| 171 | SRP1848-G06 | CDR-H2 | Chothia | TPAGGA |
| 172 | SRP1848-G07 | CDR-H2 | Chothia | TPAGGA |
| 173 | SRP1848-G09 | CDR-H2 | Chothia | TPAGGA |
| 174 | SRP1848-G10 | CDR-H2 | Chothia | TPAGGA |
| 175 | SRP1848-G11 | CDR-H2 | Chothia | TPAGGA |
| 176 | SRP1848-H01 | CDR-H2 | Chothia | FPIDGI |
| 177 | SRP2060-E10 | CDR-H2 | Chothia | WWDDD |
| 178 | SRP2060-E05 | CDR-H2 | Chothia | WWDDD |
| 179 | SRP2060-B01 | CDR-H2 | Chothia | WWDDD |
| 180 | SRP2060-A06 | CDR-H2 | Chothia | WWDDD |
| 181 | SRP1848-A01 | CDR-H2 | Kabat | GILPESGGTSYADSVKG |
| 182 | SRP1848-A02 | CDR-H2 | Kabat | GIYPESGATYYADSVKG |
| 183 | SRP1848-A04 | CDR-H2 | Kabat | VIYPVDGTTDYADSVKG |
| 184 | SRP1848-A06 | CDR-H2 | Kabat | GITPIDGNTDYADSVKG |
| 185 | SRP1848-A07 | CDR-H2 | Kabat | EIFPVDGTTDYADSVKG |
| 186 | SRP1848-A08 | CDR-H2 | Kabat | SIYPNDGTTDYADSVKG |
| 187 | SRP1848-A09 | CDR-H2 | Kabat | SIFPNDGTTDYADSVKG |
| 188 | SRP1848-A10 | CDR-H2 | Kabat | DIFPIDDITDYADSVKG |
| 189 | SRP1848-B01 | CDR-H2 | Kabat | EIYPVDGITDYADSVKG |
| 190 | SRP1848-B03 | CDR-H2 | Kabat | GITPIDGMTDYADSVKG |
| 191 | SRP1848-B04 | CDR-H2 | Kabat | EIYPVDGITDYADSVKG |
| 192 | SRP1848-B05 | CDR-H2 | Kabat | GISPIDGYTDYADSMKG |
| 193 | SRP1848-B06 | CDR-H2 | Kabat | GITPIDGYTDYADSVKG |
| 194 | SRP1848-B07 | CDR-H2 | Kabat | GISPYDGFTDYADSVKG |

TABLE 32-continued

Sequences

| SEQ ID NO: | Molecule | Region | Scheme | Sequence |
|---|---|---|---|---|
| 195 | SRP1848-B09 | CDR-H2 | Kabat | GITPVDGYTDYADRVKG |
| 196 | SRP1848-B10 | CDR-H2 | Kabat | EIYPRDGITDYADSVKG |
| 197 | SRP1848-B11 | CDR-H2 | Kabat | DISPIDGFTDYADSVKG |
| 198 | SRP1848-C01 | CDR-H2 | Kabat | GVTPNDGYTDYADSVKG |
| 199 | SRP1848-C03 | CDR-H2 | Kabat | EIYPIDGNTDYADSVKG |
| 200 | SRP1848-C04 | CDR-H2 | Kabat | EIYPGPGNTDYADSVKG |
| 201 | SRP1848-C05 | CDR-H2 | Kabat | DIFPIDGINDYADSVKG |
| 202 | SRP1848-C07 | CDR-H2 | Kabat | DIFPIDGITDYADSVKG |
| 203 | SRP1848-C10 | CDR-H2 | Kabat | GISPIDGYTDYADSMKG |
| 204 | SRP1848-D02 | CDR-H2 | Kabat | GITPQDGYTDYADSVKG |
| 205 | SRP1848-D03 | CDR-H2 | Kabat | DIFPNDGSTDYADSVKG |
| 206 | SRP1848-D04 | CDR-H2 | Kabat | EIYPRDGITDYADSVKG |
| 207 | SRP1848-D05 | CDR-H2 | Kabat | GISPIDGYTDYADSVKG |
| 208 | SRP1848-D07 | CDR-H2 | Kabat | GISPNDGYTDYADSVKG |
| 209 | SRP1848-D09 | CDR-H2 | Kabat | GISPNDGYTDYADSVKG |
| 210 | SRP1848-D10 | CDR-H2 | Kabat | WISPNDGTTDYADSVKG |
| 211 | SRP1848-E01 | CDR-H2 | Kabat | GITPFDGFTDYADSVKG |
| 212 | SRP1848-E02 | CDR-H2 | Kabat | EIYPNDGNTDYADSVKG |
| 213 | SRP1848-E03 | CDR-H2 | Kabat | GITPRDGFTDYADSVKG |
| 214 | SRP1848-E05 | CDR-H2 | Kabat | GITPNDGYTDYADSVKG |
| 215 | SRP1848-E06 | CDR-H2 | Kabat | GITPNDGYTDYADSVEG |
| 216 | SRP1848-E07 | CDR-H2 | Kabat | EIFPYDGSTDYADNVKG |
| 217 | SRP1848-F01 | CDR-H2 | Kabat | SIFPNDGTTDYADSVKG |
| 218 | SRP1848-F02 | CDR-H2 | Kabat | SIFPNDGTTDYADSVKG |
| 219 | SRP1848-F04 | CDR-H2 | Kabat | EIYPIDGITDYADSVKG |
| 220 | SRP1848-F05 | CDR-H2 | Kabat | EIYPNDGSTDYADSVKG |
| 221 | SRP1848-F06 | CDR-H2 | Kabat | GISPIDGNTDYADSVKG |
| 222 | SRP1848-F07 | CDR-H2 | Kabat | EIYPNDGITDYADSVKG |
| 223 | SRP1848-F08 | CDR-H2 | Kabat | EIYPVDGITDYADSVKG |
| 224 | SRP1848-F09 | CDR-H2 | Kabat | GISPLDGYTDYADSVKG |
| 225 | SRP1848-F10 | CDR-H2 | Kabat | SIFPNDGYTDYADSVKG |
| 226 | SRP1848-F11 | CDR-H2 | Kabat | GITPIDGNTDYADSVKG |
| 227 | SRP1848-G01 | CDR-H2 | Kabat | WIAPNDGSTDYADSVKG |
| 228 | SRP1848-G03 | CDR-H2 | Kabat | GITPSDGFTDYADSVKG |
| 229 | SRP1848-G04 | CDR-H2 | Kabat | YITPAGGATFYADSVKG |
| 230 | SRP1848-G06 | CDR-H2 | Kabat | YITPAGGATYYADNVKG |
| 231 | SRP1848-G07 | CDR-H2 | Kabat | YITPAGGATWYADSVKG |

TABLE 32-continued

Sequences

| SEQ ID NO: | Molecule | Region | Scheme | Sequence |
|---|---|---|---|---|
| 232 | SRP1848-G09 | CDR-H2 | Kabat | YITPAGGATFYADSVKG |
| 233 | SRP1848-G10 | CDR-H2 | Kabat | YITPAGGATYYADSVKG |
| 234 | SRP1848-G11 | CDR-H2 | Kabat | YITPAGGATWYADSVKG |
| 235 | SRP1848-H01 | CDR-H2 | Kabat | DIFPIDGITDYADSVKG |
| 236 | SRP2060-E10 | CDR-H2 | Kabat | HIWWDDDKYYHPALKG |
| 237 | SRP2060-E05 | CDR-H2 | Kabat | HIWWDDDKYYHPALKG |
| 238 | SRP2060-B01 | CDR-H2 | Kabat | HIWWDDDKYYHPALKG |
| 239 | SRP2060-A06 | CDR-H2 | Kabat | HIWWDDDKYYYPALKG |
| 240 | SRP1848-A01 | CDR-H3 | | HIYPWDWFSNYVLDY |
| 241 | SRP1848-A02 | CDR-H3 | | HLYVWDWVLDHVLDY |
| 242 | SRP1848-A04 | CDR-H3 | | GAWSWRSGYGYYIDY |
| 243 | SRP1848-A06 | CDR-H3 | | GAWSWRSGYGYYIDY |
| 244 | SRP1848-A07 | CDR-H3 | | GFWAWRSGYGYYLDY |
| 245 | SRP1848-A08 | CDR-H3 | | GSWFWRAGYGYYLDY |
| 246 | SRP1848-A09 | CDR-H3 | | GSWFWRSGYGYFLEY |
| 247 | SRP1848-A10 | CDR-H3 | | GSWSWPSGHSYYLDY |
| 248 | SRP1848-B01 | CDR-H3 | | GFWSWPSGYSYFLDY |
| 249 | SRP1848-B03 | CDR-H3 | | GSWSWPSGYSYYLDY |
| 250 | SRP1848-B04 | CDR-H3 | | GRYSWRAGYSYYLDY |
| 251 | SRP1848-B05 | CDR-H3 | | GSWFWQSGYGYYLDY |
| 252 | SRP1848-B06 | CDR-H3 | | GFWSWPSGYGYYQDY |
| 253 | SRP1848-B07 | CDR-H3 | | GSWSWPAGYGYYQDY |
| 254 | SRP1848-B09 | CDR-H3 | | GAWSWRSGYGYYMDY |
| 255 | SRP1848-B10 | CDR-H3 | | GGWHWRSGYSYYLDY |
| 256 | SRP1848-B11 | CDR-H3 | | GSWSWRAGYGYYLDY |
| 257 | SRP1848-C01 | CDR-H3 | | GSWFWRAGYGYYLDY |
| 258 | SRP1848-C03 | CDR-H3 | | GSWAWRSGYSYYLDY |
| 259 | SRP1848-C04 | CDR-H3 | | GSLSWRAGYGYYLDY |
| 260 | SRP1848-C05 | CDR-H3 | | GSWSWKAGYGYYLDY |
| 261 | SRP1848-C07 | CDR-H3 | | GSWSWPAGYGYYQDY |
| 262 | SRP1848-C10 | CDR-H3 | | GSWSWPAGYGYYLDY |
| 263 | SRP1848-D02 | CDR-H3 | | GAWSWRAGYGYYLDY |
| 264 | SRP1848-D03 | CDR-H3 | | GHWSWPSGYWYYLDY |
| 265 | SRP1848-D04 | CDR-H3 | | GYWFWRSGYGYYLDY |
| 266 | SRP1848-D05 | CDR-H3 | | GSWSWRAGYGYYLDY |
| 267 | SRP1848-D07 | CDR-H3 | | GFWAWRSGYGYYLDY |
| 268 | SRP1848-D09 | CDR-H3 | | GSWSWRHGYGYYLDY |

TABLE 32-continued

Sequences

| SEQ ID NO: | Molecule | Region | Scheme | Sequence |
|---|---|---|---|---|
| 269 | SRP1848-D10 | CDR-H3 | | GAWSRSGYGYYIDY |
| 270 | SRP1848-E01 | CDR-H3 | | GSWSWPAGYGYYQDY |
| 271 | SRP1848-E02 | CDR-H3 | | GSWSWRSGYGYYLDY |
| 272 | SRP1848-E03 | CDR-H3 | | GSWSWPAGHSYYLDY |
| 273 | SRP1848-E05 | CDR-H3 | | GFWAWRSGYGYYLDY |
| 274 | SRP1848-E06 | CDR-H3 | | GTWSWPSGHSYYLDY |
| 275 | SRP1848-E07 | CDR-H3 | | GAWSWRSGYGYYIDY |
| 276 | SRP1848-F01 | CDR-H3 | | GSWAWRAGYSYYLDY |
| 277 | SRP1848-F02 | CDR-H3 | | GSWSWQAGYGYYLDY |
| 278 | SRP1848-F04 | CDR-H3 | | GSWFWRSGYGYYLDY |
| 279 | SRP1848-F05 | CDR-H3 | | GSWAWRSGYSYFLDY |
| 280 | SRP1848-F06 | CDR-H3 | | GFWAWRSGYGYYLDY |
| 281 | SRP1848-F07 | CDR-H3 | | GSWDWRSGYSYYLDY |
| 282 | SRP1848-F08 | CDR-H3 | | GSWYWQSGYSYYLDY |
| 283 | SRP1848-F09 | CDR-H3 | | GAWSWRSGYGYYIDY |
| 284 | SRP1848-F10 | CDR-H3 | | GSWFWRSGYGYYLDY |
| 285 | SRP1848-F11 | CDR-H3 | | GSWYWRAGYGYYLDY |
| 286 | SRP1848-G01 | CDR-H3 | | GSWAWRSGYSYFLDY |
| 287 | SRP1848-G03 | CDR-H3 | | GSWSWPSGHGYFLDY |
| 288 | SRP1848-G04 | CDR-H3 | | YPYWFAGYMDY |
| 289 | SRP1848-G06 | CDR-H3 | | QPYWFAGYMDY |
| 290 | SRP1848-G07 | CDR-H3 | | YPFWFAGYMDY |
| 291 | SRP1848-G09 | CDR-H3 | | HEYWFSGYMDY |
| 292 | SRP1848-G10 | CDR-H3 | | YPYWFAGYIDY |
| 293 | SRP1848-G11 | CDR-H3 | | YPYWFSGYMDY |
| 294 | SRP1848-H01 | CDR-H3 | | GSWSWPSGMDYYLDY |
| 295 | SRP2060-E10 | CDR-H3 | | NHFPHYYGSSHWYFNV |
| 296 | SRP2060-E05 | CDR-H3 | | NHFPHYYGSSHWYFNV |
| 297 | SRP2060-B01 | CDR-H3 | | NHFPHYYGSSHWYFNV |
| 298 | SRP2060-A06 | CDR-H3 | | NHFPHYYGSSHWYFDV |
| 299 | trastuzumab | CDR-L1 | | RASQDVNTAVA |
| 300 | H6D1-LC4 | CDR-L1 | | KASQDINSYLS |
| 301 | H6D1-LC5 | CDR-L1 | | KASQDINSYLS |
| 302 | trastuzumab | CDR-L2 | | SASFLYS |
| 303 | H6D1-LC4 | CDR-L3 | | RANRLVD |
| 304 | H6D1-LC5 | CDR-L2 | | RANRLVD |
| 305 | trastuzumab | CDR-L3 | | QQHYTTPPT |

TABLE 32-continued

Sequences

| SEQ ID NO: | Molecule | Region | Scheme | Sequence |
|---|---|---|---|---|
| 306 | H6D1-LC4 | CDR-L3 | | LQYDEFPYT |
| 307 | H6D1-LC5 | CDR-L3 | | LQYDEFPYT |
| 308 | SRP1848-A01 | VH | | EVQLVESGGGLVQPGGSLRLSCAASGFNITRYSIHWVRQAPGKGLEWVAGILPESGGTSYADSVKGRFTISADTSKNTAYLQMNSLRAEDTAVYYCARHIYPWDWFSNYVLDYWGQGTLVTVSS |
| 309 | SRP1848-A02 | VH | | EVQLVESGGGLVQPGGSLRLSCAASGFNISGFRIHWVRQAPGKGLEWVAGIYPESGATYYADSVKGRFTISADTSKNTAYLQMNSLRAEDTAVYYCARHLYVWDWVLDHVLDYWGQGTLVTVSS |
| 310 | SRP1848-A04 | VH | | EVQLVESGGGLVQPGGSLRLSCAASGFNIDQSSIHWVRQAPGKGLEWVGVIYPVDGTTDYADSVKGRFTISADTSKNTAYLQMNSLRAEDTAVYYCARGAWSRSGYGYYIDYWGQGTLVTVSS |
| 311 | SRP1848-A06 | VH | | EVQLVESGGGLVQPGGSLRLSCAASGFNIGNSYIHWVRQAPGKGLEWVGGITPIDGNTDYADSVKGRFTISADTSKNTAYLQMNSLRAEDTAVYYCARGAWSRSGYGYYIDYWGQGTLVTVSS |
| 312 | SRP1848-A07 | VH | | EVQLVESGGGLVQPGGSLRLSCAASGFNIGYHSIHWVRQAPGKGLEWVGEIFPVDGTTDYADSVKGRFTISADTSKNTAYLHMNSLRAEDTAVYYCARGFWAWRSGYGYYLDYWGQGTLVTVSS |
| 313 | SRP1848-A08 | VH | | EVQLVESGGGLVQPGGSLRLSCAASGSNIRKHSIHWVRQAPGKGLEWVGSIYPNDGTTDYADSVKGRFTISADTSKNTAYLQMNSLRAEDTAVYYCARGSWFWRAGYGYYLDYWGQGTLVTVSS |
| 314 | SRP1848-A09 | VH | | EVQLVESGGGLVQPGGSLRLSCAASGFNIRKQSIHWVRQAPGKGLEWVGSIFPNDGTTDYADSVKGRFTISADTSKNTAYLQVNSLRAEDTAVYYCARGSWFWRSGYGYFLEYWGQGTLVTVSS |
| 315 | SRP1848-A10 | VH | | EVQLVESGGGLVQPGGSLRLSCAASGFNIRKYSIHWARQAPGKGLEWVGDIFPIDDITDYADSVKGRFTISADTSKNTAYLQMNSLRAEDTAVYYCARGSWSWPSGHSYYLDYWGQGTLVTVSS |
| 316 | SRP1848-B01 | VH | | EVQLVESGGGLVQPGGSLRLSCAASGFNIRNYSIHWVRQAPGKGLEWVGEIYPVDGITDYADSVKGRFTISADTSKNTAYLQMNSLRAEDTAVYYCARGFWSWPSGYSYFLDYWGQGTLVTVSS |
| 317 | SRP1848-B03 | VH | | EVQLVESGGGLVQPGGSLRLSCAASGFNISMKYIHWVRQAPGKGLEWVGGITPIDGMTDYADSVKGRFTISADTSKNTAYLQMNSLRAEDTAVYYCARGSWSWPSGYSYYLDYWGQGTLVTVSS |
| 318 | SRP1848-B04 | VH | | EVQLVESGGGLVQPGGSLRLSCAASSFNISNHSIHWVRQAPGKGLEWVGEIYPVDGITDYADSVKGRFTISADTSKNTAYLQMNSLRAEDTAVYYCARGRYSWRAGYSYYLDYWGQGTLVTVSS |
| 319 | SRP1848-B05 | VH | | EVQLVESGGGLVQPGGSLRLSCAASGFNISNYYIHWVRQAPGKGLEWVGGI5P1DGYTDYADSMKGRFTISADTSKNTAYLQMS |

TABLE 32-continued

Sequences

| SEQ ID NO: | Molecule | Region | Scheme | Sequence |
|---|---|---|---|---|
| | | | | SLRAEDTAVYYCARGSWFWQSGYGYYLD YWGQGTLVTVSS |
| 320 | SRP1848-B06 | VH | | EVQLVESGGGLVQPGGSLRLSCAASGFN ISNYYIHWVRQAPGKGLEWVGGITPIDG YTDYADSVKGRFTISADTSKNTAYLQMN SLRAEDTAVYYCARGFWSPSGYGYYQD YWGQGTLVTVSS |
| 321 | SRP1848-B07 | VH | | EVQLVESGGGLVQPGGSLRLSCAASGFN ISRFYIHWVRQAPGKGLEWVGISPYDG FTDYADSVKGRFTISADTSKNTAYLQMN SLRAEDTAVYYCARGSWSWPAGYGYYQD YWGQGTLVTVSS |
| 322 | SRP1848-B09 | VH | | EVQLVESGGGLVQPGGSLRLSCAAGGFN ITNYYIHWVRQAPGKGLEWVGGITPVDG YTDYADRVKGRFTISADTSKNTAYLQMN SLRAEDTAVYYCARGAWSRSGYGYYMD YWGQGTLVTVSS |
| 323 | SRP1848-B10 | VH | | EVQLVESGGGLVQPGGSLRLSCAASGFN TTTKSIHWVRQAPGKGLEWVGEIYPRDG ITDYADSVKGRFTISADTSKNTAYLQMN SLRAEDTAVYYCARGGWHWRSGYSYYLD YWGQGTLVTVSS |
| 324 | SRP1848-B11 | VH | | EVQLVESGGGLVQPGGSLRLSCAASGFN IGNNSIHWVRQAPGKGLEWVGDISPIDG FTDYADSVKGRFTISADTSKNTAYLQMN SLRAEDTAVYYCARGSWSWRAGYGYYLD YWGQGTLVTVSS |
| 325 | SRP1848-C01 | VH | | EVQLVESGGGLVQPGGSLRLSCAASGFN IGNSYIHWVRQAPGKGLEWVGGVTPNDG YTDYADSVKGRFTISADTSKNTTYLQMN SLRAEDTAVYYCARGSWFWRAGYGYYLD YWGQGALVTVSS |
| 326 | SRP1848-C03 | VH | | EVQLVESGGGLVQPGGSLRLSCAASGFN IGVYSIHWVRQAPGKGLEWVGEIYPIDG NTDYADSVKGRFTISADTSKNTAYLQMN SLRAEDTAVYYCARGSWAWRSGYSYYLD YWGQGTLVTVSS |
| 327 | SRP1848-C04 | VH | | EVQLVESGGGLVQPGGSLRLSCAASGFN IRHYSIHWVRQAPGKGLEWVGEIYPGPG NTDYADSVKGRFTISADTSKNTAYLQMN SLRAEDTAVYYCARGSLSWRAGYGYYLD YWGQGTLVTVSS |
| 328 | SRP1848-C05 | VH | | EVQLVESGGGLVQPGGSLRLSCAASGFN IRKYSIHWVRQAPGKGLEWVGDIFPIDG INDYADSVKGRFTISADTSKNTAYLQMN SLRAEDTAVYYCARGSWSKAGYGYYLD YWGQGTLVTVSS |
| 329 | SRP1848-C07 | VH | | EVQLVESGGGLVQPGGSLRLSCAASGFN IRKYSIHWVRQAPGKGLEWVGDIFPIDG ITDYADSMKGRFTISADTSKNTAYLQMN SLRAEDTAVYYCARGSWSWPAGYGYYQD YWGQGTLVTVSS |
| 330 | SRP1848-C10 | VH | | EVQLVESGGGLVQPGGSLRLSCAASGFN IRTYYIHWVRQAPGKGLEWVGGISPIDG YTDYADSVKGRFTISADTSKNTAYLQMN SLRAEDTAVYYCARGSWSWPAGYGYYLD YWGQGTLVTVSS |
| 331 | SRP1848-D02 | VH | | EVQLVESGGGLVQPGGSLRLSCAASGFN ISHNYIHWVRQAPGKGLEWVGGITPQDG YTDYADSVKGRFTISADTSKNTAYLQMN RLRAEDTAVYYCARGAWSWRAGYGYYLD YWGQGTLVTVSS |

TABLE 32-continued

Sequences

| SEQ ID NO: | Molecule | Region | Scheme | Sequence |
|---|---|---|---|---|
| 332 | SRP1848-D03 | VH | | EVQLVESGGGVVQPGGSLRLSCAASGFN IRYFSIHWVRQAPGKGLEWVGDIFPNDG STDYADSVKGRFTISADTSKNTAYLQMN SLRAEETAVYYCARGHWSPSGYWYYLD YWGQGTLVTVSS |
| 333 | SRP1848-D04 | VH | | EVQLVESGGGLVQPGGSLRSCAASGFN ISHYSIHWVRQAPGKGLEWVGEIYPRDG ITDYADSVKGRFTISADTSKNTAYLQMN SLSAEDTAVYYCARGYWFWRSGYGYYLD YWGQGTLVTVSS |
| 334 | SRP1848-D05 | VH | | EVQLVESGGGLVQPGGSLRLSCAASGFN ISISYIHWVRQAPGKGLEWVGGISPIDG YTDYADSVKGRFTISADTSKNTAYLQMN SLRAEDTAVYYCARGSWSWRAGYGYYLD YWGQGTLVTVSS |
| 335 | SRP1848-D07 | VH | | EVQLVESGGGLVQPGGSLRLSCAASGFN ISKYYIHWVRQAPGKGLEWVGGISPNDG YTDYADSVKGRFAISADTSKNTAYLQMN SLRAEDTAVYYCARGFWAWRSGYGYYLD YWGQGTLVTVSS |
| 336 | SRP1848-D09 | VH | | EVQLVESGGGLVQPGGSLRLSCAASGFN ISNYYIHWVRQAPGKGLEWVGGISPNDG YTDYADSVKGRFTISADTSKNTAYLQMN SLRAEDTAVYYCARGSWSWRHGYGYYLD YWGQGTLVTVSS |
| 337 | SRP1848-D10 | VH | | EVQLVESGGGLVQPGGSLRLSCAASGFN ISRNSIHWVRQAPGKGLEWVGWISPNDG TTDYADSVKGRFTISADGSKNTAYLQMN SLRAEDTAVYYCARGAWSWRSGYGYYID YWGQGTLVTVSS |
| 338 | SRP1848-E01 | VH | | EVQLVESGGGLVQPGGSLRLSCAASGFN ITNKYIHWVRQAPGKGLEWVGGITPFDG FTDYADSVKGRFTISADTSKNTAYLQMN SLRAEDTAVYYCARGSWSWPAGYGYYQD YWGQGTLVTVSS |
| 339 | SRP1848-E02 | VH | | EVQLVESGGGLVQPGGSLRLSCAASGFN IGKYSIHWVRQAPGKGLEWVGEIYPNDG NTDYADSVKGRFTISADTSKNTAYLQMN SLRAEDTAVYYCARGSWSWRSGYGYYLD YWGQGTLVTVSS |
| 340 | SRP1848-E03 | VH | | EVQLVESGGGLAQPGGSLRLSCAASGFN IGNYYIHWVRQAPGKGLEWVGGITPRDG FTDYADSVKGRFTISADTSKNTAYLQVN SLRAEDTAVYYCARGSWSWPAGHSYYLD YWGQGTLVTVSS |
| 341 | SRP1848-E05 | VH | | EVQLVESGGGLVQPGGSLRVSCAASGFN IGVYYIHWVRQAPGKGLEWVGGITPNDG YTDYADSVKGRFTISADTSKNTAYLQMN SLRAEDTAVYYCARGFWAWRSGYGYYLD YWGQGTLVTVSS |
| 342 | SRP1848-E06 | VH | | EVQLVESGGGLVQPSGSLRLSCAASGFN INRYYIHWVRQAPGKGLEWVGGITPNDG YTDYADSVEGRFTTSADTSKNTAYLQMN SLRAEDTAVYYCARGTWSWPSGHSYYLD YWGQGTLVTVSS |
| 343 | SRP1848-E07 | VH | | EVQLVESGGGLVQPGGSLRLSCAASGFN IRKSSIHWVRQAPGKGLEWVGEIPYDG STDYADNVKGRFTISADTSKNTAYLQMN SLRAEDTAVYYCARGAWSWRSGYGYYID YWGQGTLVTVSS |

TABLE 32-continued

Sequences

| SEQ ID NO: | Molecule | Region | Scheme | Sequence |
|---|---|---|---|---|
| 344 | SRP1848-F01 | VH | | EVQLVESGGGLVQPGGSLRLSCAASGFN IRTYSIHWVRQAPGKGLEWVGSIFPNDG TTDYADSVKGRFTISADTSKNTAYLQMN SLRAEDTAVYYCARGSWAWRAGYSYYLD YWGQGTLVTVSS |
| 345 | SRP1848-F02 | VH | | EVQLVESGGGLVQPGGSLRLSCAASGFN IRTYSIHWVRQAPGKGLEWVGSIFPNDG TTDYADSVKGRLTISADTSKNTAYLQMN SLRAEDTAVYYCARGSWSWQAGYGYYLD YWGQGTLVTVSS |
| 346 | SRP1848-F04 | VH | | EVQLVESGGGLVQPGGSLRLSCAASGFN ISNYSIHWVRQAPGKGLEWVGEIYPIDG ITDYADSVKGRFTISADTSKNTAYLQMN SLRAEDTAVYYCARGSWFWRSGYGYYLD YWGQGTLVTVSS |
| 347 | SRP1848-F05 | VH | | EVQLVESGGGLVQPGGSLRLSCAASGFN ISKSSIHWVRQAPGKGLEWVGEIYPNDG STDYADSVKGRFTISADTSKNTAYLQMN SLRAEDTAVYYCARGSWAWRSGYSYFLD YWGQGTLVTVSS |
| 348 | SRP1848-F06 | VH | | EVQLVESGGGLVQPGGSLRLSCAASGFN ISLSYIHWVRQAPGKGLEWVGGISPIDG NTDYADSVKGRFTISADTSKNTAYLQMN SLRAEDTAVYYCARGFWAWRSGYGYYLD YWGQGTLVTVSS |
| 349 | SRP1848-F07 | VH | | EVQLVESGGGLVQPGGSLRLSCAASGFN ISNHSIHWVRQAPGKGLEWVGEIYPNDG ITDYADSVKGRFTISADTSKNTAYLQMN SLSAEDTAVYYCARGSWDWRSGYSYYLD YWGQGTLVTVSS |
| 350 | SRP1848-F08 | VH | | EVQLVESGGGLVQPGGSLRLSCAAGGFN ISNHSIHWVRQAPGKGVEWVGEIYPVDG ITDYADSVKGRFTISADTSKNTAYLRMN SLRAEDTAVYYCARGSWYWQSGYSYYLD YWGQGTLVTVSS |
| 351 | SRP1848-F09 | VH | | EVQLVESGGGLVQPGGSLRLSCAASGFN ISNHYIHWVRQAPGKGLEWVGGISPLDG YTDYADSVKGRFTISADTSKNTAYLQMN SLRAEDTAVYYCARGAWSWRSGYGYYID YWGQGTLVTVSS |
| 352 | SRP1848-F10 | VH | | EVQLVESGGGLVQPGGSLRLSCAASGFN ISNNSIHWVRQAPGKGLEWVGSIFPNDG YTDYADSVKGRFTISADTSKNTAYLQMN SLRAEDTAVYYCARGSWFWRSGYGYYLD YWGQGTLVTVSS |
| 353 | SRP1848-F11 | VH | | EVQLVESGGGLVQPGGSLRLSCAASGFN ISNNYIHWVRQAPGKGLEWVGGITPIDG NTDYADSVKGRFTISADTSMNTAYLQMN SLRAEDTAVYYCARGSWYWRAGYGYYLD YWGQGALVTVSS |
| 354 | SRP1848-G01 | VH | | EVQLVESGGGLVQPGGSLRLSCAASGFN ISRHSIHWVRQAPGKGLEWVGWIAPNDG STDYADSVKGRFTISADTSKNTAYLQMN SLRAEDTAVYYCARGSWAWRSGYSYFLD YWGQGTLVTVSS |
| 355 | SRP1848-G03 | VH | | EVQLVESGGGLVQPGGSLRLSCAASGFN ISTYYIHWVRQAPGKGLEWVGGITPSDG FTDYADSVKGRSTISADTSKNTAYLQMN SLRAEDTAVYYCARGSWSWPSGHGYFLD YWGQGTLVTVSS |

TABLE 32-continued

Sequences

| SEQ ID NO: | Molecule | Region | Scheme | Sequence |
|---|---|---|---|---|
| 356 | SRP1848-G04 | VH | | EVQLVESGGGLVQPGGSLRLSCAASGFN IHSTDIHWVRQAPGKGLEWVAYITPAGG ATFYADSVKGRFTISADTSKNTAYLQMN SLRAEDTAVYYCARYPYWFAGYMDYWGQ GTLVTVSS |
| 357 | SRP1848-G06 | VH | | EVQLVESGGGLVQPGGSLRLSCAASGFN IRSTDIHWVRQAPGKGLEWVAYITPAGG ATYYADNVKGRFTISADTSKNTAYLQMN SLRAEDTAVYYCARQPYWFAGYMDYWGQ GTLVTVSS |
| 358 | SRP1848-G07 | VH | | EVQLVESGGGLVQPGGSLRLSCAASGFN IHSTDIHWVRQAPGKGLEWVAYITPAGG ATWYADSVKGRFTISADTSKNTAYLQMN SLRAEDTAVYYCARYPFWFAGYMDYWGQ GTLVTVSS |
| 359 | SRP1848-G09 | VH | | EVQLVESGGGLVQPGGSLRLSCAASGFN IRGTDIHWVRQAPGKGLEWVAYITPAGG ATFYADSVKGRFTISADTSKNTAYLQMN SLRAEDTAVYYCARHEYWFSGYMDYWGQ GTLVTVSS |
| 360 | SRP1848-G10 | VH | | EVQLVESGGGLVQPGSSLRLSCAASGFN IRSTDIHWVRQAPGKGLEWVAYITPAGG ATYYADSVKGRFTISADTSKNTAYLQMN SLRAEDTAVYYCARYPYWFAGYIDYWGQ GTLVTVSS |
| 361 | SRP1848-G11 | VH | | EVQLVESGGGLVQPGGSLRLSCAASGFN ISSTDIHWVRQAPGKGLEWVAYITPAGG ATWYADSVKGRFTISADTSKNTAYLQMN SLRAEDTAVYYCARYPYWFSGYMDYWGQ GTLVTVSS |
| 362 | SRP1848-H01 | VH | | EVQLVESGGGLVQPGGSLRLSCAASGFN IRTQSIHWVRQAPGKGLEWIGDIFPIDG ITDYADSVKGRFTISADTSKNTAYLQMN SLRAEDTAVYYCARGSWSWPSGMDYYLD YWGQGTLVTVSS |
| 363 | SRP2060-E10 | VH | | EVQLLESGGGLVQPGGSLRLSCAFSGFS LSTFGMGVGWVRQAPGKGLEWVSHIWWD DDKYYHPALKGRFTISKDNSKNTVYLQM NSLRAEDTAVYYCGRNHFPHYYGSSHWY FNVWGQGTTVTVSS |
| 364 | SRP2060-E05 | VH | | EVQLLESGGGLVQPGGSLRLSCAFSGFS LSTFGMGVGWVRQAPGKGLEWVSHIWWD DDKYYHPALKGRFTVSKDNSKNTVYLQM NSLRAEDTAVYYCGRNHFPHYYGSSHWY FNVWGQGTTVTVSS |
| 365 | SRP2060-B01 | VH | | EVQLLESGGGLVQPGGSLRLSCALSGFS LSTFGMGVGWVRQATGKGLEWVSHIWWD DDKYYHPALKGRFTISKDNSKNTVHLQM NSLRAEDTAVYYCGRNHFPHYYGSSHWY FNVWGQGTTVTVSS |
| 366 | SRP2060-A06 | VH | | EVQLLESGGGLVQPGGSLRLSCAFSGFS LSTFGMGVGWVRQAPGKGLEWVGHIWWD DDKYYYPALKGRFTISKDNSKNTVYLQM NSLRAEDTAVYYCGRNHFPHYYGSSHWY FDVWGQGTTVTVSS |
| 367 | trastuzumab | VL | | DIQMTQSPSSLSASVGDRVTITCRASQD VNTAVAWYQQKPGKAPKLLIYSASFLYS GVPSRFSGSRSGTDFTLTISSLQPEDFA TYYCQQHYTTPPTFGQGTKVEIK |
| 368 | H6D1-LC4 | VL | | EIVMTQSPATLSLSPGERATLSCKASQD INSYLSWYQQKPGQAPRLLIYRANRLVD |

TABLE 32-continued

Sequences

| SEQ ID NO: | Molecule | Region | Scheme | Sequence |
|---|---|---|---|---|
| | | | | GIPARFSGSGSGTDYTLTISSLEPEDFA VYYCLQYDEFPYTFGGGTKVEIK |
| 369 | H6D1-LC5 | VL | | DIQMTQSPSTLSASVGDRVTITCKASQD INSYLSWYQQKPGKAPKLLIYRANRLVD GVPSRFSGSGSGTEFTLTISSLQPDDFA TYYCLQYDEFPYTFGGGTKVEIK |
| 370 | Human IgG1 HC Constant | | | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLFPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSREEMTKNQVSLTCLV KGFYPSDIAVEWESNGQPENNYKTTPPV LDSDGSFFLYSKLTVDKSRWQQGNVFSC SVMHEALHNHYTQKSLSLSPGK |
| 371 | Human IgG LC Constant Ckappa | | | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 372 | Mouse IgG1 HC Constant | | | AKTTPPSVYPLAPGSAAQTNSMVTLGCL VKGYFPEPVTVTWNSGSLSSGVHTFPAV LQSDLYTLSSSVTVPSSTWPSETVTCNV AHPASSTKVDKKIVPRDCGCKPCICTVP EVSSVFIFPPKPKDVLTITLTPKVTCVV VDISKDDPEVQFSWFVDDVEVHTAQTQP REEQFNSTFRSVSELPIMHQDWLNGKEF KCRVNSAAFPAPIEKTISKTKGRPKAPQ VYTIPPPKEQMAKDKVSLTCMITDFFPE DITVEWQWNGQPAENYKNTQPIMDTDGS YFVYSKLNVQKSNWEAGNTFTCSVLHEG LHNHHTEKSLSHSPG |
| 373 | Mouse IgG LC Constant Ckappa | | | RADAAPTVSIFPPSSEQLTSGGASVVCF LNNFYPKDINVKWKIDGSERQNGVLNSW TDQDSKDSTYSMSSTLTLIKDEYERHNS YTCEATHKTSTSPIVKSFNRNEC |
| 374 | Kappa LC | | | HMTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 375 | Lambda LD | | | GQPKAAPSVTLFPPSSEELQANKATLVC LISDFYPGAVTVAWKADSSPVKAGVETT TPSKQSNNKYAASSYLSLTPEQWKSHRS YSCQVTHEGSTVEKTVAPTECS |
| 376 | FlagHis Tag | | | GSGDYKDDDDKGSGHHHHHH |
| 377 | Linker | | | GGGGSGGGGSGGGGS |
| 378 | Linker | | | AAGSDQEPKSS |
| 379 | 1848-B10-VH-(G4S)3-VL | scFv | | MEVQLVESGGGLVQPGGSLRLSCAASGF NITTKSIHWVRQAPGKGLEWVGEIYPRD GITDYADSVKGRFTISADTSKNTAYLQM NSLRAEDTAVYYCARGGWHWRSGYSYYL DYWGQGTLVTVSSGGGGSGGGGSGGGGS DIQMTQSPSSLSASVGDRVTITCRASQD VNTAVAWYQQKPGKAPKLLIYSASFLYS GVPSRFSGSRSGTDFTLTISSLQPEDFA TYYCQQHYTTPPTFGQGTKVEIK |
| 380 | 1848-B10-VL-(G4S)3-VH | scFv | | MDIQMTQSPSSLSASVGDRVTITCRASQ DVNTAVAWYQQKPGKAPKLLIYSASFLY SGVPSRFSGSRSGTDFTLTISSLQPEDF ATYYCQQHYTTPPTFGQGTKVEIKGGGG |

TABLE 32-continued

Sequences

| SEQ ID NO: | Molecule | Region | Scheme | Sequence |
|---|---|---|---|---|
| | | | | SGGGGSGGGGSEVQLVESGGGLVQPGGS LRLSCAASGFNITTKSIHWVRQAPGKGL EWVGEIYPRDGITDYADSVKGRFTISAD ISKNTAYLQMNSLRAEDTAVYYCARGGW HWRSGYSYYLDYWGQGTLVTVSS |
| 381 | 1848-B10-VH-(G4S)3-VL | | scFv-Fc | MEVQLVESGGGLVQPGGSLRLSCAASGF NITTKSIHWVRQAPGKGLEWVGEIYPRD GITDYADSVKGRFTISADTSKNTAYLQM NSLRAEDTAVYYCARGGWHWRSGYSYYL DYWGQGTLVTVSSGGGGSGGGGSGGGGS DIQMTQSPSSLSASVGDRVTITCRASQD VNTAVAWYQQKPGKAPKLLIYSASFLYS GVPSRFSGSRSGTDFTLTISSLQPEDFA TYYCQQHYTTPPTFGQGTKVEIKAAGSD QEPKSSDKTHTCPPCPAPELLGGPSVFL FPPKPKDTLMISRIPEVTCVVVDVSHED PEVKFNWYVDGVEVHNAKTKPREEQYNS TYRVVSVLTVLHQDWLNGKEYKCKVSNK ALPAPIEKTISKAKGQPREPQVYTLPPS REEMTKNQVSLTCLVKGFYPSDIAVEWE SNGQPENNYKTTPPVLDSDGSFFLYSKL TVDKSRWQQGNVFSCSVMHEALHNHYTQ KSLSLSPGK |
| 382 | 1848-B10-VL-(G4S)3-VH | | scFv-Fc | MDIQMTQSPSSLSASVGDRVTITCRASQ DVNTAVAWYQQKPGKAPKLLIYSASFLY SGVPSRFSGSRSGTDFTLTISSLQPEDF ATYYCQQHYTTPPTFGQGTKVEIKGGGG SGGGGSGGGGSEVQLVESGGGLVQPGGS LRLSCAASGFNITTKSIHWVRQAPGKGL EWVGEIYPRDGITDYADSVKGRFTISAD TSKNTAYLQMNSLRAEDTAVYYCARGGW HWRSGYSYYLDYWGQGTLVTVSSAAGSD QEPKSSDKTHTCPPCPAPELLGGPSVFL FPPKPKDTLMISRIPEVTCVVVDVSHED PEVKFNWYVDGVEVHNAKTKPREEQYNS TYRVVSVLTVLHQDWLNGKEYKCKVSNK ALPAPIEKTISKAKGQPREPQVYTLPPS REEMTKNQVSLTCLVKGFYPSDIAVEWE SNGQPENNYKTTPPVLDSDGSFFLYSKL TVDKSRWQQGNVFSCSVMHEALHNHYTQ KSLSLSPGK |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibody conjugate comprising an antibody that specifically binds to folate receptor alpha (FOLR1) linked site-specifically to at least one payload moiety, wherein the antibody comprises:
   (i) a $V_H$ comprising: a CDR-H1 comprising one of SEQ ID NOs: 58 and 117; a CDR-H2 comprising one of SEQ ID NOs: 176 and 235; and a CDR-H3 comprising SEQ ID NO: 294; and
   (ii) a $V_L$ comprising: a CDR-L1 comprising SEQ ID NO: 299; a CDR-L2 comprising SEQ ID NO: 302; and a CDR-L3 comprising SEQ ID NO: 305,
   and wherein the antibody comprises one or more non-natural amino acids at sites selected from the group consisting of: HC-F404, HC-Y180, and LC-K42 according to the Kabat or EU numbering scheme of Kabat.

2. The antibody conjugate of claim 1, wherein the one or more non-natural amino acids is selected from the group consisting of p-acetyl-L-phenylalanine, O-methyl-L-tyrosine, an -3-(2-naphthyl)alanine, 3-methyl-phenylalanine, O-4-allyl-L-tyrosine, 4-propyl-L-tyrosine, a tri-O-acetyl-GlcNAcβ-serine, L-Dopa, fluorinated phenylalanine, isopropyl-L-phenylalanine, p-azido-L-phenylalanine, p-azido-methyl-L-phenylalanine, formula (30):

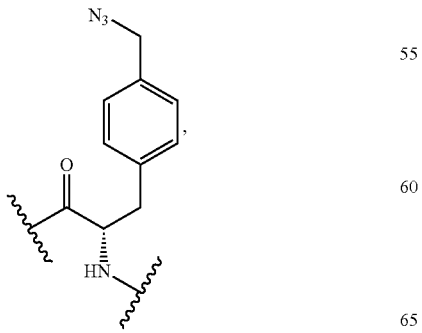

formula (56):

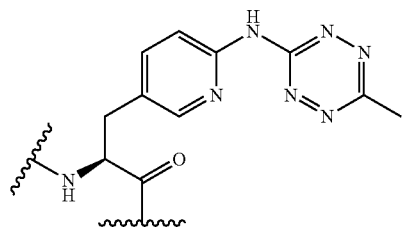 [SMILES: *N[C@@H](Cc1ccc(Nc2nnc(C)nn2)nc1)C(*)=O]

p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine.

3. The antibody conjugate of claim 1, wherein a residue of the one or more non-natural amino acids is linked to the payload moiety via a linker that is cleavable.

4. The antibody conjugate of claim 2, wherein the non-natural amino acid residue is a residue of formula (30):

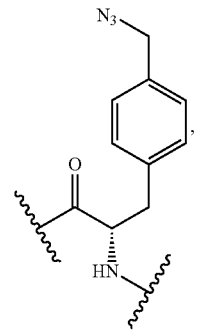 [SMILES: *N[C@@H](Cc1ccc(CN=[N+]=[N-])cc1)C(*)=O]

or formula (56):

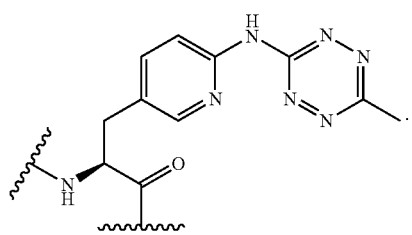 [SMILES: *N[C@@H](Cc1ccc(Nc2nnc(C)nn2)nc1)C(*)=O]

5. The antibody conjugate of claim 1, wherein the payload moiety is selected from the group consisting of maytansines, hemiasterlins, amanitins, and auristatins.

6. The antibody conjugate of claim 1, wherein the payload moiety is selected from the group consisting of DM1, hemiasterlin, amanitin, MMAF, and MMAE.

7. The antibody conjugate of claim 1, wherein the antibody comprises a $V_H$ region comprising SEQ ID NO: 362, or a variant thereof having 7 or fewer amino acid substitutions, and a $V_L$ region comprising SEQ ID NO: 367, or a variant thereof having 7 or fewer amino acid substitutions.

8. The antibody of claim 7, wherein the amino acid substitutions are conservative amino acid substitutions.

9. The antibody conjugate of claim 1, wherein the antibody comprises a non-natural amino acid at site HC-F404.

10. The antibody conjugate of claim 1, wherein the antibody comprises non-natural amino acids at sites HC-F404 and HC-Y180.

11. The antibody conjugate of claim 1, wherein the antibody comprises non-natural amino acids at sites HC-F404 and LC-K42.

12. The antibody conjugate of claim 9, wherein the non-natural amino acids are selected from the group consisting of para-azidomethylphenylalanine and p-azidomethyl-L-phenylalanine.

13. The antibody conjugate of claim 11, wherein the non-natural amino acids are selected from the group consisting of para-azidomethylphenylalanine and para-azidomethyl-L-phenylalanine.

14. The antibody conjugate of claim 1, wherein the antibody conjugate has the structure of Conjugate P:

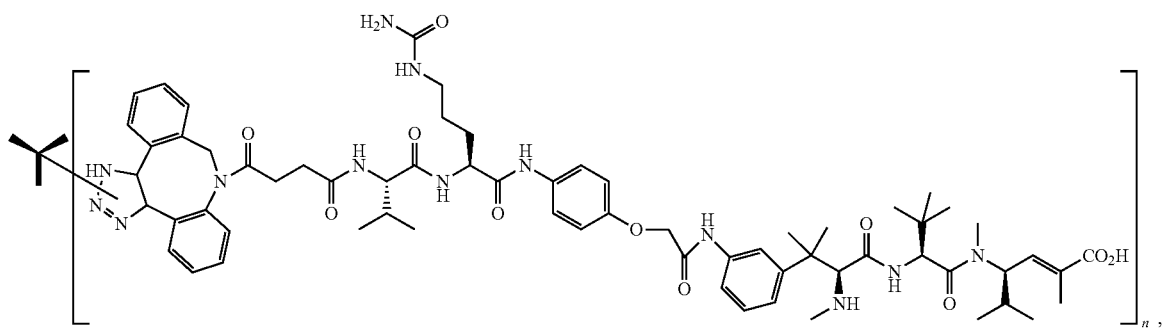

wherein n is an integer from 1 to 6.

15. The antibody conjugate of claim 1, wherein the antibody comprises a $V_H$ region comprising SEQ ID NO: 362, a $V_L$ region comprising SEQ ID NO: 367, a non-natural amino acid at each of sites HC-F404 and HC-Y180, wherein the non-natural amino acid is para-azidomethylphenylalanine, and wherein the antibody conjugate has the structure of Conjugate P:

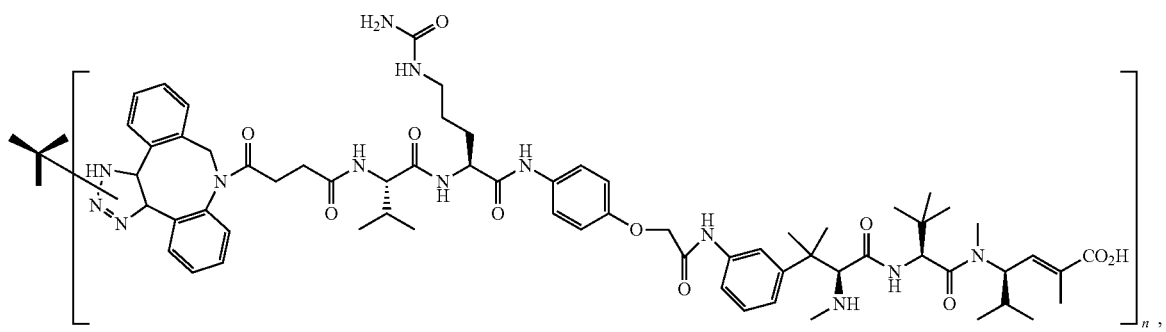

wherein n is an integer from 1 to 4, and wherein at least one bracketed structure is covalently bonded to the side chain of para-azidomethylphenylalanine at HC-F404 and at least one bracketed structure is covalently bonded to the side chain of para-azidomethylphenylalanine at HC-Y180.

16. The antibody conjugate of claim 1, further comprising at least one constant region domain comprising a sequence selected from SEQ ID NOs: 370, 371, and 372.

17. The antibody conjugate of claim 1, wherein the antibody is a monoclonal antibody selected from the group consisting of: an IgA, an IgD, an IgE, an IgG, and an IgM.

18. The antibody conjugate of claim 1, wherein the antibody is humanized or human.

19. The antibody conjugate of claim 1, wherein the antibody is aglycosylated.

20. The antibody conjugate of claim 1, wherein the antibody is an antibody fragment selected from the group consisting of: an Fv fragment, a Fab fragment, a F(ab')$_2$ fragment, a Fab' fragment, an scFv (sFv) fragment, and an scFv-Fc fragment.

21. A pharmaceutical composition comprising the antibody conjugate of claim 1 and a pharmaceutically acceptable carrier.

22. A method of treating a cancer that overexpresses folate receptor alpha, comprising administering to the subject an effective amount of an antibody conjugate of claim 1.

23. A method of treating a cancer that overexpresses folate receptor alpha, comprising administering to the subject an effective amount of, or a pharmaceutical composition of claim 21.

24. The method of claim 22, wherein the cancer is selected from the group consisting of: triple-negative breast cancer (TNBC), ovarian cancer, and endometrial cancer.

* * * * *